(12) United States Patent
Gite et al.

(10) Patent No.: US 8,114,587 B2
(45) Date of Patent: Feb. 14, 2012

(54) METHODS FOR THE DETECTION OF COLORECTAL CANCER

(75) Inventors: Sadanand Gite, Arlington, MA (US); Jennifer A. McCullough, Southbridge, MA (US); Kenneth J. Rothschild, Newton, MA (US)

(73) Assignee: Ambergen, Inc., Watertown, MA (US)

( * ) Notice: Subject to any disclaimer, the term of this patent is extended or adjusted under 35 U.S.C. 154(b) by 823 days.

(21) Appl. No.: 11/159,776

(22) Filed: Jun. 23, 2005

(65) Prior Publication Data

US 2007/0003936 A1 Jan. 4, 2007

(51) Int. Cl.
 C12Q 1/68 (2006.01)
 C07H 21/02 (2006.01)
 C07H 21/04 (2006.01)
(52) U.S. Cl. .......... 435/6; 536/23.1; 536/24.3; 536/25.4
(58) Field of Classification Search ..... 435/6; 536/23.1, 536/24.3
See application file for complete search history.

(56) References Cited

U.S. PATENT DOCUMENTS

| | | | | | |
|---|---|---|---|---|---|
| 3,996,006 | A | * | 12/1976 | Pagano | 422/50 |
| 4,333,734 | A | * | 6/1982 | Fleisher | 436/66 |
| 4,935,342 | A | * | 6/1990 | Seligson et al. | 435/6 |
| 5,106,582 | A | * | 4/1992 | Baker | 422/58 |
| 5,192,501 | A | * | 3/1993 | Guadagno et al. | 422/56 |
| 5,217,874 | A | * | 6/1993 | Guadagno et al. | 435/28 |
| 5,416,025 | A | * | 5/1995 | Krepinsky et al. | 436/63 |
| 5,702,913 | A | * | 12/1997 | Guadagno | 435/28 |
| 5,744,306 | A | * | 4/1998 | Murtagh et al. | 435/6 |
| 5,747,344 | A | * | 5/1998 | Cleator | 436/66 |
| 6,037,465 | A | * | 3/2000 | Hillebrand et al. | 536/25.42 |
| 6,187,591 | B1 | * | 2/2001 | Krepinsky et al. | 436/63 |
| 6,413,747 | B1 | * | 7/2002 | Kato et al. | 435/91.2 |
| 6,448,002 | B1 | * | 9/2002 | Hillebrand et al. | 435/6 |
| 7,195,878 | B2 | * | 3/2007 | Cleator | 435/6 |
| 7,312,060 | B2 | * | 12/2007 | Rothschild et al. | 435/194 |
| 2006/0068400 | A1 | * | 3/2006 | Cleator | 435/6 |
| 2007/0072214 | A1 | * | 3/2007 | Garvin et al. | 435/6 |
| 2008/0241940 | A1 | * | 10/2008 | LaStella | 436/66 |

OTHER PUBLICATIONS

Ahlquist, et al. Gastroenterology 2000; 119:1219-1227.*
Hemoccult II Sensa Product Instructions. Beckman Coulter. Oct. 2002.*
Wells et al. Clinica Chimica Acta 2003; 331:127-134.*
Gite, et al. Nature Biotechnology 2003; 21:194-197.*
Somers, et al. Clinical Chemistry 1998; 44(7): 1404-1409.*
Den Dunnen et al., The protein Truncation Test : A Review. Human Mutation 14 : 95-102 (1999).*
Gite et al., A high-throughput nonisotopic protein truncation test. Nature Biotechnology 21( 2) : 194-197 (Electronic Publication : Jan. 2003).*
Gyllensten Ch. 36 in PCR Protocols : A Guide to Methods and Applications. Eds. Innis et al. Academic Press San Diego, CA (1990).*
Nollau et al., Isolation of DNA from stool and bodily fluids for PCR amplification. Biotechniques 20(5) : 784-787 (1996).*
Rengucci et al., Multiple detection of genetic alterations in tumors and stool. Clinical Cancer Research 7 : 590-593 (2001).*
Rodrigues et al., p53 mutations in colorectal cancer. PNAS 87 : 7555-7559 (1990).*
Roest et al. Protein truncation test (PTT) for rapid detection of translation-terminating mutations. Human Moleclar Genetics 2 : 1719-1721 (1993).*
Sirdansky et al.. Identification of ras oncogene mutaions in the stool of patients with curable colorectal tumors. Science 256: 102-105 (1992).*
Smith-Raven et al. Detection of c-Ki-ras mutations in faecal samples from sporadic colorectal cancer patients. Gut 36 : 81-86 (1995).*
Somers et al., A rapid, reliable method for detection of known point mutations: point-EXACCT . Nucleic Acids Research 22(22), 4840-4841(1994).*
Villa et al. Identification of subjects at risk for Colorectal Carcinoma through a test based on K-ras determination in the stool. Gasteroenterology 110: 1346-1353 (1996).*
Winawer, S.J. , Colorectal Screening comes of age. NEJM 328(19) : 1416-1417 (1993).*
Winawer et al. Colorectal Cancer Screening. J. Of the National Cancer Institute 83(4) : 243-253 (1991).*

* cited by examiner

*Primary Examiner* — Ethan Whisenant
(74) *Attorney, Agent, or Firm* — Medlen & Carroll, LLP

(57) ABSTRACT

This invention relates to non-radioactive markers that facilitate the detection and analysis of nascent proteins translated within cellular or cell-free translation systems. Nascent proteins containing these markers can be rapidly and efficiently detected, isolated and analyzed without the handling and disposal problems associated with radioactive reagents. Preferred markers are dipyrrometheneboron difluoride (4,4-difluoro-4-bora-3a,4a-diaza-s-indacene) dyes.

21 Claims, 86 Drawing Sheets

```
  1 meepqsdpsv epplsqetfs dlwkllpenn vlsplpsqam ddlmlspddi eqwftedpgp
 61 deaprmpeaa prvapapaap tpaapapaps wplsssvpsq ktyqgsygfr lgflhsgtak
121 svtctyspal nkmfcqlakt cpvqlwvdst pppgtrvram aiykqsqhmt evvrrcphhe
181 rcsdsdglap pqhlirvegn lrveylddrn tfrhsvvvpy eppevgsdct tihynymcns
241 scmggmnrrp iltiitleds sgnllgrnsf evrvcacpgr drrteeenlr kkgephhelp
301 pgstkralpn ntssspqpkk kpldgeyftl qirgrerfem frelnealel kdaqagkepg
361 gsrahsshlk skkgqstsrh kklmfktegp dsd
```

Figure 10

```
   1 ccacctgaag tccaaaaagg gtcagtctac ctcccgccat aaaaaactca tgttcaagac
  61 agaagggcct gactcagact gacattctcc acttcttgtt ccccactgac agcctcccac
 121 ccccatctct ccctcccctg ccatttggg ttttgggtct ttgaacccctt gcttgcaata
 181 ggtgtgcgtc agaagcaccc aggacttcca tttgctttgt cccggggctc cactgaacaa
 241 gttggcctgc actggtgttt tgttgtgggg aggaggatgg ggagtaggac ataccagctt
 301 agatttttaag gttttttactg tgagggatgt ttgggagatg taagaaatgt tcttgcagtt
 361 aagggttagt ttacaatcag ccacattcta ggtaggggcc cacttcaccg tactaaccag
 421 ggaagctgtc cctcactgtt gaattttctc taacttcaag gcccatatct gtgaaatgct
 481 ggcatttgca cctacctcac agagtgcatt gtgagggtta atgaaataat gtacatctgg
 541 ccttgaaacc accttttatt acatggggtc tagaacttga cccccttgag ggtgcttgtt
 601 ccctctccct gttggtcggt gggttggtag tttctacagt tgggcagctg gttaggtaga
 661 gggagttgtc aagtctctgc tggcccagcc aaaccctgtc tgacaacctc ttggtgaacc
 721 ttagtaccta aaaggaaatc tcaccccatc ccacaccctg gaggatttca tctcttgtat
 781 atgatgatct ggatccacca agacttgttt tatgctcagg gtcaatttct ttttcttt
 841 tttttttttt tttcttttc tttgagactg ggtctcgctt tgttgcccag gctggagtgg
 901 agtggcgtga tcttggctta ctgcagcctt tgcctcccg gctcgagcag tcctgcctca
 961 gcctccggag tagctgggac cacaggttca tgccaccatg gccagccaac ttttgcatgt
1021 tttgtagaga tggggtctca cagtgttgcc caggctggtc tcaaactcct gggctcaggc
1081 gatccacctg tctcagcctc ccagagtgct gggattacaa ttgtgagcca ccacgtccag
1141 ctggaagggt caacatcttt tacattctgc aagcacatct gcattttcac cccacccttc
1201 ccctccttct ccctttttat atcccatttt tatatcgatc tcttattta caataaaact
1261 ttgctgccac ctgtgtgtct gagggtg
```

Figure 11

Panel A
Panel B
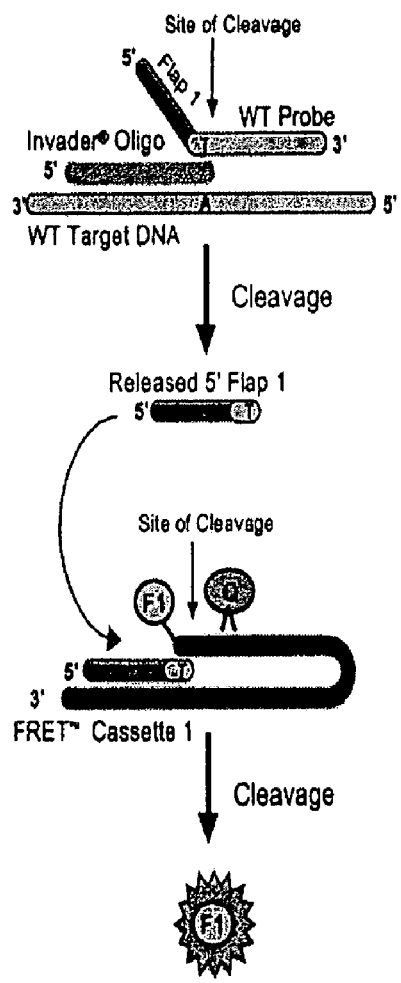
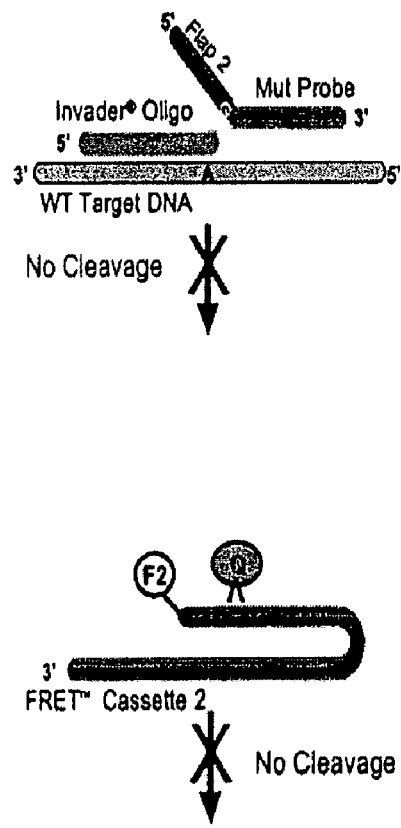
Figure 14

Panel A
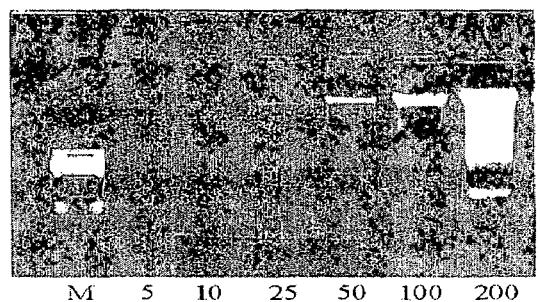
Panel B
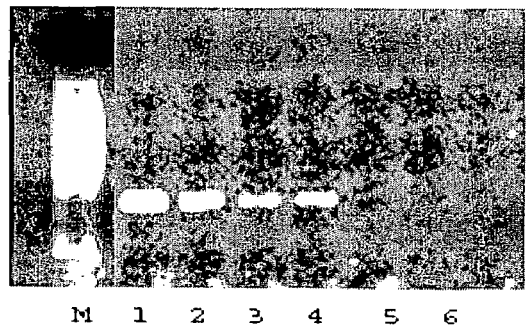
Panel C
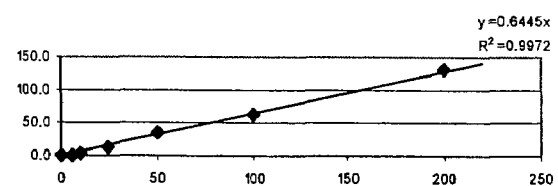
Figure 17

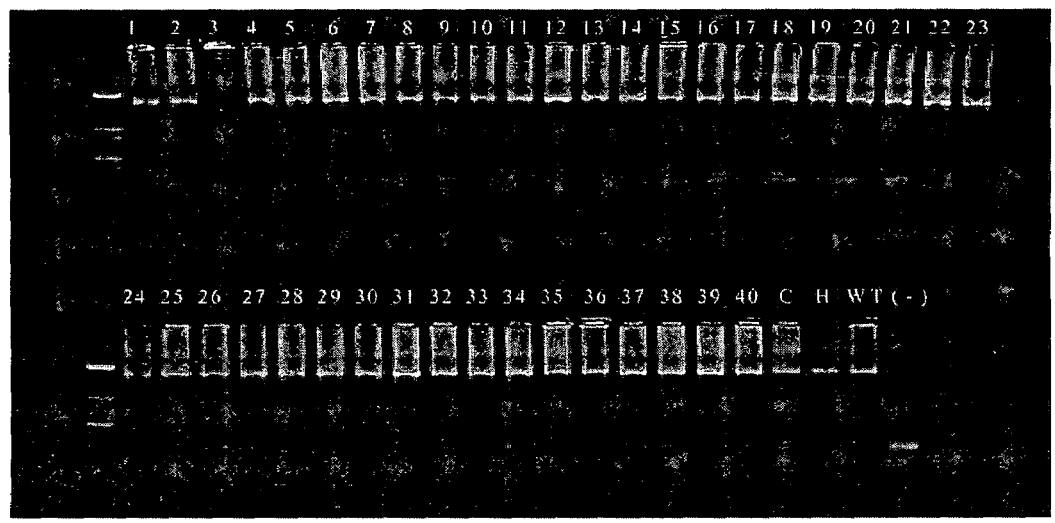
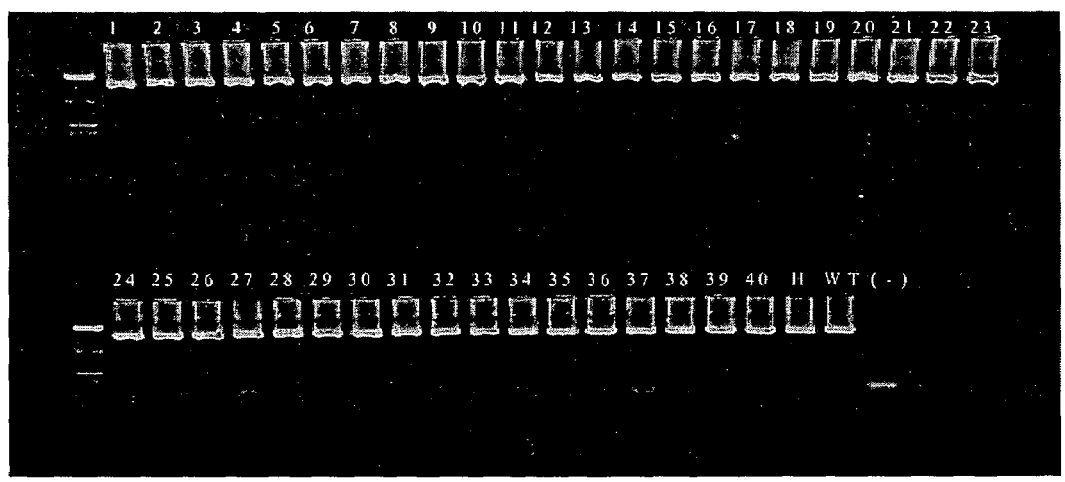
Figure 28

5'-VSV-HSV-Tag

3'-P53-Tag

▬▬ Primer Hybridization Region
▬▬ HSV Binding Sequence
▬▬ VSV Detection Sequence
▬▬ P53 Detection Sequence

Figure 30

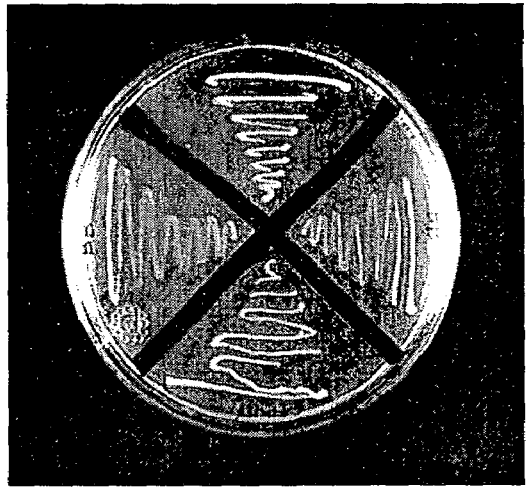 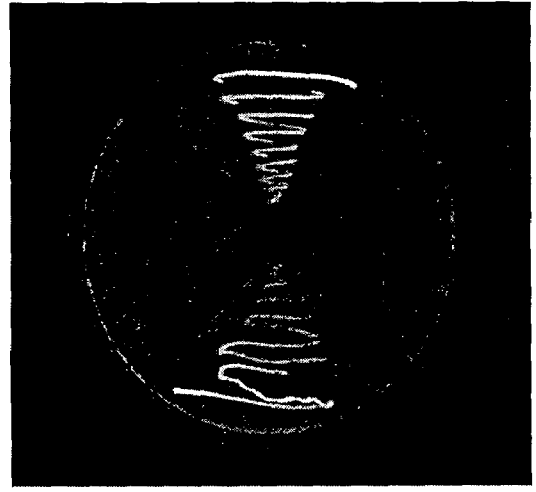
White Light UV-Light
Figure 57

| NIH Sample | mg Stool | 1-Step PCR | 2-Step PCR | FOBT |
|---|---|---|---|---|
| 1 | 2.6 | - | + | + |
| 2 | 3.9 | - | + | - |
| 3 | 2.3 | - | - | + |
| 4 | 1.5 | - | + | + |
| 5 | 1.4 | - | + | + |
| 6 | 1.9 | - | + | + |
| 7 | 2.3 | - | + | + |
| 8 | 1.7 | - | + | + |
| 9 | 1.8 | + | + | + |
| 10 | 10.4 | - | + | + |
| 11 | 13.7 | - | + | - |
| 12 | 1.9 | - | + | + |
| 13 | 0.5 | + | + | + |
| 14 | 1.7 | + | + | - |
| 15 | 4.1 | + | + | - |
| 16 | 1 | - | + | + |
| 17 | 1.7 | + | + | + |
| 18 | 1.5 | - | + | + |
| 19 | 2 | - | + | + |
| 20 | 1 | + | + | + |
| 21 | 0.8 | - | + | + |
| 22 | 1.5 | - | + | + |
| 23 | 3.7 | + | + | + |
| 24 | 2.6 | - | + | + |
| 25 | 1.7 | + | + | + |
| 26 | 4.1 | - | + | + |
| 27 | 2.2 | - | + | - |
| 28 | 2.1 | - | - | + |
| 29 | 1.9 | - | + | + |
| 30 | 5.4 | - | + | + |
| 31 | 3.6 | - | + | + |
| 32 | 3.3 | - | + | + |
| 33 | 1.6 | + | + | + |

Figure 80

```
                          SEQUENCE LISTING

<160> NUMBER OF SEQ ID NOS: 105

<210> SEQ ID NO 1
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: n can be a or g.

<400> SEQUENCE: 1 gccnccatgg                                                              10

<210> SEQ ID NO 2
<211> LENGTH: 9
<212> TYPE: RNA
<213> ORGANISM: Artificial Sequence
<220> FEATURE:
<223> OTHER INFORMATION: Synthetic

<400> SEQUENCE: 2 uaaggaggu                                                                9

<210> SEQ ID NO 3
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(14)
<223> OTHER INFORMATION: n is a, c, g, t or u
<220> FEATURE:
<221> NAME/KEY: misc_feature
<222> LOCATION: (15)..(19)
<223> OTHER INFORMATION: n can be a, c, t, or g and some or all may be
      present or absent.

<400> SEQUENCE: 3
uaaggaggun nnnnnnnnna ug                                                 22

<210> SEQ ID NO 4
<211> LENGTH: 17
<212> TYPE: PRT
<213> ORGANISM: Artificial Sequence
<220> FEATURE:
<223> OTHER INFORMATION: Synthetic

<400> SEQUENCE: 4

Trp Glu Ala Ala Ala Arg Glu Ala Cys Cys Arg Glu Cys Cys Ala Arg
1               5                   10                  15

Ala
```

```
<210> SEQ ID NO 5
<211> LENGTH: 6
<212> TYPE: PRT
<213> ORGANISM: Artificial Sequence
<220> FEATURE:
<223> OTHER INFORMATION: Synthetic

<400> SEQUENCE: 5

His His His His His His
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic

<400> SEQUENCE: 6

Glu Gln Lys Leu Ile Ser Glu Glu Asp Leu
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Synthetic

<400> SEQUENCE: 7

Asp Tyr Lys Asp Asp Asp Asp Lys
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic

<400> SEQUENCE: 8

Trp Ser His Pro Gln Phe Glu Lys
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic

<400> SEQUENCE: 9

Tyr Pro Tyr Asp Val Pro Asp Tyr Ala
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic

<400> SEQUENCE: 10

Met Trp Ser Pro Gln Phe Glu Lys
1               5

<210> SEQ ID NO 11
<211> LENGTH: 111
```

```
<212> TYPE: DNA
<213> ORGANISM: Artificial Sequence
<220> FEATURE:
<223> OTHER INFORMATION: Synthetic

<400> SEQUENCE: 11
gaattctaat acgactcact atagggttaa ctttaagaag gagatataca tatggaacaa    60
aaattaatct cggaagagga tttggcagat tctgatatta atattaaaac c            111

<210> SEQ ID NO 12
<211> LENGTH: 30
<212> TYPE: DNA
<213> ORGANISM: Artificial Sequence
<220> FEATURE:
<223> OTHER INFORMATION: Synthetic

<400> SEQUENCE: 12
agcttcatta atgatggtga tggtggtgac                                     30

<210> SEQ ID NO 13
<211> LENGTH: 94
<212> TYPE: DNA
<213> ORGANISM: Artificial Sequence
<220> FEATURE:
<223> OTHER INFORMATION: Synthetic

<400> SEQUENCE: 13
ggatcctaat acgactcact atagggagac caccatggaa caaaaattaa tatcggaaga    60
ggatttgaat gtttctccat acaggtcacg ggga                                94

<210> SEQ ID NO 14
<211> LENGTH: 50
<212> TYPE: DNA
<213> ORGANISM: Artificial Sequence
<220> FEATURE:
<223> OTHER INFORMATION: Synthetic

<400> SEQUENCE: 14
ttattaatga tggtgatggt ggtgtctgta ggaatggtat ctcgttttc                50

<210> SEQ ID NO 15
<211> LENGTH: 114
<212> TYPE: DNA
<213> ORGANISM: Artificial Sequence
<220> FEATURE:
<223> OTHER INFORMATION: Synthetic

<400> SEQUENCE: 15
ggatcctaat acgactcact atagggagac caccatggga caccaccatc accatcacgg    60
agattacaaa gatgacgatg acaaagagga gccgcagtca gatcctagcg tcga          114

<210> SEQ ID NO 16
<211> LENGTH: 68
<212> TYPE: DNA
<213> ORGANISM: Artificial Sequence
<220> FEATURE:
<223> OTHER INFORMATION: Synthetic

<400> SEQUENCE: 16
attattacaa atcctcttcc gagattaatt tttgttcgtc tgagtcaggc ccttctgtct    60
tgaacatg                                                             68

<210> SEQ ID NO 17
<211> LENGTH: 30
```

```
<212> TYPE: DNA
<213> ORGANISM: Artificial Sequence
<220> FEATURE:
<223> OTHER INFORMATION: Synthetic

<400> SEQUENCE: 17
ctcattcagc tctcggaaca tctcgaagcg                                          30

<210> SEQ ID NO 18
<211> LENGTH: 58
<212> TYPE: DNA
<213> ORGANISM: Artificial Sequence
<220> FEATURE:
<223> OTHER INFORMATION: Synthetic

<400> SEQUENCE: 18
ggatcctaat acgactcact atagggagac caccatggat gcatgtggaa ctttgtgg          58

<210> SEQ ID NO 19
<211> LENGTH: 28
<212> TYPE: DNA
<213> ORGANISM: Artificial Sequence
<220> FEATURE:
<223> OTHER INFORMATION: Synthetic

<400> SEQUENCE: 19
gaggatccat tagatgaagg tgtggacg                                            28

<210> SEQ ID NO 20
<211> LENGTH: 115
<212> TYPE: DNA
<213> ORGANISM: Artificial Sequence
<220> FEATURE:
<223> OTHER INFORMATION: Synthetic

<400> SEQUENCE: 20
ggatcctaat acgactcact atagggagac caccatgcac caccatcacc atcacggagg         60
agattacaaa gatgacgatg acaaagtttc tccatacagg tcacggggag ccaat            115

<210> SEQ ID NO 21
<211> LENGTH: 67
<212> TYPE: DNA
<213> ORGANISM: Artificial Sequence
<220> FEATURE:
<223> OTHER INFORMATION: Synthetic

<400> SEQUENCE: 21
attattacaa atcctcttcc gagattaatt tttgttcact tctgccttct gtaggaatgg         60
tatctcg                                                                  67

<210> SEQ ID NO 22
<211> LENGTH: 99
<212> TYPE: DNA
<213> ORGANISM: Artificial Sequence
<220> FEATURE:
<223> OTHER INFORMATION: Synthetic

<400> SEQUENCE: 22
ggatcctaat acgactcact atagggagac caccatgggc tacaccgaca tcgagatgaa         60
ccgcctggca aggtttctcc atacaggtca cggggagcc                               99

<210> SEQ ID NO 23
<211> LENGTH: 60
<212> TYPE: DNA
<213> ORGANISM: Artificial Sequence
```

```
<220> FEATURE:
<223> OTHER INFORMATION: Synthetic

<400> SEQUENCE: 23
ttattacagc agcttgtgca ggtcgctgaa ggtacttctg ccttctgtag gaatggtatc    60

<210> SEQ ID NO 24
<211> LENGTH: 9
<212> TYPE: PRT
<213> ORGANISM: Artificial Sequence
<220> FEATURE:
<223> OTHER INFORMATION: Synthetic

<400> SEQUENCE: 24

Thr Phe Ser Asp Leu His Lys Leu Leu
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic

<400> SEQUENCE: 25

Thr Phe Ser Asp Leu Tyr Lys Leu Leu
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic

<400> SEQUENCE: 26

Thr Phe Ser Asp Leu Gly Lys Leu Leu
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic

<400> SEQUENCE: 27

Thr Phe Ser Asp Leu Asn Lys Leu Leu
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic

<400> SEQUENCE: 28

Thr Phe Ser Asp Leu Phe Lys Leu Leu
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic
```

```
<400> SEQUENCE: 29

Thr Phe Ser Asp Leu Asp Lys Leu Leu
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic

<400> SEQUENCE: 30

Thr Phe Ser Asp Leu Thr Lys Leu Leu
1               5

<210> SEQ ID NO 31
<211> LENGTH: 10
<212> TYPE: PRT
<213> ORGANISM: Artificial Sequence
<220> FEATURE:
<223> OTHER INFORMATION: Synthetic

<400> SEQUENCE: 31

Glu Thr Phe Ser Asp Leu His Lys Leu Leu
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic

<400> SEQUENCE: 32

Gln Glu Thr Phe Ser Asp Leu His Lys Leu Leu
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic

<400> SEQUENCE: 33

Ser Gln Glu Thr Phe Ser Asp Leu His Lys Leu Leu
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Synthetic

<400> SEQUENCE: 34

Leu Ser Gln Glu Thr Phe Ser Asp Leu His Lys Leu Leu
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Synthetic

<400> SEQUENCE: 35
```

```
Glu Thr Phe Ser Asp Leu His Lys Leu Leu Pro
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Synthetic

<400> SEQUENCE: 36

Gln Glu Thr Phe Ser Asp Leu His Lys Leu Leu Pro
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Synthetic

<400> SEQUENCE: 37

Ser Gln Glu Thr Phe Ser Asp Leu His Lys Leu Leu Pro
1               5                   10

<210> SEQ ID NO 38
<211> LENGTH: 15
<212> TYPE: PRT
<213> ORGANISM: Artificial Sequence
<220> FEATURE:
<223> OTHER INFORMATION: Synthetic

<400> SEQUENCE: 38

Leu Ser Gln Glu Thr Phe Ser Asp Leu His Lys Leu Leu Pro Glu
1               5                   10                  15

<210> SEQ ID NO 39
<211> LENGTH: 11
<212> TYPE: PRT
<213> ORGANISM: Artificial Sequence
<220> FEATURE:
<223> OTHER INFORMATION: Synthetic

<400> SEQUENCE: 39

Tyr Thr Asp Ile Glu Met Asn Arg Leu Gly Lys
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Synthetic

<400> SEQUENCE: 40

Tyr Ala Asp Ile Glu Met Asn Arg Leu Gly Lys
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Synthetic

<400> SEQUENCE: 41

Tyr Thr Asp Ile Glu Met Asn Arg Ser Gly Lys
1               5                   10
```

```
<210> SEQ ID NO 42
<211> LENGTH: 11
<212> TYPE: PRT
<213> ORGANISM: Artificial Sequence
<220> FEATURE:
<223> OTHER INFORMATION: Synthetic

<400> SEQUENCE: 42

Tyr Thr Asp Ile Glu Met Asn Arg Leu Ser Lys
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Synthetic

<400> SEQUENCE: 43

Tyr Ser Asp Ile Glu Met Asn Arg Ser Gly Lys
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Synthetic

<400> SEQUENCE: 44

Tyr Ala Asp Ile Glu Met Asn Arg Leu Leu Lys
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Synthetic

<400> SEQUENCE: 45

Tyr Thr Asp Ile Glu Met Asn Arg Ser Ser Lys
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Synthetic

<400> SEQUENCE: 46

Tyr Ala Asp Ile Glu Met Asn Arg Ser Gly Lys
1               5                   10

<210> SEQ ID NO 47
<211> LENGTH: 30
<212> TYPE: DNA
<213> ORGANISM: Artificial Sequence
<220> FEATURE:
<223> OTHER INFORMATION: Synthetic

<400> SEQUENCE: 47
tttttggttg gcactcttac ttaccggagc                                    30

<210> SEQ ID NO 48
```

```
<211> LENGTH: 30
<212> TYPE: DNA
<213> ORGANISM: Artificial Sequence
<220> FEATURE:
<223> OTHER INFORMATION: Synthetic

<400> SEQUENCE: 48
agatgcttgc tggacctggt ccattatctt                                     30

<210> SEQ ID NO 49
<211> LENGTH: 1288
<212> TYPE: DNA
<213> ORGANISM: Artificial Sequence
<220> FEATURE:
<223> OTHER INFORMATION: Synthetic

<400> SEQUENCE: 49
ccacctgaag tccaaaaagg gtcagtctac ctcccgccat aaaaaactca tgttcaagac    60
agaagggcct gactcagact gacattctcc acttcttgtt ccccactgac agcctcccac   120
ccccatctct ccctcccctg ccattttggg ttttgggtct ttgaacccct gcttgcaata   180
ggtgtgcgtc agaagcaccc aggacttcca tttgctttgt cccggggctc cactgaacaa   240
gttggcctgc actggtgttt tgttgtgggg aggaggatgg ggagtaggac ataccagctt   300
agattttaag gttttttactg tgagggatgt ttgggagatg taagaaatgt tcttgcagtt   360
aagggttagt ttacaatcag ccacattcta ggtaggggcc cacttcaccg tactaaccag   420
ggaagctgtc cctcactgtt gaattttctc taacttcaag gcccatatct gtgaaatgct   480
ggcatttgca cctacctcac agagtgcatt gtgagggtta atgaaataat gtacatctgg   540
ccttgaaacc accttttatt acatggggtc tagaacttga ccccccttgag ggtgcttgtt   600 ccctctccct gttggtcggt gggttggtag tttctacagt tgggcagctg gttaggtaga   660
gggagttgtc aagtctctgc tggcccagcc aaaccctgtc tgacaacctc ttggtgaacc   720
ttagtaccta aaaggaaatc tcaccccatc ccacaccctg gaggatttca tctcttgtat   780
atgatgatct ggatccacca agacttgttt tatgctcagg gtcaatttct ttttctttt   840 ttttttttt tttcttttc tttgagactg ggtctcgctt tgttgcccag gctggagtgg   900
agtggcgtga tcttggctta ctgcagcctt tgcctccccg gctcgagcag tcctgcctca   960
gcctccggag tagctgggac cacaggttca tgccaccatg gccagccaac ttttgcatgt  1020
tttgtagaga tggggtctca cagtgttgcc caggctggtc tcaaactcct gggctcaggc  1080
gatccacctg tctcagcctc ccagagtgct gggattacaa ttgtgagcca ccacgtccag  1140
ctggaagggt caacatcttt tacattctgc aagcacatct gcattttcac cccacccttc  1200
ccctccttct ccctttttat atcccatttt tatatcgatc tcttatttta caataaaact  1260
ttgctgccac ctgtgtgtct gagggggtg                                    1288

<210> SEQ ID NO 50
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa can be alanine, arginine, asparagine,
      aspartic acid, cysteine, glutamine, glutamic acid, glycine,
      histidine, isoleucine, leucine, lysine, methionine, phenylalanine,
      proline, serine, threonine, tyrosine, or valine.

<400> SEQUENCE: 50
```

```
Thr Phe Ser Asp Leu Xaa Lys Leu Leu
1               5

<210> SEQ ID NO 51
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(10)
<223> OTHER INFORMATION: Xaa can be any amino acid and all or some may
      be present or absent.
<220> FEATURE:
<221> NAME/KEY: MISC_FEATURE
<222> LOCATION: (16)..(16)
<223> OTHER INFORMATION: Xaa can be alanine, arginine, asparagine,
      aspartic acid, cysteine, glutamine, glutamic acid, glycine,
      histidine, isoleucine, leucine, lysine, methionine, phenylalanine,
      proline, serine, threonine, tyrosine, or valine.

<400> SEQUENCE: 51

Xaa Xaa Xaa Xaa Xaa Xaa Xaa Xaa Xaa Xaa Thr Phe Ser Asp Leu Xaa
1               5                   10                  15

Lys Leu Leu

<210> SEQ ID NO 52
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(10)
<223> OTHER INFORMATION: X can be any amino acid and all or some may be
      present or absent.
<220> FEATURE:
<221> NAME/KEY: MISC_FEATURE
<222> LOCATION: (16)..(16)
<223> OTHER INFORMATION: Xaa can be alanine, arginine, asparagine,
      aspartic acid, cysteine, glutamine, glutamic acid, glycine,
      histidine, isoleucine, leucine, lysine, methionine, phenylalanine,
      proline, serine, threonine, tyrosine, or valine.
<220> FEATURE:
<221> NAME/KEY: MISC_FEATURE
<222> LOCATION: (20)..(29)
<223> OTHER INFORMATION: X can be any amino acid and all or some may be
      present or absent.

<400> SEQUENCE: 52

Xaa Xaa Xaa Xaa Xaa Xaa Xaa Xaa Xaa Xaa Thr Phe Ser Asp Leu Xaa
1               5                   10                  15

Lys Leu Leu Xaa Xaa Xaa Xaa Xaa Xaa Xaa Xaa Xaa Xaa
            20                  25

<210> SEQ ID NO 53
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa can be Serine or Alanine.

<400> SEQUENCE: 53

Tyr Xaa Asp Ile Glu Met Asn Arg Leu Gly Lys
1               5                   10
```

```
<210> SEQ ID NO 54
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Xaa can be Serine.

<400> SEQUENCE: 54

Tyr Thr Asp Ile Glu Met Asn Arg Xaa Gly Lys
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Xaa can be Serine or Leucine.

<400> SEQUENCE: 55

Tyr Thr Asp Ile Glu Met Asn Arg Leu Xaa Lys
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa can be Serine or Alanine.
<220> FEATURE:
<221> NAME/KEY: MISC_FEATURE
<222> LOCATION: (9)..(9)
<223> OTHER INFORMATION: Xaa can be Serine.

<400> SEQUENCE: 56

Tyr Xaa Asp Ile Glu Met Asn Arg Xaa Gly Lys
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa can be Serine or Alanine.
<220> FEATURE:
<221> NAME/KEY: MISC_FEATURE
<222> LOCATION: (9)..(9)
<223> OTHER INFORMATION: Xaa can be Glycine or Serine.
<220> FEATURE:
<221> NAME/KEY: misc_feature
<222> LOCATION: (10)..(10)
<223> OTHER INFORMATION: Xaa can be any naturally occurring amino acid

<400> SEQUENCE: 57

Tyr Xaa Asp Ile Glu Met Asn Arg Leu Xaa Lys
1               5                   10
```

```
<210> SEQ ID NO 58
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Xaa can be Serine.
<220> FEATURE:
<221> NAME/KEY: MISC_FEATURE
<222> LOCATION: (10)..(10)
<223> OTHER INFORMATION: Xaa can be Leucine or Serine.

<400> SEQUENCE: 58

Tyr Thr Asp Ile Glu Met Asn Arg Xaa Xaa Lys
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa can be Serine or Alanine.
<220> FEATURE:
<221> NAME/KEY: MISC_FEATURE
<222> LOCATION: (9)..(9)
<223> OTHER INFORMATION: Xaa can be Serine.
<220> FEATURE:
<221> NAME/KEY: MISC_FEATURE
<222> LOCATION: (10)..(10)
<223> OTHER INFORMATION: Xaa can be Glycine, Leucine, or Serine.

<400> SEQUENCE: 59

Tyr Xaa Asp Ile Glu Met Asn Arg Xaa Xaa Lys
1               5                   10

<210> SEQ ID NO 60
<211> LENGTH: 24
<212> TYPE: DNA
<213> ORGANISM: Artificial Sequence
<220> FEATURE:
<223> OTHER INFORMATION: Synthetic

<400> SEQUENCE: 60
agtggcatta taagccccag tgat                                          24

<210> SEQ ID NO 61
<211> LENGTH: 24
<212> TYPE: DNA
<213> ORGANISM: Artificial Sequence
<220> FEATURE:
<223> OTHER INFORMATION: Synthetic

<400> SEQUENCE: 61
agcatttact gcagcttgct tagg                                          24

<210> SEQ ID NO 62
<211> LENGTH: 24
<212> TYPE: DNA
<213> ORGANISM: Artificial Sequence
<220> FEATURE:
<223> OTHER INFORMATION: Synthetic

<400> SEQUENCE: 62
```

```
tggtaactca ctgggacgga acag                                          24

<210> SEQ ID NO 63
<211> LENGTH: 24
<212> TYPE: DNA
<213> ORGANISM: Artificial Sequence
<220> FEATURE:
<223> OTHER INFORMATION: Synthetic

<400> SEQUENCE: 63
ctcgcttagt gctccctggg ggca                                          24

<210> SEQ ID NO 64
<211> LENGTH: 21
<212> TYPE: DNA
<213> ORGANISM: Artificial Sequence
<220> FEATURE:
<223> OTHER INFORMATION: Synthetic

<400> SEQUENCE: 64
ggcctgctga aaatgactga a                                             21

<210> SEQ ID NO 65
<211> LENGTH: 21
<212> TYPE: DNA
<213> ORGANISM: Artificial Sequence
<220> FEATURE:
<223> OTHER INFORMATION: Synthetic

<400> SEQUENCE: 65
ctctattgtt ggatcatatt c                                             21

<210> SEQ ID NO 66
<211> LENGTH: 98
<212> TYPE: DNA
<213> ORGANISM: Artificial Sequence
<220> FEATURE:
<223> OTHER INFORMATION: Synthetic

<400> SEQUENCE: 66
gacgacacag gaagcagatt ctgctaatac cctgcaaata gcagaaataa aagaaaagat   60
tggaactagg tcagctgaag atcctgtgag cgaagttc                           98

<210> SEQ ID NO 67
<211> LENGTH: 32
<212> TYPE: DNA
<213> ORGANISM: Artificial Sequence
<220> FEATURE:
<223> OTHER INFORMATION: Synthetic

<400> SEQUENCE: 67
acggacgcgg agagaaaaga ttggaactag tc                                 32

<210> SEQ ID NO 68
<211> LENGTH: 45
<212> TYPE: DNA
<213> ORGANISM: Artificial Sequence
<220> FEATURE:
<223> OTHER INFORMATION: Synthetic

<400> SEQUENCE: 68
caggaagcag attctgctaa taccctgcaa atagcagaaa taaat                   45

<210> SEQ ID NO 69
<211> LENGTH: 76
```

```
<212> TYPE: DNA
<213> ORGANISM: Artificial Sequence
<220> FEATURE:
<223> OTHER INFORMATION: Synthetic

<400> SEQUENCE: 69
tcttcagctg acctagttcc aatctttct tttatttctg ctatttgcag ggtattagca      60
gaatctgctt cctgtg                                                     76

<210> SEQ ID NO 70
<211> LENGTH: 28
<212> TYPE: DNA
<213> ORGANISM: Artificial Sequence
<220> FEATURE:
<223> OTHER INFORMATION: Synthetic

<400> SEQUENCE: 70
cgcgccgagg agattggaac taggtcag                                        28

<210> SEQ ID NO 71
<211> LENGTH: 71
<212> TYPE: DNA
<213> ORGANISM: Artificial Sequence
<220> FEATURE:
<223> OTHER INFORMATION: Synthetic

<400> SEQUENCE: 71
tcttcagctg acctagttcc aatctttat ttctgctatt tgcagggtat tagcagaatc      60
tgcttcctgt g                                                          71

<210> SEQ ID NO 72
<211> LENGTH: 90
<212> TYPE: DNA
<213> ORGANISM: Artificial Sequence
<220> FEATURE:
<223> OTHER INFORMATION: Synthetic

<400> SEQUENCE: 72
atgaaccgcc tgggcaaggg aggaggagga cagcctgaac tcgctccaga ggatccggaa      60
gatgtttctc catacaggtc acggggagcc                                       90

<210> SEQ ID NO 73
<211> LENGTH: 30
<212> TYPE: DNA
<213> ORGANISM: Artificial Sequence
<220> FEATURE:
<223> OTHER INFORMATION: Synthetic

<400> SEQUENCE: 73
agatgcttgc tggacctggt ccattatctt                                       30

<210> SEQ ID NO 74
<211> LENGTH: 85
<212> TYPE: DNA
<213> ORGANISM: Artificial Sequence
<220> FEATURE:
<223> OTHER INFORMATION: Synthetic

<400> SEQUENCE: 74
ggatcctaat acgactcact atagggagac caccatgggc tacaccgaca tcgagatgaa      60
ccgcctgggc aagggaggag gagga                                            85

<210> SEQ ID NO 75
<211> LENGTH: 60
```

```
<212> TYPE: DNA
<213> ORGANISM: Artificial Sequence
<220> FEATURE:
<223> OTHER INFORMATION: Synthetic

<400> SEQUENCE: 75
ttattacagc agcttgtgca ggtcgctgaa ggtacttctg ccttctgtag gaatggtatc        60

<210> SEQ ID NO 76
<211> LENGTH: 90
<212> TYPE: DNA
<213> ORGANISM: Artificial Sequence
<220> FEATURE:
<223> OTHER INFORMATION: Synthetic

<400> SEQUENCE: 76
atgaaccgcc tgggcaaggg aggaggagga cagcctgaac tcgctccaga ggatccggaa        60
gataatgcat gtggaacttt gtggaatctc                                        90

<210> SEQ ID NO 77
<211> LENGTH: 54
<212> TYPE: DNA
<213> ORGANISM: Artificial Sequence
<220> FEATURE:
<223> OTHER INFORMATION: Synthetic

<400> SEQUENCE: 77
ggcgtaatca ggcacgtcat agggatacct cttggcatta gatgaaggtg tgga             54

<210> SEQ ID NO 78
<211> LENGTH: 85
<212> TYPE: DNA
<213> ORGANISM: Artificial Sequence
<220> FEATURE:
<223> OTHER INFORMATION: Synthetic

<400> SEQUENCE: 78
ggatcctaat acgactcact atagggagac caccatgggc tacaccgaca tcgagatgaa        60
ccgcctgggc aagggaggag gagga                                             85

<210> SEQ ID NO 79
<211> LENGTH: 60
<212> TYPE: DNA
<213> ORGANISM: Artificial Sequence
<220> FEATURE:
<223> OTHER INFORMATION: Synthetic

<400> SEQUENCE: 79
ttattacagc agcttgtgca ggtcgctgaa ggtggcgtaa tcaggcacgt catagggata        60

<210> SEQ ID NO 80
<211> LENGTH: 133
<212> TYPE: DNA
<213> ORGANISM: Artificial Sequence
<220> FEATURE:
<223> OTHER INFORMATION: Synthetic

<400> SEQUENCE: 80
ggatcctaat acgactcact atagggagac caccatgtac accgacatcg agatgaaccg        60
cctgggcaag ggaggacagc ctgaactcgc tccagaggat ccggaagata atgcatgtgg       120
aactttgtgg aat                                                         133

<210> SEQ ID NO 81
<211> LENGTH: 60
```

```
<212> TYPE: DNA
<213> ORGANISM: Artificial Sequence
<220> FEATURE:
<223> OTHER INFORMATION: Synthetic

<400> SEQUENCE: 81
ttattacagc agcttgtgca ggtcgctgaa ggtacttctg ccttctgtag gaatggtatc    60

<210> SEQ ID NO 82
<211> LENGTH: 80
<212> TYPE: DNA
<213> ORGANISM: Artificial Sequence
<220> FEATURE:
<223> OTHER INFORMATION: Synthetic

<400> SEQUENCE: 82
taatacgact cactataggg aggaggacag ctatggacta caaggacgac gatgacaagg    60
gacaaagcag taaaaccgaa                                                80

<210> SEQ ID NO 83
<211> LENGTH: 68
<212> TYPE: DNA
<213> ORGANISM: Artificial Sequence
<220> FEATURE:
<223> OTHER INFORMATION: Synthetic

<400> SEQUENCE: 83
tttttttttt atgcgtagtc tggtacgtcg tatgggtatt tatttatagc cttttgaggc    60
tgaccact                                                             68

<210> SEQ ID NO 84
<211> LENGTH: 80
<212> TYPE: DNA
<213> ORGANISM: Artificial Sequence
<220> FEATURE:
<223> OTHER INFORMATION: Synthetic

<400> SEQUENCE: 84
taatacgact cactataggg aggaggacag ctatggacta caaggacgac gatgacaagc    60
aggaagcaga ttctgctaat                                                80

<210> SEQ ID NO 85
<211> LENGTH: 68
<212> TYPE: DNA
<213> ORGANISM: Artificial Sequence
<220> FEATURE:
<223> OTHER INFORMATION: Synthetic

<400> SEQUENCE: 85
tttttttttt atgcgtagtc tggtacgtcg tatgggtatt tatttatctg cagtctgctg    60
gatttggt                                                             68

<210> SEQ ID NO 86
<211> LENGTH: 22
<212> TYPE: DNA
<213> ORGANISM: Artificial Sequence
<220> FEATURE:
<223> OTHER INFORMATION: Synthetic

<400> SEQUENCE: 86
aggcaaagtc cttcacagaa tg                                             22

<210> SEQ ID NO 87
<211> LENGTH: 24
```

```
<212> TYPE: DNA
<213> ORGANISM: Artificial Sequence
<220> FEATURE:
<223> OTHER INFORMATION: Synthetic

<400> SEQUENCE: 87
cttgattgtc tttgctcact ttgt                                              24

<210> SEQ ID NO 88
<211> LENGTH: 31
<212> TYPE: DNA
<213> ORGANISM: Artificial Sequence
<220> FEATURE:
<223> OTHER INFORMATION: Synthetic

<400> SEQUENCE: 88
agatgggcaa gacccaaaca cataatagaa g                                      31

<210> SEQ ID NO 89
<211> LENGTH: 33
<212> TYPE: PRT
<213> ORGANISM: Artificial Sequence
<220> FEATURE:
<223> OTHER INFORMATION: Synthetic

<400> SEQUENCE: 89

Met Asp Tyr Lys Asp Asp Asp Lys Asn Phe Pro Phe Phe Glu
1               5                   10                  15

Thr Leu Lys Leu Ser Ser Arg Val Tyr Pro Tyr Asp Val Pro Asp Tyr
                20                  25                  30

Ala

<210> SEQ ID NO 90
<211> LENGTH: 27
<212> TYPE: DNA
<213> ORGANISM: Artificial Sequence
<220> FEATURE:
<223> OTHER INFORMATION: Synthetic

<400> SEQUENCE: 90
ccggtagaaa aaatcagtaa aggagaa                                           27

<210> SEQ ID NO 91
<211> LENGTH: 28
<212> TYPE: DNA
<213> ORGANISM: Artificial Sequence
<220> FEATURE:
<223> OTHER INFORMATION: Synthetic

<400> SEQUENCE: 91
ttctcctttt actgattttt tctaccgg                                          28

<210> SEQ ID NO 92
<211> LENGTH: 42
<212> TYPE: DNA
<213> ORGANISM: Artificial Sequence
<220> FEATURE:
<223> OTHER INFORMATION: Synthetic

<400> SEQUENCE: 92
agcttgcatg cctgaaggtc gactctagag gatccccggg ta                          42

<210> SEQ ID NO 93
<211> LENGTH: 43
<212> TYPE: DNA
<213> ORGANISM: Artificial Sequence
```

```
<220> FEATURE:
<223> OTHER INFORMATION: Synthetic

<400> SEQUENCE: 93
accggtaccc ggggatcctc tagagtcgac cttcaggcat gca                    43

<210> SEQ ID NO 94
<211> LENGTH: 40
<212> TYPE: DNA
<213> ORGANISM: Artificial Sequence
<220> FEATURE:
<223> OTHER INFORMATION: Synthetic

<400> SEQUENCE: 94
ggagctcata agcttctctg gacaaagcag taaaaccgaa                        40

<210> SEQ ID NO 95
<211> LENGTH: 41
<212> TYPE: DNA
<213> ORGANISM: Artificial Sequence
<220> FEATURE:
<223> OTHER INFORMATION: Synthetic

<400> SEQUENCE: 95
atgagctcca ccggtgcgcc ttctgtagga atggtatctc g                      41

<210> SEQ ID NO 96
<211> LENGTH: 41
<212> TYPE: DNA
<213> ORGANISM: Artificial Sequence
<220> FEATURE:
<223> OTHER INFORMATION: Synthetic

<400> SEQUENCE: 96
atgacgtcct ctagagcacg tgatgacttt gttggcatgg c                      41

<210> SEQ ID NO 97
<211> LENGTH: 42
<212> TYPE: DNA
<213> ORGANISM: Artificial Sequence
<220> FEATURE:
<223> OTHER INFORMATION: Synthetic

<400> SEQUENCE: 97
atgagcctcc ggtaccgcac gtgatgactt tgttggcatg gc                     42

<210> SEQ ID NO 98
<211> LENGTH: 42
<212> TYPE: DNA
<213> ORGANISM: Artificial Sequence
<220> FEATURE:
<223> OTHER INFORMATION: Synthetic

<400> SEQUENCE: 98
atgagcctcc cccggggcac gtgatgactt tgttggcatg gc                     42

<210> SEQ ID NO 99
<211> LENGTH: 41
<212> TYPE: DNA
<213> ORGANISM: Artificial Sequence
<220> FEATURE:
<223> OTHER INFORMATION: Synthetic

<400> SEQUENCE: 99
tgattacgcc aagctcatct ggacaaagca gtaaaaccga a                      41
```

```
<210> SEQ ID NO 100
<211> LENGTH: 39
<212> TYPE: DNA
<213> ORGANISM: Artificial Sequence
<220> FEATURE:
<223> OTHER INFORMATION: Synthetic

<400> SEQUENCE: 100
ccggggatcc tctagacgtg atgactttgt tggcatggc                             39

<210> SEQ ID NO 101
<211> LENGTH: 100
<212> TYPE: DNA
<213> ORGANISM: Artificial Sequence
<220> FEATURE:
<223> OTHER INFORMATION: Synthetic

<400> SEQUENCE: 101
ggatcctaat acgactcact atagggagac caccatgggc tacaccgaca tcgagatgaa     60
ccgcctgggc aagtctggac aaagcagtaa aaccgaacat                          100

<210> SEQ ID NO 102
<211> LENGTH: 60
<212> TYPE: DNA
<213> ORGANISM: Artificial Sequence
<220> FEATURE:
<223> OTHER INFORMATION: Synthetic

<400> SEQUENCE: 102
ttattacagc agcttgtgca ggtcgctgaa ggtacgtgat gactttgttg gcatggcaga     60

<210> SEQ ID NO 103
<211> LENGTH: 23
<212> TYPE: DNA
<213> ORGANISM: Artificial Sequence
<220> FEATURE:
<223> OTHER INFORMATION: Synthetic

<400> SEQUENCE: 103
acgtcatgtg gatcagccta ttg                                             23

<210> SEQ ID NO 104
<211> LENGTH: 23
<212> TYPE: DNA
<213> ORGANISM: Artificial Sequence
<220> FEATURE:
<223> OTHER INFORMATION: Synthetic

<400> SEQUENCE: 104
ggtaattttg aagcagtctg ggc                                             23

<210> SEQ ID NO 105
<211> LENGTH: 78
<212> TYPE: DNA
<213> ORGANISM: Artificial Sequence
<220> FEATURE:
<223> OTHER INFORMATION: Synthetic

<400> SEQUENCE: 105
atgaccatga ttacgccaag cttgcatgcc tgcaggtcga ctctagagga tccccgggta     60
ccggtagaaa aaatgagt                                                   78
```

METHODS FOR THE DETECTION OF COLORECTAL CANCER

FIELD OF THE INVENTION

This invention relates to non-radioactive markers that facilitate the detection and analysis of nascent proteins translated within cellular or cell-free translation systems. Nascent proteins containing these markers can be rapidly and efficiently detected, isolated and analyzed without the handling and disposal problems associated with radioactive reagents.

BACKGROUND OF THE INVENTION

There exists an urgent need to develop an effective non-invasive method of detecting colorectal cancer (CRC), the second leading cause of cancer deaths in the U.S and Western world. Such non-invasive testing, if instituted for a large segment of the population, could result in a dramatic reduction in the approximately 55,000 deaths per year due to this disease. The American Cancer Society recommends that individuals over the age of fifty with normal risk be screened at one- to five-year intervals using one or more of the tests available. However, these methods are of limited effectiveness as described below.

What is needed is a non-invasive, convenient, low-cost and sensitive test for colorectal cancer that does not require specialized medical procedures.

Typical cells from which cell-free extracts or in vitro extracts are made are Escherichia coli cells, wheat germ cells, rabbit reticulocytes, insect cells and frog oocytes. Aminoacylation or charging of tRNA results in linking the carboxyl terminal of an amino acid to the 2'-(or 3'-)hydroxyl group of a terminal adenosine base via an ester linkage. This process can be accomplished either using enzymatic or chemical methods. Normally a particular tRNA is charged by only one specific native amino acid. This selective charging, termed here enzymatic aminoacylation, is accomplished by aminoacyl tRNA synthetases. A tRNA which selectively incorporates a tyrosine residue into the nascent polypeptide chain by recognizing the tyrosine UAC codon will be charged by tyrosine with a tyrosine-aminoacyl tRNA synthetase, while a tRNA designed to read the UGU codon will be charged by a cysteine-aminoacyl tRNA synthetase.

Special tRNAs, such as tRNAs which have suppressor properties, suppressor tRNAs, have been used in the process of site-directed non-native amino acid replacement (SNAAR) (C. Noren et al., Science 244:182-188, 1989). In SNAAR, a unique codon is required on the mRNA and the suppressor tRNA, acting to target a non-native amino acid to a unique site during the protein synthesis (PCT WO90/05785). However, the suppressor tRNA must not be recognizable by the aminoacyl tRNA synthetases present in the protein translation system (Bain et al., Biochemistry 30:5411-21, 1991). Furthermore, site-specific incorporation of non-native amino acids is not suitable in general for detection of nascent proteins in a cellular or cell-free protein synthesis system due to the necessity of incorporating non-sense codons into the coding regions of the template DNA or the mRNA.

In certain cases, a non-native amino acid can be formed after the tRNA molecule is aminoacylated using chemical reactions which specifically modify the native amino acid and do not significantly alter the functional activity of the aminoacylated tRNA (Promega Technical Bulletin No. 182; tRN-$A^{nscend}$TM: Non-radioactive Translation Detection System, September 1993). These reactions are referred to as post-aminoacylation modifications. For example, the $\epsilon$-amino group of the lysine linked to its cognate tRNA (tRNA$^{LYS}$), could be modified with an amine specific photoaffinity label (U. C. Krieg et al., Proc. Natl. Acad. Sci. USA 83:8604-08, 1986). These types of post-aminoacylation modifications, although useful, do not provide a general means of incorporating non-native amino acids into the nascent proteins. The disembodiment is that only those non-native amino acids that are derivatives of normal amino acids can be incorporated and only a few amino acid residues have side chains amenable to chemical modification. More often, post-aminoacylation modifications can result in the tRNA being altered and produce a non-specific modification of the $\epsilon$-amino group of the amino acid (e.g. in addition to the $\epsilon$-amino group) linked to the tRNA. This factor can lower the efficiency of incorporation of the non-native amino acid linked to the tRNA. Non-specific, post-aminoacylation modifications of tRNA structure could also compromise its participation in protein synthesis. Incomplete chain formation could also occur when the $\epsilon$-amino group of the amino acid is modified.

In certain other cases, a nascent protein can be detected because of its special and unique properties such as specific enzymatic activity, absorption or fluorescence. This approach is of limited use since most proteins do not have special properties with which they can be easily detected. In many cases, however, the expressed protein may not have been previously characterized or even identified, and thus, its characteristic properties are unknown.

SUMMARY OF THE INVENTION

One embodiment of the present invention contemplates a method, comprising: a) providing: a fecal specimen on a surface, the surface comprising guaiac, the specimen comprising DNA; b) isolating at least a portion of the DNA to create isolated DNA, and c) testing the isolated DNA for mutations. In one embodiment, the dry weight of the fecal specimen is less than 10 mg. In one embodiment, the testing of step (c) comprises using an assay with a sensitivity capable of measuring 1 mutant gene out of 50 wild type genes. In one embodiment, the method further comprises prior to step (c), amplifying one or more regions of the isolated DNA. In one embodiment, the amplifying comprises performing a polymerase chain reaction. In one embodiment, the testing results in the detection of a mutation. In one embodiment, the detected mutation is in one or more of the genes selected from a group consisting of the APC, K-RAS, p53 and beta-catenine genes. In one embodiment, the surface is part of a slide contained in a commercial kit used for fecal occult blood testing. In one embodiment, the kit is selected from the group consisting of Hemoccult® Sensa®, Hemoccult II®, Colo-Screen®, Color-Rect®, Hemachek®, Quick-Cult® and Sensa®. In one embodiment, the assay comprises a HTS-PTT assay. In another embodiment, the assay comprises an Invader® assay. In yet another embodiment, the assay comprises a Point-EXACCT assay.

Another embodiment of the present invention contemplates a method, comprising: a) providing a fecal specimen on a surface, the surface comprising anti-hemoglobin antibody, the specimen comprising DNA; b) isolating at least a portion of the DNA to create isolated DNA; and c) testing the isolated DNA for mutations. In one embodiment, the dry weight of the fecal specimen is less than 10 mg. In one embodiment, the testing of step (c) comprises using an assay with a sensitivity capable of measuring 1 mutant gene out of 50 wild type genes. In one embodiment, the method further comprises prior to step (c), amplifying one or more regions of the isolated DNA. In one embodiment, the amplifying comprises performing a polymerase chain reaction. In one embodiment, the testing results in the detection of a mutation. In one embodiment, the detected mutation is in one or more of the genes selected from a group consisting of the APC, K-RAS, p53 and beta-catenine genes. In one embodiment, the surface is part of a component of a commercial kit used for fecal occult blood testing. In one embodiment, the kit is selected from the group consisting of HemoQuant®, HemeSelect® and FlexSure®. In one embodiment, the assay comprises a HTS-PTT assay. In another embodiment, the assay comprises an Invader® assay. In yet another embodiment, the assay comprises a Point-EXACCT assay.

Another embodiment of the present invention contemplates a method, comprising: a) providing: i) deoxyribonucleic acid from a fecal specimen; ii) a cleavage means; and iii) first and second oligonucleotides that contain regions of homology with a gene selected from a group consisting of the APC, K-RAS, p53 and beta-catenine genes; b) contacting said deoxyribonucleic acid with the first and second oligonucleotides such that the first and second oligonucleotides anneal to the gene, wherein a region of overlap exists between the first and second oligonucleotides; and c) reacting the cleavage means with the region of overlap so that one or more cleavage products are produced. In one embodiment, the cleavage means is an enzyme. In one embodiment, the enzyme is a nuclease. In one embodiment, the deoxyribonucleic acid is obtained from a fecal specimen provided on a surface. In one embodiment, the surface is part of a component of a commercial kit used for fecal occult blood testing. In another embodiment, the surface comprises guaiac. In yet another embodiment, the surface comprises anti-hemoglobin antibody. In one embodiment, the dry weight of said fecal specimen is less than 10 mg. In one embodiment, the deoxyribonucleic acid is rendered substantially single-stranded prior to step (b). In one embodiment, the method further comprises the step of (d) detecting the one or more cleavage products. In one embodiment, the detecting of said one or more cleavage products indicates a mutation in the region of the gene.

Another embodiment of the present invention contemplates a method, comprising: a) providing; i) a fecal specimen comprising deoxyribonucleic acid; ii) a nuclease; iii) primers capable of amplifying a portion of a gene selected from a group consisting of the APC, K-RAS, p53 and beta-catenine genes; and iv) first and second oligonucleotides that contain regions of homology with said portion of a gene; and b) treating said fecal specimen under conditions such that isolated deoxyribonucleic acid is generated; c) contacting said isolated deoxyribonucleic acid with said primers under conditions such that a portion of said gene is amplified so as to create amplified deoxyribonucleic acid; d) contacting said amplified deoxyribonucleic acid with said first and second oligonucleotides such that said first and second oligonucleotides anneal to said amplified deoxyribonucleic acid, wherein a region of overlap exists between said first and second oligonucleotides; and e) reacting said nuclease with said region of overlap so that one or more cleavage products are produced. In one embodiment, the fecal specimen is provided on a surface. In one embodiment, the surface is part of a component of a kit used for fecal occult blood testing. In another embodiment, the surface comprises guaiac. In yet another embodiment, the surface comprises anti-hemoglobin antibody. In one embodiment, the dry weight of the fecal specimen is less than 10 mg. In one embodiment, the amplified deoxyribonucleic acid is rendered substantially single-stranded prior to step (d). In one embodiment, the method further comprises the step of (f) detecting the one or more cleavage products. In one embodiment, the detecting of the one or more cleavage products indicates a mutation in said region of the gene.

Another embodiment of the invention is directed to methods for labeling nascent proteins at their amino terminus. An initiator tRNA molecule, such as methionine-initiator tRNA or formylmethionine-initiator tRNA is misaminoacylated with a fluorescent moiety (e.g. a BODIPY moiety) and introduced to a translation system. The system is incubated and marker is incorporated at the amino terminus of the nascent proteins. Nascent proteins containing marker can be detected, isolated and quantitated. Markers or parts of markers may be cleaved from the nascent proteins which substantially retain their native configuration and are functionally active.

It is not intended that the present invention be limited to a particular translation system. In one embodiment, a cell-free translation system is selected from the group consisting of *Escherichia coli* lysates, wheat germ extracts, insect cell lysates, rabbit reticulocyte lysates, frog oocyte lysates, dog pancreatic lysates, human cell lysates, mixtures of purified or semi-purified translation factors and combinations thereof. It is also not intended that the present invention be limited to the particular reaction conditions employed. However, typically the cell-free translation system is incubated at a temperature of between about 25° C. to about 45° C. The present invention contemplates both continuous flow systems or dialysis systems.

Another embodiment of the invention is directed to compositions comprised of nascent proteins translated in the presence of markers, isolated and, if necessary, purified in a cellular or cell-free translation system. Compositions may further comprise a pharmaceutically acceptable carrier and be utilized as an immunologically active composition such as a vaccine, or as a pharmaceutically active composition such as a drug, for use in humans and other mammals.

The present invention contemplates a variety of methods wherein the three markers (e.g. the N- and C-terminal markers and the affinity markers) are introduced into a nascent protein. In one embodiment, the method comprises: a) providing i) a misaminoacylated initiator tRNA molecule which only recognizes the first AUG codon that serves to initiate protein synthesis, said misaminoacylated initiator tRNA molecule comprising a first marker, and ii) a nucleic acid template encoding a protein, said protein comprising a C-terminal marker and (in some embodiments) an affinity marker; b) introducing said misaminoacylated initiator tRNA to a translation system comprising said template under conditions such that a nascent protein is generated, said protein comprising said first marker, said C-terminal marker and (in some embodiments) said affinity marker. In one embodiment, the method further comprises, after step b), isolating said nascent protein.

The present invention also contemplates embodiments where only two markers are employed (e.g. a marker at the N-terminus and a marker at the C-terminus). In one embodiment, the nascent protein is non-specifically bound to a solid support (e.g. beads, microwells, strips, etc.), rather than by the specific interaction of an affinity marker. In this context, "non-specific" binding is meant to indicate that binding is not driven by the uniqueness of the sequence of the nascent protein. Instead, binding can be by charge interactions as well as hydrophilic or hydrophobic interactions. In one embodiment, the present invention contemplates that the solid support is modified (e.g. functionalized to change the charge of the surface) in order to capture the nascent protein on the surface of the solid support. In one embodiment, the solid support is poly-L-lysine coated. In yet another embodiment, the solid support is nitrocellulose (e.g. strips, nitrocellulose containing microwells, etc.) or alternatively polystyrene. Regardless of the particular nature of the solid support, the present invention contemplates that the nascent protein containing the two markers is captured under conditions that permit the ready detection of the markers.

In both the two marker and three marker embodiments described above, the present invention contemplates that one or more of the markers will be introduced into the nucleic acid template by primer extension or PCR. In one embodiment, the present invention contemplates a primer comprising (on or near the 5'-end) a promoter, a ribosome binding site ("RBS"), and a start codon (e.g. ATG), along with a region of complementarity to the template. In another embodiment, the present invention contemplates a primer comprising (on or near the 5'-end) a promoter, a ribosome binding site ("RBS"), a start codon (e.g. ATG), a region encoding an affinity marker, and a region of complementarity to the template. It is not intended that the present invention be limited by the length of the region of complementarity; preferably, the region is greater than 8 bases in length, more preferably greater than 15 bases in length, and still more preferably greater than 20 bases in length.

It is also not intended that the present invention be limited by the ribosome binding site. In one embodiment, the present invention contemplates primers comprising the Kozak sequence, a string of non-random nucleotides (consensus sequence 5'-GCCA/GCCATGG-3') (SEQ ID NO:1) which are present before the translation initiating first ATG in majority of the mRNAs which are transcribed and translated in eukaryotic cells. See M. Kozak, *Cell* 44:283-292 (1986). In another embodiment, the present invention contemplates a primer comprising the prokaryotic mRNA ribosome binding site, which usually contains part or all of a polypurine domain UAAGGAGGU (SEQ ID NO:2) known as the Shine-Dalgarno (SD) sequence found just 5' to the translation initiation codon: mRNA 5'-UAAGGAGGU-$N_{5-10}$-AUG. (SEQ ID NO:3)

For PCR, two primers are used. In one embodiment, the present invention contemplates as the forward primer a primer comprising (on or near the 5'-end) a promoter, a ribosome binding site ("RBS"), and a start codon (e.g. ATG), along with a region of complementarity to the template. In another embodiment, the present invention contemplates as the forward primer a primer comprising (on or near the 5'-end) a promoter, a ribosome binding site ("RBS"), a start codon (e.g. ATG), a region encoding an affinity marker, and a region of complementarity to the template. The present invention contemplates that the reverse primer, in one embodiment, comprises (at or near the 5'-end) one or more stop codons and a region encoding a C-terminus marker (such as a HIS-tag).

Another embodiment of the invention is directed to methods for detecting by electrophoresis (e.g. capillary electrophoresis) the interaction of molecules with nascent proteins which are translated in a translation system. A tRNA misaminoacylated with a detectable marker is added to the protein synthesis system. The system is incubated to incorporate the detectable marker into the nascent proteins. One or more specific molecules are then combined with the nascent proteins (either before or after isolation) to form a mixture containing nascent proteins/molecule conjugates. Aliquots of the mixture are then subjected to capillary electrophoresis. Nascent proteins/molecule conjugates are identified by detecting changes in the electrophoretic mobility of nascent proteins with incorporated markers.

Another embodiment of the present invention contemplates an oligonucleotide, comprising a 5' portion, a middle portion contiguous with said 5' portion, and a 3' portion contiguous with said middle portion, wherein i) said 5' portion comprises a sequence corresponding to a promoter, ii) said middle portion comprises a sequence corresponding to a ribosome binding site, a start codon, and a sequence coding for an epitope marker, wherein said epitope marker consists of a portion of the p53 amino acid sequence or variant thereof, and iii) said 3' portion comprises a sequence complementary to a portion of the APC gene (or another gene whose truncated products are associated with disease, i.e. a "disease related gene"). In one embodiment, said oligonucleotide is less than one hundred bases in length. In another embodiment, said oligonucleotide has the sequence set forth in SEQ ID NO: 22. In one embodiment, said 5' portion is between ten and forty bases in length (preferably between eight and sixty bases in length, and more preferably between fifteen and thirty bases in length). In one embodiment, said middle portion is between ten and three thousand bases in length (preferably between eight and sixty bases in length, and more preferably between fifteen and thirty bases in length). In one embodiment, said 3' portion is between ten and three thousand bases in length (preferably between eight and sixty bases in length, and more preferably between fifteen and thirty bases in length). In one embodiment, said sequence complementary to the portion of the APC gene is greater than 15 bases in length. In another embodiment, said sequence complementary to the portion of the APC gene is greater than 20 bases in length. In one embodiment, said sequence coding for an epitope marker codes for the amino acid sequence selected from SEQ ID NOS:24-38. In another embodiment, said sequence coding for an epitope marker codes for the amino acid sequence selected from SEQ ID NOS: 39-46.

Another embodiment of the present invention contemplates an oligonucleotide, comprising a 5' portion, a middle portion contiguous with said 5' portion, and a 3' portion contiguous with said middle portion, wherein i) said 5' portion comprises at least one stop codon, ii) said middle portion comprises a sequence encoding for an epitope marker, wherein said epitope marker consists of a portion of the VSV-G amino acid sequence or variant thereof, and iii) said 3' portion comprises a sequence complementary to a portion of the APC gene (or another gene whose truncated products are associated with disease). In one embodiment, said oligonucleotide is less than one hundred bases in length. In another embodiment, said oligonucleotide has the sequence set forth in SEQ ID NO: 23. In one embodiment, said 5' portion is between ten and forty bases in length (preferably between eight and sixty bases in length, and more preferably between fifteen and thirty bases in length). In one embodiment, said middle portion is between ten and forty bases in length (preferably between eight and sixty bases in length, and more preferably between fifteen and thirty bases in length). In one embodiment, said 3' portion is between ten and forty bases in length (preferably between eight and sixty bases in length, and more preferably between fifteen and thirty bases in length). In one embodiment, said sequence complementary to the portion of the APC gene is greater than 15 bases in length. In another embodiment, said sequence complementary to the portion of the APC gene is greater than 20 bases in length. In one embodiment, said sequence coding for an epitope marker codes for the amino acid sequence selected from SEQ ID NOS:24-38. In another embodiment, said sequence coding for an epitope marker codes for the amino acid sequence selected from SEQ ID NOS: 39-46.

Another embodiment of the present invention contemplates a kit, comprising: a) a first oligonucleotide comprising a 5' portion, a middle portion contiguous with said 5' portion, and a 3' portion contiguous with said middle portion, wherein i) said 5' portion comprises a sequence corresponding to a promoter, ii) said middle portion comprises a sequence corresponding to a ribosome binding site, a start codon, and a sequence coding for a first epitope marker, and iii) said 3' portion comprises a sequence complementary to a first portion of the APC gene (or other disease related gene); b) a second oligonucleotide comprising a 5' portion, a middle portion contiguous with said 5' portion, and a 3' portion contiguous with said middle portion, wherein i) said 5' portion comprises at least one stop codon, ii) said middle portion comprises a sequence encoding for a second epitope marker, and iii) said 3' portion comprises a sequence complementary to a second portion of the APC gene (or other disease related gene), wherein either said first epitope marker or said second epitope marker consist of a portion of the p53 amino acid sequence or variant thereof. In one embodiment, said sequence coding for said first epitope marker codes for the amino acid sequence selected from SEQ ID NOS: 39-46. In one embodiment, said sequence coding for said second epitope marker codes for the amino acid sequence selected from SEQ ID NOS: 24-38. In one embodiment, said first oligonucleotide has the sequence set forth in SEQ ID NO: 22. In one embodiment, said second oligonucleotide has the sequence set forth in SEQ ID NO: 23. In one embodiment, said kit further comprises a polymerase. In another embodiment, said kit further comprises a misaminoacylated tRNA. In another embodiment, said kit further comprises antibodies directed against said epitopes.

Another embodiment of the present invention contemplates a method of introducing coding sequence for one or more epitope markers into nucleic acid, comprising: a) providing: a first oligonucleotide primer comprising a 5' portion, a middle portion contiguous with said 5' portion, and a 3' portion contiguous with said middle portion, wherein 1) said 5' portion comprises a sequence corresponding to a promoter, 2) said middle portion comprises a sequence corresponding to a ribosome binding site, a start codon, and a sequence coding for a first epitope marker, and 3) said 3' portion comprises a sequence complementary to a first portion of the APC gene (or other disease related gene); ii) a second oligonucleotide primer comprising a 5' portion, a middle portion contiguous with said 5' portion, and a 3' portion contiguous with said middle portion, wherein 1) said 5' portion comprises at least one stop codon, 2) said middle portion comprises a sequence encoding for a second epitope marker, and 3) said 3' portion comprises a sequence complementary to a second portion of the APC gene (or other disease related gene), wherein either said first epitope marker or said second epitope marker consist of a portion of the p53 amino acid sequence or variant thereof; iii) a polymerase; and iv) template nucleic acid comprising a region of the APC gene (or other disease related gene), said region comprising at least said first portion of the APC gene; and b) mixing said template nucleic acid with said first primer, second primer and said polymerase under conditions such that amplified template is produced, said amplified template comprising said sequence coding for an epitope marker. In one embodiment, said first and said second oligonucleotide are each less than one hundred bases in length. In one embodiment, said sequence complementary to a portion of the APC gene of said first and said second oligonucleotide is 10 bases or greater, but preferably greater than 15 bases in length. In another embodiment, said sequence complementary to a portion of the APC gene of said first and said second oligonucleotide is greater than 20 bases in length. In one embodiment, said first oligonucleotide has the sequence set forth in SEQ ID NO: 22 and said second oligonucleotide has the sequence set forth in SEQ ID NO: 23. Not intending to limit the present invention, it is understood by one skilled in the art, that "a region of the APC gene" is larger than "a portion of the APC gene" (just as "regions" of any other gene associated with disease are larger than "portions" of the same). For example, a region of the APC gene may comprise, but is not limited to, the region coding for amino acids 1098-1696 (i.e., segment 3).

Another embodiment of the invention contemplates incorporation of three epitope tags into a nascent protein and their use for capture and detection of prematurely truncated protein translated from disease related genes.

Other embodiments and advantages of the invention are set forth, in part, in the description which follows and, in part, will be obvious from this description, or may be learned from the practice of the invention.

DEFINITIONS

To facilitate understanding of the invention, a number of terms are defined below.

The term "substantially single-stranded", as used herein, refers to a nucleic acid molecule that exists primarily as a single strand of nucleic acid in contrast to a double-stranded target which exists as two strands of nucleic acid which are held together by inter-strand base pairing interactions.

The term "cleavage means", as used herein, refers to any means which is capable of cleaving a cleavage structure, including but not limited to enzymes. The cleavage means may include a native DNA polymerase having 5' nuclease activity (e.g., Taq DNA polymerase, E. coli DNA polymerase I) and, more specifically, a modified DNA polymerase having 5' nuclease but lacking synthetic activity. The ability of 5' nucleases to cleave naturally occurring structures in nucleic acid templates (structure-specific cleavage) is useful to detect internal sequence differences in nucleic acids without prior knowledge of the specific sequence of the nucleic acid. In this manner, they are structure-specific enzymes. The cleavage means is not restricted to enzymes having solely 5' nuclease activity. The cleavage means may include nuclease activity provided from a variety of sources including the Cleavase® enzymes, the FEN-1 endonucleases (including RAD2 and XPG proteins), Taq DNA polymerase and E. coli DNA polymerase I. The cleavage means of the present invention cleave a nucleic acid molecule in response to the formation of cleavage structures; it is not necessary that the cleavage means cleave the cleavage structure at any particular location within the cleavage structure.

The term "cleavage products", as used herein, refers to products generated by the reaction of a cleavage means with a cleavage structure (i.e., for example, the treatment of a cleavage structure with a cleavage means).

The term "target nucleic acid", as used herein, refers to a nucleic acid molecule which contains a sequence which has at least partial complementarity with at least one probe oligonucleotide. The target nucleic acid may comprise single- or double-stranded DNA or RNA.

The term "probe oligonucleotide", as used herein, refers to an oligonucleotide which interacts with a target nucleic acid to form a complex. The complex may also comprise a cleavage structure.

The term "invader oligonucleotide", as used herein, refers to an oligonucleotide that hybridizes to a target nucleic acid such that its 3' end positions the site of structure-specific nuclease cleavage within an adjacently hybridized oligonucleotide probe. In one embodiment its 3' end has at least one nucleotide of sequence that is identical to the first target-complementary nucleotide of the adjacent probe; these nucleotides will compete for hybridization to the same nucleotide in a complementary target nucleic acid. In another embodiment, the invader oligonucleotide has a single 3' mismatched nucleotide, and hybridizes to an adjacent, but not overlapping, site on the target nucleic acid.

The term "DNA", as used herein, refers to a polynucleotide (i.e., an oligonucleotide) comprising deoxyribonucleic acid.

The term "mutation", as used herein, refers to any nucleic acid sequence variation as compared to the wild type sequence.

The term "polymerase chain reaction" (PCR) (Mullis et al., U.S. Pat. No. 4,683,195 and Mullis, U.S. Pat. No. 4,683,202) (both patents hereby incorporated by reference), as used herein, refers to a general method for increasing the concentration of a sequence within a nucleic acid target in a mixture of genomic DNA without cloning or purification.

The term "amplifying", as used herein, refers to a PCR method wherein the target sequence is introduced to a molar excess of two oligonucleotide primers which are complementary to their respective strands of the double-stranded target sequence to the DNA mixture containing the desired target sequence. The mixture is denatured and then allowed to hybridize. Following hybridization, the primers are extended with polymerase so as to form complementary strands. The steps of denaturation, hybridization, and polymerase extension can be repeated as often as needed, in order to obtain relatively high concentrations of a segment of the desired target sequence.

The term "molecular diagnostic assay", as used herein, refers to any "testing" procedure that results in the detection of a gene mutation. For example, the detected mutation may reside in a gene including, but not limited to, the APC, K-RAS, p53 or beta-catenine genes. "Testing" for a mutation may be performed by assays including, but not limited to, a HTS-PTT assay, an Invader® assay or a Point-EXACCT assay.

The term "commercial kit", as used herein, refers to a product available for sale that comprises a fecal occult blood test. Preferably, a "commercial kit" comprises a plurality of "components" including, but not limited to, applicator sticks, surfaces, slides, guaiac-coated slides or anti-hemoglobin antibody-coated slides. While not intending to limit the present invention, a "commercial kit" compatible with at least one embodiment of the present invention includes, but is not limited to, Hemoccult® Sensa®, Hemoccult II®, Colo-Screen®, Color-Rect®, Hemachek®, Quick-Cult®, Sensa®, HemoQuant®, HemeSelect® or FlexSure®.

The term "surface", as used herein, refers to any material capable of adhering a fecal specimen (i.e., for example, glass or paper). In one embodiment, the "surface" comprising a fecal specimen is dehydrated (i.e., for example, by drying) and subsequently extracted for DNA. Alternatively, the "surface" may contain one or more substances such as, but not limited to, guaiac or anti-hemoglobin antibody. In one embodiment, a glass slide comprises a "surface" as contemplated by the present invention.

The term "fecal specimen", as used herein, refers to a portion of a stool of less than 10 mg (dry weight). In one embodiment, a fecal specimen ranges approximately between 0.1 μg to less than 10 mg, preferably between approximately 1.0 μg to 5 mg, and more preferably between approximately 3.0 μg and 1 mg.

The term "homology" or "homologous", as used herein, refers to a degree of identity. There may be partial homology or complete homology. A partially identical sequence is one that is less than 100% identical to another sequence.

The term "portion" may refer to a relatively small segment of a protein or an oligonucleotide. Specifically, a portion of a protein refers to a range of between 5-100 contiguous amino acids while a portion of a nucleic acid refers to a range of between 15-300 contiguous nucleic acids.

The term "region" may refer to a relatively large segment of a protein or an oligonucleotide. Specifically, a region of a protein refers to a range of between 101-1700 contiguous amino acids which a region of an oligonucleotides refers to a range of between 303-5100 contiguous nucleic acids.

The term "contiguous" refers to a continuous, finite, sequence of units wherein each unit has physical contact with at least one other unit in the sequence. For example, a contiguous sequence of amino acids are physically connected by peptide bonds and a contiguous sequence of nucleic acids are physically connect by phosphodiester bonds.

The term "sequence corresponding to a promoter" refers to a non-coding nucleic acid region that is responsible for the regulation of transcription (an open reading frame) of the DNA coding for the protein of interest.

The term "sequence corresponding to a ribosome binding site" refers to a coding nucleic acid region that, when transcribed, allows the binding a mRNA in such a manner that translation occurs.

The term "gene" refers to a DNA sequence that comprises control and coding sequences necessary for the production of a polypeptide or precursor. The polypeptide can be encoded by a full length coding sequence or by any portion of the coding sequence so long as the desired enzymatic activity is retained.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "oligonucleotide" as used herein is defined as a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may have 5' and 3' ends.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to have on its 3' end a region that is "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

As used herein, the terms "hybridize" and "hybridization" refers to the annealing of a complementary sequence to the target nucleic acid. The ability of two polymers of nucleic acid containing complementary sequences to find each other and anneal through base pairing interaction is a well-recognized phenomenon. Marmur and Lane, Proc. Natl. Acad. Sci. USA 46:453 (1960) and Doty et al., Proc. Natl. Acad. Sci. USA 46:461 (1960). The terms "annealed" and "hybridized" are used interchangeably throughout, and are intended to encompass any specific and reproducible interaction between an oligonucleotide and a target nucleic acid, including binding of regions having only partial complementarity.

The complement of a nucleic acid sequence as used herein refers to an oligonucleotide which, when aligned with the nucleic acid sequence such that the 5' end of one sequence is paired with the 3' end of the other, is in "antiparallel association." The term "complement" or "complementary" does not imply or limit pairing to the sense strand or the antisense strand of a gene; the term is intended to be broad enough to encompass either situation. Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

The stability of a nucleic acid duplex is measured by the melting temperature, or "$T_m$." The $T_m$ of a particular nucleic acid duplex under specified conditions is the temperature at which on average half of the base pairs have disassociated.

The term "probe" as used herein refers to an oligonucleotide which forms a duplex structure or other complex with a sequence in another nucleic acid, due to complementarity or other means of reproducible attractive interaction, of at least one sequence in the probe with a sequence in the other nucleic acid.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like. As noted above, an oligonucleotide primer need not be perfectly complementary to a target or template sequence. A primer need only have a sufficient interaction with the template that it can be extended by template-dependent synthesis.

As used herein, the term "poly-histidine tract" or (HIS-tag) refers to the presence of two to ten histidine residues at either the amino- or carboxy-terminus of a nascent protein A polyhistidine tract of six to ten residues is preferred. The polyhistidine tract is also defined functionally as being a number of consecutive histidine residues added to the protein of interest which allows the affinity purification of the resulting protein on a nickel-chelate column, or the identification of a protein terminus through the interaction with another molecule (e.g. an antibody reactive with the HIS-tag).

As used herein, the term "marker" is used broadly to encompass a variety of types of molecules (e.g. introduced into proteins using methods and compositions of the present invention) which are detectable through spectral properties (e.g. fluorescent markers) or through functional properties (e.g. affinity markers). An epitope marker or "epitope tag" is a marker of the latter type, functioning as a binding site for antibody or other types of binding molecules (e.g. receptors, lectins and other ligands). Of course, if the epitope marker is used to immobilize the nascent protein, the epitope marker is also an affinity marker.

As used herein, the term "total tRNA" is used to describe a mixture comprising misaminoacylated marker tRNA molecules representing each amino acid. This mixture has a distinct advantage over the limited ability of misaminoacylated lys-tRNA to reliably incorporate in large variety of proteins. It is contemplated that "total tRNA" will provide a homogenous insertion of affinity markers in all nascent proteins.

As used herein, the term "VSV-derived epitope" refers to any amino acid sequence comprising the wild type sequence (i.e., SEQ ID NO:39) or mutations thereof, wherein said mutations include, but are not limited to, site-specific mutations, deletions, additions, substitutions and truncations.

As used herein, the term "p53-derived epitope" refers to any amino acid sequence comprising the wild type sequence (i.e., SEQ ID NO:24) or mutations thereof, wherein said mutations include, but are not limited to, site-specific mutations, frameshift mutations, deletions, additions, substitutions and truncations.

As used herein, the term "VSV variant" refers to any amino acid sequence that differs from the wild type sequence (i.e., SEQ ID NO: 39) in at least one, but not more than three residues.

As used herein, the term "p53 variant" refers to any amino acid sequence that differs from the wild type sequence (i.e., SEQ ID NO: 24) in at least one, but not more than three residues.

BRIEF DESCRIPTION OF THE DRAWINGS

FIG. 2 shows the incorporation of BODIPY-FL into various proteins. FIG. 2A shows the results visualized using laser based Molecular Dynamics FluorImager 595, while

FIG. 6 shows Western blot analysis of in vitro translated triple-epitope-tagged wild-type p53 (RT-PCR derived DNA).

FIG. 8 shows the detection of in vitro translated BODIPY-labeled proteins by Western blotting.

FIG. 10 displays the amino acid sequence for the full-length wild-type cellular tumor antigen p53 (Accession No.: DNHU53) (SEQ ID NO: 48)

FIG. 11 displays the nucleic acid sequence of the human phosphoprotein p53 gene exon 11 encoding the full length wild-type cellular tumor antigen p53 (Accession No.: M13121 N00032) (SEQ ID NO: 49).

FIG. 14 shows a diagrammatic representation of one embodiment of a molecular diagnostic assay (i.e., for example, Invader®). Panel A: A WT probe hybridizes to a WT Target DNA while in competition with an Invader® Oligo-T. A transient trinary complex creates a single base (T) overlap that generates a cleavage site which releases 5' Flap 1 having a 3'-thymidine (5'-Flap 1-T) from the WT probe. 5' Flap 1-T subsequently hybridizes with FRET Cassette 1 that generates a cleavage site next to fluorescent marker (F1). Once cleaved from FRET Cassette 1, F1 consequently generates a fluorescent signal. Panel B: A Mutant probe hybridizes to a WT Target DNA while in competition with an Invader® Oligo-T. No transient trinary complex is formed, and therefore, does not create a single base overlap. Flap 2, therefore, is not cleaved and released. Consequently, no fluorescent signal is generated.

FIG. 17 shows exemplary data from one embodiment of a DNA extraction method (i.e., for example, Quiagen). Panel A: Shows DNA extracted from varying amounts of fecal specimens; M: markers; 5 mg, 10 mg, 25 mg, 50 mg, 100 mg, 200 mg. Panel B: Shows PCR product DNA from extracted from varying amounts of fecal specimens; M: markers; Lane 1: 200 mgs, Lane 2: 100 mg, Lane 3: 50 mg, Lane 4: 20 mg, Lane 5: 10 mg and Lane 6: 5 mg. Panel C: Shows a representative proportionality relationship between the fecal specimen quantity and the nanograms/microliter (i.e., ng/µl) of extracted DNA.

FIG. 28 shows exemplary example of PCR amplification of APC segment 2 from patient's genomic DNA using universal primers. Top panel represents the results from first PCR while bottom panel shows the results obtained after second PCR. Lane 1-40 corresponds to different DNA samples. M is a marker.

FIG. 30 shows exemplary example of One-Step Long-Primer PCR Strategy. Detection and binding tags are incorporated into the APC product using a single 5'-long Tan and 3'-Tag primer set.

FIG. 57 shows exemplary example of screening of recombinants using white and UV-light. Insert with GFP shows strong green fluorescent while clones without GFP show white phenotype.

FIG. 80 shows exemplary data using very small amounts of stool material isolated from an NIH stool sample repository.

DESCRIPTION OF THE INVENTION

Figure 1:
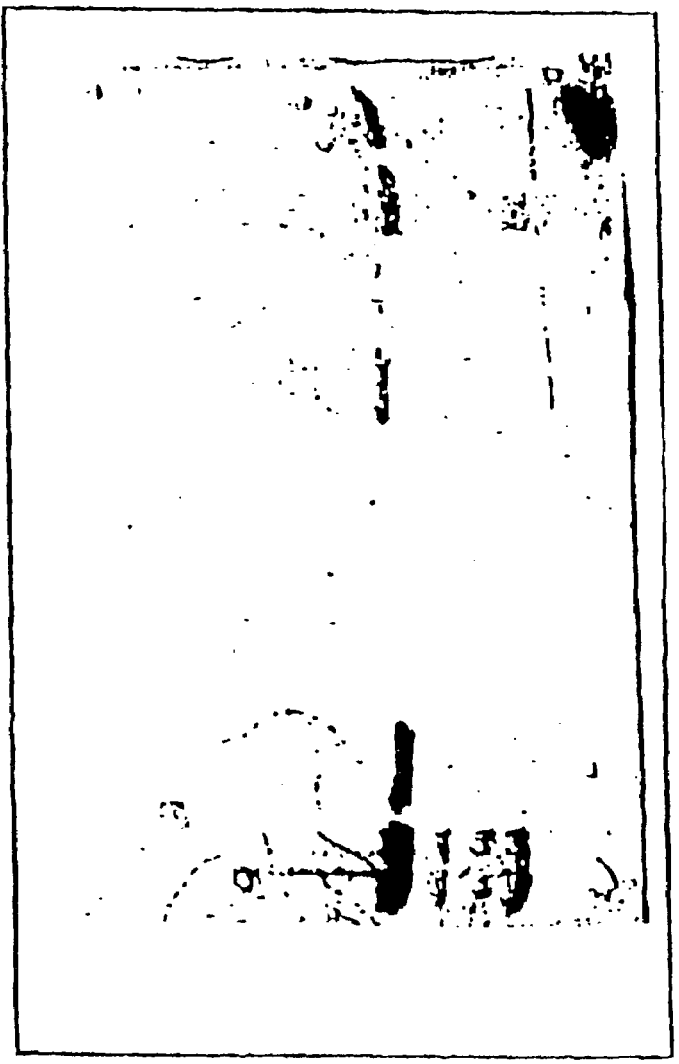
FIG. 1 is a photograph of a gel showing the incorporation of various fluorescent molecules into hemolysin during translation.
Figure 2A:
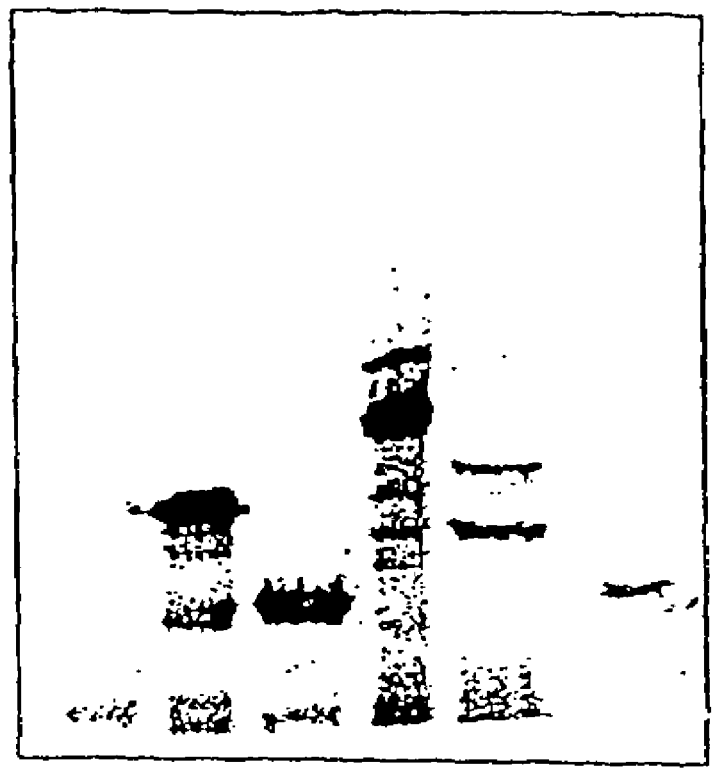
Figure 2B:
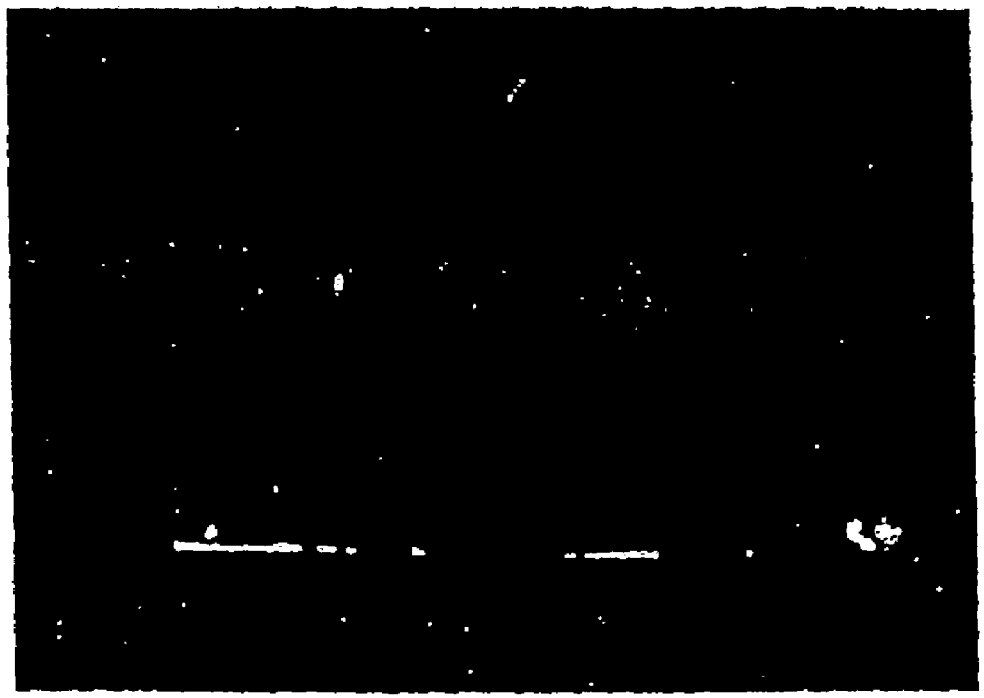
FIG. 2B shows the results visualized using a UV-transilluminator.
Figure 3A:
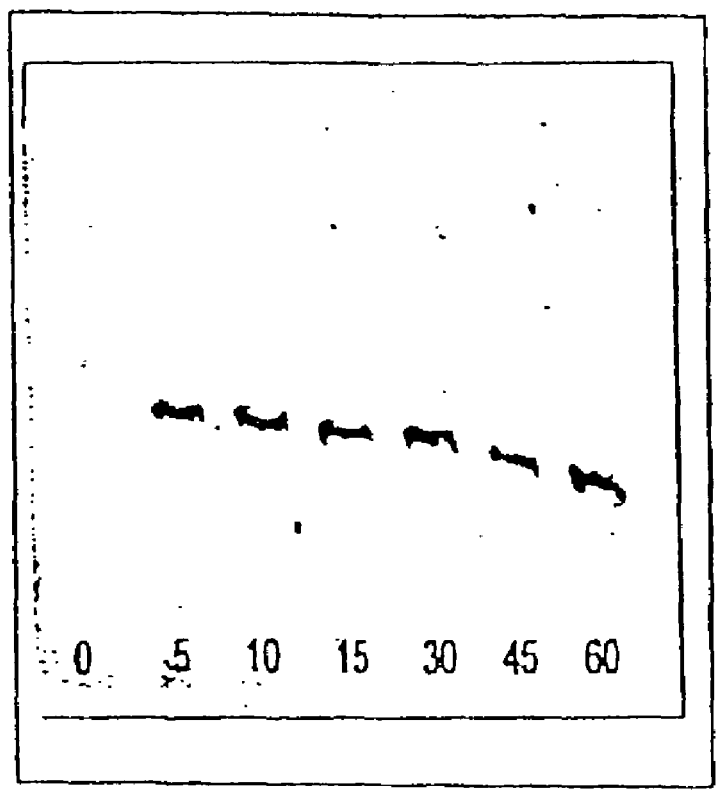
FIG. 3A shows a time course of fluorescence labeling.
Figure 3B:
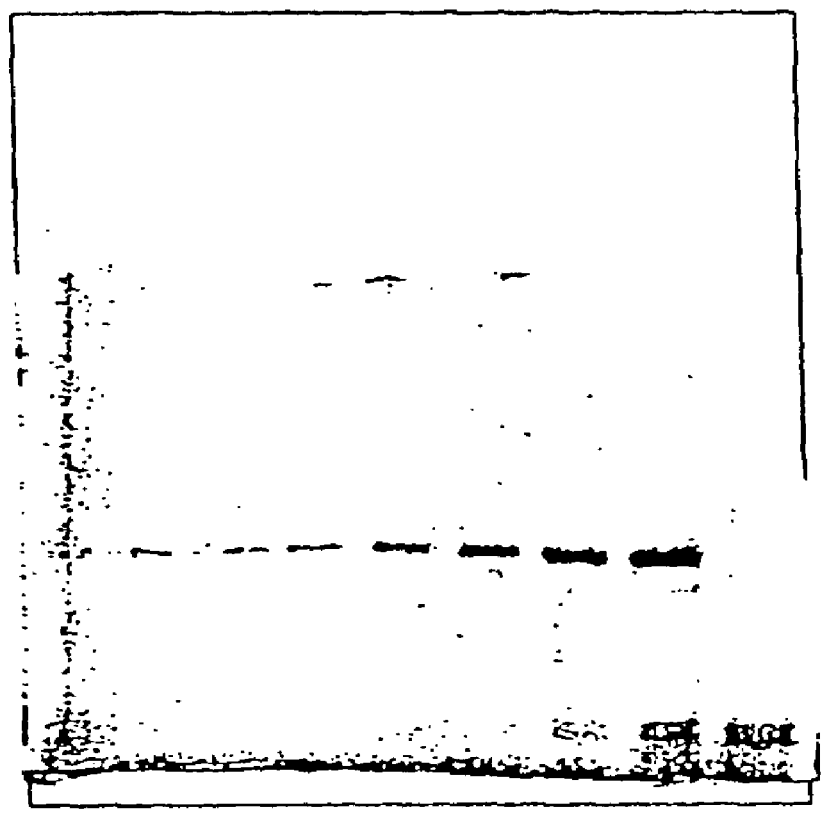
FIG. 3B shows the SDS-PAGE results of various aliquots of the translation mixture, demonstrating the sensitivity of the system.

As embodied and described herein, the present invention comprises methods for the non-radioactive labeling and detection of the products of new or nascent protein synthesis, and methods for the isolation of these nascent proteins from preexisting proteins in a cellular or cell-free translation system. In addition, no prior knowledge of the protein sequence or structure is required which would involve, for example, unique suppressor tRNAs. Further, the sequence of the gene or mRNA need not be determined. Consequently, the existence of non-sense codons or any specific codons in the coding region of the mRNA is not necessary. Any tRNA can be used, including specific tRNAs for directed labeling, but such specificity is not required. Unlike post-translational labeling, nascent proteins are labeled with specificity and without being subjected to post-translational modifications which may effect protein structure or function.

Any proteins that can be expressed by translation in a cellular or cell-free translation system may be nascent proteins and consequently, labeled, detected and isolated by the methods of the invention. Examples of such proteins include enzymes such as proteolytic proteins, cytokines, hormones, immunogenic proteins, carbohydrate or lipid binding proteins, nucleic acid binding proteins, human proteins, viral proteins, bacterial proteins, parasitic proteins and fragments and combinations. These methods are well adapted for the detection of products of recombinant genes and gene fusion products because recombinant vectors carrying such genes generally carry strong promoters which transcribe mRNAs at fairly high levels. These mRNAs are easily translated in a translation system.

Translation systems may be cellular or cell-free, and may be prokaryotic or eukaryotic. Cellular translation systems include whole cell preparations such as permeabilized cells or cell cultures wherein a desired nucleic acid sequence can be transcribed to mRNA and the mRNA translated.

Cell-free translation systems are commercially available and many different types and systems are well-known. Examples of cell-free systems include prokaryotic lysates such as *Escherichia coli* lysates, and eukaryotic lysates such as wheat germ extracts, insect cell lysates, rabbit reticulocyte lysates, frog oocyte lysates and human cell lysates.

Cell-free systems may also be coupled transcription/translation systems wherein DNA is introduced to the system, transcribed into mRNA and the mRNA translated as described in *Current Protocols in Molecular Biology* (F. M. Ausubel et al. editors, Wiley Interscience, 1993), which is hereby specifically incorporated by reference. RNA transcribed in eukaryotic transcription system may be in the form of heteronuclear RNA (hnRNA) or 5'-end caps (7-methyl guanosine) and 3'-end poly A tailed mature mRNA, which can be an advantage in certain translation systems. For example, capped mRNAs are translated with high efficiency in the reticulocyte lysate system.

tRNA molecules chosen for misaminoacylation with marker do not necessarily possess any special properties other than the ability to function in the protein synthesis system. Due to the universality of the protein translation system in living systems, a large number of tRNAs can be used with both cellular and cell-free reaction mixtures. Specific tRNA molecules which recognize unique codons, such as nonsense or amber codons (UAG), are not required.

tRNAs molecules used for aminoacylation are commercially available from a number of sources and can be prepared using well-known methods from sources including *Escherichia coli*, yeast, calf liver and wheat germ cells (Sigma Chemical; St. Louis, Mo.; Promega; Madison, Wis.; Boehringer Mannheim Biochemicals; Indianapolis, Ind.). Their isolation and purification mainly involves cell-lysis, phenol extraction followed by chromatography on DEAE-cellulose. Amino-acid specific tRNA, for example $tRNA^{fMet}$, can be isolated by expression from cloned genes and overexpressed in host cells and separated from total tRNA by techniques such as preparative polyacrylamide gel electrophoresis followed by band excision and elution in high yield and purity (Seong and RajBhandary, Proc. Natl. Acad. Sci. USA 84:334-338, 1987). Run-off transcription allows for the production of any specific tRNA in high purity, but its applications can be limited due to lack of post-transcriptional modifications (Bruce and Uhlenbeck, Biochemistry 21:3921, 1982).

Misaminoacylated tRNAs are introduced into the cellular- or cell-free protein synthesis system. In the cell-free protein synthesis system, the reaction mixture contains all the cellular components necessary to support protein synthesis including ribosomes, tRNA, rRNA, spermidine and physiological ions such as magnesium and potassium at appropriate concentrations and an appropriate pH. Reaction mixtures can be normally derived from a number of different sources including wheat germ, *E. coli* (S-30), red blood cells (reticulocyte lysate,) and oocytes, and once created can be stored as aliquots at about +4° C. to −70° C. The method of preparing such reaction mixtures is described by J. M. Pratt (*Transcription and Translation*, B. D. Hames and S. J. Higgins, Editors, p. 209, IRL Press, Oxford, 1984) which is hereby incorporated by reference. Many different translation systems are commercially available from a number of manufacturers.

The misaminoacylated tRNA is added directly to the reaction mixture as a solution of predetermined volume and concentration. This can be done directly prior to storing the reaction mixture at −70° C. in which case the entire mixture is thawed prior to initiation of protein synthesis or prior to the initiation of protein synthesis. Efficient incorporation of markers into nascent proteins is sensitive to the final pH and magnesium ion concentration. Reaction mixtures are normally about pH 6.8 and contain a magnesium ion concentration of about 3 mM. These conditions impart stability to the base-labile aminoacyl linkage of the misaminoacylated tRNA. Aminoacylated tRNAs are available in sufficient quantities from the translation extract. Misaminoacylated tRNAs charged with markers are added at between about 1.0 µg/ml to about 1.0 mg/ml, preferably at between about 10 µg/ml to about 500 µg/ml, and more preferably at about 150 µg/ml.

Translations in cell-free systems generally require incubation of the ingredients for a period of time. Incubation times range from about 5 minutes to many hours, but is preferably between about thirty minutes to about five hours and more preferably between about one to about three hours. Incubation may also be performed in a continuous manner whereby reagents are flowed into the system and nascent proteins removed or left to accumulate using a continuous flow system (A. S. Spirin et al., Sci. 242:1162-64, 1988). This process may be desirable for large scale production of nascent proteins. Incubations may also be performed using a dialysis system where consumable reagents are available for the translation system in an outer reservoir which is separated from larger components of the translation system by a dialysis membrane [Kim, D., and Choi, C. (1996) *Biotechnol Prog* 12, 645-649]. Incubation times vary significantly with the volume of the translation mix and the temperature of the incubation. Incubation temperatures can be between about 4° C. to about 60° C., and are preferably between about 15° C. to about 50° C., and more preferably between about 25° C. to about 45° C. and even more preferably at about 25° C. or about 37° C. Certain markers may be sensitive to temperature fluctuations and in such cases, it is preferable to conduct those incubations in the non-sensitive ranges. Translation mixes will typically comprise buffers such as Tris-HCl, Hepes or another suitable buffering agent to maintain the pH of the solution between about 6 to 8, and preferably at about 7. Again, certain markers may be pH sensitive and in such cases, it is preferable to conduct incubations outside of the sensitive ranges for the marker. Translation efficiency may not be optimal, but marker utility will be enhanced. Other reagents which may be in the translation system include dithiothreitol (DTT) or 2-mercaptoethanol as reducing agents, RNasin to inhibit RNA breakdown, and nucleoside triphosphates or creatine phosphate and creatine kinase to provide chemical energy for the translation process.

The misaminoacylated tRNA can be formed by natural aminoacylation using cellular enzymes or misaminoacylation such as chemical misaminoacylation. One type of chemical misaminoacylation involves truncation of the tRNA molecule to permit attachment of the marker or marker precursor. For example, successive treatments with periodate plus lysine, pH 8.0, and alkaline phosphatase removes 3'-terminal residues of any tRNA molecule generating tRNA-OH-3' with a mononucleotide or dinucleotide deletion from the 3'-terminus (Neu and Heppel, J. Biol. Chem. 239:2927-34, 1964). Alternatively, tRNA molecules may be genetically manipulated to delete specific portions of the tRNA gene. The resulting gene is transcribed producing truncated tRNA molecules (Sampson and Uhlenbeck, Proc. Natl. Acad. Sci. USA 85:1033-37, 1988). Next, a dinucleotide is chemically linked to a modified amino acid or other marker by, for example, acylation. Using this procedure, markers can be synthesized and acylated to dinucleotides in high yield (Hudson, J. Org. Chem. 53:617-624, 1988; Happ et al., J. Org. Chem. 52:5387-91, 1987).

Markers are basically molecules which will be recognized by the enzymes of the translation process and transferred from a charged tRNA into a growing peptide chain. To be useful, markers must also possess certain physical and physio-chemical properties. Therefore, there are multiple criteria which can be used to identify a useful marker. First, a marker must be suitable for incorporation into a growing peptide chain. This may be determined by the presence of chemical groups which will participate in peptide bond formation. Second, markers should be attachable to a tRNA molecule. Attachment is a covalent interaction between the 3'-terminus of the tRNA molecule and the carboxy group of the marker or a linking group attached to the marker and to a truncated tRNA molecule. Linking groups may be nucleotides, short oligonucleotides or other similar molecules and are preferably dinucleotides and more preferably the dinucleotide CA. Third, markers should have one or more physical properties that facilitate detection and possibly isolation of nascent proteins. Useful physical properties include a characteristic electromagnetic spectral property such as emission or absorbance, magnetism, electron spin resonance, electrical capacitance, dielectric constant or electrical conductivity.

Useful markers are native amino acids coupled with a detectable label, detectable non-native amino acids, detectable amino acid analogs and detectable amino acid derivatives. Labels and other detectable moieties may be ferromagnetic, paramagnetic, diamagnetic, luminescent, electrochemiluminescent, fluorescent, phosphorescent, chromatic or have a distinctive mass. Fluorescent moieties which are useful as markers include dansyl fluorophores, coumarins and coumarin derivatives, fluorescent acridinium moieties and benzopyrene based fluorophores. Preferably, the fluorescent marker has a high quantum yield of fluorescence at a wavelength different from native amino acids and more preferably has high quantum yield of fluorescence can be excited in both the UV and visible portion of the spectrum. Upon excitation at a preselected wavelength, the marker is detectable at low concentrations either visually or using conventional fluorescence detection methods. Electrochemiluminescent markers such as ruthenium chelates and its derivatives or nitroxide amino acids and their derivatives are preferred when extreme sensitivity is desired (J. DiCesare et al., BioTechniques 15:152-59, 1993). These markers are detectable at the femtomolar ranges and below.

In addition to fluorescent markers, a variety of markers possessing other specific physical properties can be used to detect nascent protein production. In general, these properties are based on the interaction and response of the marker to electromagnetic fields and radiation and include absorption in the UV, visible and infrared regions of the electromagnetic spectrum, presence of chromophores which are Raman active, and can be further enhanced by resonance Raman spectroscopy, electron spin resonance activity and nuclear magnetic resonances and use of a mass spectrometer to detect presence of a marker with a specific molecular mass. These electromagnetic spectroscopic properties are preferably not possessed by native amino acids or are readily distinguishable from the properties of native amino acids. For example, the amino acid tryptophan absorbs near 290 nm, and has fluorescent emission near 340 nm when excited with light near 290 nm. Thus, tryptophan analogs with absorption and/or fluorescence properties that are sufficiently different from tryptophan can be used to facilitate their detection in proteins.

The coumarin derivative can be used most advantageously if it misaminoacylates the tryptophan-tRNA, either enzymatically or chemically. When introduced in the form of the misaminoacylated tryptophan-tRNA, the coumarin amino acid will be incorporated only into tryptophan positions. By controlling the concentration of misaminoacylated tRNAs or free coumarin derivatives in the cell-free synthesis system, the number of coumarin amino acids incorporated into the nascent protein can also be controlled. This procedure can be utilized to control the amount of most any markers in nascent proteins.

Markers can be chemically synthesized from a native amino acid and a molecule with marker properties which cannot normally function as an amino acid. For example a highly fluorescent molecule can be chemically linked to a native amino acid group. The chemical modification can occur on the amino acid side-chain, leaving the carboxyl and amino functionalities free to participate in a polypeptide bond formation. Highly fluorescent molecules (e.g. dansyl chloride) can be linked to the nucleophilic side chains of a variety of amino acids including lysine, arginine, tyrosine, cysteine, histidine, etc., mainly as a sulfonamide for amino groups or sulfate bonds to yield fluorescent derivatives. Such derivatization leaves the ability to form peptide bond intact, allowing the normal incorporation of dansyllysine into a protein.

One group of fluorophores with members possessing several favorable properties (including favorable interactions with components of the protein translational synthesis system) is the group derived from dipyrromethenboron difluoride derivatives (BODIPY). Compared to a variety of other commonly used fluorophores with advantageous properties such as high quantum yields, some BODIPY compounds have the additional unusual property that they are highly compatible with the protein synthesis system. The core structure of all BODIPY fluorophores is 4,4-difluoro-4-bora-3a,4a-diaza-s-indacene. See U.S. Pat. Nos. 4,774,339; 5,187,288; 5,248,782; 5,274,113; 5,433,896; 5,451,663, all hereby incorporated by reference. All BODIPY fluorophores have several desirable properties for a marker (Molecular Probes Catalog, pages 13-18) including a high extinction coefficient, high fluorescence quantum yield, spectra that are insensitive to solvent polarity and pH, narrow emission bandwidth resulting in a higher peak intensity compared to other dyes such as fluorescein, absence of ionic charge and enhanced photostability compared to fluorescein. The addition of substituents to the basic BODIPY structure which cause additional conjugation can be used to shift the wavelength of excitation or emission to convenient wavelengths compatible with the means of detection.

A variety of BODIPY molecules are commercially available in an amine reactive form which can be used to derivatize aminoacylated tRNAs to yield a misaminoacylated tRNA with a BODIPY marker moiety. One example of a compound from this family which exhibits superior properties for incorporation of a detectable marker into nascent proteins is 4,4-difluoro-5,7-dimethyl-4-bora-3a,4a-diaza-s-indacene (BODIPY-FL). When the sulfonated N-hydroxysuccinimide (NHS) derivative of BODIPY-FL is used to misaminoacylate an $E.\ coli$ initiator tRNA$^{fmet}$, the nascent protein produced can be easily detected on polyacrylamide gels after electrophoresis using a standard UV-transilluminator and photographic or CCD imaging system. This can be accomplished by using purified tRNA$^{fmet}$ which is first aminoacylated with methionine and then the α-amino group of methionine is specifically modified using N-hydroxysuccinimide BODIPY. Before the modification reaction, the tRNA$^{fmet}$ is charged maximally (>90%) and confirmed by using $^{35}$S-methionine and acid-urea gels [Varshney, U., Lee, C. P., and RajBhandary, U. L. 1991. Direct analysis of aminoacylation levels of tRNA in vitro. $J.\ Biol.\ Chem.$ 266:24712-24718].

It has previously been shown that fluorescent markers such as 3-N-(7-nitrobenz-2-oxa-1,3-diazol-4-yl)-2,3,-diamino-proprionic acid (NBD-DAP) and coumarin could be incorporated into proteins using misaminoacylated tRNAs. However, detection of nascent proteins containing these markers was only demonstrated using highly sensitive instrumentation such a fluorescent spectrometer or a microspectrofluorometer and often require indirect methods such as the use of fluorescence resonance energy transfer (FRET) (Turcatti, G., Nemeth, K., Edgerton, M. D., Meseth, U., Talabot, F., Peitsch, M., Knowles, J., Vogel, H., and Chollet, A. (1996) $J\ Biol\ Chem$ 271(33), 19991-8; Kudlicki, W., Odom, O. W., Kramer, G., and Hardesty, B. (1994) $J\ Mol\ Biol$ 244(3), 319-31). Such instruments are generally not available for routine use in a molecular biology laboratory and only with special adaptation can be equipped for measurement of fluorescent bands on a gel.

An additional advantage of BODIPY-FL as a marker is the availability of monoclonal antibodies directed against it which can be used to affinity purify nascent proteins containing said marker. One example of such a monoclonal antibody is anti-BODIPY-FL antibody (Cat# A-5770, Molecular Probes, Eugene, Oreg.). This combined with the ability incorporate BODIPY-FL into nascent proteins with high efficiency relative to other commercially available markers using misaminoacylated tRNAs facilitates more efficient isolation of the nascent protein. These antibodies against BODIPY-FL can be used for quantitation of incorporation of the BODIPY into the nascent protein.

A marker can also be modified after the tRNA molecule is aminoacylated or misaminoacylated using chemical reactions which specifically modify the marker without significantly altering the functional activity of the aminoacylated tRNA. These types of post-aminoacylation modifications may facilitate detection, isolation or purification, and can sometimes be used where the modification allow the nascent protein to attain a native or more functional configuration.

Fluorescent and other markers have detectable electromagnetic spectral properties that can be detected by spectrometers and distinguished from the electromagnetic spectral properties of native amino acids. Spectrometers which are most useful include fluorescence, Raman, absorption, electron spin resonance, visible, infrared and ultraviolet spectrometers. Other markers, such as markers with distinct electrical properties can be detected by an apparatus such as an ammeter, voltmeter or other spectrometer. Physical properties of markers which relate to the distinctive interaction of the marker with an electromagnetic field is readily detectable using instruments such as fluorescence, Raman, absorption, electron spin resonance spectrometers. Markers may also undergo a chemical, biochemical, electrochemical or photochemical reaction such as a color change in response to external forces or agents such as an electromagnetic field or reactant molecules which allows its detection.

One class of fluorescent markers contemplated by the present invention is the class of small peptides that can specifically bind to molecules which, upon binding, are detectable. One example of this approach is the peptide having the sequence of WEAAAREACCRECCARA (SEQ ID NO: 4). This sequence (which contains four cysteine residues) allows the peptide to specifically bind the non-fluorescent dye molecule 4',5'-bis(1,3,2-dithioarsolan-2-yl) fluorescein (FLASH, which stands for fluorescein arsenic helix binder). This dye has the interesting property that, upon binding, it becomes fluorescent. In other words, fluorescence is observed only when this specific peptide sequence is present in the nascent protein. So by putting the peptide sequence at the N- or C-terminal, one can easily monitor the amount of protein synthesized. This peptide sequence can be introduced by designing the nucleic acid primers such that they carry a region encoding the peptide sequence.

After protein synthesis in a cell-free system, the reaction mixture, which contains all of the biomolecules necessary for protein synthesis as well as nascent proteins, is loaded onto a gel which may be composed of polyacrylamide or agarose (R. C. Allen et al., $Gel\ Electrophoresis\ and\ Isoelectric\ Focusing\ of\ Proteins$, Walter de Gruyter, New York 1984). This mixture also contains the misaminoacylated tRNAs bearing the marker as well as uncharged tRNAs. Subsequent to loading the reaction mixture, a voltage is applied which spatially separates the proteins on the gel in the direction of the applied electric field. The proteins separate and appear as a set of discrete or overlapping bands which can be visualized using a pre- or post-gel staining technique such as Coomassie blue staining. The migration of the protein band on the gel is a function of the molecular weight of the protein with increasing distance from the loading position being a function of decreasing molecular weight. Bands on the gel which contain nascent proteins will exhibit fluorescence when excited at a suitable wavelength. These bands can be detected visually, photographically or spectroscopically and, if desired, the nascent proteins purified from gel sections.

For example, if BODIPY-FL is used as a marker, nascent proteins will fluoresce at 510 nm when excited by UV illumination. This fluorescence can be detected visually by simply using a standard hand-held UV illuminator or a transilluminator. Approximately 10 nanograms (ng) of the protein alpha-hemolysin is detectable using this method. Also useful are electronic imaging devices which can rapidly screen and identify very low concentrations of markers such as a fluorescent scanner based on a low-temperature CCD imager. In this case as low as 0.3 ng of protein can be detected.

The molecular weight and quantity of the nascent protein can be determined by comparison of its band-position on the gel with a set of bands of proteins of predetermined molecular weight which are fluorescently labeled. For example, a nascent protein of molecular weight 25,000 could be determined because of its relative position on the gel relative to a calibration gel containing the commercially available standard marker proteins with known quantities and with known molecular weights (bovine serum albumin, 66 kD; porcine heart fumarase, 48.5 kD; carbonic anhydrase, 29 kD, β-lactoglobulin, 18.4 kD; α-lactoglobulin, 14.2 kD; Sigma Chemical; St. Louis, Mo.).

Other methods of protein separation are also useful for detection and subsequent isolation and purification of nascent proteins containing markers. For example, proteins can be separated using capillary electrophoresis, isoelectric focusing, low pressure chromatography and high-performance or fast-pressure liquid chromatography (HPLC or FPLC). In these cases, the individual proteins are separated into fractions which can be individually analyzed by fluorescent detectors at the emission wavelengths of the markers. Alternatively, on-line fluorescence detection can be used to detect nascent proteins as they emerge from the column fractionation system. A graph of fluorescence as a function of retention time provides information on both the quantity and purity of nascent proteins produced.

Another embodiment of the invention is directed to a method for labeling, detecting and, if desired, isolating and purifying nascent proteins, as described above, containing cleavable markers. Cleavable markers comprise a chemical structure which is sensitive to external effects such as physical or enzymatic treatments, chemical or thermal treatments, electromagnetic radiation such as gamma rays, x-rays, ultraviolet light, visible light, infrared light, microwaves, radio waves or electric fields. The marker is aminoacylated to tRNA molecules as before using conventional technology or mis-aminoacylated and added to a translation system. After incubation and production of nascent proteins, marker can be cleaved by the application of specified treatments and nascent proteins detected. Alternatively, nascent proteins may also be detected and isolated by the presence or absence of the cleaved marker or the chemical moiety removed from the marker.

Cleavable markers can facilitate the isolation of nascent proteins. For example, one type of a cleavable marker is photocleavable biotin coupled to an amino acid. This marker can be incorporated into nascent proteins and the proteins purified by the specific interaction of biotin with avidin or streptavidin. Upon isolation and subsequent purification, the biotin is removed by application of electromagnetic radiation and nascent proteins utilized in useful applications without the complications of an attached biotin molecule. Other examples of cleavable markers include photocleavable coumarin, photocleavable dansyl, photocleavable dinitrophenyl and photocleavable coumarin-biotin. Photocleavable markers are cleaved by electromagnetic radiation such as UV light, peptidyl markers are cleaved by enzymatic treatments, and pyrenyl fluorophores linked by disulfide bonds are cleaved by exposure to certain chemical treatments such as thiol reagents.

For enzymatic cleavage, markers introduced contain specific bonds which are sensitive to unique enzymes of chemical substances. Introduction of the enzyme or chemical into the protein mixture cleaves the marker from the nascent protein. When the marker is a modified amino acid, this can result in the production of native protein forms. Thermal treatments of, for example, heat sensitive chemical moieties operate in the same fashion. Mild application of thermal energy, such as with microwaves or radiant heat, cleaves the sensitive marker from the protein without producing any significant damage to the nascent proteins.

Nonsense or frameshift mutations, which result in a truncated gene product, are prevalent in a variety of disease-related genes. Den Dunnen et al., *The Protein Truncation Test: A Review*. Hum Mutat 14:95-102 (1999). Specifically, these diseases include: i) APC (colorectal cancer), Powell et al., *Molecular Diagnosis Of Familial Adenomatous Polyposis*. N Engl J Med 329:1982-1987 (1993); van der Luijt et al., *Rapid Detection Of Translation-Terminating Mutations At The Adenomatous Polyposis Coli (APC) Gene By Direct Protein Truncation Test*. Genomics 20:1-4 (1994); Traverso et al., *Detection Of APC Mutations In Fecal DNA From Patients With Colorectal Tumors*. N Engl J Med 346:311-320 (2002); Kinzler et al., *Identification Of A Gene Located At Chromosome 5q21 That Is Mutated In Colorectal Cancers*. Science 251:1366-1370 (1991); and Groden et al., *Identification And Characterization Of The Familial Adenomatous Polyposis Coli Gene*. Cell 66:589-600 (1991); ii) BRCA1 and BRCA2 (breast and ovarian cancer), Hogervosrt et al., *Rapid Detection Of BRCA1 Mutations By The Protein Truncation Test*. Nat Genet 10:208-212 (1995); Garvin et al., *A Complete Protein Truncation Test For BRAC1 and BRAC2*. Eur J Hum Genet 6:226-234 (1998); Futreal et al., *BRAC1 Mutations In Primary Breast And Ovarian Carcinomas*. Science 266:120-122 (1994); iii) polycystic kidney disease, Peral et al., *Identification Of Mutations In the Duplicated Region Of The Polycystic Kidney Disease 1 Gene (PKD1) By A Novel Approach*. Am J. Hum Genet 60:1399-1410 (1997); iv) neurofibromatosis (NF1 and NF2), Hein et al., *Distribution Of 13 Truncating Mutations In The Neurofibromatosis 1 Gene*. Hum Mol Genet 4:975-981 (1995); Parry et al., *Germ-line Mutations In The Neurofibromatosis 2 Gene: Correlations With Disease Severity And Retinal Abnormalities*. Am J Hum Genet 59:529-539 (1996); and v) Duchenne muscular dystrophy (DMD), Roest et al., *Protein Truncation Test (PTT) To Rapidly Screen The DMD gene For Translation Terminating Mutations*. Neuromuscul Disord 3:391-394 (1993). Such chain truncating mutations can be detected using the protein truncation test (PTT). This test is based on cell-free coupled transcription-translation of PCR (RT-PCR) amplified portions of the target gene (target mRNA) followed by analysis of the translated product(s) for shortened polypeptide fragments. However, conventional PTT is not easily adaptable to high throughput applications since it involves SDS-PAGE followed by autoradiography or Western blot. It is also subject to human error since it relies on visual inspection to detect mobility shifted bands. To overcome these limitations, we have developed the first high throughput solid-phase protein truncation test (HTS-PTT). HTS-PTT uses a combination of misaminoacylated tRNAs (Rothschild et al., *tRNA-Mediated Protein Engineering*. Curr Opin Biotechnol 10:64-70 (1999); and Gite et al., *Ultrasensitive Fluorescence-Based Detection Of Nascent Proteins In Gels*. Anal Biochem 279:218-225 (2000)), which incorporate affinity tags for surface capture of the cell-free expressed protein fragments, and specially designed PCR primers, which introduce N- and C-terminal markers for measuring the relative level of shortened polypeptide produced by the chain truncation mutation. After cell-free translation of the protein fragments, capture and detection is accomplished in a single-well using a standard 96-well microtiter plate ELISA format and chemiluminescence readout. The technique is demonstrated for the detection of chain truncation mutations in the APC gene using DNA or RNA from cancer cell lines as well as DNA of individuals pre-diagnosed with familial adenomatous polyposis (FAP). HTP-PTT can also provide a high throughput method for non-invasive colorectal cancer screening when used in conjunction with methods of enriching/amplifying low-abundance mutant DNA. Traverso et al. (2002).

A. Detection of Mutations

Detection of mutations is an increasingly important area in clinical diagnosis, including but not limited to the diagnosis of cancer and/or individuals disposed to cancer. The protein truncation test (PTT) is a technique for the detection of nonsense and frameshift mutations which lead to the generation of truncated protein products. Genes associated with Duchenne muscular dystrophy, adenomatous polyposis coli, human mutL homologue and human nutS homologue (both involved in colon cancer), and BRAC1 (involved in familial breast cancer) can now be screened for mutations in this manner, along with others (see Table 1).

Typically, the PTT technique involves the incorporation of a T7 promoter site, ribosome binding site, and an artificial methionine start site into a PCR product covering the region of the gene to be investigated. The PCR product is then transcribed and translated using either an in vitro rabbit reticulocyte lysate or wheat germ lysate system, to generate a protein corresponding to the region of the gene amplified. The presence of a stop codon in the sequence, generated by a nonsense mutation or a frameshift, will result in the premature termination of protein translation, producing a truncated protein that can be detected by standard gel electrophoresis (e.g. SDS-PAGE) analysis combined with radioactive detection.

There are drawbacks to the technique as currently practiced. One of the most important problems involves the identification of the product of interest. This is made difficult because of nonspecific radiolabeled products. Attempts to address these problems have been made. One approach is to introduce an affinity tag after the start site and before the region encoding the gene of interest. See Rowan and Bodmer, "Introduction of a myc Reporter Taq to Improve the Quality of Mutation Detection Using the Protein Truncation Test," Human Mutation 9:172 (1997). However, such approaches still have the disadvantage that they rely on electrophoresis.

The present invention contemplates a gel-free truncation test (GFTT), wherein two or three markers are introduced into the nascent protein. The present invention contemplates both pre-natal and post-natal testing to determine predisposition to disease. In a preferred embodiment of the invention, the novel compositions and methods are directed to the detection of frameshift or chain terminating mutations. In order to detect such mutations, a nascent protein is first synthesized in a cell-free or cellular translation system from message RNA or DNA coding for the protein which may contain a possible mutation. The nascent protein is then separated from the cell-free or cellular translation system using an affinity marker located at or close to the

TABLE 1

Applications of PTT in Human Molecular Genetics

| Disease References | % Truncating Mutations | Gene |
|---|---|---|
| Familial Adenomatous Polyposis | 95% | APC |
| Hereditary desmold disease | 100% | APC |
| Ataxia telangiectasia | 90% | ATM |
| Hereditary Breast and Ovarian Cancer | 90% | BRCA1 |
|  | 90% | BRCA2 |
| Cystic Fibrosis | 15% | CFTR |
| Duchenne Muscular Dystrophy | 95% | DMD |
| Emery-Dreifuss Muscular Dystrophy | 80% | EMD |
| Fanconi anaemia | 80% | FAA |
| Hunter Syndrome | ~50% | IDS |
| Hereditary non-polyposis colorectal cancer | ~80% | hMSH2 |
|  | ~70% | hMLH1 |
| Neurofibromatosis type 1 | 50% | NF1 |
| Neurofibromatosis type 2 | 65% | NF2 |
| Polycystic Kidney Disease | 95% | PKD1 |
| Rubinstein-Taybi Syndrome | 10% | RTS |

The percentage of truncating mutations reported which should be detectable using PTT.

N-terminal end of the protein. The protein is then analyzed for the presence of a detectable marker located at or close to the N-terminal of the protein (N-terminal marker). A separate measurement is then made on a sequence dependent detectable marker located at or close to the C-terminal end of the protein (C-terminal marker).

A comparison of the measurements from the C-terminal marker and N-terminal marker provides information about the fraction of nascent proteins containing frameshift or chain terminating mutations in the gene sequence coding for the nascent protein. The level of sequence dependent marker located near the C-terminal end reflects the fraction of protein which did not contain chain terminating or out-of-frame mutations. The measurement of the N-terminal marker provides an internal control to which measurement of the C-terminal marker is normalized. Normalizing the level of the C-terminal marker to the N-terminal marker eliminates the inherent variabilities such as changes in the level of protein expression during translation that can undermine experimental accuracy. Separating the protein from the translation mixture using an using an affinity marker located at or close to the N-terminal end of the protein eliminates the occurrence of false starts which can occur when the protein is initiated during translation from an internal AUG in the coding region of the message. A false start can lead to erroneous results since it can occurs after the chain terminating or out-of-frame mutation. This is especially true if the internal AUG is in-frame with the message. In this case, the peptide C-terminal marker will still be present even if message contains a mutation.

In one example, a detectable marker comprising a non-native amino acid or amino acid derivative is incorporated into the nascent protein during its translation at the amino terminal (N-terminal end) using a misaminoacylate initiator tRNA which only recognizes the AUG start codon signaling the initiation of protein synthesis. One example of a detectable marker is the highly fluorescent compound BODIPY FL. The marker might also be photocleavable such as photocleavable coumarin or photocleavable biotin. The nascent protein is then separated from the cell-free or cellular translation system by using a coupling agent which binds to an affinity marker located adjacent to the N-terminal of the protein. One such affinity marker is a specific protein sequence known as an epitope. An epitope has the property that it selectively interacts with molecules and/or materials containing acceptor groups. There are many epitope sequences reported in the literature including HisX6 (HHHHHH) (SEQ ID NO: 5) described by ClonTech and C-myc (EQKLISEEDL) (SEQ ID NO:6) described by Roche-BM, Flag (DYKDDDDK) (SEQ ID NO:7) described by Stratagene), SteptTag (WSHPQFEK) (SEQ ID NO:8) described by Sigma-Genosys and HA Tag (YPYDVPDYA) (SEQ ID NO:9) described by Roche-BM.

Once the nascent protein is isolated from the translation system, it is analyzed for presence of the detectable marker incorporated at the N-terminal of the protein. The protein is then analyzed for the presence of a sequence specific marker located near the C-terminal end of the protein. In normal practice, such a sequence specific marker will consist of a specific sequence of amino acids located near the C-terminal end of the protein which is recognized by a coupling agent. For example, an antibody can be utilized which is directed against an amino acid sequence located at or near C-terminal end of the nascent protein can be utilized. Such antibodies can be labeled with a variety of markers including fluorescent dyes that can be easily detected and enzymes which catalyze detectable reactions that lead to easily detectable substrates. The marker chosen should have a different detectable property than that used for the N-terminal marker. An amino acid sequence can also comprise an epitope which is recognized by coupling agents other than antibodies. One such sequence is 6 histidines sometimes referred to as a his-tag which binds to cobalt complex coupling agent.

A variety of N-terminal markers, affinity markers and C-terminal markers are available which can be used for this embodiment. The N-terminal marker could be BODIPY, affinity marker could be StrepTag and C-terminal marker could be a HisX6 tag. In this case, after translation, the reaction mixture is incubated in streptavidin coated microtiter plate or with streptavidin coated beads. After washing unbound material, the N-terminal marker is directly measured using a fluorescence scanner while the C-terminal marker can be quantitated using anti-hisX6 antibodies conjugated with a fluorescent dye (like rhodamine or Texas Red) which has optical properties different than BODIPY, thus facilitating simultaneous dual detection.

In a different example, the N-terminal marker could be a biotin or photocleavable biotin incorporated by a misaminoacylated tRNA, the affinity marker could be a His X6 tag and the C-terminal had C-myc marker. In this case, after the translation, the reaction mixture is incubated with metal chelating beads or microtiter plates (for example Talon, ClonTech). After washing the unbound proteins, the plates or beads can be subjected to detection reaction using streptavidin conjugated fluorescence dye and C-myc antibody conjugated with other fluorescent dye. In addition, one can also use chemiluminescent detection method using antibodies which are conjugated with peroxidases.

It will be understood by those skilled in the area of molecular biology and biochemistry that the N-terminal marker, affinity marker and C-terminal marker can all consist of epitopes that can be incorporated into the nascent protein by designing the message or DNA coding for the nascent protein to have a nucleic acid sequence corresponding to the particular epitope. This can be accomplished using known methods such as the design of primers that incorporate the desired nucleic acid sequence into the DNA coding for the nascent protein using the polymerase chain reaction (PCR). It will be understood by those skilled in protein biochemistry that a wide variety of detection methods are available that can be used to detect both the N-terminal marker and the C-terminal markers. Additional examples include the use of chemiluminescence assays where an enzyme which converts a non-chemiluminescent substrate to a chemiluminescent product is conjugated to an antibody that is directed against a particular epitope.

There are a variety of additional affinity markers, N-terminal markers and C-terminal markers available for this embodiment. The affinity marker could be biotin or photocleavable biotin, N-terminal marker could be StepTag and C-terminal the C-myc epitope. In this case, after the translation, the reaction mixture is incubated with streptavidin coated beads or microtiter plates coated with streptavidin. After washing the unbound proteins, the plates or beads can be subjected to detection reaction using anti-his 6 antibodies conjugated with a fluorescent dye (like rhodamine or Texas Red) and C-myc antibody conjugated with other another fluorescent dye such as BODIPY. In addition, one can also use chemiluminescent detection method using antibodies which are conjugated with peroxidases. Even in case of peroxidases conjugated antibodies, one can use fluorescent substrates and use FluorImager like device to quantitate N-terminal and C-terminal labels.

For optimal effectiveness, the N-terminal marker and affinity marker should be placed as close as possible to the N-terminal end of the protein. For example, if an N-terminal marker is incorporated using a misaminoacylated initiator, it will be located at the N-terminal amino acid. In this case, the affinity marker should be located immediately adjacent to the N-terminal marker. Thus, if a BODIPY marker which consists of a BODIPY conjugated to methionine is incorporated by a misaminoacylated initiator tRNA, it should be followed by an epitope sequence such as SteptTag (WSHPQFEK) (SEQ ID NO:8) so that the entire N-terminal sequence will be BODIPY-MWSPQFEK (SEQ ID NO: 10). However, for specific cases it may be advantageous to add intervening amino acids between the BODIPY-M and the epitope sequence in order to avoid interaction between the N-terminal marker and the affinity marker or the coupling agent which binds the affinity marker. Such interactions will vary depending on the nature of the N-terminal marker, affinity marker and coupling agent.

For optimal effectiveness, the C-terminal marker should be placed as close as possible to the C-terminal end of protein. For example, if a His-X6 tag is utilized, the protein sequence would terminate with 6 His. In some cases, an epitope may be located several residues before the C-terminal end of the protein in order to optimize the properties of the nascent protein. This might occur for example, if a specific amino acid sequence is necessary in order to modify specific properties of the nascent protein that are desirable such as its solubility or hydrophobicity.

In the normal application of this method, the ratio of the measured level of N-terminal and C-terminal markers for a nascent protein translated from a normal message can be used to calculate a standard normalized ratio. In the case of a message which may contain a mutation, deviations from this standard ratio can then be used to predict the extent of mutations. For example, where all messages are defective, the ratio of the C-terminal marker to the N-terminal marker is expected to be zero. On the other hand, in the case where all messages are normal, the ratio is expected to be 1. In the case where only half of the message is defective, for example for a patient which is heterozygote for a particular genetic defect which is chain terminating or causes an out-of-frame reading error, the ratio would be ½.

There are several unique advantages of this method compared to existing techniques for detecting chain terminating or out-of-frame mutations. Normally, such mutations are detected by analyzing the entire sequence of the suspect gene using conventional DNA sequencing methods. However, such methods are time consuming, expensive and not suitable for rapid throughput assays of large number of samples. An alternative method is to utilize gel electrophoresis, which is able to detect changes from the expected size of a nascent protein. This approach, sometimes referred to as the protein truncation test, can be facilitated by using non-radioactive labeling methods such as the incorporation of detectable markers with misaminoacylated tRNAs. However, in many situations, such as high throughput screening, it would be desirable to avoid the use of gel electrophoresis which is time-consuming (typically 60-90 minutes). In the present method, the need for performing gel electrophoresis is eliminated. Furthermore, since the approach depends on comparison of two detectable signals from the isolated nascent protein which can be fluorescent, luminescent or some combination thereof, it is highly amenable to automation.

B. Reporter Groups

Another embodiment of the invention is directed to a method for monitoring the synthesis of nascent proteins in a cellular or a cell-free protein synthesis system without separating the components of the system. These markers have the property that once incorporated into the nascent protein they are distinguishable from markers free in solution or linked to a tRNA. This type of marker, also called a reporter, provides a means to detect and quantitate the synthesis of nascent proteins directly in the cellular or cell-free translation system.

One type of reporters previously described in U.S. Pat. No. 5,643,722 (hereby incorporated by reference) has the characteristic that once incorporated into the nascent protein by the protein synthesizing system, they undergo a change in at least one of their physical or physio-chemical properties. The resulting nascent protein can be uniquely detected inside the synthesis system in real time without the need to separate or partially purify the protein synthesis system into its component parts. This type of marker provides a convenient non-radioactive method to monitor the production of nascent proteins without the necessity of first separating them from pre-existing proteins in the protein synthesis system. A reporter marker would also provide a means to detect and distinguish between different nascent proteins produced at different times during protein synthesis by addition of markers whose properties are distinguishable from each other, at different times during protein expression. This would provide a means of studying differential gene expression.

A tRNA molecule is misaminoacylated with a reporter (R) which has lower or no fluorescence at a particular wavelength for monitoring and excitation. The misaminoacylated tRNA is then introduced into a cellular or cell-free protein synthesis system and the nascent proteins containing the reporter analog are gradually produced. Upon incorporation of the reporter into the nascent protein (R*), it exhibits an increased fluorescence at known wavelengths. The gradual production of the nascent protein is monitored by detecting the increase of fluorescence at that specific wavelength.

Reporters are not limited to those non-native amino acids which change their fluorescence properties when incorporated into a protein. These can also be synthesized from molecules that undergo a change in other electromagnetic or spectroscopic properties including changes in specific absorption bands in the UV, visible and infrared regions of the electromagnetic spectrum, chromophores which are Raman active and can be enhanced by resonance Raman spectroscopy, electron spin resonance activity and nuclear magnetic resonances. In general, a reporter can be formed from molecular components which undergo a change in their interaction and response to electromagnetic fields and radiation after incorporation into the nascent protein.

In the present invention, reporters may also undergo a change in at least one of their physical or physio-chemical properties due to their interaction with other markers or agents which are incorporated into the same nascent protein or are present in the reaction chamber in which the protein is expressed. The interaction of two different markers with each other causes them to become specifically detectable. One type of interaction would be a resonant energy transfer which occurs when two markers are within a distance of between about 1 angstrom (A) to about 50 A, and preferably less than about 10 A. In this case, excitation of one marker with electromagnetic radiation causes the second marker to emit electromagnetic radiation of a different wavelength which is detectable. A second type of interaction would be based on electron transfer between the two different markers which can only occur when the markers are less than about 5 A. A third interaction would be a photochemical reaction between two markers which produces a new species that has detectable properties such as fluorescence. Although these markers may also be present on the misaminoacylated tRNAs used for their incorporation into nascent proteins, the interaction of the markers occurs primarily when they are incorporated into protein due to their close proximity. In certain cases, the proximity of two markers in the protein can also be enhanced by choosing tRNA species that will insert markers into positions that are close to each other in either the primary, secondary or tertiary structure of the protein. For example, a tyrosine-tRNA and a tryptophan-tRNA could be used to enhance the probability for two different markers to be near each other in a protein sequence which contains the unique neighboring pair tyrosine-tryptophan.

In one embodiment of this method, a reporter group is incorporated into a nascent protein using a misaminoacylated tRNA so that when it binds to a coupling agent, the reporter group interacts with a second markers or agents which causes them to become specifically detectable. Such an interaction can be optimized by incorporating a specific affinity element into the nascent protein so that once it interacts with a coupling agent the interaction between the reporter group and the second marker is optimized. Such an affinity element might comprise a specific amino acid sequence which forms an epitope or a normative amino acid. In one example, the reporter group is incorporated at the N-terminal of the nascent protein by using a misaminoacylated tRNA. The epitope is incorporated into the nascent protein so that when it interacts with the coupling agent the reporter comes into close proximity with a second marker which is conjugated to the coupling agent.

One type of interaction between the markers that is advantageously used causes a fluorescence resonant energy transfer which occurs when the two markers are within a distance of between about 1 angstrom (A) to about 50 A, and preferably less than about 10 A. In this case, excitation of one marker with electromagnetic radiation causes the second marker to emit electromagnetic radiation of a different wavelength which is detectable. This could be accomplished, for example, by incorporating a fluorescent marker at the N-terminal end of the protein using the $E.\ coli$ initiator tRNA$^{fmet}$. An epitope is then incorporated near the N-terminal end such as the SteptTag (WSHPQFEK) (SEQ ID NO:8) described by Sigma-Genosys. Streptavidin is then conjugated using known methods with a second fluorescent marker which is chosen to efficiently undergo fluorescent energy transfer with marker 1. The efficiency of this process can be determined by calculating the a Forster energy transfer radius which depends on the spectral properties of the two markers. The marker-streptavidin complex is then introduced into the translation mixture. Only when nascent protein is produced does fluorescent energy transfer between the first and second marker occur due to the specific interaction of the nascent protein StrepTag epitope with the streptavidin.

The criteria for the selection of a reporter group (acceptor) include small size, high fluorescence quantum yield, photostability and insensitivity to environment. The criteria for choosing a quencher molecules are minimal background when both molecules (F and Q) are present on the tRNA molecules and its availability in suitable reactive form.

There are a variety of dyes which can be used as marker pairs in this method that will produce easily detectable signals when brought into close proximity. Previously, such dye pairs have been used for example to detect PCR products by hybridizing to probes labeled with a dye on one probe at the 5'-end and another at the 3'-end. The production of the PCR product brings a dye pair in close proximity causing a detectable FRET signal. In one application the dyes, fluorescein and LC 640 were utilized on two different primers (Roche Molecular Biochemicals-). When the fluorescein is excited by green light (around 500 nm) that is produced by a diode laser, the LC 640 emits red fluorescent light (around 640 nm) which can be easily detected with an appropriate filter and detector. In the case of nascent proteins, the pair of dyes BODIPY FL and LC 640 would function in a similar manner. For example, incorporation of the BODIPY FL on the N-terminal end of the protein and the labeling of a binding agent with LC 640 which is directed against an N terminal epitope would allow detection of the production of nascent proteins.

As stated above, a principal advantage of using reporters is the ability to monitor the synthesis of proteins in cellular or a cell-free translation systems directly without further purification or isolation steps. Reporter markers may also be utilized in conjunction with cleavable markers that can remove the reporter property at will. Such techniques are not available using radioactive amino acids which require an isolation step to distinguish the incorporated marker from the unincorporated marker. With in vitro translation systems, this provides a means to determine the rate of synthesis of proteins and to optimize synthesis by altering the conditions of the reaction. For example, an in vitro translation system could be optimized for protein production by monitoring the rate of production of a specific calibration protein. It also provides a dependable and accurate method for studying gene regulation in a cellular or cell-free systems.

C. Affinity Markers

Another embodiment of the invention is directed to the use of markers that facilitate the detection or separation of nascent proteins produced in a cellular or cell-free protein synthesis system. Such markers are termed affinity markers and have the property that they selectively interact with molecules and/or materials containing acceptor groups. The affinity markers are linked by aminoacylation to tRNA molecules in an identical manner as other markers of non-native amino acid analogs and derivatives and reporter-type markers as described. These affinity markers are incorporated into nascent proteins once the misaminoacylated tRNAs are introduced into a translation system.

An affinity marker facilities the separation of nascent proteins because of its selective interaction with other molecules which may be biological or non-biological in origin through a coupling agent. For example, the specific molecule to which the affinity marker interacts, referred to as the acceptor molecule, could be a small organic molecule or chemical group such as a sulfhydryl group (—SH) or a large biomolecule such as an antibody. The binding is normally chemical in nature and may involve the formation of covalent or non-covalent bonds or interactions such as ionic or hydrogen bonding. The binding molecule or moiety might be free in solution or itself bound to a surface, a polymer matrix, or a reside on the surface of a substrate. The interaction may also be triggered by an external agent such as light, temperature, pressure or the addition of a chemical or biological molecule which acts as a catalyst.

The detection and/or separation of the nascent protein and other preexisting proteins in the reaction mixture occurs because of the interaction, normally a type of binding, between the affinity marker and the acceptor molecule. Although, in some cases some incorporated affinity marker will be buried inside the interior of the nascent protein, the interaction between the affinity marker and the acceptor molecule will still occur as long as some affinity markers are exposed on the surface of the nascent protein. This is not normally a problem because the affinity marker is distributed over several locations in the protein sequence.

Affinity markers include native amino acids, non-native amino acids, amino acid derivatives or amino acid analogs in which a coupling agent is attached or incorporated. Attachment of the coupling agent to, for example, a non-native amino acid may occur through covalent interactions, although non-covalent interactions such as hydrophilic or hydrophobic interactions, hydrogen bonds, electrostatic interactions or a combination of these forces are also possible. Examples of useful coupling agents include molecules such as haptens, immunogenic molecules, biotin and biotin derivatives, and fragments and combinations of these molecules. Coupling agents enable the selective binding or attachment of newly formed nascent proteins to facilitate their detection or isolation. Coupling agents may contain antigenic sites for a specific antibody, or comprise molecules such as biotin which is known to have strong binding to acceptor groups such as streptavidin. For example, biotin may be covalently linked to an amino acid which is incorporated into a protein chain. The presence of the biotin will selectively bind only nascent proteins which incorporated such markers to avidin molecules coated onto a surface. Suitable surfaces include resins for chromatographic separation, plastics such as tissue culture surfaces for binding plates, microtiter dishes and beads, ceramics and glasses, particles including magnetic particles, polymers and other matrices. The treated surface is washed with, for example, phosphate buffered saline (PBS), to remove non-nascent proteins and other translation reagents and the nascent proteins isolated. In some case these materials may be part of biomolecular sensing devices such as optical fibers, chemfets, and plasmon detectors.

Affinity markers can also comprise cleavable markers incorporating a coupling agent. This property is important in cases where removal of the coupled agent is required to preserve the native structure and function of the protein and to release nascent protein from acceptor groups. In some cases, cleavage and removal of the coupling agent results in production of a native amino acid. One such example is photocleavable biotin coupled to an amino acid.

A lysine-tRNA is misaminoacylated with photocleavable biotin-lysine, or chemically modified to attach a photocleavable biotin amino acid. The misaminoacylated tRNA is introduced into a cell-free protein synthesizing system and nascent proteins produced. The nascent proteins can be separated from other components of the system by streptavidin-coated magnetic beads using conventional methods which rely on the interaction of beads with a magnetic field. Alternatively, agarose beads coated with streptavidin, avidin and there derivatives be utilized. Nascent proteins are released then from beads by irradiation with UV light of approximately 280 nm wavelength. Once a nascent protein is released from by light it can be analyzed in solution (homogenous phase) or transferred to another surface such as nitrocellulose, polystyrene or glass for analysis (solid phase analysis) (non-specific binding surface or chemically activated). In one embodiment which involves solid phase analysis, neutravidin-coated agarose beads are used to capture nascent proteins produced in a cell-free rabbit reticulocyte protein synthesis system and the beads then separated from the synthesis system by centrifugation and washing. The nascent protein is then transferred to the surface of a microplate well by inserting the beads directly into the well and illuminating thereby facilitating transfer to the well surface.

In one experimental demonstration, nascent proteins (p53 and alpha-tubulin) were produced in a rabbit reticulocyte protein synthesis system supplemented with elongator tRNA misaminoacylated with a photocleavable biotin derivatized lysine. Without further processing, the nascent proteins were then specifically captured on NeutrAvidin biotin-binding agarose beads. After washing, the bead suspension containing the immobilized nascent protein was added directly to the wells of a high-protein-binding polystyrene micro-well plate. The UV release was performed directly in the wells of the plate thereby allowing subsequent and immediate non-specific adsorption of the released target protein onto the surface of the well. This approach, which is facilitated by photocleavable biotin, eliminates the need for stabilizers/additives (e.g., proteins like albumin or non-ionic detergents) normally required when handling small quantities of pure soluble target protein separately in tubes or vials. Elimination of such stabilizers/additives facilitates non-specific immobilization of the isolated target proteins and direct transfer of the target protein from the beads to the well of the plate minimizes handling and non-specific losses. Furthermore, this approach eliminates the need for plates coated with proteinaceous capture elements and therefore should provide certain advantages (e.g. lower background/interference from capture elements in the plate-based immunoassay).

Nascent proteins, including those which do not contain affinity-type markers, may be isolated by more conventional isolation techniques. Some of the more useful isolation techniques which can be applied or combined to isolate and purify nascent proteins include chemical extraction, such as phenol or chloroform extract, dialysis, precipitation such as ammonium sulfate cuts, electrophoresis, and chromatographic techniques. Chemical isolation techniques generally do not provide specific isolation of individual proteins, but are useful for removal of bulk quantities of non-proteinaceous material. Electrophoretic separation involves placing the translation mixture containing nascent proteins into wells of a gel which may be a denaturing or non-denaturing polyacrylamide or agarose gel. Direct or pulsed current is applied to the gel and the various components of the system separate according to molecular size, configuration, charge or a combination of their physical properties. Once distinguished on the gel, the portion containing the isolated proteins removed and the nascent proteins purified from the gel. Methods for the purification of protein from acrylamide and agarose gels are known and commercially available.

Chromatographic techniques which are useful for the isolation and purification of proteins include gel filtration, fast-pressure or high-pressure liquid chromatography, reverse-phase chromatography, affinity chromatography and ion exchange chromatography. These techniques are very useful for isolation and purification of proteins species containing selected markers.

A marker group can also be incorporated at the N terminal by using a mutant tRNA which does not recognize the normal AUG start codon. In some cases this can lead to a higher extent of specific incorporation of the marker. For example, the mutant of initiator tRNA, where the anticodon has been changed from CAU→CUA (resulting in the change of initiator methionine codon to amber stop codon) has shown to act as initiator suppressor tRNA (Varshney U, RajBhandary U L, Proc Natl Acad Sci USA 1990 February; 87(4):1586-90; Initiation of protein synthesis from a termination codon). This tRNA initiates the protein synthesis of a particular gene when the normal initiation codon, AUG is replaced by the amber codon UAG. Furthermore, initiation of protein synthesis with UAG and tRNA(fMet$^{CUA}$) was found to occur with glutamine and not methionine. In order to use this tRNA to introduce a marker at the N terminal of a nascent protein, this mutant tRNA can be enzymatically aminoacylated with glutamine and then modified with suitable marker. Alternatively, this tRNA could be chemically aminoacylated using modified amino acid (for example methionine-BODIPY). Since protein translation can only be initiated by this protein on messages containing UAG, all proteins will contain the marker at the N-terminal end of the protein.

D. Mass Spectrometry

Mass spectrometry measures the mass of a molecule. The use of mass spectrometry in biology is continuing to advance rapidly, finding applications in diverse areas including the analysis of carbohydrates, proteins, nucleic acids and biomolecular complexes. For example, the development of matrix assisted laser desorption ionization (MALDI) mass spectrometry (MS) has provided an important tool for the analysis of biomolecules, including proteins, oligonucleotides, and oligosachamides [Karas, 1987 #6180; Hillenkamp, 1993 #6175]. This technique's success derives from its ability to determine the molecular weight of large biomolecules and non-covalent complexes (>500,000 Da) with high accuracy (0.01%) and sensitivity (sub-femtomole quantities). Thus far, it has been found applicable in diverse areas of biology and medicine including the rapid sequencing of DNA, screening for bioactive peptides and analysis of membrane proteins.

Another embodiment of the invention contemplates using mass spectrometry for detection of the mutations. This includes but is not limited to the chain truncation, deletion, addition, frameshift and missense mutations.

Mass spectrometry has become increasingly attractive as an analytical technique in biomedical research. For example, mass spectrometry holds substantial potential for use in the rapid screening of disease causing genetic defects (Koster, H., Tang, K., Fu, D.-J., Braun, A., van den Boom, D., Smith, C. L. Cotter, R. J. and Cantor, C. R., A strategy for rapid and efficient DNA sequencing by mass spectrometry. *Nature Biotechnol.* 1996. 14. 1123-1128). Instead of sequencing an entire gene in order to detect the presence of a mutation, mass spectrometry can identify a mutation on the basis of changes in the mass. Very high throughputs are obtained because separation times are measured in microseconds rather than minutes or hours (Ross, P. L., P. A. Davis, and P. Belgrader, Analysis of DNA fragments from conventional and microfabricated PCR devices using delayed extraction MALDI-TOF mass spectrometry. *Anal Chem*, 1998. 70(10). 2067-2073). However, there still exist several major barriers to widespread application of mass spectrometry for DNA analysis. First, unlike proteins, DNA undergoes facile fragmentation in a mass spectrometer, especially when vaporized using MALDI-MS (Schneider, K. and B. T. Chait, Increased stability of nucleic acids containing 7-deaza-guanosine and 7-deaza-adenosine may enable rapid DNA sequencing by matrix-assisted laser desorption mass spectrometry. *Nucleic Acids Res*. 1995. 23(9), 1570-1575). Second, lengthy pre-isolation/purification steps are often required prior to MALDI-MS analysis, due to a number of factors including the formation of cation adducts with the acidic phosphate groups.

These problems can be overcome if the peptide product of the DNA, rather than the DNA itself, is analyzed by mass spectrometry. Larger test sequences can be scanned, while remaining in the effective mass range of the instrument, because the process of transcribing and translating DNA into protein reduces the mass by a factor of 10 (e.g. 3 bases of single stranded DNA have a mass of roughly 1000 Daltons, while the amino acid residue encoded by these 3 bases has a mass of roughly 100 Daltons). Secondly, each peptide will give a single peak on the MALDI-TOF mass spectrum resulting in only one peak per amplicon for the wild type sequence and one additional peak when a sequence variant is present. Thus, a peptide-based approach can be multiplexed without generating overly complex spectra. In contrast, DNA based mass spectrometric scanning produces a mass ladder of dideoxy terminated DNA strands for each amplicon and, as with electrophoresis based sequencing, cannot be multiplexed.

The MASSIVE-PRO approach for detection of chain truncating mutations is based on the utilization of advanced methods for cell-free protein expression along with the ability of mass spectrometry to simultaneously detect changes in the amino acid sequence of multiple peptides. DNA is isolated from a patient fecal sample and specific regions of a gene (i.e., for example, an APC gene) are PCR amplified using specifically designed primers that allow translation of encoded peptide fragments in a cell-free protein synthesis system. Nascent proteins are affinity purified and their mass is detected by MALDI-TOF which allows identifying low levels of mutations (i.e., for example, one characteristic of colorectal cancer). See FIG. 33.

Figure 33:
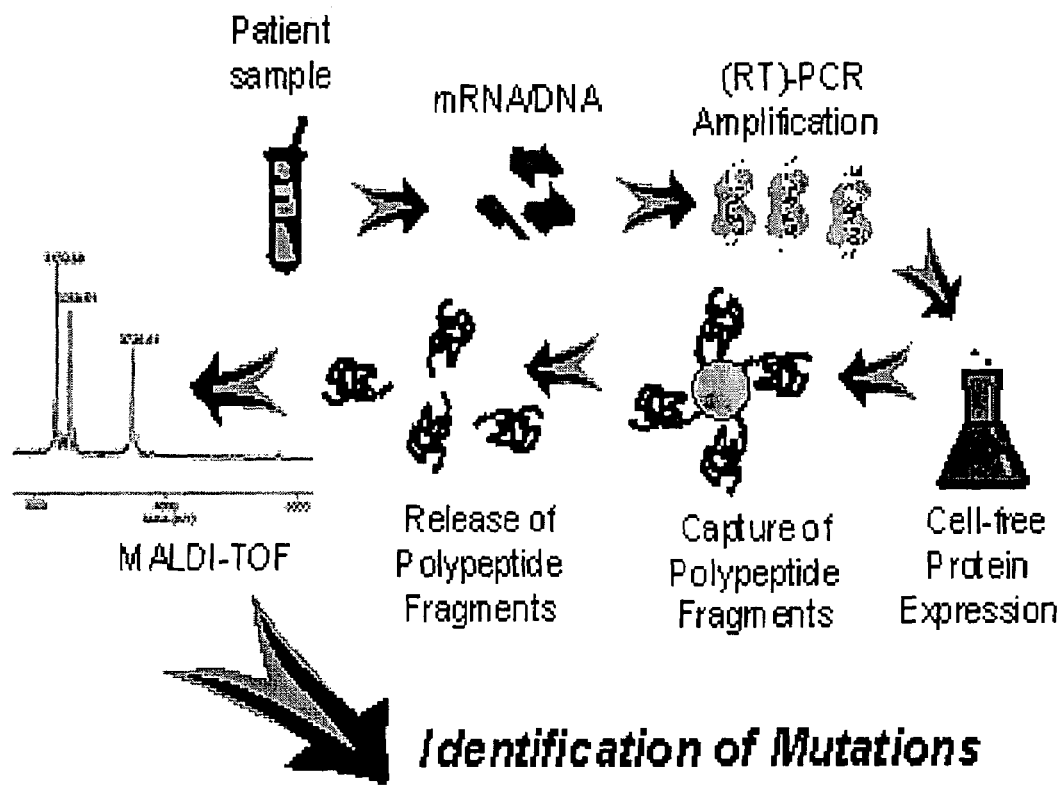
FIG. 33 shows one embodiment of a MASSIVE-PRO assay.

The overall approach is illustrated in FIG. 33 and described below:
  1. Specific region of the genomic mRNA or DNA is amplified by PCR using specially designed internal primers that encode for promoters, capture epitopes and start/stop codons.
  2. The resulting PCR products are added to a cell-free protein transcription/translation system. In some cases this mixture will contain misaminoacylated tRNAs to facilitate incorporation of special affinity/detection tags. In order to minimize proteolysis of fragments and increase yields, a reconstituted *E. coli* expression system (RECES) is utilized.
  3. The expressed peptides are purified by capturing on beads or other solid-phase media via an incorporated N-terminal affinity tag (e.g. affinity epitopes and/or modified amino acids).
  4. A second C-terminal affinity tag is incorporated for elimination of full-length peptides.
  5. The purified peptides are then released from the solid support and deposited on a MALDI plate. The utilization of photocleavable affinity tags such as PC-biotin, which can be incorporated using misaminoacylated tRNAs provides a rapid method of polypeptide capture and release.
  6. Mass spectrometry is performed on the peptide mixtures to detect mass shifted fragments which indicate variations in the sequence when compared to a reference sample.

Compared to the existing technology of electrophoresis-based DNA sequencing, mass spectrometry offers the potential of much higher throughput because separation times are measured in microseconds rather than tens of minutes to hours. Perhaps most important is the ability of MASSIVE-PRO to detect mutant sequences present in low concentration. Compared to the limit of 20-25% sensitivity for mutant sequences in direct sequencing, MASSIVE-PRO is likely to detect mutations at levels well-below 1%. In addition, unlike DNA sequencing, changes in the mass of several peptides can be simultaneously detected, opening the possibility of multiplexed analysis. Based on initial studies, the estimated costs for mass spectrometry based mutation detection for the APC gene is likely to be significantly less expensive than DNA sequencing due to the ability to perform high level (3-5 fold) multiplexing.

Markers incorporated by misaminoacylated tRNAs into nascent proteins, especially at a specific position such at the N-terminal can be used for the detection of nascent proteins by mass spectrometry. Without such a marker, it can be very difficult to detect a band due to a nascent protein synthesized in the presence of a cellular or cell-free extract due the presence of many other molecules of similar mass in the extract. For example, in some cases less than 0.01% of the total protein mass of the extract may comprise the nascent protein(s).

Detection by mass spectrometry of a nascent protein produced in a translation system is also very difficult if the mass of the nascent protein produced is not known. This might situation might occur for example if the nascent protein is translated from DNA where the exact sequence is not known. One such example is the translation of DNA from individuals which may have specific mutations in particular genes or gene fragments. In this case, the mutation can cause a change in the protein sequence and even result in chain truncation if the mutation results in a stop codon. In one embodiment a tRNA misaminoacylated with a marker of a known mass is added to the protein synthesis system. The synthesis system is then incubated to produce the nascent proteins. The mass spectrum of the protein synthesis system is then measured. The presence of the nascent protein can be directly detected by identifying peaks in the mass spectrum of the protein synthesis system which correspond to the mass of the unmodified protein and a second band at a higher mass which corresponds to the mass of the nascent protein plus the modified amino acid containing the mass of the marker.

There are several steps that can be taken to optimize the efficient detection of nascent proteins using this method. The mass of the marker should exceed the resolution of the mass spectrometer, so that the increased in mass of the nascent protein can be resolved from the unmodified mass. For example, a marker with a mass exceeding 100 daltons can be readily detected in proteins with total mass up to 100,000 using both matrix assisted laser desorption (MALDI) or electrospray ionization (ESI) techniques. The amount of misaminoacylated tRNA should be adjusted so that the incorporation of the mass marker occurs in approximately 50% of the total nascent protein produced. An initiator tRNA is preferable for incorporation of the mass marker since it will only be incorporated at the N-terminal of the nascent protein, thus avoiding the possibility that the nascent protein will contain multiple copies of the mass marker.

One example of this method is the incorporation of the marker BODIPY-FL, which has a mass of 282, into a nascent protein using a misaminoacylated initiator tRNA. Incorporation of this marker into a nascent protein using a misaminoacylated initiator tRNA causes a band to appear at approximately 282 daltons above the normal band which appears for the nascent protein. Since the incorporation of the marker is less than one per protein due to competition of non-misaminoacylated $E.$ $coli$ $tRNA^{fmet}$, a peak corresponding to the unmodified protein also appears. Identification of these two bands separated by the mass of the marker allows initial identification of the band due to the nascent protein. Further verification of the band due to the nascent protein can be made by adjusting the level of the misaminoacylated initiator tRNA in the translation mixture. For example, if the misaminoacylated initiator tRNA is left out, than only a peak corresponding to the unmodified protein appears in the mass spectrum of the protein synthesis system. By comparing the mass spectrum from the protein synthesis system containing and not containing the misaminocylated tRNA with the BODIPY-FL, the presence of the nascent protein can be uniquely identified, even when a protein with similar or identical mass is already present in the protein synthesis system.

For the purpose of mass spectrometric identification of nascent proteins, it is sometimes advantageous to utilize a photocleavable marker. In this case, peaks due to nascent proteins in the mass spectrum can be easily identified by measuring and comparing spectra from samples of the protein synthesis system that have been exposed and not exposed to irradiation which photocleaves the marker. Those samples which are not exposed to irradiation will exhibit bands corresponding the mass of the nascent protein which has the incorporated mass marker, whereas those samples which are exposed to irradiation will exhibit bands corresponding to the mass of the nascent proteins after removal of the mass marker. This shift of specific bands in the mass spectrum due to irradiation provides a unique identifier of bands which are due to the nascent proteins in the protein synthesis system.

Markers with affinity properties which are incorporated by misaminoacylated tRNAs into nascent proteins can also be very useful for the detection of such proteins by mass spectrometry. Such markers can be used to isolate nascent proteins from the rest of the cell-free or cellular translation system. In this case, the isolation of the nascent proteins from the rest of the cell-free mixture removes interference from bands due to other molecules in the protein translation system. An example of this approach is the incorporation of photocleavable biotin into the N-terminal end of a nascent proteins using misaminoacylated tRNA. When this marker is incorporated onto the N-terminal end of a nascent protein using an $E.$ $coli$ $tRNA^{met}$, it provides a convenient affinity label which can be bound using streptavidin affinity media such as streptavidin agarose. Once the nascent protein is separated by this method from the rest of the protein synthesis system, it can be released by UV-light and analyzed by mass spectrometry. In the case of MALDI mass spectrometry, release of the nascent protein can most conveniently be accomplished by using the UV-laser excitation pulses of the MALDI system. Alternatively, the sample can be irradiated prior to mass spectrometric analysis in the case of MALDI or ESI mass spectrometry.

E. Electrophoresis

Another embodiment of the invention is directed to methods for detecting by electrophoresis the interaction of molecules or agents with nascent proteins which are translated in a translation system. This method allows a large number of compounds or agents to be rapidly screened for possible interaction with the expressed protein of specific genes, even when the protein has not been isolated or its function identified. It also allows a library of proteins expressed by a pool of genes to be rapidly screened for interaction with compounds or agents without the necessity of isolating these proteins or agents. The agents might be part of a combinatorial library of compounds or present in a complex biological mixture such as a natural sample. The agents might interact with the nascent proteins by binding to them or to cause a change in the structure of the nascent protein by chemical or enzymatic modification.

In addition to gel electrophoresis, which measures the electrophoretic mobility of proteins in gels such as polyacrylamide gel, this method can be performed using capillary electrophoresis. CE measures the electrophoretic migration time of a protein which is proportional to the charge-to-mass ratio of the molecule. One form of CE, sometimes termed affinity capillary electrophoresis, has been found to be highly sensitive to interaction of proteins with other molecules including small ligands as long as the binding produces a change in the charge-to-mass ratio of the protein after the binding event. The highest sensitivity can be obtained if the protein is conjugated to a marker with a specifically detectable electromagnetic spectral property such as a fluorescent dye. Detection of a peak in the electrophoresis chromatogram is accomplished by laser induced emission of mainly visible wavelengths. Examples of fluorescent dyes include fluorescein, rhodamine, Texas Red and BODIPY.

It is very difficult to detect a nascent protein synthesized in a cellular or cell-free extract by CE without subsequent isolation and labeling steps due the need for high sensitivity detection and the presence of many other molecules of similar mass/charge ratio in the extract. For example, in typical cases less than 0.01% of the total protein mass of the extract may comprise the nascent protein(s). Other molecules with similar electrophoretic migration times as the nascent protein may be present in the mixture. Such molecules will overlap with peaks due to the nascent protein.

It is also very difficult using conventional methods of CE to detect the interaction of molecules with nascent proteins produced in a cell free or cellular synthesis system. Affinity capillary electrophoresis has been found to be sensitive to interaction of proteins with other molecules including small ligands as long as the binding produces a change in the charge-to-mass ratio of the protein after the binding event. However, the selective addition of a marker such as a fluorescent dye to a nascent protein is not possible using conventional means because most markers reagents will nonspecifically label other molecules in the protein synthesis system besides the nascent proteins. Even after a nascent protein has been isolated, it is often difficult to uniformly label the protein with a marker so that the charge/mass ratio of each labeled protein remains the same. In the most advantageous form of labeling, a highly fluorescent marker is incorporated at only one specific position in the protein thus avoiding a set of proteins with different electrophoretic mobilities.

In one embodiment of the invention a tRNA misaminoacylated with a detectable marker is added to the protein synthesis system. The system is incubated to incorporate the detectable marker into the nascent proteins. One or more molecules (agents) are then combined with the nascent proteins (either before or after isolation) to allow agents to interact with nascent proteins. Aliquots of the mixture are then subjected to electrophoresis. Nascent proteins which have interacted with the agents are identified by detecting changes in the electrophoretic mobility of nascent proteins with incorporated markers. In the case where the agents have interacted with the nascent proteins, the proteins can be isolated and subsequently subjected to further analysis. In cases where the agents have bound to the nascent proteins, the bound agents can be identified by isolating the nascent proteins.

In one example of this method, the fluorescent marker BODIPY-FL is used to misaminoacylate an *E. coli* initiator tRNA$^{fmet}$ as previously described. The misaminoacylated tRNA is then added to a protein synthesis system and the system incubated to produce nascent protein containing the BODIPY-FL at the N-terminal. A specific compound which may bind to the nascent protein is then added to the protein synthesis system at a specific concentration. An aliquot from the mixture is then injected into an apparatus for capillary electrophoresis. Nascent proteins in the mixture are identified by detection of the fluorescence from the BODIPY-FL using exciting light from an Argon laser tuned to 488 nm. Interaction of the specific compound is determined by comparing the electrophoretic mobility measured of the nascent protein exposed to the specific compound with a similar measurement of the nascent protein that has not been exposed. The binding strength of the compound can then be ascertained by altering the concentration of the specific compounds added to the protein synthesis system and measuring the change in the relative intensity of bands assigned to the uncomplexed and complexed nascent protein.

G. Multiple Misaminoacylated tRNAs

It may often be advantageous to incorporate more than one marker into a single species of protein. This can be accomplished by using a single tRNA species such as a lysine tRNA misaminoacylated with both a marker such as dansyllysine and a coupling agent such as biotin-lysine. Alternatively, different tRNAs which are each misaminoacylated with different markers can also be utilized. For example, the coumarin derivative could be used to misaminoacylate a tryptophan tRNA and a dansyl-lysine used to misaminoacylate a lysine tRNA.

One use of multiple misaminoacylated tRNAs is in the combined isolation and detection of nascent proteins. For example, biotin-lysine marker could be used to misaminoacylate one tRNA and a coumarin marker used to misaminoacylate a different tRNA. Magnetic particles coated with streptavidin which binds the incorporated lysine-biotin would be used to isolate nascent proteins from the reaction mixture and the coumarin marker used for detection and quantitation.

I. Kits

Another embodiment of the invention is directed to diagnostic kits or aids containing, preferably, a cell-free translation containing specific misaminoacylated tRNAs which incorporate markers into nascent proteins coded for by mRNA or genes, requiring coupled transcription-translation systems, and are only detectably present in diseased biological samples. Such kits may be useful as a rapid means to screen humans or other animals for the presence of certain diseases or disorders. Diseases which may be detected include infections, neoplasias and genetic disorders. Biological samples most easily tested include samples of blood, serum, tissue, urine or stool, prenatal samples, fetal cells, nasal cells or spinal fluid. In one example, misaminoacylate fmet-tRNAs could be used as a means to detect the presence of bacteria in biological samples containing prokaryotic cells. Kits would contain translation reagents necessary to synthesize protein plus tRNA molecules charged with detectable non-radioactive markers. The addition of a biological sample containing the bacteria-specific genes would supply the nucleic acid needed for translation. Bacteria from these samples would be selectively lysed using a bacteria directed toxin such as Colicin E1 or some other bacteria-specific permeabilizing agent. Specific genes from bacterial DNA could also be amplified using specific oligonucleotide primers in conjunction with polymerase chain reaction (PCR), as described in U.S. Pat. No. 4,683,195, which is hereby specifically incorporated by reference. Nascent proteins containing marker would necessarily have been produced from bacteria. Utilizing additional markers or additional types of detection kits, the specific bacterial infection may be identified.

The present invention also contemplates kits which permit the GFTT described above. For example, the present invention contemplates kits to detect specific diseases such as familial adenomatous polyposis. In about 30 to 60% of cases of familial adenomatous polyposis, the diseased tissues also contain chain terminated or truncated transcripts of the APC gene (S. M. Powell et al., N. Engl. J. Med. 329:1982-87, 1993). Chain termination occurs when frameshift cause a stop codon such as UAG, UAA or UGA to appear in the reading frame which terminates translation. Using misaminoacylated tRNAs which code for suppressor tRNAs, such transcripts can be rapidly and directly detected in inexpensive kits. These kits would contain a translation system, charged suppressor tRNAs containing detectable markers, for example photocleavable coumarin-biotin, and appropriate buffers and reagents. Such a kit might also contain primers or "pre-primers," the former comprising a promoter, RBS, start codon, a region coding an affinity tag and a region complementary to the template, the latter comprising a promoter, RBS, start codon, and region coding an affinity tag—but lacking a region complementary to the template. The pre-primer permits ligation of the region complementary to the template (allowing for customization for the specific template used). A biological sample, such as diseased cells, tissue or isolated DNA or mRNA or PCR products of the DNA, is added to the system, the system is incubated and the products analyzed. Analysis and, if desired, isolation is facilitated by a marker such as coumarin or biotin which can be specifically detected by its fluorescence using streptavidin coupled to HRP. Such kits provide a rapid, sensitive and selective non-radioactive diagnostic assay for the presence or absence of the disease.

J. Colorectal Cancer PTT Detection

The present invention contemplates the isolation, detection and identification of expressed proteins having an altered primary amino acid sequence. One example of an altered primary sequence is a protein chain truncation. A protein chain truncation is most easily explained by a frameshift mutation that generates a stop codon (i.e., AUG) within the open reading frame. The resulting translation of the mRNA from this mutated gene synthesizes a nonfunctional or malfunctional protein. One example of such a truncated protein is derived from the APC gene, and is known to be a diagnostic marker for colorectal cancer. Rothschild et al., "Methods for the Detection, Analysis and Isolation of Nascent Proteins", U.S. patent application Ser. No. 10/339,712 (herein incorporated by reference).

Many attempts have been reported to detect and analyze biological samples using a noninvasive diagnostic marker of colorectal cancer. Currently, the most reliable method to identify and treat colorectal cancer requires a colonoscopy. While colonoscopy is not a high risk procedure, except for the associated general anesthesia, it is expensive and there is a serious problem regarding obtaining compliance for one time or repeated testing due to the invasive nature of the examination and the extensive bowel preparation required. One possible non-invasive source of diagnostic markers is fecal matter.

It should be understood that fecal matter is not the only source of diagnostic markers contemplated by the present invention. For example, urine samples may also be used to provide the necessary DNA source to conduct assay embodiments contemplated herein. Su et al., "Human Urine Contains Small, 150, 250 Nucleotide-Sized, Soluble DNA Derived From The Circulation And May Be Useful In the Detection Of Colorectal Cancer" *J Mol Diag* 6:101-107 (2004). Other DNA sources include, but are not limited to, blood serum or buccal cells.

The Protein Truncation Test (PTT) was first reported by Roest et al., *Protein Truncation Test (PTT) For Rapid Detection Of Translation-Terminating Mutations*. Hum Mol Genet 2:1719-1721 (1993), and applied to the detection of truncating mutations in the APC gene by Powell et al., *Molecular Diagnosis Of Familial Adenomatous Polyposis*. N Engl J Med 329:1982-1987 (1993). In traditional PTT, the region of the gene to be analyzed is amplified by PCR (or RT-PCR for an mRNA template) using a primer pair that incorporates additional sequences into the PCR amplicons required for efficient cell-free translation. The amplified DNA is then added to a cell-free transcription-translation extract along with radioactive amino acids ($^{35}$S-methionine or $^{14}$C-leucine). The expressed protein is analyzed by SDS-PAGE and autoradiography. Chain truncation mutations are detected by the presence of a lower molecular weight (increased mobility) species relative to the wild-type (WT) protein band. Non-radioactive Western blot-based PTT-methods utilizing a combination of N-terminal and C-terminal epitopes have also been reported. Rowan et al., *Introduction Of A myc Reporter Tag To Improve The Quality Of Mutation Detection Using The Protein Truncation Test*. Hum Mutat 9:172-176 (1997); de Koning Gans et al., *A Protein Truncation Test For Emery-Dreifuss Muscular Dystrophy (EMU): Detection Of N-Terminal Truncating Mutations*. Neuromuscul Disord 9:247-250 (1999); and Kahamnn et al., *A Non-Radioactive Protein Truncation Test For The Sensitive Detection Of All Stop And Frameshift Mutations*. Hum Mutat 19:165-172 (2002). However, these approaches still involve lengthy steps of SDS-PAGE, electroblotting and membrane-based immunoassay.

Capillary electrophoreses provides an alternative to traditional SDS-PAGE gels. For example, a translation carried out in presence of BODIPY-FL tRNA results in a nascent protein (WT or mutant) having incorporated the BODIPY-FL. As with SDS-PAGE, a mutant protein expressing a premature termination codon, will have faster mobility when using CE (i.e., a truncated protein As an alternative to SDS-PAGE based PTT, the present invention contemplates a high throughput solid-phase protein truncation test (HTS-PTT) that is compatible with multi-well or microarray formats. Amplified DNA corresponding to the region of interest in the target gene is first generated using PCR with primers that incorporate N- and C-terminal epitope tags as well as a T7 promoter, Kozak sequence and start codon (ATG) in the amplicons. (see Example 10). The resulting amplified DNA is subsequently added to a cell-free protein expression system. (see Example 11). As an initial evaluation of HTS-PTT, an ELISA-based multi-well assay was developed to detect truncating mutations in a region of the APC gene (segment 3; amino acids 1098-1696) using genomic DNA as a PCR template. Extensive screening of various epitope tag sequences including His-6, c-myc, P53 (derived from the P53 sequence), FLAG, VSV-G, Fil-16 (filamin derived) and StrepTag was performed in order to determine which were optimal with respect to signal-to-noise ratio. Based on this, VSV-G and a P53-derived tag were chosen as the N- and C-terminal epitopes, respectively. The target protein was expressed using a cell-free transcription-translation system in the presence of a misaminoacylated tRNAs (biotin-lysyl-tRNA and/or BODIPY-FL-lysyl-tRNA) designed to incorporate lysine residues modified with biotin or a fluorophore (BODIPY-FL) at random lysine positions. In order to enhance throughput, the nascent APC segment 3 was selectively captured from the reaction mixture via the incorporated biotin onto a 96-well ELISA plate and simultaneously treated with the appropriate antibodies in a single step. Furthermore, to increase accuracy, the N- and C-terminal epitope tags were measured in the same well plate using differentially labeled antibodies (HRP and alkaline phosphatase (AP), respectively).

While heterozygous mutations in germ-line cells are expected to comprise 50% of the total DNA in a sample, sporadic mutations are often present in significantly lower abundance, such as the case of stool samples from individuals with colorectal cancer. Traverso et al., *Detection Of APC Mutations In Fecal DNA From Patients With Colorectal Tumors*. N Engl J. Med 346:311-320 (2002); Deuter et al., *Detection Of APC Mutations In Stool DNA Of Patients With Colorectal Cancer By HD-PCR*. Hum Mutat, 11:84-89 (1998); and Doolittle et al., *Detection Of The Mutated K-Ras Biomarker In Colorectal Carcinoma*. Exp Mol Pathol 70:289-301 (2001). One recent approach which can detect as low as 0.40% mutant DNA relative to WT, termed digital PTT, was utilized as part of a non-invasive assay for colorectal tumors. A key feature of this approach is the serial dilution of DNA prior to PCR amplification, so that each reaction contains no more than 4 copies of the APC gene. Detection of a mutation thus requires that the PTT assay have sensitivity sufficient to detect 1 out of 4 (25%) mutated copies of the gene. 144 individual cell-free translation reactions were performed for each patient sample and each reaction then analyzed by SDS-PAGE and autoradiography. Traverso et al. (2002). However, it would be desirable to replace the radioactive gel-based analyses with HTS-PTT in order to more efficiently screen such large numbers of samples per patient.

Figure 9:
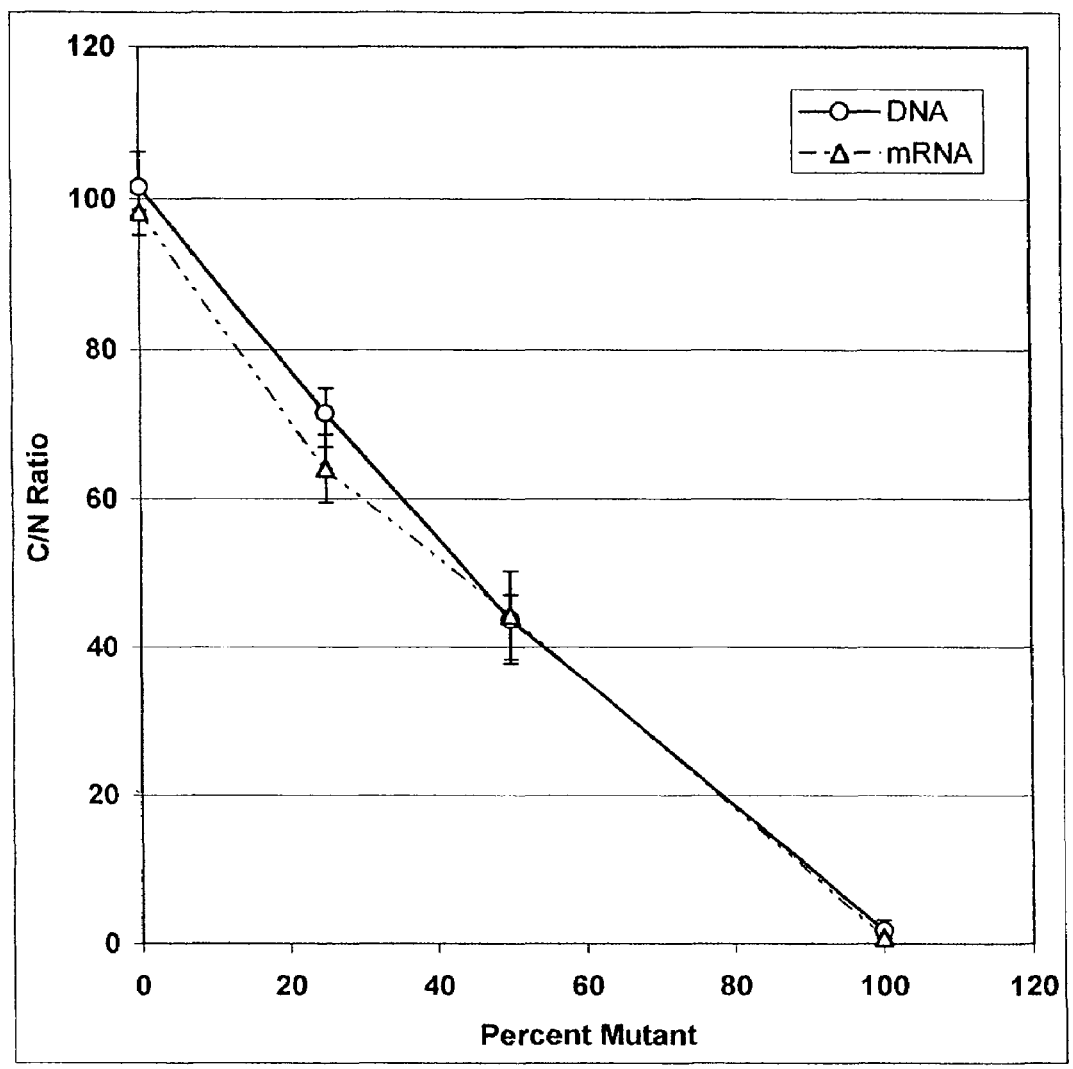
FIG. 9 displays HTS-PTT truncation mutation detection in APC gene at various dilutions of WT:C3 DNA (circles-solid line) or mRNA (triangles-broken line). The DNA were mixed prior to PCR. The mRNA were mixed prior to isolation. All data points represent an average of $\geq 3$ replicates and error bars indicate the standard deviation.

In an experiment designed to measure the sensitivity of HTS-PTT, various amounts of amplified WT and mutant APC DNA (cell-line C3) were mixed and translated as described earlier. As expected, the C/N terminal ratio decreased with increasing levels of mutant DNA (FIG. 9). C/N terminal ratios were 100±6 (WT) versus 70±4 (25% mutant mixture; 3 WT:1 mutant) and 42±4 (50% mutant mixture; 1 WT:1 mutant). An unpaired two-tailed t-test shows that the difference in raw C/N terminal ratios between the WT and WT:mutant mixtures is statistically significant with p values of $1\times10^{-11}$ for WT versus 50% mixture and $1\times10^{-8}$ for WT versus 25% mixture (n=7). These results indicated that HTS-PTT may be suitable to replace the radioactive gel-based analysis in the digital PTT. Specifically, the above results indicated that the C/N ratio for the 50% and 25% mutant mixture deviate slightly from expected values of 0.5 and 0.75, respectively. This deviation may possibly be due to unequal binding and N-terminal accessibility of the full-length and truncated fragments.

Experiments were also carried out using mRNA isolated from cell line C3 which was then amplified using RT-PCR. The results (FIG. 9, broken line) are very similar to those obtained using DNA as starting material (C/N terminal ratios for mRNA based HTS-PTT were 100±5, 64±3, 44±3 for WT, 25% mutant mixture and 50% mutant mixture, respectively). This demonstrates the suitability of the HTS-PTT for analyzing chain truncating mutation using mRNA. However, it is noted that most clinical laboratories normally avoid the use of mRNA for PTT analysis because of problems such as the process of nonsense mediated mRNA decay, can make detection of the mutated allele difficult in some cases. Frieschmeyer et al., *Nonsense-Mediated mRNA Decay In Health And Disease*, Hum Mol Genet 8:1893-1900 (1999).

Several improvements are envisioned for the basic HTS-PTT approach presented herein. The use of biotin-lysyl-tRNA to incorporate biotin affinity tags at lysine residues would result in no capture if the chain truncation occurs upstream of the first lysine. This problem and the overall efficiency of capture can be improved if a tRNA mixture containing most, or all, of the normal cellular tRNAs is misaminoacylated with a biotin-labeled amino acid (i.e., tRNA$^{TOTAL}$). This "total tRNA mixture" is then used instead of lysyl-tRNA, thereby making the biotin incorporation less dependent on the amino acid sequence of the nascent protein. It may also be possible to incorporate an affinity tag uniquely at the first residue in the sequence, thereby ensuring capture of any size truncated protein. This has been achieved for the case of an *E. coli* expression system using a suppressor initiator tRNA in conjunction with a nonsense codon for initiation. Because the HTS-PTT is not limited by the resolution of SDS-PAGE, it is possible to reduce the number of cell-free reactions per patient sample by translating larger segments of the target gene (or the whole gene itself). In fact, initial studies indicate that HTS-PTT analysis of fragments of at least 140 kDa in size is possible. Finally, the HTS-PTT is not limited to a multi-well ELISA/chemiluminescence format. For example, a microarray format is possible where the target proteins are captured on NeutrAvidin™ coated glass slides and detected using fluorescently labeled antibodies.

In contrast to traditional methods of PTT, the HTS-PTT described herein is non-isotopic, rapid and amenable to automation. The high throughput capabilities of the HTS-PTT should be useful in order to facilitate population-wide colorectal cancer (CRC) screening and other diseases that have prevalent truncation mutations.

The present invention contemplates the isolation, detection and identification of mutated genes by methods that do not require extensive and expensive purification, isolation and sequencing procedures. Furthermore, the present invention contemplates the use of nucleic acid material from any tissue or fluid sample, and is not restricted to fecal samples. Specifically, sample DNA from a patient suspected of having cancer is amplified by PCR using primers comprising sequences encoding a N-terminal and C-terminal epitope. The epitope-containing sample DNA is placed in a translation system (i.e., resulting in the production of mRNA followed by protein synthesis) containing at least one misaminoacylated marker tRNA. The marker is inserted into the nascent peptide for affinity capture following protein synthesis. It is not intended that the tRNA be limited to a single misaminoacylated tRNA (i.e., for example, lysine). The present invention contemplates the misaminoacylation of all amino acid tRNA's with a marker (i.e., the "total tRNA" embodiment or tRNA$^{TOTAL}$). This approach uniformly labels any length of any nascent protein with the affinity marker. Importantly, even if an amino acid in the C-terminal or N-terminal epitope receives a marker, the expected 1% incorporation rate (i.e., due to a low misaminoacylated tRNA concentration) will not reduce the ability to detect the affected epitope.

The present invention identifies a gene mutation by the ratio of detected N-terminal and C-terminal epitopes present in the nascent proteins. The epitopes may be identified by detection with enzyme-conjugated antibodies.

One embodiment of the present invention contemplates an HTS-PTT test combined with a DNA-based method of detecting specific mutations in one or more genes that have been associated with the series of genetic changes which result in neoplastic transformation of normal colonic epithelium to benign adenomas and subsequently to malignant adenocarcinomas (Seung Myung Dong et al., *J. Natl. Cancer Inst.*, 93:858-865 (2001)). It is also advantageous to utilize DNA-based assays which are compatible with the HTS-PTT platform and can be easily implemented in a clinical laboratory. For example, the TaqMan® assay and Invader® assay can be implemented on a 96, 384 or 1536 well luminescent/fluorescent reader to detect missense, deletion and insertion mutations which commonly occur in many genes, including APC. Even in cases where a large panel of known mutations is screened using DNA-based probes (specifically designed for those mutations) a significant percentage (i.e., approximately 20%) of de novo mutations are likely to appear in the APC gene and not be detected (Gavert et. al., *Molecular Analysis Of The APC Gene In 71 Israeli Families: 17 Novel Mutations.*, Hum Mutat 19(6):664 (2002). These mutations can be detected using HTS-PTT. In contrast, such a panel combined with PTT is likely to detect such new mutations in the APC gene.

K. p53 Variants

The present invention contemplates PCR-mediated incorporation of a p53 epitope variant into a diagnostic protein. In one embodiment, the present invention contemplates variants of the general formula:

T F S D L [x] K L L (SEQ ID NO:50), wherein [x] can be any amino acid other than W.

Examples of such variants include (but are not limited to):

| | |
|---|---|
| TFSDLHKLL | (SEQ ID NO:24) |
| TFSDLYKLL | (SEQ ID NO:25) |
| TFSDLGKLL | (SEQ ID NO:26) |
| TFSDLNKLL | (SEQ ID NO:27) |
| TFSDLFKLL | (SEQ ID NO:28) |
| TFSDLDKLL | (SEQ ID NO:29) |
| TFSDLTKLL | (SEQ ID NO:30) |

In another embodiment, the present invention contemplates variants of the general formula:

[z]$_y$ T F S D L [x] K L L (SEQ ID NO:51), wherein [x] can be any amino acid other than W, [z] can be any amino acid including but not limited to the amino acids corresponding to the wild-type sequence, and y is an integer between 1 and 10.

Examples of such variants include (but are not limited to):

| | |
|---|---|
| ETFSDLHKLL | (SEQ ID NO:31) |
| QETFSDLHKLL | (SEQ ID NO:32) |
| SQETFSDLHKLL | (SEQ ID NO:33) |
| LSQETFSDLHKLL | (SEQ ID NO:34) |

In another embodiment, the present invention contemplates variants of the general formula:

[z]$_y$ T F S D L [x] K L L [z]$_y$ (SEQ ID NO:52), wherein [x] can be any amino acid other than W, [z] can be any amino acid including but not limited to the amino acids corresponding to the wild-type sequence, and y is an integer between 1 and 10.

Examples of such variants include (but are not limited to):

```
ETFSDLHKLLP         (SEQ ID NO:35)
QETFSDLHKLLP        (SEQ ID NO:36)
SQETFSDLHKLLP       (SEQ ID NO:37)
LSQETFSDLHKLLPE     (SEQ ID NO:38)
```

L. VSV-G Variants

The present invention contemplates PCR-mediated incorporation of an eleven amino acid VSV-G epitope (residues 497-506) and variants thereof, into a diagnostic protein. This particular epitope is known to bind both monovalent and polyclonal antibodies and affects intracellular transport to the cell membrane. Kries, T. E., *Microinjected Antibodies Against The Cytoplasmic Domain Of Vesicular Stomatitis Virus Glycoprotein Block It's Transport To The Cell Surface.* EMBO J, 5(5):931-941 (1986). The incorporation of this VSV-G epitope into amphotropic leukemia virus envelope glycoprotein retained compatibility with envelope processing, transport and incorporation, although some temperature-sensitive mutants were generated. Battini et al., *Definition Of A 14-Amino Acid Peptide Essential For The Interaction Between The Murine Leukemia Virus Amphotropic Envelope Glycoprotein And Its Receptor.* J. Virol., 72(1):428-435 (1998).

By "variants" it is meant that the sequence need not comprise the exact sequence; up to three (3) amino acid substitutions are contemplated. For example, Leu or Ser may be substituted for the Gly; Ser may be substituted for the Leu; and Ser or Ala may be substituted for the T.

In one embodiment, the present invention contemplates the wild type sequence:
Y T D I E M N R L G K (SEQ ID NO:39)

In another embodiment, the present invention contemplates variants of the general formula:
Y [x] D I E M N R L G K (SEQ ID NO:53), wherein [x] can be S or A.

An example of such a variant includes, but is not limited to:
Y A D I E M N R L G K (SEQ ID NO:40)

In another embodiment, the present invention contemplates variants of the general formula:
Y T D I E M N R [y] G K (SEQ ID NO:54), wherein [y] can be S.

An examples of such a variant includes, but is not limited to:
Y T D I E M N R S G K (SEQ ID NO:41)

In another embodiment, the present invention contemplates variants of the general formula:
Y T D I E M N R L [z] K (SEQ ID NO:55), wherein [z] can be S or L.

An examples of such a variant includes, but is not limited to:
Y T D I E M N R L S K (SEQ ID NO:42)

In another embodiment, the present invention contemplates variants of the general formula:
Y [x] D I E M N R [y] G K (SEQ ID NO:56), wherein [x] can be S or A and [y] can be S.

An examples of such a variant includes, but is not limited to:
Y S D I E M N R S G K (SEQ ID NO:43)

In another embodiment, the present invention contemplates variants of the general formula:
Y [x] D I E M N R L [z] K (SEQ ID NO:57), wherein [x] can be S or A and [z] can be G or S.

An examples of such a variant includes, but is not limited to:
Y A D I E M N R L L K (SEQ ID NO:44)

In another embodiment, the present invention contemplates variants of the general formula;
Y T D I E M N R [y] [z] K (SEQ ID NO:58), wherein [y] can be S and [z] can be L or S.

An examples of such a variant includes, but is not limited to:
Y T D I E M N R S S K (SEQ ID NO:45)

In another embodiment, the present invention contemplates variants of the general formula;
Y [x] D I E M N R [y] [z] K (SEQ ID NO:59), wherein [x] can be S or A; [y] can be S and [z] can be G, L or S.

An examples of such a variant includes, but is not limited to:
Y A D I E M N R S G K (SEQ ID NO:46)

Another embodiment of the present invention contemplates a method for rapidly measuring cDNA library expression products. In this approach, the products were identified by Expression ELISA Assay.

Briefly, this method quickly assesses the product of the translation reaction in a high throughput manner. After the deconvolution of the cDNA pool, single colonies were grown and the DNA was isolated using standard mini-prep methods. The high-throughput ELISA-PTT assay was then used to rapidly screen the DNA from several clones in order to determine if the DNA was expressed.

Current methods for early detection of colorectal cancer include the endoscopic colorectal examination (colonoscopy) and the fecal occult-blood test (FOBT). An important feature of any colorectal assay suitable for population screening is the method of specimen collection. For example, procedures which are similar to FOBT (e.g., smears on slides performed by individuals at home) are well accepted (e.g., several million FOBT assays performed per year).

1. Colonoscopy

Colonoscopy is the current gold standard for early detection of CRC. The colonoscopy procedure is clinically reliable and allows both the identification and removal of colorectal cancer polyps in a single procedure. The colonoscopy procedure is, however, invasive, requires sedation, requires trained experts, and is preceded by extensive patient bowl preparation including the intake of large volumes of liquid, application of laxatives and restrictions on diet and certain medicines. As such, colonoscopy has a low compliance rate, high cost ($1,000-3,000/test) and risk of complications. Alternatively, a simpler colonoscopy procedure (i.e., flexible sigmoidoscopy) only costs $400/test and is widely used. Unfortunately, even when administered in conjunction with FOBT, at least 50% of possible tumors in the colon are missed. Flexible sigmoidoscopy still requires unpleasant bowl preparation and trained experts but does not require a sedative.

2. Fecal Occult-Blood Test

The detection of fecal occult blood has been part of medical diagnoses for many years. Baker et al., "Test For Fecal Occult Blood", U.S. Pat. No. 5,391,498 (1995); and Pagano J. F., "Specimen Test Slide" U.S. Pat. No. 3,996,006 (1976) (both patents hereby incorporated by reference). For example, the '006 patent discloses test slides (marketed under the trademark Hemoccult®) having a specimen receiving sheet between a front panel and a rear panel with openings in the front and rear panels and pivotal covers or flaps to cover these openings. The specimen receiving sheet is generally an absorbent paper impregnated with a gum guaiac (a natural resin extract from the wood of *Guaiacum officiale*) reagent. Oxidation of the gum guaiac by hydrogen peroxide produces blue-colored compounds. The heme portion of the hemoglobin, if present in fecal specimen, has peroxidase activity which catalyzes the oxidation of guaiaconic acid by hydrogen peroxide to form a highly conjugated blue quinine compound. The hemoglobin catalyzed oxidation of the guaiac extract coated paper is used clinically to detect occult blood in feces by the appearance of a blue color when the fecal material is placed in contact with the guaiac coated paper.

Briefly, the Hemoccult® test procedure comprises:
1. A specimen of fecal matter is smeared onto the guaiac paper through an opening of the front panel.
2. The panel is then covered and the flap of the rear panel is opened.
3. A developing solution such as hydrogen peroxide is applied to the guaiac paper via the corresponding opening in the rear panel.
4. If blood is present in the fecal matter, the guaiac reaction will color the paper blue.

Fecal occult blood tests (FOBT) have been used extensively to screen for the presence of colorectal cancer with an estimated 5 million tests performed each year. FOBT is currently favored by the medical community, has a very high patient compliance (~75%), is user-friendly and has an overall low cost. FOBT requires only a small smear of fecal material on a slide that affords an easy method to transport specimens.

While the test may result in a modest reduction in CRC mortality rates, its overall value has been questioned, partially due the high rate of false positives and negatives. For example, almost ⅔ of people who die from colon cancer have a negative FOBT. Specifically, this high false negative rate can be explained by the fact that FOBT misses almost all advanced adenomas. Advanced adenomas are known to have either an absence of, or intermittent, bleeding. A change of diet or drug use restrictions are often associated with the implementation of the FOBT. For example, in the case of the Hemoccult II® Sensa® test, the instructions include the following:
1. For seven days before and during the stool collection period avoid non-steroidal anti-inflammatory drugs such as ibuprofen, naproxen or aspirin (more than one adult aspirin a day).
2. For three days before and during the stool collection period avoid vitamin C in excess of 250 mg a day from supplements, and citrus fruits and juices.
3. For three days before and during stool collection period avoid red meats (beef, lamb and liver).

FOBT utilizes small fecal material specimens that are sufficient to detect stool blood, which is one symptom associated with colorectal cancer. These small amounts of fecal specimens collected by FOBT avoid offensive odors, minimize storage requirements and facilitate transportation that are problematic when large stool samples are required by other diagnostic cancer methods. In addition, because of the small fecal specimens required, the collection methods available are inexpensive, user friendly and simple.

In spite of the small specimen size, a typical FOBT test (i.e., for example, Hemoccult® Sensa®, Beckman-Coulter, Inc.) can detect 0.3 mg hemoglobin/gm of feces. In the case of the Hemoccult® Sensa® test, sampling comprises using an applicator stick which is provided in a kit to smear a thin layer of fecal specimen on guaiac-coated paper, wherein the paper is incorporated onto a slide. For increased accuracy, the patient provides fecal specimens on three separate days from three separate stools on three different slides. Additionally, separate fecal specimens are required from two different sections of each stool. Slides containing fecal specimens can be stored up to 14 days without preservatives at room temperature before developing.

Due to the simplicity of the FOBT tests the compliance rate is very high. For example, the Hemoccult® Sensa® test is reported to have a compliance rate of approximately 75%. Paaso B. T., "Community-Based Colorectal Cancer Screening," *Point of Care* 1:20-27, (2002). However, as discussed previously, FOBT suffers from very high rates of false positives and negatives. In one embodiment, the present invention contemplates combining a molecular diagnostic test (i.e., for example, a DNA mutation analysis) with an FOBT wherein the molecular diagnostic test sampling procedure is very similar or identical to the FOBT sampling procedure. Another embodiment of the present invention contemplates eliminating the need for collection of whole stools or large stool samples (e.g., approximately 30 grams) requiring specialized sampling, handling and transportation procedures. In one embodiment, an FOBT kit comprising a molecular diagnostic test increases the diagnostic accuracy for detection of colorectal cancer or precancerous polyps.

One skilled in the art realizes therefore, that despite current reliance of the medical community on both colonoscopy and the FOBT to diagnose colorectal cancer, both procedures have critical deficiencies that are remedied by various embodiments of the present invention.

3. DNA Extraction and Mutation Analysis a. Current Methods

Current methods for the extraction and isolation of DNA of fecal specimens typically require a stool sizes ranging from 400 mg-4 g. Practically, however, patients are often required to provide large stool portions, or even whole stools, for laboratory analysis in order to facilitate multiple sampling. This large size requirement introduces the need for specialized collection and transportation procedures which increases the cost of the overall test and decreases user-friendliness.

For example, PreGen™ Plus is a fecal material DNA extraction protocol designed to detect the presence of mutations characteristic of colorectal cancer. Specifically, the manufacturer describes its use as:
1. A test for the detection of clinically significant colorectal neoplasia in asymptomatic, average-risk patients 50 years old and older;
2. An adjunctive test for those patients who receive an FOBT, flexible sigmoidoscopy, or colonoscopy;
3. A test that is expected to enhance current methods for early detection of colorectal cancer.

Figure 12:
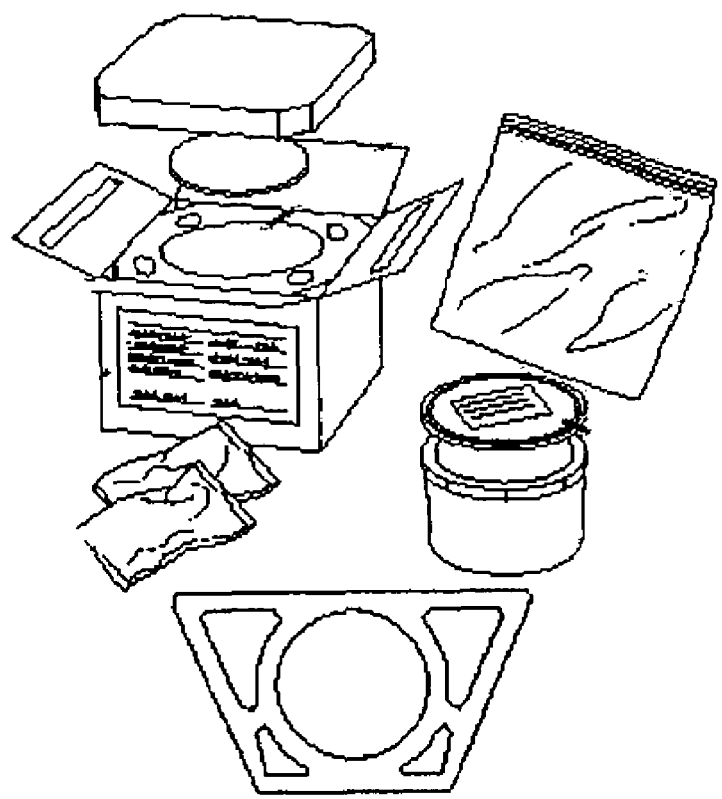
FIG. 12 illustrates the cumbersome specimen collection materials required for the LabCorp PreGen™ DNA extraction test procedure.

Unfortunately, PreGen™ Plus requires fecal collection and transportation using only a PreGen™ Plus "specimen collection and transport kit" that involves cumbersome procedures, including:
1. Shipment of a specimen collection kit in a large cardboard shipping carton to the patient. (See FIG. 12)
2. Use of a specimen collection container mounted on a toilet using a flat plastic bracket.
3. Collection of the entire bowel movement in the specimen container of at least 30 grams.
4. Specimen refrigeration or freezing.
5. Placement of a lid on container with label.
6. Sealing of specimen container in plastic bag.
7. Insertion of freezer packs into the shipment box.
8. Placement of plastic bag within shipment box having a foam cooler lid.
9. Delivery of the shipment box containing the frozen specimen to the patient's physician's office or nearest LabCorp patient service center.

The present invention contemplates one embodiment wherein fecal specimen collection for a DNA extraction and a molecular diagnostic assay is performed in an identical manner as that for an FOBT, wherein the specimens are much smaller than those currently used for fecal DNA extraction and isolation procedures. (i.e., for example, in the 1-3 microgram (μg) range). Preferably, the fecal specimen collection method allows convenient, patient-friendly, and simple procedures to transport the specimen to the analysis laboratory.

A number of studies have shown the effectiveness of CRC screening by using fecal material DNA extraction assays to detect one or more mutations in a specific gene or one or more mutations in a panel of specific genes (multi-target) in known cancer patients. In one single-gene study, a mutation cluster region within the APC gene was analyzed. Cancer was detected in 17 of 28 mutated patients (61%) and large adenomas were detected in 9 of 18 mutated patients (50%). The 28 control patients had no false positive results.

In one multi-target study, advanced adenomas were detected in 8 of 11 mutated patients (73%) whereas none were detected by simultaneously administered FOBTs. Another multi-target study detected invasive colorectal cancer in 33 of 52 mutated patients (63.5%, 95% confidence interval (CI), 49.0%-76.4%), including node-negative disease (Stage I/II; American Joint Committee on Cancer) in 26 of 36 mutated patients (72.2%) and advanced disease (Stage III/IV, American Joint Committee on Cancer) in 7 of 16 mutated patients (43.7%). Further, advanced adenomas (lesions containing high-grade dysplasia, villous adenomas, or tubular adenomas >1 cm in size) were detected in 16 of 28 mutated patients (57.1%; 95% CI, 37.2%-75.5%), including high-grade dysplasia in 6 of 7 mutated patients (85.7%) and advanced adenomas in 10 of 21 mutated patients (47.6%).

Overall specificity in the above study was 96.2% (95% CI, 92.7%-98.4%) in patients with either no colorectal lesions or diminutive polyps (i.e., an overall false positive rate of approximately 4%). In conclusion, the current multi-target DNA mutation assay panels have a better sensitivity in the detection of cancer than that reported with use of an FOBT (i.e., for example, Hemoccult® II) having similar specificity. Other studies detecting K-RAS gene mutations show a sensitivity of approximately 40% that is still superior to an FOBT alone.

4. Molecular Diagnostic Assays

One embodiment of the present invention comprises a molecular diagnostic assay comprising DNA extraction, isolation and mutation detection procedures that are superior to current DNA extraction colorectal detection methods to diagnose colorectal cancer. In one embodiment, the present invention contemplates a method of identifying a patient having colorectal cancer by using an FOBT fecal specimen collection kit, extracting DNA from the fecal specimen, amplifying the DNA by PCR and testing to identify a mutation known to cause cancer (i.e., for example, colorectal cancer) by a molecular diagnostic assay. Testing with molecular diagnostic assays avoid the invasiveness of colonoscopies and the low sensitivity and reliability of the FOBT. In one embodiment, testing with a molecular diagnostic assay detects DNA mutations from small fecal specimens (i.e., for example, 1-3 micrograms).

Figure 13:
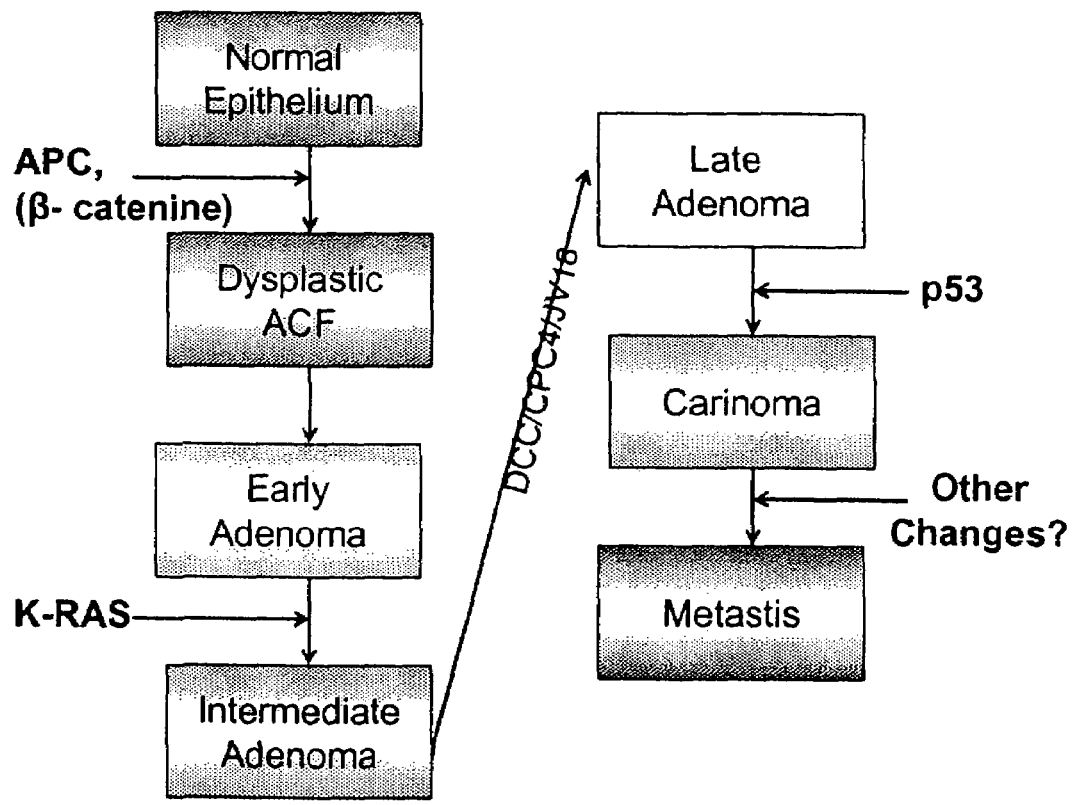
FIG. 13 shows a diagrammatic representation of probable genetic changes which are believed to occur at different steps in colorectal cancer tumorigenesis.

Mutations that cause colorectal cancer are known in several genes. (See FIG. 13) In one embodiment, a molecular diagnostic assay detects at least one mutation in the adenomatous polyposis (APC) gene. Although it is not necessary to understand the mechanism of an invention, it is believed that APC mutations play an early role in initiating the cancerous transformation of a colon cell. In another embodiment, testing with a molecular diagnostic assay detects at least one mutation in the p53 gene. In another embodiment, testing with a molecular diagnostic assay detects at least one mutation in the K-RAS gene. In another embodiment, testing with a molecular diagnostic assay detects at least one mutation in the β-catenine gene. In one embodiment, testing with a molecular diagnostic assay is performed in conjunction with the FOBT, under conditions that the probability of accurately diagnosing colorectal cancer is increased. In another embodiment, testing with a molecular diagnostic assay is performed in conjunction with a colonoscopy procedure, under conditions that the probability of accurately diagnosing colorectal cancer is increased.

One embodiment of the present invention contemplates testing with a panel of molecular diagnostic assays, wherein said panel is selected to increase the sensitivity of diagnosing colorectal cancer. Although it is not necessary to understand the mechanism of an invention, it is believed that a panel of molecular diagnostic assays can be designed to evaluate genes containing high frequency mutations, e.g. hot-spots, such that inclusion of only a few of such "hot-spot mutations" are required in order to increase sensitivity over FOBT.

One skilled in the art would realize that a variety of other molecular diagnostic assays might also detect mutations in fecal DNA other than those described in the present invention. For example, such assays may include, but are not limited to, the use of in vitro protein expression in conjunction with fluorotags and HTS-PTT.

As mentioned above, one embodiment of the present invention contemplates combining the advantages of FOBT with the advantages of a molecular diagnostic assay. For example: i) the FOBT advantages include, but are not limited to, providing a convenient method of fecal specimen collection and detecting fecal blood present in stool; and ii) the molecular diagnostic assay advantages include, but are not limited to, a significantly reduced fecal specimen size, wherein the reduced fecal specimen size is still capable of providing extracted DNA sufficient for PCR and mutation detection. In one embodiment, testing with a molecular diagnostic assay has sufficient sensitivity to detect at least 1 mutant gene out of 50 wild-type (WT) genes. In another embodiment, testing with a molecular diagnostic assay has sufficient sensitivity to detect at least 1 mutant gene out of 100 WT genes. Although it is not necessary to understand the mechanism of an invention, it is believed that the reliable detection of colorectal cancer DNA in a fecal specimen depends upon a low concentration of exfoliated DNA originating from cancerous or pre-cancerous cells when compared to the relatively high concentration of DNA derived from normal untransformed cells. This low ratio of mutated DNA in fecal material from cancerous patients requires currently used DNA extraction and mutation identification methods to handle large stool samples (i.e., from 30 grams to including whole stools). Additionally, many currently used DNA extraction and mutation identification methods implement complex isolation procedures based on DNA hybridization to isolate target gene sequences from the total DNA in stool samples in order to increase sensitivity of the mutation detection methodology.

In one embodiment, the present invention contemplates a method for testing with a molecular diagnostic assay on extracted DNA from a fecal specimen size lower than currently used methods. In one embodiment, the quantity of fecal specimen for a molecular diagnostic assay is equivalent to that collected during an FOBT. In one embodiment, a fecal specimen collected for a molecular diagnostic assay comprises sampling a small portion of a stool (i.e., for example, approximately 1-10 mgs dry weight, but more preferably 1-3 mgs dry weight) using a simple implement (i.e., for example, a wooden stick) by smearing the fecal specimen on the surface of a slide. In one embodiment, the slide comprises a surface having a first layer comprising gum guaiac. In another embodiment, the surface comprises a second layer comprising anti-hemoglobin antibody. In one embodiment, the slide is provided in a Hemoccult® Sensa® test kit (Beckman Coulter). In one embodiment, the present invention contemplates testing with a molecular diagnostic assay capable of detecting a DNA mutation comprising a fecal specimen of approximately 3 micrograms.

One embodiment of the present invention contemplates a method comprising testing with a molecular diagnostic assay using small quantities of human fecal specimens (i.e., for example, similar to current requirements for FOBT) and detecting the presence of DNA mutations characteristic of colorectal cancer or adenomas. For example, in contrast to currently used fecal DNA extraction, isolation and detection protocols, described previously, which requires whole stool specimens or large stool samples in the range of 200 mg-40 g, the present invention contemplates collecting and extracting DNA from a fecal specimen in the range of approximately between 1-100 mg. A more preferable embodiment contemplates using a 1-10 mg fecal specimen, and even more preferably a 1-3 mg fecal specimen.

One embodiment of the present invention contemplates a method to detect fecal DNA mutations, comprising: a) providing; i) a small fecal specimen, wherein said specimen is completely compatible with a concurrent FOBT analysis; ii) a test slide, wherein the slide is compatible with the FOBT analysis and iii) a molecular diagnostic assay; b) collecting the small fecal specimen with a small implement (i.e., for example, a stick); c) smearing the fecal specimen onto the test slide; d) drying the fecal specimen on the test slide; e) storing the fecal specimen for up to five days; f) transporting the fecal specimen to a testing laboratory; g) removing the fecal specimen from the slide using a liquid medium; h) extracting the fecal DNA from the fecal specimen; i) isolating the DNA by a separation procedure (i.e., for example, gel electrophoresis); j) amplifying the isolated DNA by PCR; and h) detecting mutations in the amplified DNA by testing with the molecular diagnostic assay under conditions that the mutation is detected in a ratio of 1:20 cells, preferably in a ratio of 1:50 cells and more preferably in a ratio of 1:100 cells.

Another embodiment of the present invention contemplates a method using a standard FOBT kit to collect small fecal specimens followed by testing with a molecular diagnostic assay to extract fecal DNA and detect mutations characteristic of colorectal cancer. In one embodiment, the FOBT kit comprises a Hemoccult II® Sensa® slide, wherein kit instructions comprise the following steps:

1. Remove slide from paper dispensing envelope. Using a ball-point pen, write your name, age, and address on the front of the slide Do not tear the sections apart.
2. Fill in specimen collection date on section 1 before a bowel movement. Flush toilet and allow to refill. Unfold flushable collection tissue and float it on surface of water. (You may also use any clean, dry container to collect your specimen.) Let stool fall onto collection tissue. Collect specimen before it contacts the toilet bowl water.
3. Open front of section 1. Use one stick to collect a small specimen. Apply a thin smear covering Box A. Collect second specimen from different part of stool with same stick. Apply a thin smear covering Box B. If used, flush collection tissue; discard stick in a waste container. Do not flush stick.
4. Close and secure front flap of section 1 by inserting it under tab. Store slide in any paper envelope until the next day.
5. Repeat steps 2-4 for the next two days, using sections 2 and 3. After completing the last section, store the slide overnight in any paper envelope overnight. The next day, remove slide from the paper envelope and place in the Mailing Pouch. Seal pouch carefully and immediately return to your doctor or laboratory.

In addition to the convenience of collecting small amounts of fecal specimens using FOBT kits there are a variety of other intrinsic advantages which are important in facilitating analysis of human DNA. The use of slides, (i.e., where a fecal specimen is smeared on the slide surface) promotes the preservation of the specimen by dehydration (i.e., drying). In particular, a fecal specimen dries more rapidly as a thin layer or smear due to the increased surface-to-volume ratio relative to pellets of fecal matter or whole stool. Dry stool is known to promote the ability to perform a molecular diagnostic assay. Machiels et al., "New Protocol For DNA Extraction Of Stool" *Biotechniques* 28:286-290 (2000). In addition to the promotion of drying by application of thin fecal specimens on a surface, the utilization of an absorbent medium such as, but not limited to, guaiac paper further promotes drying of the fecal specimen. One advantage of applying FOBT sampling procedures to PCR amplification protocols is that the FOBT instructions explicitly require avoidance of conditions which do not promote drying (i.e., for example, Hemoccult II® Sensa® Step 4 is designed to promote drying). FOBT instructions also state that fecal specimens are not to be placed in any moisture-proof materials such as plastic bags (which prevent drying) or in the refrigerator at any time.

Other embodiments of applying FOBT sampling procedures to PCR amplification protocols to detect DNA mutations characteristic of colorectal cancer include, but are not limited to, i) collecting fecal specimens from different portions of the stool and ii) collecting fecal specimens on different days. Both of these embodiments improve the sensitivity of the mutation detection analysis as it is known that DNA derived from cancerous lesions or adenomas may not be uniformly mixed within a whole stool.

In one embodiment, the present invention contemplates a method of detecting a DNA mutation characteristic of colorectal cancer, comprising: a) providing, i) an FOBT compatible surface, wherein the surface comprises guaiac paper; and ii) a fecal specimen, wherein said specimen comprises DNA; b) recovering the fecal specimen from the FOBT compatible medium using a liquid medium; c) isolating the DNA from the fecal specimen; d) amplifying a discrete region of the DNA, wherein the region corresponds to a gene having a mutation characteristic of colorectal cancer; and e) detecting the mutation by testing with a molecular diagnostic assay, wherein the mutation is detected with a sensitivity of 1:20.

Numerous embodiments of molecular diagnostic assays are contemplated by this invention. In one embodiment, the assay comprises sufficient sensitivity to detect a small percentage of mutant genes in the presence of an abundance of the normal un-mutated (wild type: WT) genes. Although it is not necessary to understand the mechanism of an invention, it is believed that isolated cells including, but not limited to, those collected from tissues, blood, stool, spinal fluid, saliva, urine and other bodily fluids utilized for the early detection of cancer usually contain a small percentage of mutant cells in a large background of normal cells. Sun et al., "Detection Of Tumor Mutations In The Presence Of Excess Amounts of Normal DNA, *Nature Biotechnology*, 20:186-189 (2002). One skilled in the art recognizes that a variety of testing assays are capable of detecting small fractions of mutants in the presence of excess amounts of normal DNA. Some assays are designed to detect specific and known mutations. Other assays scan entire regions of a DNA sequence and reveal any alterations from the WT sequence, including those mutations which were previously unknown.

a. Primer Extension

In one embodiment, the present invention contemplates a molecular diagnostic assay comprising primer extension. Goelet et al., "Method For Determining Nucleotide Identity Through Primer Extension" U.S. Pat. No. 5,888,819 (1999); and Goelet et al., "Method For Determining Nucleotide Identity Through Extension Of Immobilized Primer" U.S. Pat. No. 6,004,744 (1999) (both patents hereby incorporated by reference). In one embodiment, the primer extension comprises at least two different terminators of a nucleic acid template-dependent primer extension reaction. In another embodiment, the identity of a nucleotide base at a specific position in a nucleic acid of interest is identified.

In one embodiment, the primer extension determines the presence of a specific nucleotide sequence. In another embodiment, the primer extension determines the absence of a specific nucleotide sequence. In one embodiment, primer extension determines a genotype. In another embodiment, primer extension determines the identity of different alleles.

One skilled in the art would recognize that there are many methods to practice primer extension. One instructive example, based on the '819 patent, comprises: (a) treating a sample containing the nucleic acid of interest, if the nucleic acid is double-stranded, so as to obtain unpaired nucleotide bases spanning the specific position, or directly employing step (b) if the nucleic acid of interest is single-stranded; (b) contacting the sample from step (a), with an oligonucleotide primer which is fully complementary to and which hybridizes specifically to a stretch of nucleotide bases present in the nucleic acid of interest immediately adjacent to the nucleotide base to be identified, under high stringency hybridization conditions, so as to form a duplex between the primer and the nucleic acid of interest such that the nucleotide base to be identified is the first unpaired base in the template immediately downstream of the 3' end of the primer in said duplex; and (c) contacting the duplex from step (b), in the absence of dATP, dCTP, dGTP, or dTTP, with at least two different terminators of a nucleic acid template-dependent, primer extension reaction capable of specifically terminating the extension reaction in a manner strictly dependent upon the identity of the unpaired nucleotide base in the template immediately downstream of the 3' end of the primer wherein one of said terminators is complementary to said nucleotide base to be identified and wherein at least one of said terminators is labeled with a detectable marker; wherein said contacting is under conditions sufficient to permit base pairing of said complementary terminator with the nucleotide base to be identified and occurrence of a template-dependent primer extension reaction sufficient to incorporate said complementary terminator onto the 3' end of the primer to thereby extend said 3' end of said primer by one terminator; (d) determining the presence and identity of the nucleotide base at the specific position in the nucleic acid of interest by detecting the detectable marker of said incorporated terminator while said terminator is incorporated at the 3' end of the extended primer, and wherein said detection is conducted in the absence of non-terminator nucleotides.

While not intending to limit the present invention, primer extension may be combined with other embodiments of the present invention to attain sensitivities useful for detection of mutations present in fecal DNA and in particular with gene sequences associated with colorectal cancer. In one embodiment, primer extension comprises a microarray that is capable of detecting colorectal cancer mutations. For example, a p53 gene chip is known that spans exons 2-9 plus two introns from both strands. Primer extension was successfully performed using a p53 gene chip on samples from patients having esophageal cancer that comprised either freshly extracted genomic DNA or paraffin-embedded archival DNA samples. The detection sensitivity of a p53 gene chip was reported as at least 5% mutant p53 DNA in the presence of 95% wild type DNA (i.e., a 1:20 mutant/WT ratio). Tonisson et al., "Evaluating The Arrayed Primer Extension Resequencing Assay Of TP53 Tumor Suppressor Gene" *Proc Natl Acad Sci USA* 99:5503-5508 (2002).

In another embodiment, primer extension comprises mass spectrometry that is capable of detecting a small percentage of mutant cells (i.e., for example, colorectal cancer cells) within a large background of WT cells. In one embodiment, fecal DNA extracts are amplified using peptide nucleic acid (PNA)-directed PCR clamping reactions in which mutated DNA is preferentially enriched to generate PCR-amplified mutated DNA fragments. In another embodiment, the PCR-amplified mutated DNA fragments are then sequenced by primer extension. In one embodiment, the sequenced mutated fragments are identified using matrix-assisted-laser-desorption/ionization (MALDI) time-of-flight (MALDI-TOF) mass spectrometry. Preferably, as few as 3 copies of mutant alleles are detectable in the presence of a 10,000-fold excess of normal alleles (i.e., a 0.03:100 mutant/WT ratio).

Although it is not necessary to understand the mechanism of an invention, it is believed that the sensitivity of primer extension allows the detection of small percentages of mutant genes in the presence of an abundance of the normal (i.e., non-mutated or wild type) genes. It is further believed that this detection method has a variety of embodiments that can analyze PCR products obtained from DNA extracted from fecal specimens that are compatible with conventional FOBT analysis. In one embodiment, fecal DNA is smeared or dried on a surface in a quantity ranging between approximately 1-10 mg.

b. Invader® Assay

One embodiment of the present invention contemplates a method comprising collecting a fecal DNA extract and detecting a mutated DNA sequence using an Invader® assay. The mechanism of Invader® is depicted in FIG. 14. Briefly, two oligonucleotides (a discriminatory primary probe and an Invader® Oligo) are designed to hybridize to the DNA to form an overlapping structure. First, a trinary heteroduplex structure is formed between a first Invader® Oligo, discriminatory primary probe and the target DNA. Once the trinary heteroduplex is formed, a specially designed 5' flap on the discriminatory primary probe is released by the Cleavase® enzyme. This 5' flap becomes a target-specific product and hybridizes to a fluorophore/quencher-containing fluorescence resonance energy transfer (FRET) DNA cassette to create a second overlapping heteroduplex. This second heteroduplex is then cleaved by a Cleavase® enzyme to release the fluorophore. Once separated from the quencher molecule, the free fluorophore generates a fluorescence signal. The fluorescent signal is then amplified as these two concurrent hybridization reactions cycle and the concentration of free fluorophore increases. Advantages of this assay over those commonly used in the art include, but are not limited to, exceptional accuracy, ease of use, high-throughput and scalability.

Figure 15:
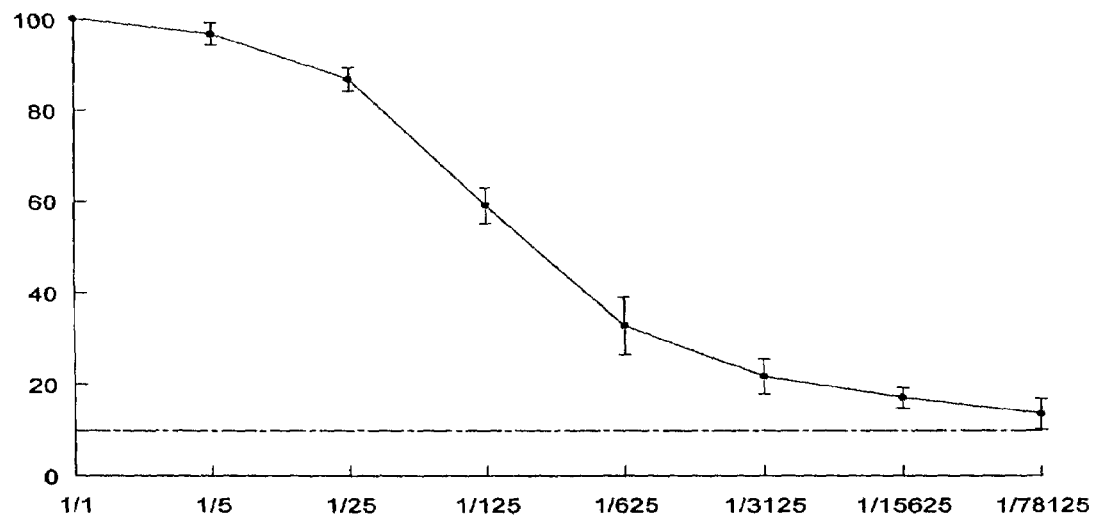
FIG. 15 shows exemplary data from one embodiment of a molecular diagnostic assay (i.e., for example, Point-EX-ACCT). K-RAS mutations were detected at various mutant/WT ratios from cell line DNA (i.e., A549: homozygote GGT→AGT and HL60 (WT)). The Y-axis measures the relative optical density of a marker signal and the X-axis identifies the specific cell line ratios assayed.

The basic steps involved in carrying out one embodiment of the Invader® assay are as follows:
Step 1: Accurate quantitation of DNA (Picogreen, Mol. Probes)
Step 2: Reaction set-up (Various DNA concentration)
Step 3: Incubation at 63° C. for 10 min to 4 hours
Step 4: Arresting the reaction by cooling the plate
Step 5: Reading the two color fluorescence
Step 6: Determining the Fold-Over-Zero (FOZ) ratio
Step 7: If counts are not enough, continue the reaction
Step 8: Reading the fluorescence again.
Step 9: Determining the FOZ ratio c. Exonuclease Amplification Coupled Capture Techniques Another embodiment of the present invention contemplates the extraction of fecal DNA compatible with a DNA sequencing technique comprising the detection of point mutations using Exonuclease Amplification Coupled Capture Techniques (i.e., Point-EXACCT). In one embodiment, the Point-EXACCT assay detects mutations that are present in low concentrations within a fecal specimen. The Point-EXACCT assay is known in the art as capable of detecting K-RAS mutations in the sputum of patients having adenocarcinoma of the lung. For example, WT K-RAS (HL60) and mutant K-RAS (A549) cells were mixed in a various ratios (1/1 to 1/78125) followed by DNA isolation. The K-RAS gene was then PCR-amplified from this isolated DNA and sequenced by the Point-EXACCT assay. The results indicated that the Point-EXACCT assay detected 1 mutant gene out of 15,000 WT genes (See FIG. 15).

Although it is not necessary to understand the mechanism of an invention, it is believed that the Point-EXACCT assay provides a highly sensitive method for the detection of known point mutations. Further, it is believed that the Point-EXACCT assay comprises: i) PCR amplification of the target DNA; ii) exonuclease digestion of PCR product; iii) hybridization of the target DNA to a mutation-specific detection probe; and iv) enzymatic ligation (i.e., for example, by T4 DNA ligase). Preferably, when a mutation-specific probe hybridizes and ligation occurs, a signal is generated. In one embodiment, a double-stranded product (i.e., for example, DNA) is converted to single-stranded product (i.e., for example, ssDNA using T7 gene 6 exonuclease), whereby the sensitivity of nucleotide sequencing and point mutation detection is enhanced.

6. Proteolysis

Another embodiment of the present invention contemplates one embodiment comprising a method for reducing and eliminating proteolysis of in vitro expressed proteins and protein fragments. In one embodiment, the proteins and protein fragments are molecular diagnostic assay probes. Reduction and elimination of protein and protein fragment proteolysis includes, but is not limited to, addition of proteolytic inhibitors, removal of proteolytic factors, physical inactivation of proteolytic factors (i.e., for example, by heat, light and physical binding), proteolytic-resistant expressed polypeptide sequences, modification of expressed polypeptides using non-native amino acids which increase resistance to proteolysis including, but not limited to, modifications of the polypeptide on the N-terminal and C-terminal end.

One skilled in the art would recognize that the problem of proteolysis occurring during the in vitro expression of proteins for diagnostic purposes has not been solved. In one embodiment of the present invention, proteolytic processes that hinder the use of in vitro expressed diagnostic proteins and diagnostic protein fragments are reduced.

One embodiment of the present invention contemplates a variety of embodiments comprising the in vitro expression of a protein or protein fragment from a DNA or mRNA template, wherein proteolysis of the protein or protein fragment is reduced in downstream isolation and/or detection steps. In one embodiment, the expressed protein or protein fragment may be isolated and/or detected using specifically incorporated epitope tags. In one embodiment, the incorporated epitope tags may be recognized by specific antibodies. In another embodiment, the incorporated epitope tags may be recognized by binding agents such as, but not limited to, biotin or photocleavable biotin through the use of misaminoacylated tRNAs.

Figure 16:
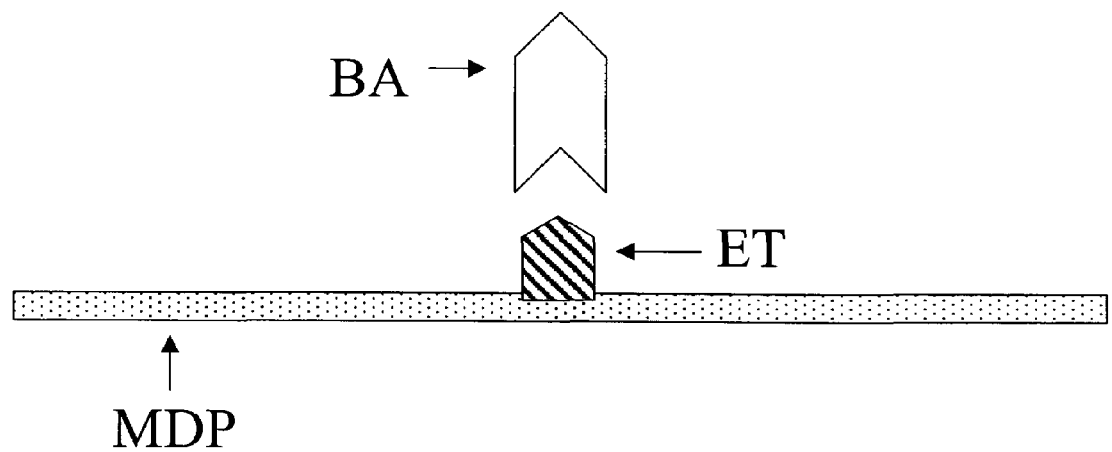
FIG. 16 shows one embodiment of a molecular diagnostic assay probe (MDP) comprising an epitope tag (ET) and an epitope binding agent (BA).

One embodiment of the present invention contemplates a series of molecular diagnostic assay probes comprising an epitope tag (i.e., for example, avidin) and an epitope binding agent (i.e., for example, biotin). (See FIG. 16). Although it is not necessary to understand the mechanism of an invention, it is believed that the molecular diagnostic assay probe will allow the measurement and quantitation of proteolytic activity in a plurality of in vitro protein expression systems. Further, it is believed that proteolytic measurement will allow the development of methods to reduce the proteolytic activity.

M. Fluorescent In Situ High-Sensitivity Protein Truncation Test (FISH-PTT)

In one embodiment, the present invention contemplates a novel method for screening protein truncation mutations with very high sensitivity Nonsense or frame-shift mutations, which result in a truncated gene product, are prevalent in a variety of disease-related genes, including APC (colorectal cancer), BRCA1 and BRCA2 (breast and ovarian cancer, PKD1 (polycystic kidney disease), NF1 and NF2 (neurofibromatosis) and DMD (Duchenne muscular dystrophy). Such protein truncating mutations can be detected using the protein truncation test (PTT). This test is based on cell-free coupled transcription-translation of PCR (RT-PCR) amplified portions of the target gene (target mRNA) followed by analysis of the translated product(s) for shortened polypeptide fragments. However, conventional PTT is not easily adaptable to high throughput applications since it involves SDS-PAGE followed by autoradiography or Western blot. It is also subject to human error since it relies on visual inspection to detect mobility shifted bands. To overcome these limitations, we recently reported an advanced protein truncation test termed as "ELISA-PTT" (Gite, S., Lim, M., Carlson, R., Olejnik, J., Zehnbauer, B., and Rothschild, K. (2003) Nat Biotechnol 21, 194-197). ELISA-PTT is non-isotopic, sensitive, rapid and amenable to high throughput. Though ELISA-PTT removes most of the aforementioned limitations of traditional gel-based PTT, its sensitivity is still not very high (~25%) i.e. capability of picking up 1 mutant copy out of 4 total copies.

While heterozygous mutations in germ-line cells are expected to comprise 50% of the total DNA in a sample, stool or polyp samples from patient may contain a mixture of cells/DNA for which only some of them contain mutations. As mentioned before, the feasibility of detecting 25% mutant population has already been demonstrated (Gite, S., Lim, M., Carlson, R., Olejnik, J., Zehnbauer, B., and Rothschild, K. (2003) Nat Biotechnol 21, 194-197). Recently, Vogelstein and co-workers have demonstrated detection efficiencies of chain truncation mutations as low as 0.4% relative to WT (Traverso, G., Shuber, A., Levin, B., Johnson, C., Olsson, L., Schoetz, D. J., Jr., Hamilton, S. R., Boynton, K., Kinzler, K. W., and Vogelstein, B. (2002) N Engl J Med 346, 311-320). This is possible by first diluting genomic DNA samples so that no more than 2-4 DNA templates are present in each sample prior to PCR amplification. This step is followed by translation of the amplified DNA for over 100 samples and detection using radioactive-gel based PTT. At least two non-wild type bands are required out of the entire set for a positive (mutation present) in order to correct for possible polymerase error. Unfortunately, as described in the above publication, radioactive-gel based detection is not suitable for automation of detection by gel and indeed problems are compounded for digital PTT. Even though, the ELISA-PTT removes the barrier of running 144 samples on a gel which is time consuming, still one has to do 144 PCR reactions/cell-free translation reactions per patient. This significantly adds to the running cost of this particular test.

Figure 49:
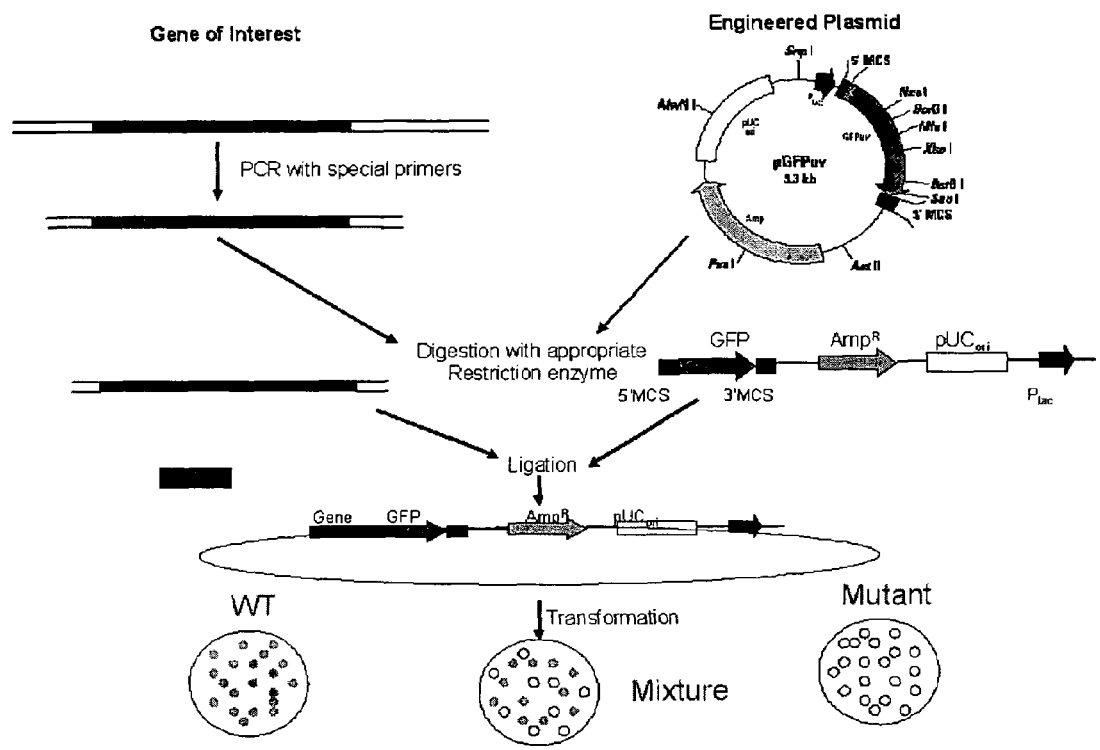
FIG. 49 shows one embodiment of a FISH-PTT assay based on traditional cloning protocol.

To avoid this problem, we have developed a novel method to screen chain truncation mutations with very high sensitivity, which we termed "FISH-PTT" which stands for "Fluorescent In Situ High-Sensitivity Protein Truncation Test". FIG. 49 shows the schematics of FISH-PTT based upon standard cloning procedures. In short, this test is based on using the plasmid coding for GFP gene and cloning the gene/gene fragment of interest, in frame, upstream of the GFP coding region. The bacterial cells (typically *E. coli*) are then transformed with the recombinant plasmid (containing Gene-GFP fusion) and the transformed cells are grown overnight on appropriate medium (Luria agar plates). The colonies obtained were then visualized and photographed under normal and UV light. The colonies containing WT gene-GFP fusion glow green when excited with UV light because the cells are expressing gene-GFP fusion. On the other hand colonies containing mutant gene-GFP fusion are white because GFP is not expressed since the fusion protein is not synthesized due to the truncation mutation present in the gene of interest which is cloned upstream of the GFP coding sequence. The details of two separate cloning methods, to achieve the same desired outcome, are described below with appropriate examples.

The bioluminescent jellyfish *Aequorea victoria* produces light when energy is transferred from Ca2+-activated photoprotein aequorin to green fluorescent protein (GFP; Shimomura, O., Johnson, F. H. & Saiga, Y. (1962) Extraction, purification and properties of aequorin, a bioluminescent protein from the luminous hydromedusan, *Aequorea*. J. Cell. Comp. Physiol. 59:223-227; Morin, J. G. & Hastings, J. W. (1971) Energy transfer in a bioluminescent system. J. Cell. Physiol. 77:313-318; Ward, W. W., Cody, C. W., Hart, R. C. & Cormier, M. J. (1980). Spectrophotometric identity of the energy transfer chromophores in *Renilla* and *Aequorea* green-fluorescent proteins. Photochem. Photobiol. 31:611-615). When expressed in either eukaryotic or prokaryotic cells and illuminated by blue or UV light, GFP yields a bright green fluorescence. Light-stimulated GFP fluorescence is species-independent and does not require any cofactors, substrates, or additional gene products from *A. victoria*. Additionally, detection of GFP and its variants can be performed in living cells and tissues as well as fixed samples.

The bacterial expression vector (pGFPuv) contains a mutant *Aequorea victoria* green fluorescent protein (a GFP variant optimized for maximal fluorescence when excited by UV light [360-400 nm]) and its expression is driven by the lac promoter. GFPuv is an UV-Optimized GFP variant and is reported to be 18 times brighter than WT GFP when expressed in *E. coli* and excited by standard UV light (Crameri, A., Whitehorn, E. A., Tate, E. & Stemmer, W. P. C. (1996) Improved green fluorescent protein by molecular evolution using DNA shuffling. Nature Biotechnol. 14:315-319).

This variant contains additional amino acid mutations which also increase the translational efficiency of the protein in *E. coli*. GFPuv contains three amino acid substitutions (Phe-99 to Ser, Met-153 to Thr, and Val-163 to Ala [based on the amino acid numbering of wt GFP]), none of which alter the chromophore sequence. The GFPuv variant is ideal for experiments in which GFP expression will be detected using UV light for chromophore excitation (e.g., for visualizing bacteria or yeast colonies). While these mutations dramatically increase the fluorescence of GFPuv through their effects on protein folding and chromophore formation, the emission and excitation maxima remain at the same wavelengths as those of WT GFP. However, GFPuv has a greater propensity to dimerize than WT GFP. GFPuv expressed in *E. coli* is a soluble, fluorescent protein even under conditions in which the majority of WT GFP is expressed in a non-fluorescent form in inclusion bodies. This GFP variant also appears to have lower toxicity than WT GFP; hence, the *E. coli* containing GFPuv grow two to three times faster than those expressing wt GFP (Crameri, A., Whitehorn, E. A., Tate, E. & Stemmer, W. P. C. (1996) Improved green fluorescent protein by molecular evolution using DNA shuffling. Nature Biotechnol. 14:315-319). Furthermore, the GFPuv gene is a synthetic GFP gene in which five rarely used Arg codons from the WT gene were replaced by codons preferred in *E. coli*. Consequently, the GFPuv gene is expressed very efficiently in *E. coli*.

GFP has been expressed as a fusion in many different proteins. In many cases, chimeric genes encoding either N- or C-terminal fusions to GFP retain the normal biological activity of the heterologous partner, as well as maintaining fluorescent properties similar to native GFP (Flach, J., Bossie, M., Vogel, J., Corbett, A., Jinks, T., Willins, D. A. & Silver, P. A. (1994) A yeast RNA-binding protein shuttles between the nucleus and the cytoplasm. Mol. Cell. Biol. 14:8399-8407; Wang, S. & Hazelrigg, T. (1994) Implications for bcd mRNA localization from spatial distribution of exu protein in *Drosophila oogenesis*. Nature 369:400-403; Marshall, J., Molloy, R., Moss, G. W. J., Howe, J. R. & Hughes, T. E. (1995) The jellyfish green fluorescent protein: a new tool for studying ion channel expression and function. Neuron 14:211-215; Stearns, T. (1995) The green revolution. Curr. Biol. 5:262-264). The use of GFP and its variants in this capacity provides a "fluorescent tag" on the protein, which allows for in vivo localization of the fusion protein. GFP fusions can provide enhanced sensitivity and resolution in comparison to standard antibody staining techniques and the GFP tag eliminates the need for fixation, cell permeabilization, and antibody incubation steps normally required when using antibodies tagged with chemical fluorophores. Lastly, use of the GFP tag permits kinetic studies of protein localization and trafficking.

EXPERIMENTAL

The following examples illustrate embodiments of the invention, but should not be viewed as limiting the scope of the invention. In some of the examples below, particular reagents and methods were employed as follows:

General Methodologies

Reagents: tRNA$^{fmet}$, aminoacyl-tRNA synthetase, amino acids, buffer salts, and RNase free water were purchased from Sigma (St. Louis, Mo.). Many of the fluorescent dyes were obtained from Molecular Probes (Eugene, Oreg.). The translation supplies including routine kits were purchased from Promega (Madison, Wis.). Sephadex G-25 was from Amersham-Pharmacia Biotech (Piscataway, N.J.). The in vitro translation kits and plasmid DNAs coding for CAT (PinPoint™) and Luciferase (pBESTluc™) were from Promega (Wisconsin-Madison, Wis.) while DHFR plasmid DNA (pQE16-DHFR) was obtained from Qiagen (Valencia, Calif.). The plasmid DNA for α-hemolysin, pT7-WT-H6-αHL was kindly supplied by Prof. Hagan Bayley (Texas A &M University) and large scale preparation of α-HL DNA was carried out using Qiagen plasmid isolation kit. The bacterioopsin plasmid DNA (pKKbop) was from the laboratory stock.

Preparation of FluoroTag tRNAs: the Purified tRNA$^{fmet}$ was First Aminoacylated with the methionine. In typical reaction, 1500 picomoles (~1.0 $OD_{260}$) of tRNA was incubated for 45 min at 37° C. in aminoacylation mix using excess of aminoacyl tRNA-synthetases. After incubation, the mixture was neutralized by adding 0.1 volume of 3 M sodium acetate, pH 5.0 and subjected to chloroform:acid phenol extraction (1:1). Ethanol (2.5 volumes) was added to the aqueous phase and the tRNA pellet obtained was dissolved in the water (25 µl). The coupling of NHS-derivatives of fluorescent molecules to the _-amino group of methionine was carried out in 50 mM sodium carbonate, pH 8.5 by incubating the aminoacylated tRNAf$^{met}$ (25 µl) with fluorescent reagent (final concentration=2 mM) for 10 min at 0° C. and the reaction was quenched by the addition of lysine (final concentration=100 mM). The modified tRNA was precipitated with ethanol and passed through Sephadex G-25 gel filtration column (0.5×5 cm) to remove any free fluorescent reagent, if present. The modified tRNA was stored frozen (−70° C.) in small aliquots in order to avoid free-thaws. The modification extent of the aminoacylated-tRNA was assessed by acid-urea gel electrophoresis. This tRNA was found to stable at least for 6 month if stored properly.

Cell free synthesis of proteins and their detection: The in vitro translation reactions were typically carried out using E. coli T7 transcription-translation system (Promega) with optimized premix. The typical translation reaction mixture (10 µl) contained 3 µl of extract, 4 µl of premix, 1 µl of complete amino acid mix, 30 picomoles of fluorescent-methionyl-tRNA and 0.5 µg of appropriate plasmid DNA. The optimized premix (1×) contains 57 mM HEPES, pH 8.2, 36 mM ammonium acetate, 210 mM potassium glutamate, 1.7 mM DTT, 4% PEG 8000, 1.25 mM ATP, 0.8 mM GTP, 0.8 mM UTP, 0.8 mM CTP, 60 mM phosphoenol pyruvate, 0.6 mM cAMP and 16 mM magnesium acetate. The translation reaction was allowed to proceed for 45 min at 37° C. For SDS-PAGE, 4-10 µl aliquot of the reaction mix was precipitated with 5-volume acetone and the precipitated proteins were collected by centrifugation. The pellet was dissolved in 1× loading buffer and subjected to SDS-PAGE after boiling for 5 min. SDS-PAGE was carried out according to Laemmli and the gel was scan using Molecular Dynamics FluorImager 595 using Argon laser as excitation source. Alternatively, the nascent proteins in polyacrylamide gels were also detected using an UV-transilluminator and the photographs were carried out using Polaroid camera fitted with green filter (Tiffen green #58, Polaroid DS34 camera filter kit).

For visualization of BODIPY-FL labeled protein, 488 nm as excitation source was used along with a 530+/−30 narrow band excitation filter. The gel was scanned using PMT voltage 1000 volts and either 100 or 200 micron pixel size.

Enzyme/Protein activities: Biological activity of α-hemolysin was carried out as follows. Briefly, various aliquots (0.5-2 µl) of in vitro translation reaction mixture were added to 500 µl of TBSA (Tris-buffered saline containing 1 mg/ml BSA, pH 7.5). To this, 25 µl of 10% solution of rabbit red blood cells (rRBCs) was added and incubated at room temperature for 20 min. After incubation, the assay mix was centrifuged for 1 min and the absorbance of supernatant was measured at 415 nm (release of hemoglobin). The equal amount of rRBCs incubated in 500 µl of TBSA is taken as control while rRBCs incubated with 500 µl of water as taken 100% lysis. The DHFR activity was measured spectrophotometrically. Luciferase activity was determined using luciferase assay system (Promega) and luminescence was measures using Packard Lumi-96 luminometer.

Purification of α-HL and measurement BODIPY-FL incorporation into α-HL: The translation of plasmid coding for α-HL ($His_6$) was carried out at 100 µl scale and the α-HL produced was purified using Talon-Sepharose (ClonTech) according manufacturer instructions. The fluorescence incorporated into α-HL was then measured on Molecular Dynamics FluorImager along with the several known concentration of free BODIPY-FL (used as standard). The amount of protein in the same sample was measured using a standard Bradford assay using Pierce Protein Assay kit (Pierce, Rockford, Ill.).

FLAG Capture Assay
Biotinylation of FLAG Antibody

A 4.4 mg/mL stock of FLAG M2 monoclonal antibody (SIGMA Chemical, St. Louis, Mo.) is diluted with equal volume of 100 mM sodium bicarbonate (~15 mM final antibody concentration). Subsequently, NHS-LC-Biotin (Pierce Chemical, Rockford, Ill.) is added from a 2 mM stock (in DMF) to a final 150 mM. The reaction is incubated for 2 hours on ice. The mixture is then clarified by centrifugation in a microcentrifuge (14,000 R.P.M.) for 2.5 minutes. Unreacted labeling reagent is removed by gel filtration chromatography.
Preparation of Flag Antibody Coated ELISA Plates NeutrAvidin™ biotin binding protein (Pierce Chemical, Rockford, Ill.) is diluted to a final concentration of 50 mg/mL in 100 mM sodium bicarbonate and used to coat Microlite (2+ white opaque 96-well ELISA plates (Dynex Technologies, Chantilly, Va.). Plates are washed with TBS-T and coated using a solution of 5 mg/mL biotinylated FLAG M2 antibody in TBS-T. Plates are washed with TBS-T and blocked in Translation Dilution Buffer (TDB) [4.5% Teleostean Gelatin, 2% non-fat milk powder, 10 mM EDTA, 0.1% Tween-20, 1.25 mg/mL pre-immune mouse IgG, 2.5 mM d-biotin, in TBS, pH 7.5.].
Binding and Detection of Target Protein Triple-epitope-tagged target proteins produced by in vitro translation using rabbit reticulocyte extract are diluted 1/25-1/75 in TDB and added to the antibody coated ELISA plates. Following capture of the target protein, plates are washed with TBS-T. Detection of c-myc is performed using a polyclonal antibody (Santa Cruz Biotechnology, Santa Cruz, Calif.) followed by a peroxidase labeled secondary antibody, whereas detection of the $His_6$ tag is achieved with a peroxidase labeled nickel chelate-based probe (India(His Probe-HRP, Pierce, Rockford, Ill.). Antibodies are diluted in TDB and the India(His Probe-HRP is diluted in TBS-T supplemented with 5 mg/mL pre-immune mouse IgG. In all cases, signal is generated using a chemiluminescent substrate system.

His-Tag Metal Affinity Capture ELISA Assay
Binding and Detection of Target Protein Triple-epitope-tagged target proteins produced by in vitro translation using rabbit reticulocyte extract are diluted 1/25-1/75 in 1% BSA/TBS-T and added to nickel chelate coated ELISA plates (Pierce Chemical, Rockford, Ill.). Following capture of the target protein, plates are washed with TBS-T and blocked with 1% BSA/TBS-T. Detection of epitope tags on the bound target protein is achieved using a monoclonal FLAG M2 antibody (SIGMA Chemical, St. Louis, Mo.) or a polyclonal c-myc antibody (Santa Cruz Biotechnology, Santa Cruz, Calif.) in conjunction with the appropriate peroxidase labeled secondary antibody. Detection of biotin incorporated into the target protein via Biotin-lysyl-tRNA$^{lys}$ is achieved using NeutrAvidin™ biotin binding protein conjugated to peroxidase (Pierce Chemical, Rockford, Ill.). The NeutrAvidin™ conjugate and all antibodies are diluted in 1% BSA/TBS-T. In all cases, signal is generated using a chemiluminescent substrate system.

Example 1

Cell-Free Translation Reactions

The incorporation mixture (100 µl) contained 50 µl of S-23 extract, 5 mM magnesium acetate, 5 mM Tris-acetate, pH 7.6, 20 mM Hepes-KOH buffer, pH 7.5; 100 mM potassium acetate, 0.5 mM DTT, 0.375 mM GTP, 2.5 mM ATP, 10 mM creatine phosphate, 60 µg/ml creatine kinase, and 100 µg/ml mRNA containing the genetic sequence which codes for bacterioopsin. Misaminoacylated PCB-lysine or coumarin amino acid-tRNA$^{lys}$ molecules were added at 170 µg/ml and concentrations of magnesium ions and ATP were optimized. The mixture was incubated at 25° C. for one hour.

Example 2

Incorporation of Various Fluorophores into α-Hemolysin

E. coli tRNA$^{fmet}$ was first quantitatively aminoacylated with methionine and the α-amino group was specifically modified using NHS-derivatives of several fluorophores. The list of fluorescent reporter molecules (fluorophores) tested and their properties are given in Table 2. Under the modification conditions, the modified Met-tRNA$^{fmet}$ is found to be stable as assessed by acid-urea gel. Since all the fluorescent molecules tested have different optical properties (excitation and emission), we have determined their relative fluorescence intensity under the condition which were used for the quantitation of gels containing nascent protein.

Fluorescent detection of nascent protein was first evaluated using α-hemolysin (α-HL) as a model protein (with C-terminal His$_6$-tag). α-HL is a relatively small protein (32 kDa) and could be produced efficiently in in vitro translation. In addition, its activity can be measured directly in the protein translation mixture using a rabbit red blood cell hemolysis assay. In vitro translation of α-HL was carried out using an E. coli T7 S30 transcription/translation extract (Promega Corp., Madison, Wis.) in the presence of several different modified methionyl-tRNA$^{fmet}$ as described above. After the reaction, an aliquot (3-5 µl) was subjected to SDS-PAGE analysis and the fluorescent bands were detected and quantitated using a FluorImager F595 (Molecular Dynamics, Sunnyvale, Calif.).

The data is presented in FIG. 1. Lane 1 is a no DNA control. Lane 2 shows the results with BODIPY-FL-SSE. Lane 3 shows the results with BODIPY-FL-SE. Lane 4 shows the results with NBD (see Table 2 for the structure). Lane 5 shows the results with BODIPY-TMR. Lane 6 shows the results with BODIPY R6G. Lanes 7, 8, 9 and 10 show the results achieved with FAM, SFX, PYMPO and TAMRA, respectively (see Table 2 for structures).

The results clearly indicate the α-HL produced in presence of BODIPY-FL-methionyl-tRNA$^{fmet}$ (lanes 2 and 3) exhibited the highest fluorescence (all the data is normalized to the BODIPY-FL-SSE. The two different BODIPY-FL reagents (BODIPY-FL sulfosuccinimidyl ester (SSE) and BODIPY-FL succinimidyl ester (SE)), differ only with respect to solubility. The next best fluorophore evaluated, 6-(tetramethylrhodamine-5-(and-6)-carboxamido)hexanoic acid, succinimidyl ester (TAMRA-X, SE), exhibited 35% of the fluorescence (corrected for relative fluorescence) of BODIPY-FL-SSE. Two other forms of BODIPY, BODIPY-TMR, SE (6-((4,4-difluoro-1,3-dimethyl-5-(4-methoxyphenyl)-4-bora-3a,4a-diaza-s-indacene-2-propionyl)amino) hexanoic acid, succinimidyl ester) and BODIPY-R6G, SE (4,4-difluoro-5-phenyl-4-bora-3a,4a-diaza-s-indacene-3-propionic acid, succinimidyl ester) exhibited less than 3% of the fluorescence of BODIPY-FL, SSE. Succinimidyl 6-(7-nitrobenz-2-oxa-1,3-diazol-4-yl)aminohexanoate (NBD-X-SE), a fluorescent molecule which has previously been incorporated into the neurokinin-2 receptor. exhibited only 6% of the BODIPY-FL-SSE. The two fluorescein analogs 5-(and-6)-carboxyfluorescein, succinimidyl-ester (FAM, SE) and 6-(fluorescein-5-(and-6) carboxamido)hexanoic acid, succinimidyl ester (SFX, SE) also showed very low fluorescence (8.4% and 4.6%, respectively relative to BODIPY-FL).

Example 3

The Modifying Reagent

In the case of post-aminoacylation modifications used to form a misaminoacylated tRNA, an important factor is the modifying reagent used to add the modification to the natural amino acid. For example, in the case of the fluorophore BODIPY FL, there are two different commercially available BODIPY FL NHS reagents known as BODIPY-FL-SE and BODIPY-FL-SSE (Molecular Probes). Both reagents are based on N-hydroxysuccinimide (NHS) as the leaving group. However, the two forms differ in aqueous solubility due to the presence in one form (SSE) of a sulfonate (sulfo) group (see Table 2 for structures). In this example, optimized reactions based on standard biochemical procedures were performed aimed at adding the BODIPY FL fluorophore to a purified tRNA$^{fmet}$ which is aminoacylated with methionine using these two different reagents. For this purpose, first the tRNA$^{fmet}$ was aminoacylated with the methionine. In typical reaction, 1500 picomoles (~1.0 OD$_{260}$) of tRNA was incubated for 45 min at 37° C. in aminoacylation mix using excess of aminoacyl tRNA-synthetases. The aminoacylation mix consisted of 20 mM imidazole-HCl buffer, pH 7.5, 150 mM NaCl, 10 mM MgCl$_2$, 2 mM ATP and 1600 units of aminoacyl tRNA-synthetase. The extent of aminoacylation was determined by acid-urea gel as well as using $^{35}$S-methionine. After incubation, the mixture was neutralized by adding 0.1 volume of 3 M sodium acetate, pH 5.0 and subjected to chloroform: acid phenol (pH 5.0) extraction (1:1). Ethanol (2.5 volumes) was added to the aqueous phase and the tRNA pellet obtained was dissolved in water (37.5 (1) and used for modification.

A. Modification of Aminoacylated tRNA with BODIPY-FL-SSE

To the above aminoacylated-tRNA solution, 2.5 (1 of 1N NaHCO$_3$ was added (final conc. 50 mM, pH=8.5) followed by 10 (1 of 10 mM solution of BODIPY-FL-SSE (Molecular Probes) in water. The mixture was incubated for 10 min at 0° C. and the reaction was quenched by the addition of lysine (final concentration=100 mM). To the resulting solution 0.1 volume of 3 M NaOAc, pH=5.0 was added and the modified tRNA was precipitated with 3 volumes of ethanol. Precipitate was dissolved in 50 ml microliters of water and purified on Sephadex G-25 gel filtration column (0.5×5 cm) to remove any free fluorescent reagent, if present. The modified tRNA was stored frozen (–70° C.) in small aliquots in order to avoid free-thaws.

B. Modification of Aminoacylated tRNA with BODIPY-FL-SE

To the above aminoacylated-tRNA solution, 2.5 (1 of 1N NaHCO$_3$ (final conc. 50 mM, pH=8.5) and 20 (1 of DMSO was added followed by 10 (1 of 10 mM solution of BODIPY-FL-SE (Molecular Probes) in DMSO. The mixture was incubated for 10 min at 0° C. and the reaction was quenched by the addition of lysine (final concentration=100 mM). To the resulting solution 0.1 volume of 3 M NaOAc, pH=5.0 was added and the modified tRNA was precipitated with 3 volumes of ethanol. Precipitate was dissolved in 50 ml of water and purified on Sephadex G-25 gel filtration column (0.5×5 cm) to remove any free fluorescent reagent, if present. The modified tRNA was stored frozen (–70° C.) in small aliquots in order to avoid free-thaws.

C. Analysis

It was found empirically using HPLC that the extent of modification of the alpha-amino group of methionine is substantially greater using the sulfonated form of NHS BODIPY FL compared to the non-sulfonated form of NHS-BODIPY FL reagent. In addition the misaminoacylated tRNA$^{fmet}$ formed using the sulfonated form was found to exhibit superior properties. When used in an optimized S30 E. coli translation systems to incorporate BODIPY FL into the protein (hemolysin using a plasmid containing the HL gene under control of a T7 promoter), the band on an SDS-PAGE gel corresponding to the expressed HL exhibited an approximately 2 times higher level of fluorescence when detected using a argon laser based fluoroimager compared to a similar system using the misaminoacylated formed using the non-sulfonated form.

Example 4

Triple Marker System

In this example, a three marker system is employed to detect nascent proteins, i.e. an N-terminus marker, a C-terminus marker, and an affinity marker (the latter being an endogenous affinity marker). The experiment involves 1) preparation of a tRNA with a marker, so that a marker can be introduced (during translation) at the N-terminus of the protein; 2) translation of hemolysin with nucleic acid coding for wild type and mutant hemolysin; and 4) quantitation of the markers.

1. Preparation of Biotin-Methionyl-tRNA$^{fmet}$

The purified tRNA$^{fmet}$ (Sigma Chemicals, St. Louis, Mo.) was first aminoacylated with methionine. The typical aminoacylation reaction contained 1500 picomoles (–1.0 OD$_{260}$) of tRNA, 20 mM imidazole-HCl buffer, pH 7.5, 10 mM MgCl$_2$, 1 mM methionine, 2 mM ATP, 150 mM NaCl and excess of aminoacyl tRNA-synthetases (Sigma). The reaction mixture was incubated for 45 min at 37° C. After incubation, the reaction mixture was neutralized by adding 0.1 volume of 3 M sodium acetate, pH 5.0 and subjected to chloroform:acid phenol extraction (1:1). Ethanol (2.5 volumes) was added to the aqueous phase and the tRNA pellet obtained was dissolved in the water (25 _l). The coupling of NHS-biotin to the α-amino group of methionine was carried out in 50 mM sodium bicarbonate buffer, pH 8.0 by incubating the aminoacylated tRNA$^{fmet}$ (25 µl) with NHS-biotin (final concentration=2 mM) for 10 min at 0° C. and the reaction was quenched by the addition of free lysine (final concentration=100 mM). The modified tRNA was precipitated with ethanol and passed through Sephadex G-25 gel filtration column (0.5×5 cm) to remove any free reagent, if present.

2. In Vitro Translation of α-HL DNA

A WT and Amber (at position 135) mutant plasmid DNA was using coding for _-hemolysin (α-HL), a 32 kDa protein bearing amino acid sequence His-His-His-His-His-His (His-6) (SEQ ID NO: 5) at its C-terminal. In vitro translation of WT and amber mutant α-HL gene (Amb 135) was carried out using E. coli T7 circular transcription/translation system (Promega Corp., Wisconsin, Wis.) in presence of Biotin-methionyl-tRNA$^{fmet}$ (AmberGen, Inc.). The translation reaction of 100 µl contained 30 µl E. coli extract (Promega Corp., Wisconsin, Wis.), 40 µl premix without amino acids, 10 µl amino acid mixture (1 mM), 5 µg of plasmid DNA coding for WT and mutant α-HL, 150 picomoles of biotin-methionyl-tRNA$^{fmet}$ and RNase-free water. The premix (1×) contains 57 mM HEPES, pH 8.2, 36 mM ammonium acetate, 210 mM potassium glutamate, 1.7 mM DTT, 4% PEG 8000, 1.25 mM ATP, 0.8 mM GTP, 0.8 mM UTP, 0.8 mM CTP, 60 mM phosphoenol pyruvate, 0.6 mM cAMP and 6 mM magnesium acetate. From the translation reaction premix, n-formyl-tetrahydrofolate (fTHF) was omitted. The translation was carried out at 37° C. for 1 hour. The translation reaction mixture incubated without DNA is taken as control. After the translation reaction mixture was diluted with equal volume of TBS (Tris-buffered saline, pH 7.5). Each sample was divided into two aliquots and processed individually as described below.

3. Preparation of Anti-α-HL Antibody Microtiter Plate

Anti-rabbit-IgG coated microtiter plate (Pierce Chemicals, Rockford, Ill.) was washed with Superblock buffer solution (Pierce) and incubated with 100 µg/ml of anti-α-HL polyclonal antibody solution (Sigma Chemicals, St. Louis, Mo.) prepared in Superblock buffer on microtiter plate shaker for 1 hour at room temperature. The plate was then washed (3 times×200 µl) with Superblock buffer and stored at 4° C. till further use.

4. Quantitation of N-Terminal (Biotin) Marker

The translation reaction mixture (50 µl) for the control, WT and amber α-HL DNA were incubated in different wells of anti-α-HL microtiter plate for 30 minutes on the shaker at room temperature. After incubation, the wells were washed 5 times (5-10 min each) with 200 µl Superblock buffer and the supernatant were discarded. To these wells, 100 µl of 1:1000 diluted streptavidin-horse radish peroxidase (Streptavidin-HRP; 0.25 mg/ml; Promega) was added and the plate was incubated at room temperature for 20 min under shaking conditions. After the incubation, excess streptavidin-HRP was removed by extensive washing with Superblock buffer (5 times×5 min each). Finally, 200 µl of substrate for HRP (OPD in HRP buffer; Pierce) was added and the HRP activity was determined using spectrophotometer by measuring absorbance at 441 nm.

5. Quantitation of C-Terminal (His-6-taq) Marker

Control, WT and Amber α-HL DNA (50 µl) were incubated in different wells of anti-α-HL microtiter plate for 30 min on the shaker at room temperature. After incubation, the wells were washed 5 times (5-10 min each) with 200 µl Superblock buffer and the supernatant were discarded. To these wells, 100 µl of 1:1000 diluted anti-His-6 antibody (ClonTech, Palo Alto, Calif.) was added to the well and incubated at room temperature for 20 min under shaking conditions. After the incubation, excess antibodies were removed with extensive washing with Superblock buffer (5 times×5 min each). Subsequently, the wells were incubated with secondary antibody (anti-mouse IgG-HRP, Roche-BM, Indianapolis, Ind.) for 20 min at room temperature. After washing excess 2$^{nd}$ antibodies, HRP activity was determined as described above.

6. Gel-Free Quantitation of N- and C-Terminal Markers

Figure 4A:
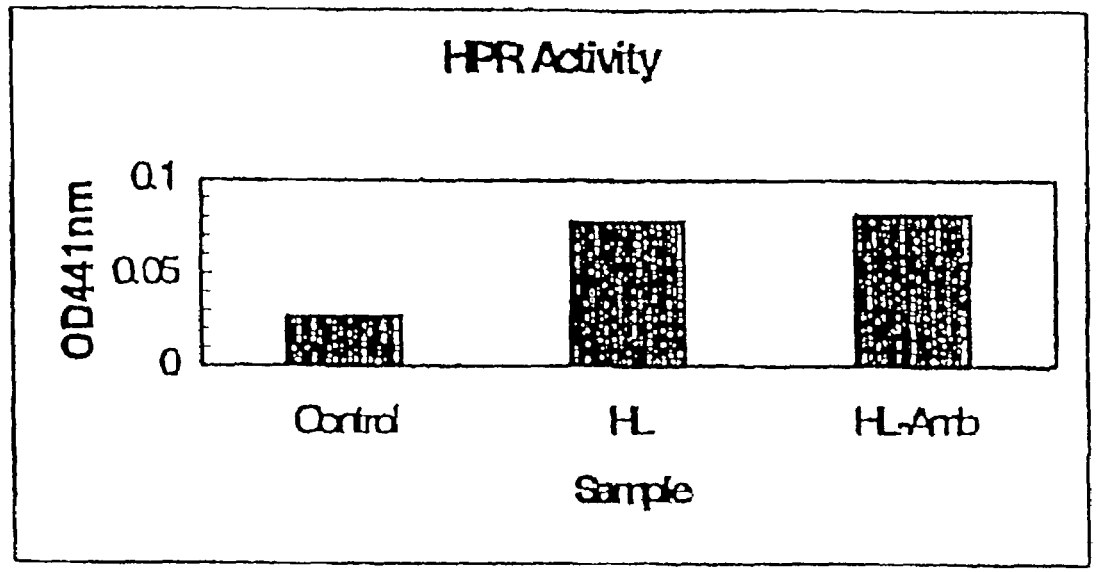
FIG. 4A is a bar graph showing gel-free quantitation of an N-terminal marker introduced into a nascent protein in accordance with the method of the present invention.
Figure 4B:
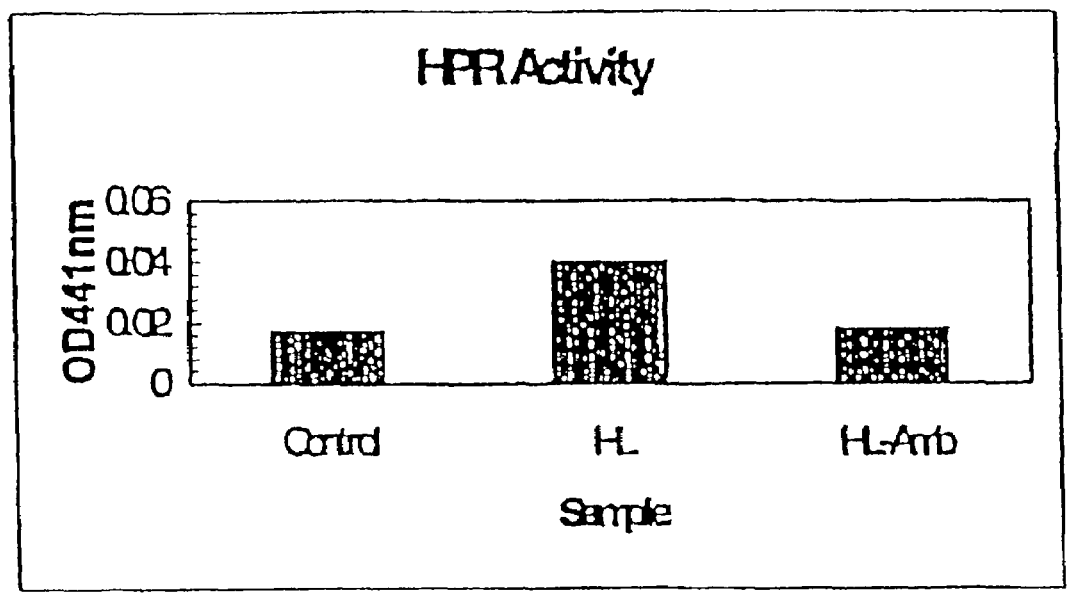
FIG. 4B is a bar graph showing gel-free quantitation of an C-terminal marker of a nascent protein quantitated in accordance with the method of the present invention.

The results of the above-described quantitation are shown in FIG. 23A (quantitation of N-terminal, Biotin marker) and FIG. 4B (quantitation of C-terminal, His-6 marker). In case of in vitro transcription/translation of WT α-HL DNA in presence of biotin-methionyl-tRNA, the protein synthesized will have translated His-6 tag at the C-terminal of the protein and some of the α-HL molecules will also carry biotin at their N-terminus which has been incorporated using biotinylated-methionine-tRNA. When the total translation reaction mixture containing α-HL was incubated on anti-α-HL antibody plate, selectively all the α-HL will bind to the plate via interaction of the antibody with the endogenous affinity marker. The unbound proteins can be washed away and the N- and C-terminal of the bound protein can be quantitated using Streptavidin-HRP and anti-His-6 antibodies, respectively. In case of WT α-HL, the protein will carry both the N-terminal (biotin) and C-terminal (His-6) tags and hence it will produce HRP signal in both the cases where streptavidin-HRP and secondary antibody-HRP conjugates against His-6 antibody used (HL, FIG. 4A). On the other hand, in case of amber mutant α-HL, only N-terminal fragment of α-HL (first 134 amino acids) will be produced and will have only N-terminal marker, biotin, but will not have His-6 marker due to amber mutation at codon number 135. As a result of this mutation, the protein produced using amber α-HL DNA will bind to the antibody plate but will only produce a signal in the case of strepavidin-HRP (HL-AMB, FIG. 4A) and not for anti-HisX6 antibodies (HL-AMB, FIG. 4B).

Example 5

Incorporation of Three Markers into Hemolysin

This is an example wherein a protein is generated in vitro under conditions where N- and C-terminal markers are incorporated along with a marker incorporated using a misaminoacylated tRNA. The Example involves 1) PCR with primers harboring N-terminal and C-terminal detectable markers, 2) preparation of the tRNA, 3) in vitro translation, 4) detection of nascent protein.

1. PCR of α-Hemolysin DNA

Plasmid DNA for α-hemolysin, pT7-WT-H6-α-HL, was amplified by PCR using following primers. The forward primer (HL-5) was: 5'-GAATTC TAATACGACTC-ACTATAGGGTTAACTTTAAGAAGG-<u>AGATATACATATG</u> GAACAAAAATTAAT-CTCGGAAGAGGATTTGGCAG-ATTCTGAT*ATTAATATTAAAACC*-3' (SEQ ID NO:11) and the reverse primer (HL-3) was: 5'-AGCTTCATTA-ATGATGGTGATGG-TGGTGAC 3' (SEQ ID NO:12). The underlined sequence in forward primer is T7 promoter, the region in bold corresponds to ribosome binding site (Shine-Dalgarno's sequence), the bold and underlined sequences involve the C-myc epitope and nucleotides shown in italics are the complimentary region of α-hemolysin sequence. In the reverse primer, the underlined sequence corresponds to that of HisX6 epitope. The PCR reaction mixture of 100 ul contained 100 ng template DNA, 0.5 uM each primer, 1 mM MgCl$_2$, 50 ul of PCR master mix (Qiagen, CA) and nuclease free water (Sigma Chemicals, St. Louis, Mo.) water. The PCR was carried out using Hybaid Omni-E thermocycler (Hybaid, Franklin, Mass.) fitted with hot-lid using following conditions: 95° C. for 2 min, followed by 35 cycles consisted of 95° C. for 1 min, 61° C. for 1 min and 72° C. for 2 min and the final extension at 72° C. for 7 min. The PCR product was then purified using Qiagen PCR clean-up kit (Qiagen, CA). The purified PCR DNA was used in the translation reaction.

2. Preparation of BODIPY-FL-lysyl-tRNA$^{lys}$

The purified tRNA$^{lys}$ (Sigma Chemicals, St. Louis, Mo.) was first aminoacylated with lysine. The typical aminoacylation reaction contained 1500 picomoles (~1.0 OD$_{260}$) of tRNA, 20 mM imidazole-HCl buffer, pH 7.5, 10 mM MgCl$_2$, 1 mM lysine, 2 mM ATP, 150 mM NaCl and excess of aminoacyl tRNA-synthetases (Sigma Chemicals, St. Louis, Mo.). The reaction mixture was incubated for 45 min at 37° C. After incubation, the reaction mixture was neutralized by adding 0.1 volume of 3 M sodium acetate, pH 5.0 and subjected to chloroform:acid phenol extraction (1:1). Ethanol (2.5 volumes) was added to the aqueous phase and the tRNA pellet obtained was dissolved in water (35 ul). To this solution 5 ul of 0.5 M CAPS buffer, pH 10.5 was added (50 mM final conc.) followed by 10 ul of 10 mM solution of BODIPY-FL-SSE. The mixture was incubated for 10 min at 0° C. and the reaction was quenched by the addition of lysine (final concentration=100 mM). To the resulting solution 0.1 volume of 3 M NaOAc, pH=5.0 was added and the modified tRNA was precipitated with 3 volumes of ethanol. Precipitate was dissolved in 50 ul of water and purified on Sephadex G-25 gel filtration column (0.5×5 cm) to remove any free fluorescent reagent, if present. The modified tRNA was stored frozen (−70° C.) in small aliquots in order to avoid free-thaws. The modification extent of the aminoacylated-tRNA was assessed by acid-urea gel electrophoresis. Varshney et al., *J. Biol. Chem.* 266:24712-24718 (1991).

3. Cell-Free Synthesis of Proteins in Eukaryotic (Wheat Germ) Translation Extracts.

The typical translation reaction mixture (20 ul) contained 10 ul of TnT wheat germ extract (Promega Corp., Wisconsin-Madison, Wis.), 0.8 ul of TnT reaction buffer, 2 ul of amino acid mix (1 mM), 0.4 ul of T7 RNA polymerase, 30 picomoles of BODIPY-FL-lysyl-tRNA$^{lys}$, 1-2 ug plasmid or PCR DNA and RNase-free water. The translation reaction was allowed to proceed for 60 min at 30° C. and reaction mixture was centrifuged for 5 min to remove insoluble material. The clarified extract was then precipitated with 5-volumes of acetone and the precipitated proteins were collected by centrifugation. The pellet was dissolved in 1× loading buffer and subjected to SDS-PAGE after boiling for 5 min. SDS-PAGE was carried out according to Laemmli, *Nature*, 227:680-685.

4. Detection of Nascent Protein

After the electrophoresis, gel was scanned using FluorImager 595 (Molecular Dymanics, Sunnyvale, Calif.) equipped with argon laser as excitation source. For visualization of BODIPY-FL labeled nascent protein, we have used 488 nm as the excitation source as it is the closest to its excitation maximum and for emission, we have used 530+/−30 filter. The gel was scanned using PMT voltage 1000 volts and either 100 or 200 micron pixel size.

Figure 5:
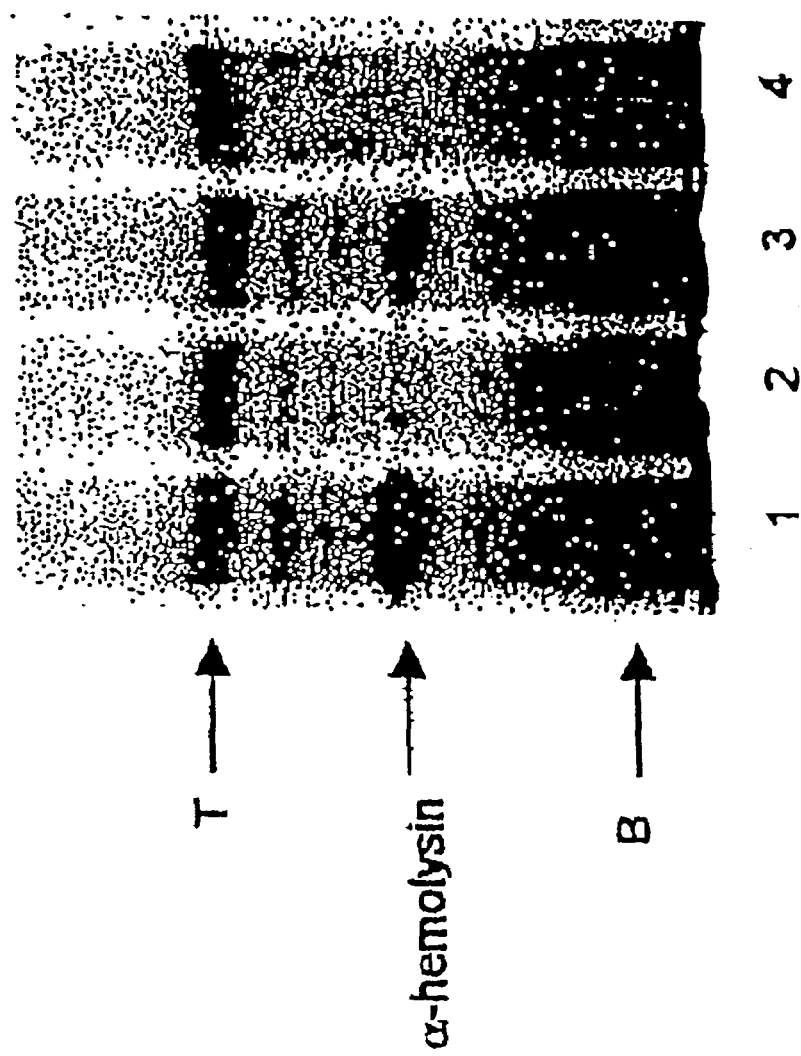
FIG. 5 are gel results of in vitro translation results wherein three markers were introduced into a nascent protein.

The results are shown in FIG. 5. It can be seen from the Figure that one can in vitro produce the protein from the PCR DNA containing desired marker(s) present. In the present case, the protein (α-hemolysin) has a C-myc epitope at N-terminal and HisX6 epitope at C-terminal. In addition, BODIPY-FL, a fluorescent reporter molecule is incorporated into the protein. Lane 1: α-Hemolysin plasmid DNA control; lane 2: no DNA control; lane 3: PCR α-hemolysin DNA and lane 4: hemolysin amber 135 DNA. The top (T) and bottom (B) bands in all the lane are from the non-specific binding of fluorescent tRNA to some proteins in wheat germ extract and free fluorescent-tRNA present in the translation reaction, respectively.

Example 6

Primer Design

It is not intended that the present invention be limited to particular primers. A variety of primers are contemplated for use in the present invention to ultimately incorporate markers in the nascent protein (as explained above). The Example involves 1) PCR with primers harboring markers, 2) in vitro translation, and 3) detection of nascent protein.

For PCR the following primers were used: forward primer: 5'GGATCC TAATACGACTCACTATAGGGAGACCACCATG GAACAAAAATTAATA TCGGAAGAGGATTTGAATGTTTCTCCATACAGGTC-ACGGGGA-3' (SEQ ID NO:13). Reverse Primer: 5'-TTAT-TAATGATGGTGATGGTGGTG TCTGTAGGAATGGTAT-CTCGTTTTTC-3' (SEQ ID NO:14) The underlined sequence in the forward primer is T7 promoter, the bold and underlined sequences involve the C-myc epitope and nucleotides shown in italics are the complimentary region of α-hemolysin sequence. In the reverse primer, the bold sequence corresponds to that of His-6 epitope and the underlined sequence corresponds to the complimentary region of the α-hemolysin sequence. A PCR reaction mixture of 100 ul can be used containing 100 ng template DNA, 0.5 uM each primer, 1 mM $MgCl_2$, 50 ul of PCR master mix (Qiagen, CA) and nuclease free water (Sigma Chemicals, St. Louis, Mo.) water. The PCR was carried out using Hybaid Omni-E thermocycler (Hybaid, Franklin, Mass.) fitted with hot-lid using following conditions: 95° C. for 2 min, followed by 35 cycles consisted of 95° C. for 1 min, 61° C. for 1 min and 72° C. for 2 min and the final extension at 72° C. for 7 min. The PCR product can then be purified using Qiagen PCR clean-up kit (Qiagen, CA). The purified PCR DNA can then be used in a variety of translation reactions. Detection can be done as described above.

Overall, the present invention contemplates a variety of primer designs based on the particular epitopes desired (see Table 4 for a list of illustrative epitopes). In general, the epitopes can be inserted as the N-terminus or C-terminus. In addition, they can be used to introduce an affinity region (i.e. a region which will bind to antibody or other ligand) into the protein.

Example 7

Antibody Detection of Primer-Encoded Epitopes

This is an example wherein a protein is generated in vitro under conditions where affinity regions are incorporated in a protein and thereafter detected. The Example involves 1) PCR with primers containing sequences that encode epitopes, 2) preparation of the tRNA, 3) in vitro translation, 4) detection of nascent protein.

1. PCR with Primer-Encoded Epitopes

The total RNA from the human colon (Clontech, Palo Alto, Calif.) was subjected to one-step RT-PCR reaction using ClonTech RT-PCR Kit. The forward Primer, PTT-T7-P53, was 5'-GGATCCTAATACGACTCACTATAGGGAG-ACCACCATGGGACAC-CACCATCACCATCACG-GAGATTACAAAGATGACGATGACAAAGAGGAGCC-GCAGTCAGATCCTAGCGTCGA-3' (SEQ ID NO:15) and the reverse primer, Myc-P53-3', was 5'-ATTATTA CAAATCCTCTTCCGAGATTAATTTTTGTTCGTCTGA-GTCAGGCCCTTCTGTCTTGAACATG-3' (SEQ ID NO:16). The underlined sequence in forward primer is T7 promoter, the nucleotides shown in italics corresponds to that of His-6 tag while the sequence in bold codes for FLAG-epitope and the rest of primer is the complementary region for P53 DNA. In the reverse primer, the underlined sequence corresponds to that of c-Myc epitope.

The RT-PCR/PCR reaction mixture of 50 μl contained 1 μg total human colon RNA, 0.5 μμM each primer, 43.5 μl of RT-PCR master mix (ClonTech) and nuclease free water (Sigma Chemicals, St. Louis, Mo.) water. The RT-PCR/PCR was carried out in PTC-150 thermocycler (MJ Research, Waltham, Mass.) using following conditions: 50° C. for 1 hour, 95° C. for 5 min followed by 40 cycles consisted of 95° C. for 45 sec, 60° C. for 1 min and 70° C. for 2 min and the final extension at 70° C. for 7 min. The PCR product was analyzed on 1% agarose gel and the PCR amplified DNA was used in the translation reaction without any further purification. The artificial C-terminal truncated mutant of P53 was prepared using the identical procedure described above except the reverse primer, 3'-P53-Mut, was 5'-CTCAT-TCAGCTCTCGGAACATC-TCGAAGCG-3' (SEQ ID NO: 17).

2. tRNA Labeling

Purified $tRNA^{lys}$ (Sigma Chemicals, St. Louis, Mo.) was first amino-acylated with lysine. The typical aminoacylation reaction (100 μl) contained 1500 picomoles (~1.0 $OD_{260}$) of tRNA, 20 mM imidazole-HCl buffer, pH 7.5, 10 mM $MgCl_2$, 1 mM lysine, 2 mM ATP, 150 mM NaCl and excess of aminoacyl tRNA-synthetases (Sigma). The reaction mixture was incubated for 45 min at 37° C. After incubation, the reaction mixture was neutralized by adding 0.1 volume of 3 M sodium acetate, pH 5.0 and subjected to chloroform:acid phenol extraction (1:1). Ethanol (2.5 volumes) was added to the aqueous phase and the tRNA pellet obtained was dissolved in the water (35 μl). To this solution 5 μl of 0.5M CAPS buffer, pH 10.5 was added (final concentration of 50 mM) followed by 10 μl of 10 mM solution of BODIPY-FL-SSE. The mixture was incubated for 10 minutes at 0° C. and the reaction was quenched by the addition of free lysine (final concentration=100 mM). To the resulting solution 0.1 volumes of 3 M NAOAc (pH=5.0) was added and the modified tRNA was precipitated with 3 volumes of ethanol. Precipitate was dissolved in 50 μl of RNase-free water and passed through Sephadex G-25 gel filtration column (0.5×5 cm) to remove any free fluorescent reagent, if present. The modified tRNA was stored frozen (−70° C.) in small aliquots in order to avoid freeze-thaws. The modification extent of the aminoacylated-tRNA was assessed by acid-urea gel electrophoresis [Varshney, U., Lee, C. P. & RajBhandary, U. L., *J. Biol. Chem.* 266, 24712-24718 (1991)] or by HPLC [*Anal. Biochem.* 279:218-225 (2000)].

3. Translation

Translation of P53 DNA (see step 1, above) was carried out in rabbit reticulocyte translation extract in presence of fluorescent-tRNA (step 2, above).

4. Detection

Once the translation was over, an aliquot (5 μl) was subjected to SDS-PAGE and the nascent proteins were visualized using FluorImager SI (Molecular Dynamics, Sunnyvale, Calif.). After visualization, the gel was soaked in the transfer buffer (12 mM Tris, 100 mM glycine and 0.01% SDS, pH 8.5) for 10 min. Proteins from the gels were then transferred to PVDF membrane by standard western blotting protocol using Bio-Rad submersion transfer unit for 1 hr. After the transfer, then membrane was reversibly stained using Ferrozine/ferrous total protein stain for 1 min to check the quality of transfer and then the membrane was blocked using amber blocking solution (4.5% v/v teleostean gelatin, 2% w/v nonfat milk powder, 0.1% w/v Tween-20 in Tris-buffered saline, pH 7.5) for 2 hours followed by overnight incubation (12-15 hours at 4° C. on constant speed shaker) with appropriately diluted antibodies. For Flag detection, we have used 2000-fold diluted anti-Flag M2 Antibody (Sigma), for His-6 detection, we have used 500-fold anti-His6 antibody (Santa-Cruz Biotech, Calif.) and for c-Myc detection, we have used 500-fold diluted anti-C-Myc antibody (Santa-Cruz Biotech, Calif.).

After primary antibody incubation, the membrane was washed with TBST (Tris-buffered saline, pH 7.5 with 0.1% Tween-20) four times (10 min each wash) and incubated with appropriately diluted secondary antibodies (10,000-fold diluted) for 1 hour at room temperature on constant speed shaker. The unbound secondary antibodies were washed with TBST (4 washes/10 min each) and the blot was visualized using an ECL-Plus chemiluminescence detection system (Amersham-Pharmacia Biotech, NJ).

Figure 6A:
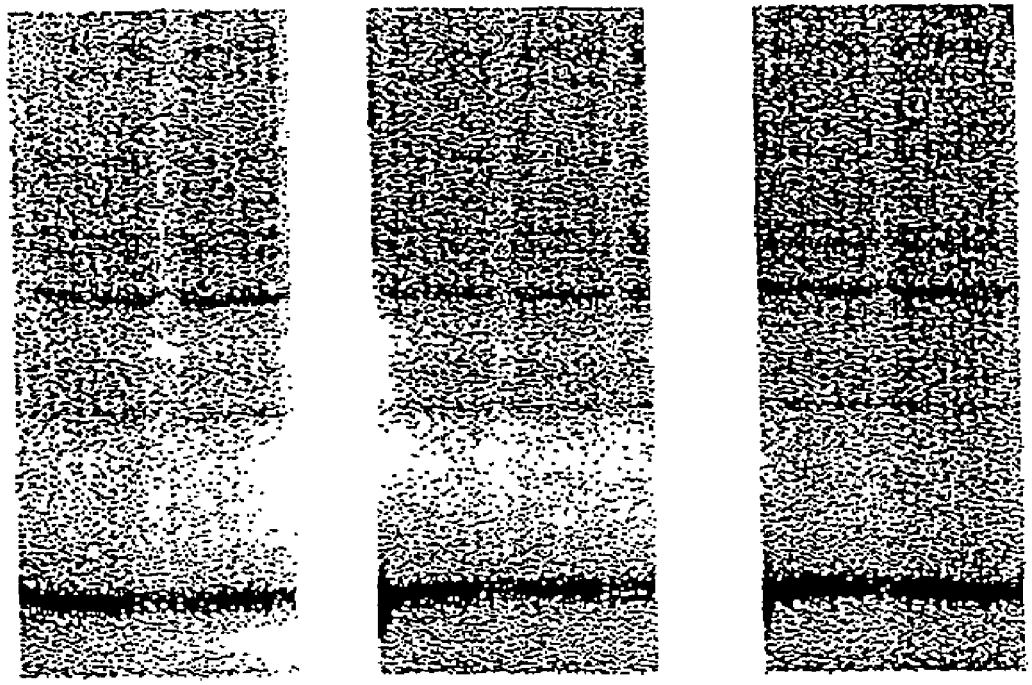
FIG. 6A shows the total protein staining.
Figure 6B:
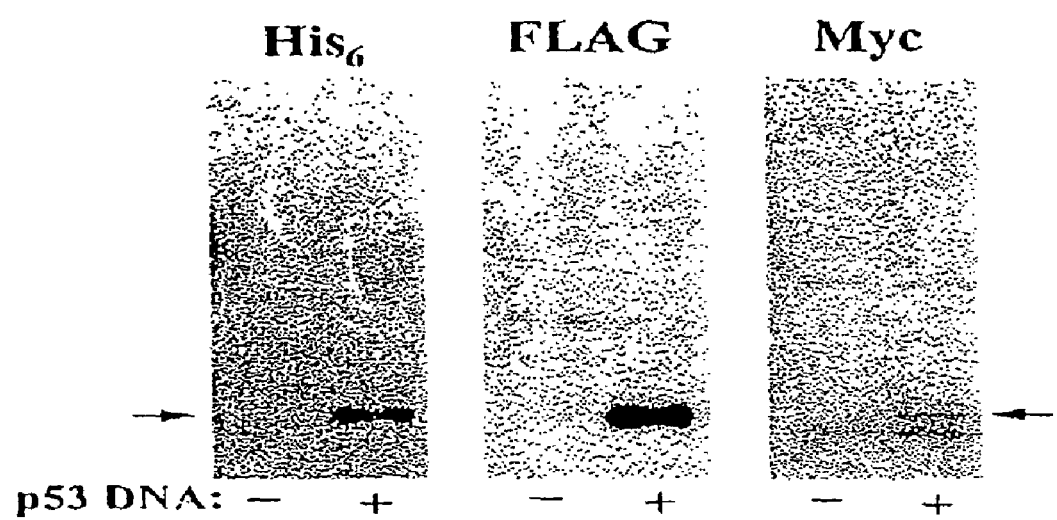
FIG. 6B presents the Western blot analysis.

The results are shown in FIGS. 6A and 30B. FIG. 6A shows the total protein stain of PVDF membranes following protein transfer from the gel for three replicate blots containing a minus DNA negative control and a plus p53 DNA sample respectively. FIG. 6B shows the same blots (total protein staining is reversible) are probed with antibodies against the three epitope tags using standard chemiluminescent Western blotting techniques. Arrows indicate the position of p53.

Example 8

Gel-Based PTT for Cancer Genes

The detection of truncating mutations in proteins was first reported by Roest and co-workers and applied to the detection of truncating mutations in the APC gene by Vogelstein, Kinzler and co-workers. Truncations in a translated protein can occur due to frameshift, splicing and point mutations which result in the occurrence of a stop codon in the reading frame of a gene. Truncated polypeptides can be detected by translating a specific region of the DNA corresponding to the target gene in an in vitro system in the presence of radioactive labels (e.g. $^{35}$S-methionine) and then analyzing the resulting polypeptide using standard PAGE. Such an approach has been reported for the analysis of truncating mutations in a variety of cancer-linked genes including BRCA1/BRCA2, ATM, MHS2, MLH1. However, the use of radioactive isotopes presents problems in terms of the time needed for detection (>5 hours), which is critical for high-throughput analysis. For this reason, it would be highly advantageous to replace radioactivity with a more rapid means of detection.

In this example, we demonstrate the feasibility of rapid truncation analysis based on the use of N-terminal tags. The present invention provides a convenient, accurate and rapid method to screen for truncation mutations in a wide range of genes of clinical significance. The Example involves 1) PCR with primers having sequences complementary to the APC gene, 2) preparation of the tRNA, 3) in vitro translation, 4) detection of nascent protein.

1. PCR of Clinical Samples

Clinical samples were submitted to the Washington University Molecular Diagnostics laboratory for screening of chain truncations in the APC gene, which are characteristic of the autosomal dominant cancer syndrome familial adenomatous polyposis (FAP). Genomic DNA was isolated and a specific region of the APC gene (Exon 15-segment 2) was first amplified by PCR using primers which incorporate a T7 promoter, and Kozak sequence into the DNA. The forward Primer, T7-APC2 was 5'-GGATCC TAATACGACTCACTATAGGG*AGACCACC*ATGGATG-CATGTGGA-ACTTTGTGG-3' (SEQ ID NO:18) and the reverse primer 3'-APC2 was 5'-GAGGAT-CCATTAGAT-GAAGGTGTGGACG-3' (SEQ ID NO:19). The underlined sequence in forward primer is T7 promoter and the sequence shown in italics corresponds to that of Kozak sequence which is necessary for efficient eukaryotic translation initiation. The PCR reaction mixture of 50 µl contained 200-500 ng template DNA (either WT or mutant), 0.5 µ$\overline{\omega}$µM each primer and 25 µl of PCR master mix (Qiagen, CA) and nuclease free water (Sigma Chemicals, St. Louis. Mo.) water. The PCR was carried out using Hybaid Omi-E thermocycler (Hybaid, Franklin, Mass.) fitted with hot-lid following conditions: 95° C. for 3 min, followed by 40 cycles consisted of 95° C. for 45 sec. 55° C. for 1 min and 72° C. for 2 min and the final extension at 72° C. for 7 min. The PCR product was analyzed on 1% agarose gel and the PCR amplified DNA was used in the translation reaction without any further purification.

2. Preparation of the tRNA

The purified tRNA$^{lys}$ (Sigma Chemicals, St. Louis, Mo.) was first amino-acylated with lysine. The typical aminoacylation reaction (100 µl) contained 1500 picomoles (~1.0 OD$_{260}$) of tRNA, 20 mM imidazole-HCl buffer, pH 7.5, 10 mM MgCl$_2$, 1 mM lysine, 2 mM ATP, 150 mM NaCl and excess of aminoacyl tRNA-synthetases (Sigma). The reaction mixture was incubated for 45 min at 37° C. After incubation, the reaction mixture was neutralized by adding 0.1 volume of 3 M sodium acetate, pH 5.0 and subjected to chloroform:acid phenol extraction (1:1). Ethanol (2.5 volumes) was added to the aqueous phase and the tRNA pellet obtained was dissolved in the water (35 µl). To this solution 5 ul of 0.5M CAPS buffer, pH 10.5 was added (final concentration of 50 mM) followed by 10 ul of 10 mM solution of BODIPY-FL-SSE. The mixture was incubating for 10 minutes at 0° C. and the reaction was quenched by the addition of free lysine (final concentration=100 mM). To the resulting solution 0.1 volumes of 3 M NAOAc (pH=5.0) was added and the modified tRNA was precipitated with 3 volumes of ethanol. Precipitate was dissolved in 50 µl of RNase-free water and passed through Sephadex G-25 gel filtration column (0.5×5 cm) to remove any free fluorescent reagent, if present. The modified tRNA was stored frozen (−70° C.) in small aliquots in order to avoid free-thaws. The modification extent of the aminoacy-lated-tRNA was assessed by acid-urea gel electrophoresis (Varshney, U., Lee, C. P. & RajBhandary, U. L., 1991 J. Biol. Chem. 266, 24712-24718).

3. Translation

The PCR products (see step 1 above) were directly added without purification to a small aliquot of a Promega rabbit reticulocyte TnT Quick system which also contained the BODIPY-Lys-tRNA (see step 2 above). More specifically, after PCR, 0.5-1 µl of PCR product was directly added to translation reaction mixture containing 8 µl of rabbit reticulocyte extract for PCR product (Promega), 0.5 µl of 1 mM complete amino acid mix, 1 µl of BODIPY-FL-Lysyl-tRNA. The translation reaction was allowed to proceed for 1 hour and the reaction product were analyzed by 14% SDS-PAGE. Imaging was performed in under 1-2 minute using a Molecular Dynamics FluorImager.

Figure 7:
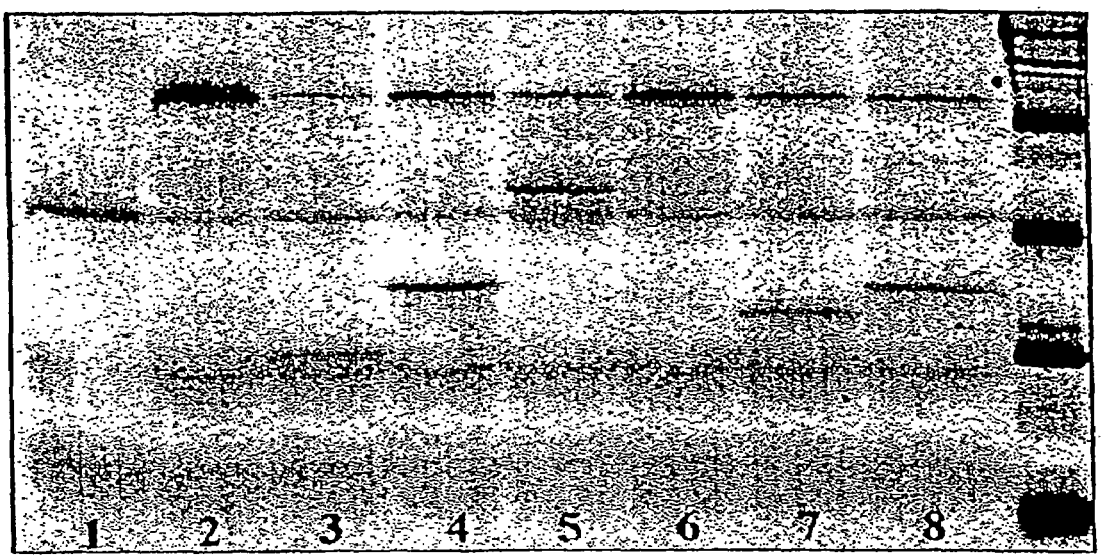
FIG. 7 shows the results for a gel-based PTT of APC Exon 15, segment 2.

FIG. 7 shows the results for analysis of several different human genomic samples using BODIPY-FL-lysyl-tRNA$^{lys}$ to incorporate a fluorescent label into fragments of the APC protein. Lane 1 is a minus DNA control. Lane 2 shows the results for wild-type DNA, while lanes 3-8 show the results for various mutant DNA isolated from patients having FAP (colon cancer). The last lane is fluorescent molecular weight markers. As seen in FIG. 7, the WT DNA (lane 2) produces a band, which corresponds to the normal Exon 15, segment 2 fragment of the APC gene. In contrast, all other lanes (except lane 6) exhibit the WT band and an additional band which corresponds to truncated fragments of Exon 15, segment 2. Thus, these individuals are heterozygous and carry one WT and one chain truncating mutation in the APC gene. In contrast, the lane 6 results indicates normal WT sequence in this region for both genes. Similar conclusion was reached independently using conventional radioactive PAGE analysis of patient samples by the University Molecular Diagnostics laboratory.

Figure 8A:
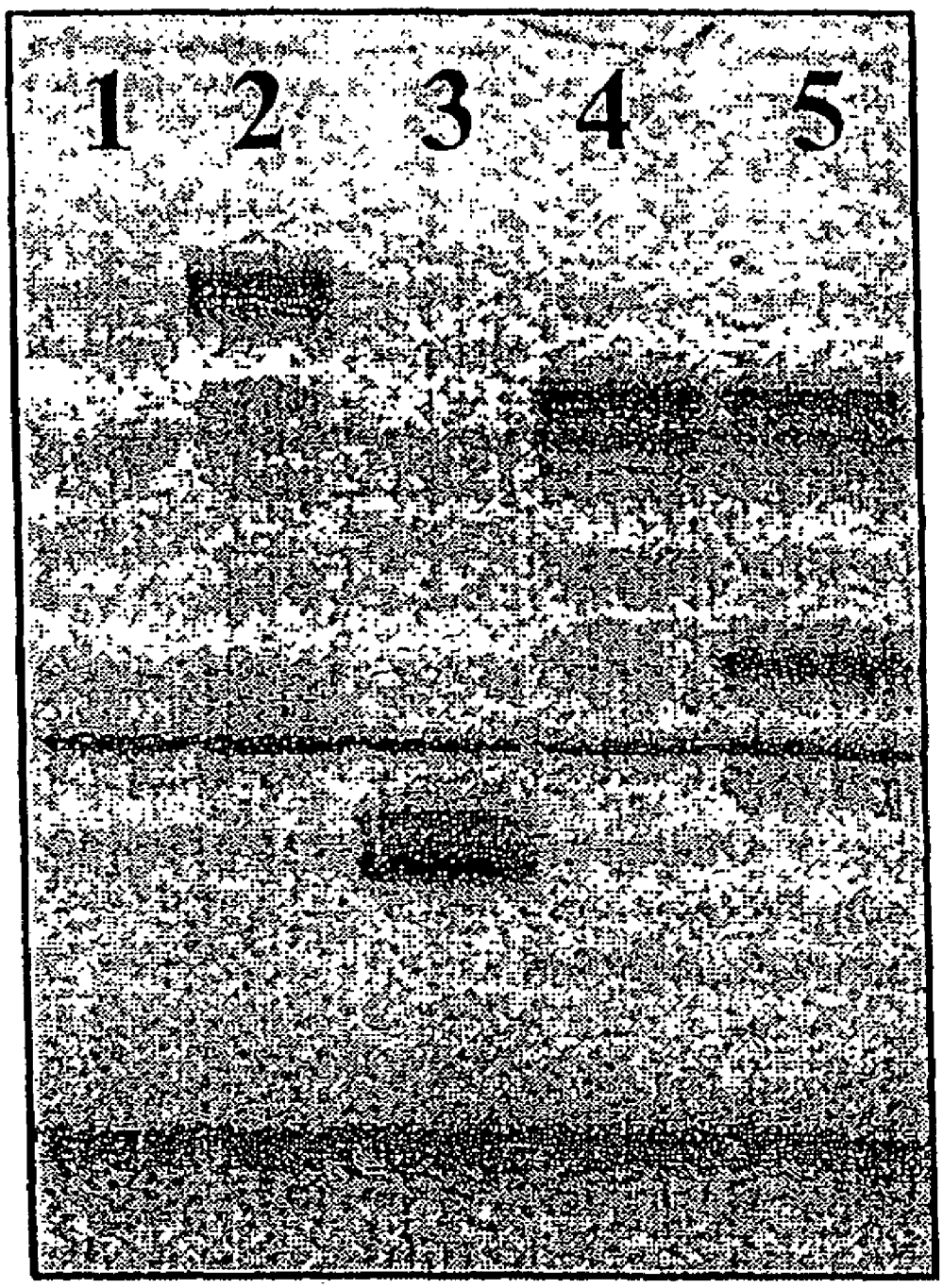
FIG. 8A shows the results by fluorescence imaging and FIG. 8B shows the results by Western blotting.
Figure 8B:
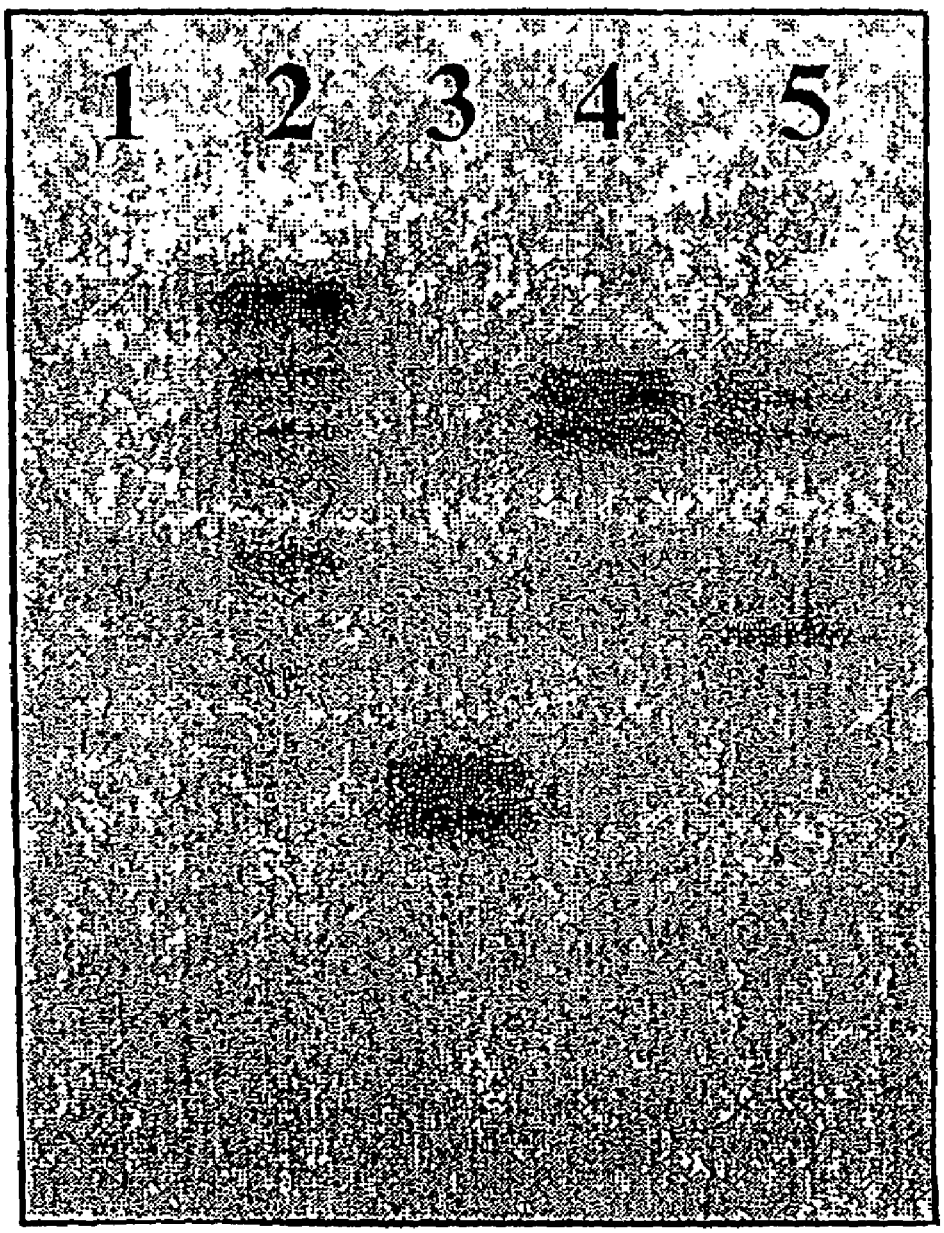

A similar analysis was performed to detect chain-truncating mutations in Exon 15-segment 3 (FIG. 8). Proteins were synthesized using the rabbit reticulocyte in vitro translation system in conjunction with BODIPY-FL-lysyl-tRNA$^{lys}$. Following separation by SDS-PAGE, translated proteins were visualized by fluorescence imaging (FIG. 8A) or by chemiluminescent Western blotting procedures using a polyclonal antibody directed against the BODIPY fluorophore (FIG. 8B). Lane 1 is a minus DNA control. Lane 2 shows the results for APC3 wild-type DNA, while lane 3 shows the results for APC3 truncated mutant. Lane 4 shows the results for APC2 wild-type DNA, while lane 5 shows the results for APC2 heterozygous mutant.

Overall, these results demonstrate the ability to replace radioactive PTT screening with fluorescent-based screening of chain truncations involved in human inherited diseases.

Example 9

Gel-Free PTT for Cancer Genes

Although the replacement of radioactivity in Example 8 (above) with fluorescent labels represents an improvement in current PTT technology, it still relies on the use of gels, which are not easily adaptable for high-throughput screening applications. For this reason, this example demonstrates a non-gel approach based on the use of chemiluminescent detection. In this approach, a cancer-linked protein or polypeptide fragment from the protein is expressed in vitro from the corresponding gene with different detection and binding tags incorporated at the N-terminal, C-terminal and between the two ends of the protein using a combination of specially designed primers and tRNAs. The detection and binding tags provide a means to quantitate the fraction of protein or protein fragment which is truncated while the tags located between the two ends of the protein can be used to determine the region of truncation. For example, a full-length protein would contain both an N and C-terminal tag, whereas a truncated protein would contain only the N-terminal tag. The signal from a tag incorporated at random lysines between the two ends of the protein (intrachain signal) would be reduced proportional to the size of the truncated fragment. It is important to also capture the protein with a marker located close to the N-terminus in order to avoid interference of chain truncations with binding.

In order to evaluate this method, we performed experiments on the APC and p53 genes containing either a WT sequence or truncating mutations. In both cases, a combination of primers and specially designed tRNAs were used to incorporate a series of markers into the target proteins during their in vitro synthesis in a rabbit reticulocyte system. After in vitro expression, the expressed protein was captured in 96-well ELISA plates using an affinity element bound to the plate. The relative amount of N-terminal, C-terminal and intrachain signal was then determined using separate chemiluminescent-based assays.

1. PCR of Cancer Genes
   A. APC Segment 3

First, the genomic DNA (WT and isolated from cell lines harboring mutant APC gene) was amplified by PCR using following primers. The forward primer, PTT-T7-APC3, was 5'-GGATCC<u>TAATACGACTCACTATAGGG</u>AGACCACCATG-CACC-*ACCATCACCATCACGGAGGAGATTA*-CAAAGATGACGATGACAAA-GTTTCTCCATACAGGT-CACGGGGAGCCAAT-3' (SEQ ID NO:20) and the reverse primer, PTT-Myc-APC3, was 5'-ATTATTACAAATCCTCTTCCAGATTAA-TTTTTGTTCACTTC-TGCCTTCTGTAGGAATGGTATCTCG-3' (SEQ ID NO:21). The underlined sequence in forward primer is T7 promoter, nucleotides shown in italics corresponds to that of His-6 tag while the nucleotides sequence shown in the bold codes for FLAG-epitope and the rest of the primer is the complementary region for APC segment 3 DNA. In the reverse primer, the underlined sequence corresponds to that of c-Myc epitope. The PCR\reaction mixture of 50 µl contained 200-500 ng template DNA (either WT or mutant), 0.5 µM each primer and 25 µl of PCR master mix (Qiagen, CA) and nuclease free water (Sigma Chemicals, St. Louis, Mo.) water. The PCR was carried out using Hybaid Omni-E thermocycler (Hybaid, Franklin, Mass.) fitted with hot-lid using following conditions: 95° C. for 3 min, followed by 40 cycles consisting of 95° C. for 45 sec, 55° C. for 1 min and 72° C. for 2 min and the final extension at 72° C. for 7 min. The PCR product was analyzed on 1% agarose gel and the PCR amplified DNA was used in the translation reaction without any further purification.

B. P53

The p53 DNA was prepared as described in Example 7 (above).

2. Preparation of the tRNA

The BODIPY-FL-lysyl-tRNA$^{lys}$ was prepared as described in Example 7 (above). Preparation of Biotin-lysyl-tRNA$^{lys}$ and PC-Biotin-lysyl-tRNA$^{lys}$ was achieved as follows. The purified tRNA$^{lys}$ (Sigma Chemicals, St. Louis, Mo.) was first aminoacylated with lysine. The typical aminoacylation reaction contained 1500 picomoles (~1.0 OD$_{260}$) of tRNA, 20 mM imidazole-HCl buffer, pH 7.5, 10 mM MgCl$_2$, 1 mM lysine, 2 mM ATP, 150 mM NaCl and excess of aminoacyl-tRNA-synthetases (Sigma Chemicals, St. Louis, Mo.). The reaction mixture was incubated for 45 min at 37° C. After incubation, the reaction mixture was neutralized by adding 0.1 volume of 3 M sodium acetate, pH 5.0 and subjected to chloroform:acid phenol extraction (1:1). Ethanol (2.5 volumes) was added to the aqueous phase and the tRNA pellet obtained was dissolved in water (35 µl). To this solution 5 µl of 0.5 M CAPS buffer, pH 10.5 was added (50 mM final conc.) followed by 10 µl of 10 mM solution of either Biotin or photocleavable-Biotin. The mixture was incubated for 10 min at 0° C. and the reaction was quenched by the addition of lysine (final concentration=100 mM). To the resulting solution 0.1 volume of 3 M NaOAc, pH=5.0 was added and the modified tRNA was precipitated with 3 volumes of ethanol. Precipitate was dissolved in 50 ul of water and purified on Sephadex G-25 gel filtration column (0.5×5 cm) to remove any free fluorescent reagent, if present. The modified tRNA was stored frozen (−70° C.) in small aliquots in order to avoid free-thaws. The modification extent of the aminoacylatedtRNA was assessed by acid-urea gel electrophoresis (Varshney, U., Lee, C. P. & RajBhandary, U. L., 1991, J. Biol. Chem. 266, 2471224718).

3. Translation

The typical translation reaction mixture (20 µl) contained 16 µl of TNT rabbit reticulocyte extract for PCR DNA (Promega, Madison, Wis.), 1 µl of amino acid mix (1 mM), 1-2 µl of PCR DNA (see APC and p53 preparation described above) and RNase-free water. For fluorescence detection, the BODIPY-FL-lysyl-tRNA$^{lys}$ was included into the translation reaction mixture. The translation reaction was allowed to proceed for 60 min at 30° C.

Example 10

Incorporation of VSV-G and p53-Derived Epitopes

Genomic DNA and RNA (WT and APC mutant) was isolated from established cell lines CaCo-2 (C1), HCT-8 (C2) and SW480 (C3) as well as from patient blood samples using commercially available kits (Qiagen, Valencia, Calif.). PCR amplification of a selected region of the APC gene (APC segment 3) was carried out using 250-500 ng of genomic DNA, 0.2 µM primer mix (forward and reverse) and 1×PCR master mix (Qiagen, Valencia, Calif.). Amplification was performed as follows: an initial cycle of denaturation at 95° C., forty cycles of denaturation at 95° C. for 45 sec, annealing at 57° C. for 45 sec, extension at 72° C. for 2 min and a final extension step at 72° C. for 10 min. RT-PCR amplification of APC gene (APC segment 3) was carried out using one-step RT-PCR/PCR kit from ClonTech (Palo Alto, Calif.). RT-PCR reaction contained 500 ng of total RNA, 0.2 µM primer mix (forward and reverse) and 1×RT-PCR master mix. Amplification conditions were the same as above with an additional initial cycle of reverse transcription at 50° C. for 1 hour. The primer pair was:
Forward: (SEQ ID NO:22)
5'-GG*ATCCTAATACGACTCACTATAGG*GAGACCACC
<u>ATG</u>GGC**TACACCGACAT-CGAGATGAACCGCCTGG-
CAA**GGTTTCTCCATACAGGTCACGGGGAGCC-3'
Reverse: (SEQ ID NO:23) 5'-*TTATTA*CAGCAGCTTGTG-
CAGGTCGCTGAAGGTACTTCTGCCTTCTGT-AG-
GAATGTATC-3'

The italicized nucleotides in the forward primer correspond to the T7 promoter, the underlined ATG is the initiation codon, the boldface nucleotide region codes for the N-terminal tag (VSV-G; YTDIEMNRLGK: SEQ ID NO:39) and the remaining nucleotide sequences correspond to the complementary region of the APC gene. In the reverse primer, the boldface nucleotides code for the C-terminal tag (P53 sequence derived tag; TFSDLHKLL: SEQ ID NO:24) while the rest of the nucleotide sequence is complementary to the APC gene and nucleotides in italics codes for 2 successive stop codons. After amplification, the quality and quantity of the PCR products was analyzed by agarose gel electrophoresis.

Example 11

Cell-Free Protein Synthesis

The cell-free reaction mixture contained 8 µl of TNT T7 Quick Rabbit Reticulocyte lysate for PCR DNA (Promega, Madison, Wis.), 0.5 µl of a complete amino acid mix and 0.5 µl of DNA (approximately 200 ng) and either 1 µl of biotin-lysyl-tRNA or a tRNA mix consisting of equal amount of Biotin-lysyl tRNA and BODIPY-FL-lysyl-tRNA. The translation reaction was allowed to proceed for 45 min at 30° C. For electrophoresis, a 4-6 µl aliquot was used for SDS-PAGE. SDS-PAGE was carried out according to Laemmli. Kahmann et al., *A Non-Radioactive Protein Truncation Test For The Sensitive Detection Of All Stop And Frameshift Mutations*, Hum Mutat 19; 165-172 (2002). After electrophoresis, polyacrylamide gels were scanned using a FluorImager SI (Molecular Dynamics, Sunnyvale, Calif.) equipped with an Argon laser as an excitation source (488 nm line) and a 530±30 nm emission filter.

Example 12

High-Throughput Solid-Phase PTT (HTS-PTT)

After the translation exemplified in Example 11, the reaction mixture was diluted 30-fold with TBS containing 0.05% Tween-20, 0.1% Triton X-100, 5% BSA, and both antibodies (anti-VSV-G-HRP (Roche Applied Sciences, Indianapolis, Ind.) at 80 ng/mL and anti-p53-alkaline phosphatase at 100 ng/mL (Santa Cruz Biotechnology, Santa Cruz, Calif.)). Subsequently, 100 µl of the diluted reaction mixture was added to each well of a NeutrAvidin™ coated 96-well plate (pre-blocked with 5% BSA) and incubated for 45 min on an orbital shaker. NeutrAvidin™ was obtained from Pierce Chemicals (Rockford, Ill.) and Microlite2+ multiwell plates were obtained from Dynex Technologies (Chantilly, Va.). The plate was washed 5× with TBS-T (TBS with 0.05% Tween-20) followed by 2× with TBS and developed using a chemiluminescent HRP substrate (Super Signal Femto, Pierce Chemicals, Rockford, Ill.). Finally, the plate was washed twice in 100 mM Tris-HCl, pH 9.5, 100 mM NaCl and 50 mM magnesium acetate, a chemiluminescent alkaline-phosphatase reaction mixture.

Example 13

Minimal Copy PCR Amplification

This example demonstrates that a single copy DNA may be amplified and isolated using HTS-PTT.

A defined amount of genomic DNA (WT APC) and cell line DNA (mutant APC) was used as the template for PCR. Low copy PCR was carried out in two sequential PCR amplifications. To test the limit of PCR, template DNA was diluted to various ratios to obtain 1-300,000 copies of DNA/µl. In the first PCR amplification, a selected region of the APC gene (APC long, 3.8 kb region) was carried out using various amounts of genomic DNA, 0.2 µM primer mix (Long 5' and Long 3') and 1×PCR master mix (Qiagen, Valencia, Calif.). Amplification was performed as follows: an initial cycle of denaturation at 95° C., forty cycles of denaturation at 95° C. for 45 sec, annealing at 57° C. for 45 sec, extension at 72° C. for 4 min and a final extension step at 72° C. for 10 min. The product after this PCR was used as the template for the second PCR reaction. PCR amplification of a selected region of the APC gene (APC-3) was carried out using 5 µl of above PCR product (after APC Long PCR), 0.2 µM primer mix (forward and reverse) and 1×PCR master mix (Qiagen, Valencia, Calif.). Amplification was performed as follows: an initial cycle of denaturation at 95° C., forty cycles of denaturation at 95° C. for 45 sec, annealing at 57° C. for 45 sec, extension at 72° C. for 4 min and a final extension step at 72° C. for 10 min.

The primer pairs were:
Long 5': 5'-TTTTTGGTTGGCACTCTTACTTACCGGAGC-3' SEQ ID NO: 47
Long 3': 5'-AGATGCTTGCTGGACCTGGTCCATTATCTT-3' SEQ ID NO: 48
Forward: SEQ ID NO: 22
5'-GGATCCTAATACGACTCACTATAGGGAGACCACC ATGGGCTACACCGACAT CGAGATGAACCGCCTG-GCAAGGTTTCTCCATACAGGTCACGGGGAGCC-3'
Reverse: SEQ ID NO: 23
5'-TTATTACAGCAGCTTGTGCAGGTCGCT-GAAGGTACTTCTGCCTTCTGTA GGAATGGTATC-3'

The italicized nucleotides in the forward primer correspond to the T7 promoter, the underlined ATG is the initiation codon, the boldface nucleotide region codes for the N-terminal tag (VSV-G; YTDIEMNRLGK, SEQ ID NO:39) and the remaining nucleotide sequences correspond to the complementary region of the APC gene. In the reverse primer, the boldface nucleotides code for the C-terminal tag (P53 sequence derived tag: TFSDLHKLL, SEQ ID NO:24). The nucleotides in italics (TTATTA) codes for 2 successive stop codons. After amplification, the quality and quantity of the PCR products were analyzed by agarose gel electrophoresis.

Example 14

DNA PCR Using a Fecal Specimen

This example illustrates one embodiment of the present invention comprising the isolation of DNA from a small specimen of fecal material that is subsequently amplified by a standard PCR protocol.

DNA was extracted from 10-200 mg of a fecal specimen using QIAamp DNA Stool Mini Kit® (Cat. No. 51504, Qiagen, Valencia, Calif.). The fecal specimens were processed in amounts of decreasing quantity to determine a minimum amount necessary to perform a successful PCR amplification of a portion of the APC gene. The extracted fecal DNA specimens were then isolated and visualized using agarose gel electrophoresis (See FIG. 17).

The top band in each lane of FIG. 17 (Panel A & Panel B) mainly represents bacterial DNA that is relatively intact. Appearing below the bacterial DNA band is a DNA smear that represents human DNA in a generally degraded condition. The human DNA appearing in each lane was then quantitated using PicoGreen® (Molecular Probes). The amount of extracted human DNA appearing in each lane varied in linear proportion with the amount of starting stool material (See FIG. 17; Panel C).

The isolated human DNA was then removed from the agarose gel and subjected to a standard PCR protocol using various primer sets, including primers which spanned at least 200 bases of the APC gene. The results of these PCR amplifications show the feasibility of using DNA extracted and isolated from small amounts of stool (e.g., similar to those compatible with current FOBT protocols). The data show that short DNA sequences (i.e., for example, 200 base pairs) are capable of PCR amplification. Specifically, the data demonstrates that DNA isolated from 5 mg of stool material generated an identifiable PCR product DNA. (See FIG. 17; Panel B—Lane 6).

Example 15

DNA Extraction Using a Fecal Specimen

This example illustrates one embodiment of the present invention comprising collecting and processing a small fecal specimen using an FOBT kit whereby DNA is subsequently extracted and isolated following a 1-4 day drying time.

Approximately 1-3 mg of stool was smeared on each of two windows of a FOBT strip comprising guaiac-coated paper (Hemoccult® or Hemoccult® Sensa®, Beckman Coulter) using an applicator stick. The FOBT strips were then closed, placed in an envelope and stored in laminar hood at room temperature until further processed. In this experiment, DNA was extracted and isolated on each of the four days immediately following fecal specimen collection, drying and storage (e.g. Day 1, Day 2, Day 3 and Day 4).

On the day of each extraction, the guaiac-coated paper was cut from the FOBT holder and placed into a 1.5 ml Eppendorf® tube. To this tube, 1.6 ml of ASL Buffer was added and the guaiac-coated paper soaked for 20-30 minutes. After the soaking step, the fecal specimen was dislodged from the paper by vortexing the tube. The DNA present in the resultant fecal specimen mixture was extracted using the QIAamp DNA Stool Mini Kit® following the manufacturer's recommended protocol (See page 22 of instruction booklet, "Isolation of DNA from Stool for Human DNA Analysis"). The quality of the extracted DNA was then checked by agarose gel electrophoresis and the DNA quantitated according to Example 14.

Figure 18:
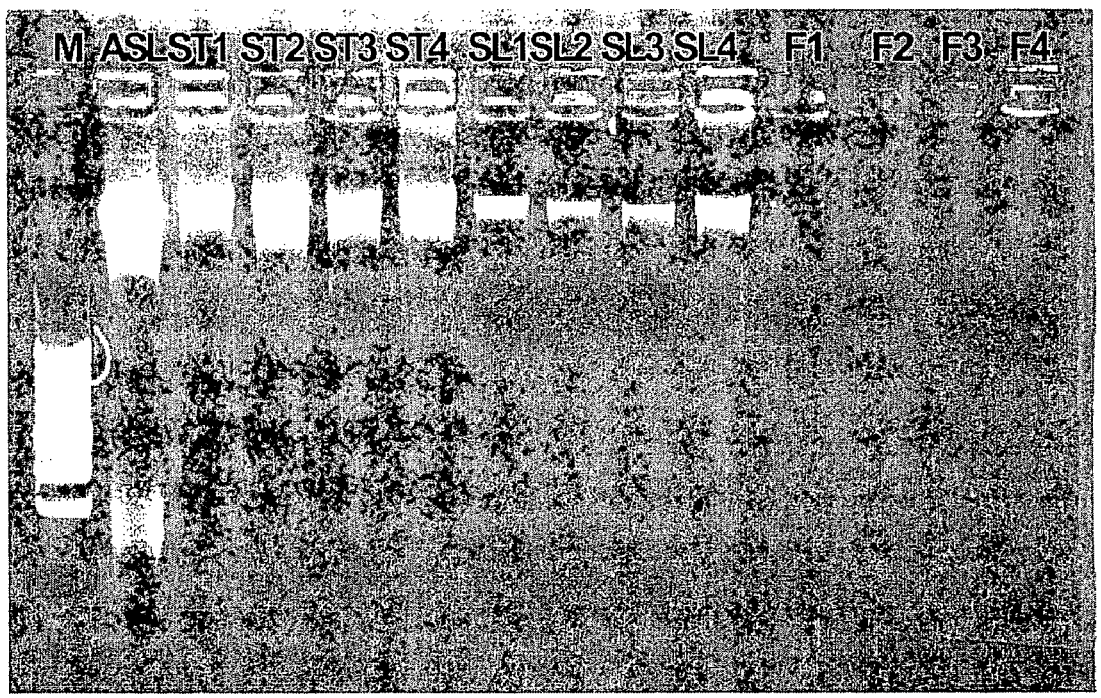
FIG. 18 shows an exemplary gel electrophoresis experiment of DNA collected and extracted using various embodiments of the present invention. ST=Star Buffer; SL=Glass Slide; F=FOBT slides; M=markers, ASL=buffer

The amount of DNA extracted from the 1-3 mg FOBT strip fecal specimens that were dried from 1-4 days was fairly constant ranging from approximately 100-200 ng. (See FIG. 18: Lane F1=Day 1 extraction/isolation; Lane F2=Day 2 extraction/isolation; Lane F3=Day 3 extraction/isolation; and Lane F4=Day 4 extraction/isolation). The percentage yield is equivalent to that generally achieved when using current DNA extraction protocols where 15,000-60,000 ng of DNA is generally extracted from 200 mg of stool sample.

Example 16

Primer-Directed DNA PCR Using a Fecal Specimen

This example demonstrates that isolated DNA from a fecal specimen provided in accordance with Example 15 is capable of primer directed PCR amplification using primers directed to approximately 150-200 bases of the APC, P53 and K-RAS genes.
APC PCR Subsequent to DNA extraction and isolation according to Example 15 the following primers were constructed to amplify a portion of the APC gene.
Sense: APC4-5: 5'-AGTGGCATTATAAGCCCCAGTGAT-3' (SEQ ID NO: 60)
Antisense: APC4-3: 5'-AGCATTTACTGCAGCTTGCT-TAGG-3'(SEQ ID NO: 61)

After an initial cycle of denaturation at 94° C. for 2 minutes; amplification was as follows: 40 cycles of denaturation at 94° C. for 20 seconds, annealing at 61.8° C. for 30 seconds, and extension at 72° C. for 1 minute. Each reaction was carried out in a total volume of 30 ul and contained: 0.5 ul of each sense (APC4-5, 10 mM) and antisense (APC4-3, 10 mM) primers, 5 ul of template DNA and 15 ul of High Fidelity PCR Master (Roche).

After PCR, fecal specimens (5 ul) were analyzed on a 2.0% agarose gel that was run at 150 V for 25 minutes. A 100 base pair ladder was used as a DNA marker standard as well as a quantitation standard. The PCR product was visualized and quantitated using a CCD-based imaging system and software (ChemImager, Alpha Innotech, San Leandro, Calif.).

Figure 19:
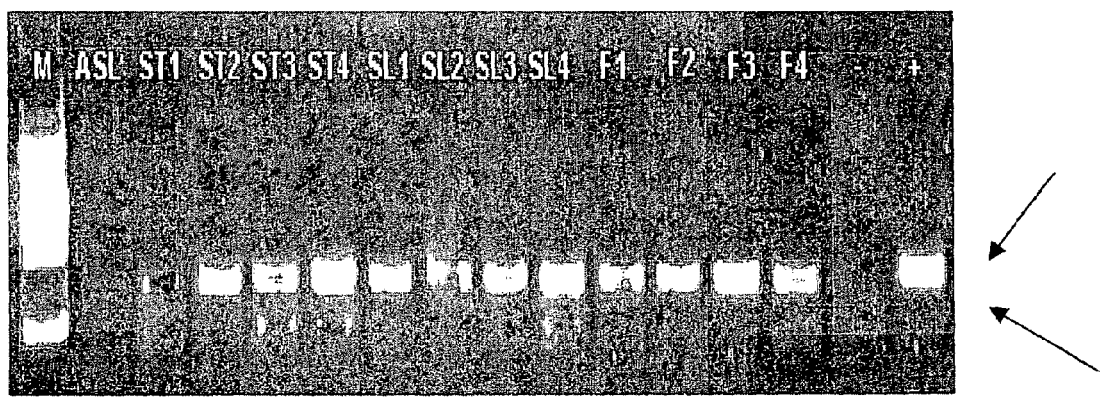
FIG. 19 shows exemplary gel electrophoresis experiment of APC PCR DNA product following collection and extraction using various embodiments of the present invention. ST=Star Buffer; SL=Glass Slide; F=FOBT slides; Top Arrow=PCR product DNA; Bottom Arrow=primers; M=markers; ASL=buffer.

PCR product DNA corresponding to at least 200 base pairs of the APC gene is clearly seen in all the lanes where the PCR was carried out using DNA extracted and isolated from FOBT strips between 1-4 days subsequent to fecal specimen collection. (See FIG. 19; Lane F1=Day 1 extraction/isolation; Lane F2=Day 2 extraction/isolation; Lane F3=Day 3 extraction/isolation; and Lane F4=Day 4 extraction/isolation). Lanes indicated with − and + are negative and positive controls, respectively. The quantitation of the above PCR product DNA ranged approximately between 40 ng to 80 ng per band in Lane F1-Lane F4 (i.e., 8-16 ng/ul; total 240-480 ng/30 ul PCR reaction).

P53 PCR

Subsequent to DNA extraction and isolation according to Example 15 the following primers were constructed to amplify a portion of the P53 gene.
Sense: P53-9-5: 5'-TGGTAACTCACTGGGACGGAA-CAG-3' (SEQ ID NO: 62)
Antisense: P53-9-3:5'-CTCGCTTAGTGCTC-CCTGGGGGCA-3' (SEQ ID NO: 63)

After an initial cycle of denaturation at 94° C. for 2 minutes; amplification was as follows: 40 cycles of denaturation at 94° C. for 20 seconds, annealing at 61.8° C. for 30 seconds, and extension at 72° C. for 1 minute. Each reaction mixture was carried out in a total volume of 30 ul and contained: 0.5 ul of each sense (P53-9-5, 10 mM) and antisense (P53-9-3, 10 mM) primers, 5 ul of template DNA and 15 ul of High Fidelity PCR Master (Roche).

After PCR, fecal specimens (5 ul) were analyzed on a 2.0% agarose gel which was run at 150V for 25 minutes. A 100 base pair ladder was used as a DNA marker standard as well as a quantitation standard. The PCR product was visualized and quantitated using a CCD-based imaging system and software (ChemImager, Alpha Innotech, San Leandro, Calif.).

Figure 20:
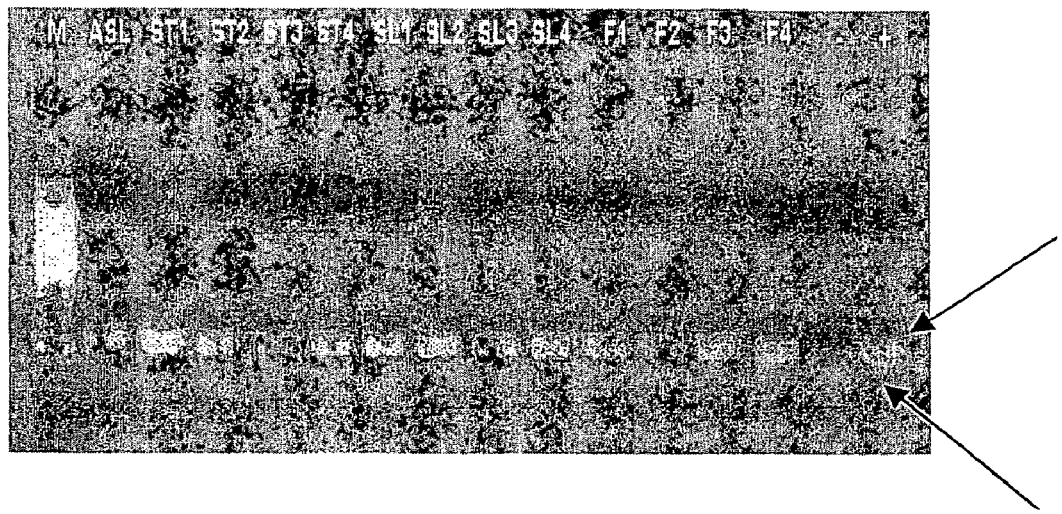
FIG. 20 shows exemplary gel electrophoresis experiment of p53 PCR DNA product following collection and extraction using various embodiments of the present invention. ST=Star Buffer; SL=Glass Slide; F=FOBT slides; Top Arrow=PCR product DNA; Bottom Arrow=primers. M=markers; ASL=buffer.

PCR product DNA corresponding to at least 150 base pairs of the P53 gene is clearly seen in all the lanes where the PCR was carried out using DNA extracted and isolated from FOBT strips between 1-4 days subsequent to fecal specimen collection. (See FIG. 20: Lane F1=Day 1 extraction/isolation; Lane F2=Day 2 extraction/isolation; Lane F3=Day 3 extraction/isolation; and Lane F4=Day 4 extraction/isolation). Lanes indicted with − and + are negative and positive controls, respectively. The quantitation of the above PCR product DNA ranged approximately between 40 ng to 80 ng per band in Lane F1-Lane F4 (i.e., 8-16 ng/ul; total 240-480 ng/30 ul PCR reaction).

K-RAS PCR

Subsequent to DNA extraction and isolation according to Example 15 the following primers were constructed to amplify a portion of the K-RAS gene.
Sense: KRAS-12F: 5'-GGCCTGCTGAAAATGACTGAA-3' (SEQ ID NO: 64)
Antisense: KRAS-12R: 5'-CTCTATTGTTGGAT-CATATTC-3' (SEQ ID NO: 65)

After an initial cycle of denaturation at 94° C. for 2 minutes; amplification was as follows: 40 cycles of denaturation at 94° C. for 20 seconds, annealing at 50.7° C. for 30 seconds, and extension at 72° C. for 1 minute. Each reaction mixture was carried out in a total volume of 30 ul and contained: 0.5 ul of each sense (KRAS-12F, 10 mM) and antisense (KRAS-12R, 10 mM) primers, 5 ul of template DNA and 15 ul of High Fidelity PCR Master (Roche).

After PCR, fecal specimens (5 ul) were analyzed on a 2.0% agarose gel which was run at 150V for 25 minutes. A 100 base pair ladder was used as a DNA marker standard as well as a quantitation standard. The PCR product was visualized and quantitated using a CCD-based imaging system and software (ChemImager, Alpha Innotech, San Leandro, Calif.).

Figure 21:
FIG. 21 shows exemplary gel electrophoresis experiment of K-RAS PCR DNA product following collection and extraction using various embodiments of the present invention. ST=Star Buffer; SL=Glass Slide; F=FOBT slides; Top Arrow=PCR product DNA; Bottom Arrow=primers. M=markers; ASL=buffer.

PCR product DNA corresponding to at least 120 base pairs of the K-RAS gene is clearly seen in all the lanes where the PCR was carried out using DNA extracted and isolated from FOBT strips between 1-4 days subsequent to fecal specimen collection. (See FIG. 21: Lane F1=Day 1 extraction/isolation; Lane F2=Day 2 extraction/isolation; Lane F3=Day 3 extraction/isolation; and Lane F4=Day 4 extraction/isolation). Lanes indicted with − and + are negative and positive controls, respectively. The quantitation of the above PCR product DNA ranged approximately between 10 ng to 20 ng per band in Lane F1-Lane F4 (i.e., 2-4 ng/ul; total 60-120 ng/30 ul PCR reaction).

Example 17

High Sensitivity Detection of Mutations

This example illustrates the detection of a single-point mutation using PCR product DNA using a protocol sold commercially under the trademark Invader® (Third Wave Technologies, Madison, Wis.).

Figure 22:
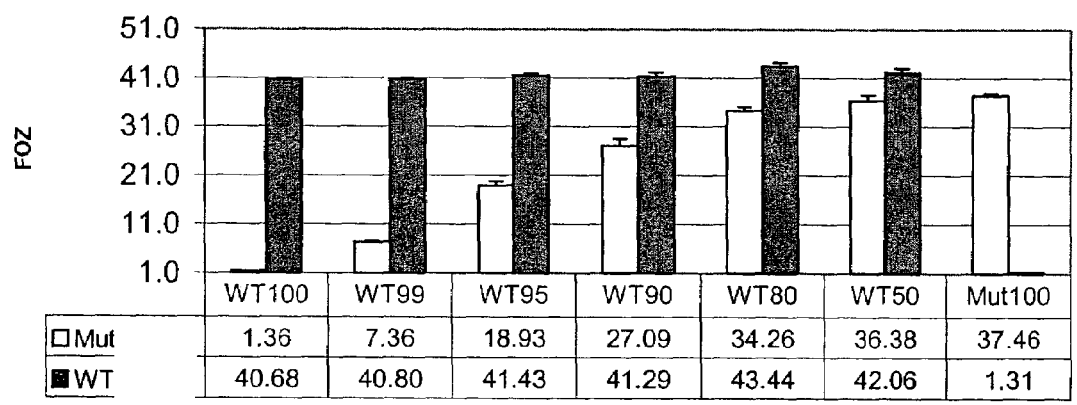
FIG. 22 shows exemplary data using various ratios of APC-1 mutant genes (open bars) and WT genes (solid bars) demonstrating the detection of a small amount of mutant genes over the large WT gene background using one embodiment of the Invader® assay. FOZ=Fold Over Zero.

This experiment evaluated the suitability of the Invader® assay to detect point mutations in DNA extracted from stool. Specifically, using DNA isolated from WT (HeLa) and mutant (LS1034) cell lines in various ratios (0.1%-10% total mutant), a mixed 1.5 KB PCR product was generated. This mixed PCR product was probed using the Invader® assay for a specific mutation designated APC-1 (e.g., Del5 at codon 1309). The results are shown in FIG. 22. Even at a sensitivity of 0.1% (i.e., detecting 1 mutant copy in 1000 WT copies) the mutations are detectable over the background; measured as Fold Over Zero (FOZ), exemplified by an experimental FOZ=2.39 versus a background FOZ=1.69. The results show that a mutant population of either 0.4% (FOZ=3.34) and 1% (FOZ=5.63) is detected with a very high confidence when the background FOZ=1.69.

The following probes and synthetic template sequences were utilized in this experiment:
APC1: Target DNA 1309 del5 (Del GAAAA)
GACGACACAGGAAGCAGATTCT-GCTAATACCCTGCAAATAGCAGAAATAAAA[GAA AA-]GATTGGAACTAGGTCAGCTGAAGATCCT-GTGAGCGAAGTTC
(SEQ ID NO: 66)
660541-Sa1P1: Probe (INS=3 12[21], $T_m$=63.35° C.)
acggacgcggagAGAAAAGATTGGAACTAGTC (SEQ ID NO: 67)
660541-Ss2I1: Invader 35 ($T_m$=77.31° C.)
CAGGAAGCAGATTCTGCTAATACCCTG-CAAATAGCAGAAATAAAt
(SEQ ID NO: 68)
660541-Ss1T1: Synthetic Target 70
TCTTCAGCTGACCTAGTTC-CAATCttttctTTTATTTCTGCTATTTG-CAGGGTATTAGCAG AATCTGCTTCCTGTG (SEQ ID NO: 69)
660541-Ss2P1: Probe (DEL=1 12 [22], $T_m$=62.14° C.)
cgcgccgaggAGATTGGAACTAGGTCAG (SEQ ID NO: 70)
660541-Ss2T1: Synthetic Target 65
TCTTCAGCTGACCTAGTTCCAATCTTT-TATTTCTGCTATTTGCAGGGTATTAGCAGAA TCT-GCTTCCTGTG (SEQ ID NO: 71)

In one embodiment, Invader® assays comprise 1 fmol of PCR product DNA (i.e., 128,000 femto-gram per 200 base pairs; 200 base pairs×640 femtograms/femtomole). In another embodiment, 60 to 500 ng of PCR product DNA (e.g., 469-3906 fmol) may be routinely obtained after a 30 ul PCR reaction (i.e., for example, approximately 2-17 ng/ul).

Example 18

Incorporation of Three Epitope Tags

This example demonstrates the method used for incorporating 3 epitope tags into PCR amplicons and their use in performing protein truncation test (VSV, HSV and P53 epitopes in APC segments as an N-terminal marker, binding element and C-terminal marker, respectively).

Genomic DNA (WT and APC mutant) was isolated from WT and APC mutant cell lines as well as from FAP patients using commercially available kits (Qiagen, Valencia, Calif.). Incorporation of three epitope tags using various primers has been achieved using two-step PCR. First, PCR amplification of a selected region of the APC gene (APC segment 3) was carried out using the following conditions: after an initial cycle of denaturation at 95° C. for 3 minutes; amplification was as follows: 35 cycles of denaturation at 95° C. for 45 seconds, annealing at 56° C. for 45 seconds and extension at 72° C. for 4 minute. The primer pair used was: Sense (HSV-APC3): 5'-ATG AAC CGC CTG GGC AAG GGA GGA GGA GGA CAG CCT GAA CTC GCT CCA GAG GAT CCG GAA GAT GTT TCT CCA TAC AGG TCA CGG GGA GCC-3' (SEQ ID NO:72) and antisense (APCLong3): 5'-AGA TGC TTGCTG GAC CTG GTC CAT TAT CTT-3' (SEQ ID NO:73). Each reaction was carried out in a total volume of 30 μL and contained: 0.5 μL of each sense (HSV-APC3, 10 mM) and antisense (APCLong3, 10 mM) primers; 1 μL of sample DNA; and 15 μL of High Fidelity PCR Master (Roche). Genomic Female DNA was used as a wild type control. After the PCR, samples (3 μL) were analyzed on a 2.0% agarose gel run at 165 volts for 70 minutes. 100 bp ladder was used as a DNA marker standard. Second PCR was carried put using the first PCR product as a template. Primers were: Sense (T7-VSV-ST1): 5' GGA TCC TAA TAC GAC TCA CTA TAG GGA GAC CAC CAT G GGC TAC ACC GAC ATC GAG ATG AAC CGC CTG GGC AAG GGA GGA GGA GGA-3' (SEQ ID NO:74) and antisense (BP53-APC3): 5'-TTA TTA CAG CAG CTT GTG CAG GTC GCT GAA GGT ACT TCT GCC TTC TGT AGG AAT GGT ATC 3' (SEQ ID NO:75). PCR conditions were as follows: after an initial cycle of denaturation at 95° C. for 3 minutes; amplification, 35 cycles of denaturation at 95° C. for 45 seconds, annealing at 56° C. for 45 seconds, and extension at 72° C. for 4 minute. Each reaction mixture was carried out in a total volume of 30 μL and contained: 0.5 μL of each sense (T7-VSV-ST1, 10 mM) and antisense (BP53-APC3, 10 mM) primers; 5 μL of PCR product from the first reaction (HSV PCR); and 15 μL of High Fidelity PCR Master (Roche). Genomic Female DNA was used as a wild type control. After the PCR, samples (3 μL) were analyzed on a 2.0% agarose gel run at 165 volts for 70 minutes. 100 bp ladder was used as a DNA marker standard.

Figure 23:
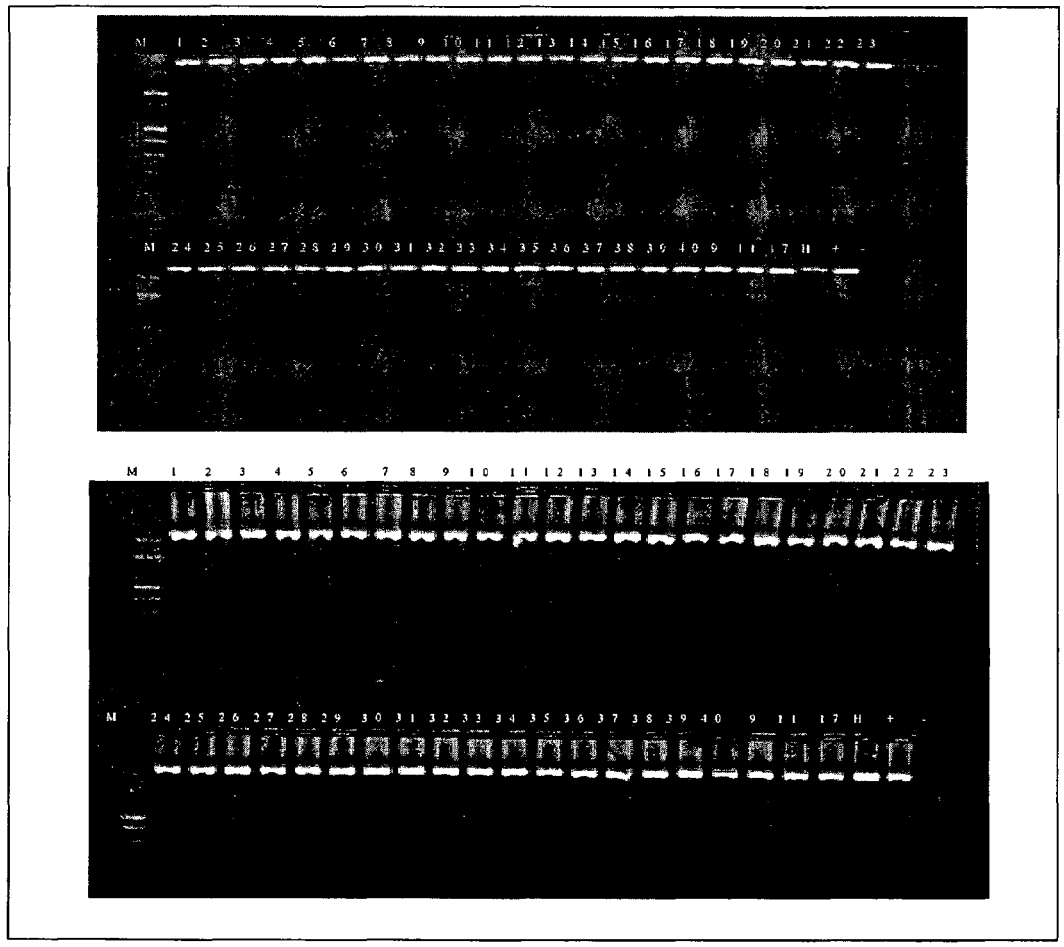
FIG. 23 shows exemplary data on gel electrophoresis experiment of APC segment 3 PCR DNA product from FAP patients. Top Panel shows the results of first PCR while bottom panel shows the results of second PCR. Lanes 1-40 correspond to different patient samples.

The results of PCR amplification of FAP patients DNA are shown in FIG. 23. Top panel shows the results of first PCR while bottom panel shows the results of second PCR. It is clear from the Figure that the amplification of patients DNA works well and produces enough DNA for downstream applications.

Example 19

SDS-PAGE Analysis of Translation of PCR Amplicon Containing Three Epitope Tags

This example utilizes VSV, HSV and P53 epitopes in APC segments as an N-terminal marker, binding element and C-terminal marker, respectively.

Cell-Free protein synthesis and SDS-PAGE: The cell-free reaction mixture contained 8 μl of TNT T7 Quick Rabbit Reticulocyte lysate for PCR DNA (Promega, Madison, Wis.), 0.5 μl of a complete amino acid mix, 0.5 μl of DNA (approximately 200 ng) and 0.5 μl of BODIPY-FL-lysyl-tRNA. The translation reaction was allowed to proceed for 45 min at 30° C. A 4-6 μl aliquot was used for SDS-PAGE electrophoresis. SDS-PAGE was carried out according to Laemmli. After electrophoresis, polyacrylamide gels were scanned using a FluorImager SI (Molecular Dynamics, Sunnyvale, Calif.) equipped with an Argon laser as an excitation source (488 nm line) and a 530±30 nm emission filter.

Figure 24:
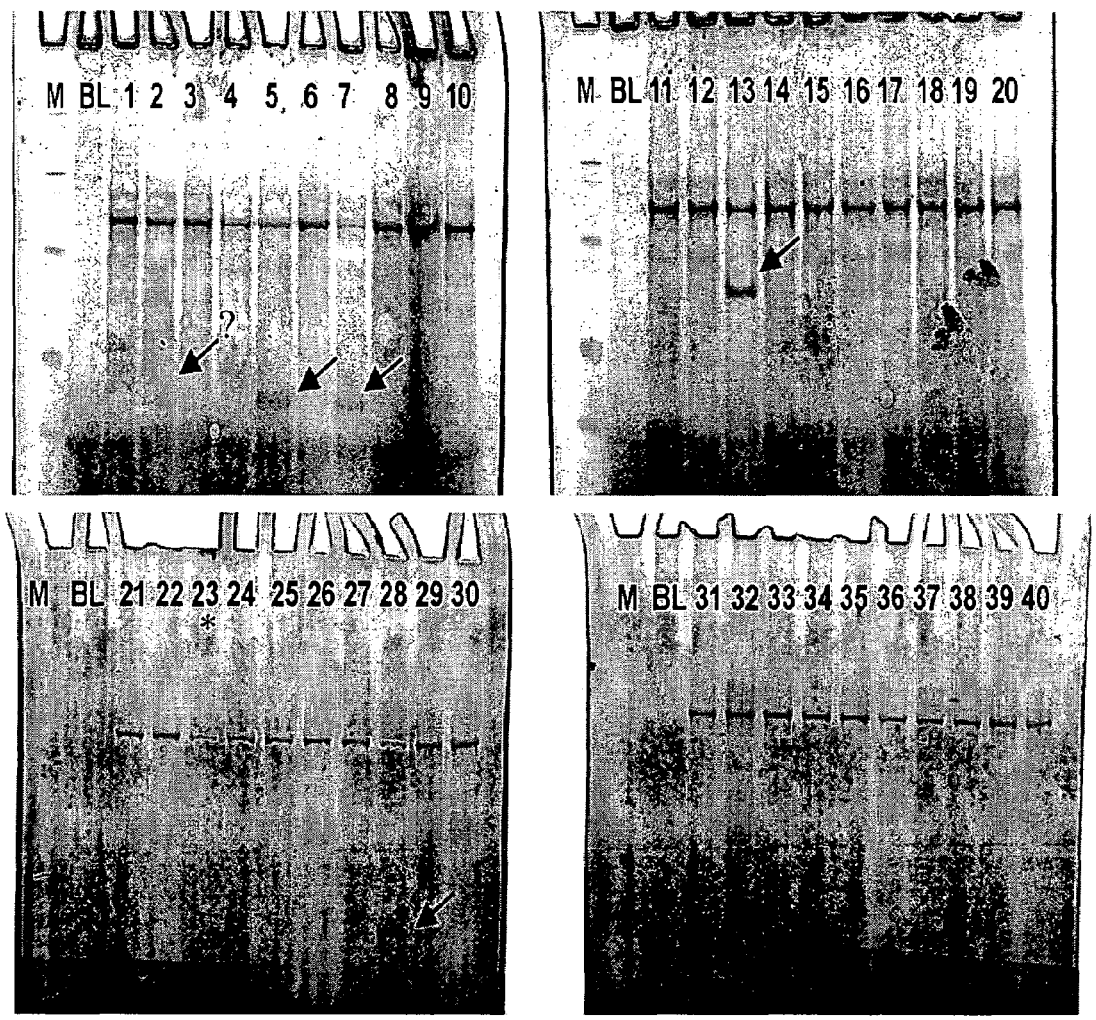
FIG. 24 shows exemplary fluorescent gel electrophoretic analysis data obtained on nascent protein synthesized using PCR amplicons corresponding to APC segment 3 DNA obtained from FAP patients DNA. Arrows indicate the position where the mutant protein migrates.

In the traditional PTT, the region of the gene to be analyzed is amplified by PCR (or RT-PCR for an mRNA template) using a primer pair that incorporates additional sequences into the PCR amplicons required for efficient cell-free translation. The amplified DNA is then added to a cell-free transcription-translation extract along with radioactive amino acids ($^{35}$S-methione or $^{14}$C-leucine). The expressed protein is analyzed by SDS-PAGE and autoradiography. Chain truncation mutations are detected by the presence of a lower molecular weight (increased mobility) species relative to the wild-type (WT) protein band. Here we demonstrate the use of Fluorotag tRNA for performing the non-isotopic PTT for APC gene. The results of gel electrophoresis of nascent protein synthesized using PCR template DNA is shown in FIG. 24. It is clear from the Figure that all the PCR template DNA produced significant fluorescently labeled proteins (either WT or mixture of WT and mutant).

Example 20

ELISA-PTT Analysis of PCR Amplicon Containing Three Epitope Tags

This example utilizes VSV, HSV and P53 epitopes in APC segments as an N-terminal marker, binding element and C-terminal marker, respectively.

Cell-Free protein synthesis and ELISA-PTT: The cell-free reaction mixture contained 8 μl of TNT T7 Quick Rabbit Reticulocyte lysate for PCR DNA (Promega, Madison, Wis.), 0.5 μl of a complete amino acid mix and 0.5 μl of DNA (approximately 200 ng). The translation reaction was allowed to proceed for 45 min at 30° C. After the translation, the reaction mixture was diluted 30-fold with TBS containing 0.05% Tween-20, 0.1% Triton X-100, 5% BSA, and both antibodies anti-VSV-G-HRP (Roche Applied Sciences, Indianapolis, Ind.) at 80 ng/mL and anti-p53-alkaline phosphatase (Santa Cruz Biotechnology, Santa Cruz, Calif.) at 100 ng/mL]. Subsequently, 100 μl of the diluted reaction mixture was added to each well of an anti-HSV antibody coated 96-well plate (pre-blocked with 5% BSA) and incubated for 45 min on an orbital shaker. Anti-HSV antibody was obtained from Novagen (Madison, Wis.) and Microlite2+ multiwell plates were obtained from Dynex Technologies (Chantilly, Va.). The plate was washed 5× with TBS-T (TBS with 0.05% Tween-20) followed by 2× with TBS and developed using a chemiluminescent alkaline-phosphatase (AP) substrate (Roche Biochemicals, Indianapolis). After the AP readings, the plate was washed 2 times with TBS and the HRP signal was measured using chemiluminescent HRP substrate (Supersignal Femto, Pierce Chemicals, Rockford, Ill.). After normalization, C/N was calculated.

Figure 25:
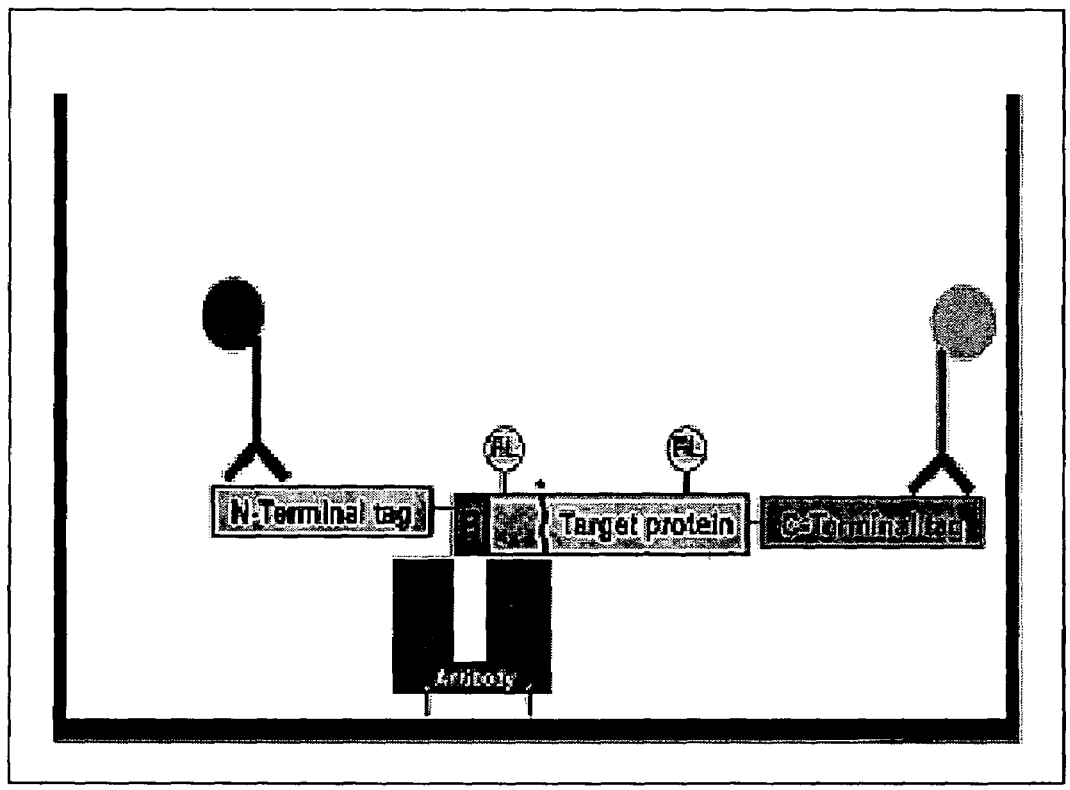
FIG. 25 shows exemplary schematics of 3-Tag ELISA-PTT.
Figure 26:
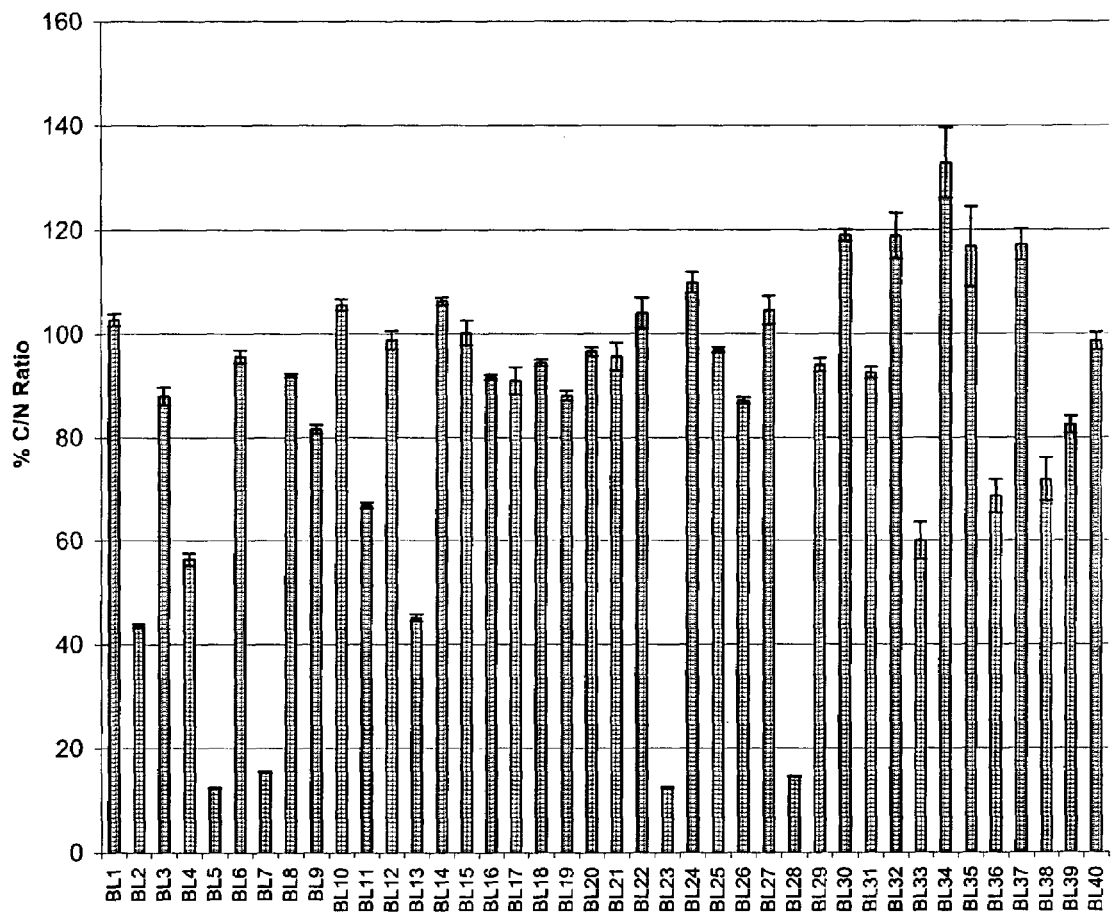
FIG. 26 shows exemplary ELISA-PTT results for APC segment 3 from FAP patients DNA. Top panel: First PCR with HSV-Tag and HA-Tag primers. Bottom panel: Second PCR with T7-VSV-p53-HA primers.

As an alternative to the SDS-PAGE based PTT, we have developed an ELISA-based high throughput protein truncation test (ELISA-PTT) that is compatible with multi-well or MicroArray formats. The schematics of ELISA-PTT are shown in the Figure C. Amplified DNA corresponding to the region of interest in the target gene is first generated using PCR with primers that incorporate N- and C-terminal epitope tags as well as a T7 promoter, Kozak sequence and start codon (ATG) in the amplicons. The resulting amplified DNA is subsequently added to a cell-free protein expression system. The cell-free transcription-translation reaction mixture is also supplemented with various misaminoacylated tRNAs carrying detection tags. As illustrated in FIG. 25, the incorporated binding tag (e.g. HSV epitope sequence) is used to capture the translated protein from the cell-free expression mixture onto a solid surface using anti-HSV antibodies. The N- and C-terminal epitope tags are used to compare the total amount of target protein bound (N-terminal signal) verses the fraction that is truncated (i.e. lacks a C-terminal). In addition, optional incorporation of a fluorescent label allows non-isotopic, direct detection of WT and truncated bands by SDS-PAGE. This feature is useful during initial assay development allowing the results of the HTS-PTT to be compared with the results from fluorescent-based SDS-PAGE. In the case of a positive diagnostic test for a chain truncating mutation, the approximate position of the mutation can be determined using the fluorescent label feature followed by local DNA sequencing to determine the exact position and nature of the mutation. The results of typical ELISA-PTT are shown in FIG. 26. It is clear from the Figure that WT and mutant samples can be clearly distinguished using percent C/N ratio. For example, almost all the WT samples, percent C/N ratios were 80-100 while percent C/N ratio for mutant samples ranged from 15 to 45.

Example 21

Development of Universal Primer Set for Second PCR for Incorporation of Three Epitope Tags This example demonstrates the strategy for developing a universal primer set for performing second PCR for incorporating 3 epitope tag into PCR amplicons and their use in performing protein truncation test (VSV, HSV and P53 epitopes in APC segments as an N-terminal marker, binding element and C-terminal marker, respectively).

Figure 27:
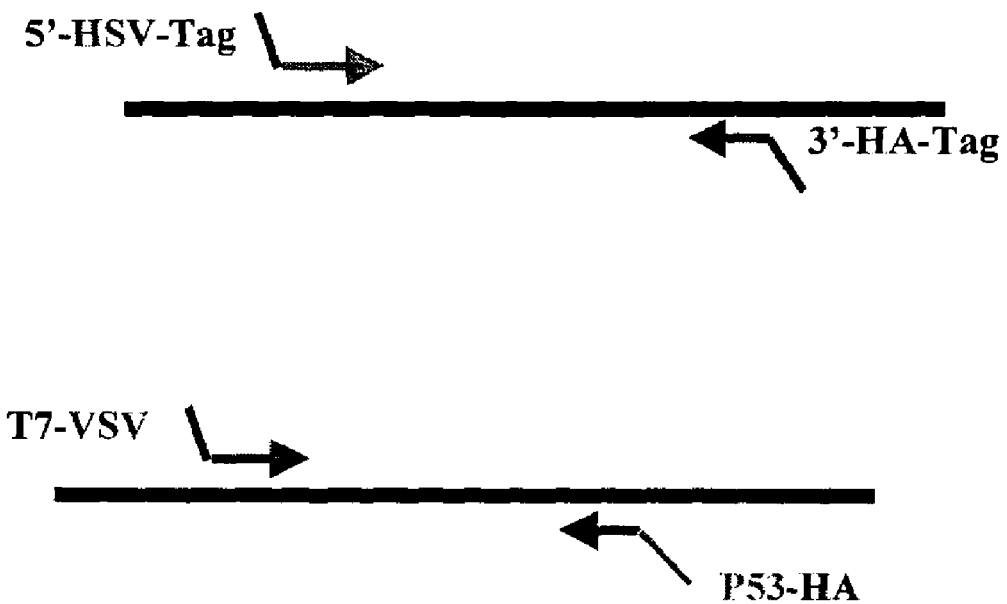
FIG. 27 shows exemplary example of 2-Step PCR using Universal Primer.

In accordance with Example 18, 2-step PCR was carried out successfully to obtain amplicons capable of producing a sufficient amount of nascent protein in cell-free translation system. However, when a significant number of different segments of the same gene of interest need to be carried out or different genes need to be analyzed, huge amounts of primer sets need to be generated and tested. For example, every segment will need at least four primers i.e. two primers for first PCR and 2 primers for second PCR. In order to avoid generation of a large number of primer pairs, we have streamlined the procedure of first PCR using a modified primer containing overlapping sequences. The schematics are shown in FIG. 27. This avoids the need to have separate primer sets for each second PCR (i.e. the same primer set can be used for the second PCR for any segment of a particular gene or any segment of any gene). The following are the details.

First PCR:
Primers: Sense (HSV-APC2): 5'-ATg AAC CgC CTg ggC AAg ggA ggA ggA ggA CAg CCT gAA CTC gCT CCA gAg gAT CCg gAA gAT AAT gCA TgT ggA ACT TTg Tgg AAT CTC 3' (SEQ ID NO:76) and Antisense (APC2—HA): 5'-GGC GTA ATC AGG CAC GTC ATA GGG ATA CCT CTT GGC ATT AGA TGA AGG TGT GGA-3' (SEQ ID NO:77).

Reaction mixture and cycling conditions: Each reaction was carried out in a total volume of 30 µL and contained: 0.5 µL of each sense (HSV-APC2, 10 mM) and antisense (APC2-HA, 10 mM) primers; 0.2 µL of genomic DNA; and 15 µL of High Fidelity PCR Master (Roche). After an initial cycle of denaturation at 95° C. for 3 minutes; amplification was as follows: 40 cycles of denaturation at 95° C. for 45 seconds, annealing at 58° C. for 45 seconds, and extension at 72° C. for 2 minutes.

Gel Analysis: Samples (5 µL) were analyzed on a 2.0% agarose gel run at 150 volts for 30 minutes. 100 bp ladder was used as a DNA marker standard.

Second PCR:
Primers: Sense (T7-VSV-ST1): 5'-GGA TCC TAA TAC GAC TCA CTA TAG GGA GAC CAC CAT G GGC TAC ACC GAC ATC GAG ATG AAC CGC CTG GGC AAG GGA GGA GGA GGA-3' (SEQ ID NO:78) and Antisense (BP53-HA): 5'-TTA TTA CAG CAG CTT GTG CAG GTC GCT GAA GGT GGC GTA ATC AGG CAC GTC ATA GGG ATA-3' (SEQ ID NO:79).

Reaction Mixture and cycling conditions: Each reaction was carried out in a total volume of 30 µL and contained: 0.5 µL of each sense (T7-VSV-ST1, 10 mM) and antisense (BP53-HA, 10 mM) primers; 1.0 µL of PCR product from the first reaction (HSV PCR); and 15 µL of High Fidelity PCR Master (Roche). After an initial cycle of denaturation at 95° C. for 3 minutes; amplification was as follows: 40 cycles of denaturation at 95° C. for 45 seconds, annealing at a 58° C. for 45 seconds, and extension at 72° C. for 2 minutes.

Gel Analysis: Samples (5 µL) were analyzed on a 2.0% agarose gel run at 150 volts for 30 minutes. 100 bp ladder was used as a DNA marker standard.

The results of first and second PCR are shown in FIG. 28. Top panel shows the results of first PCR while bottom panel shows the results of second PCR. It is clear from the Figure that the amplification of genomic DNA works well and produces enough DNA for downstream applications. By using this approach, one can limit the number of primers required to analyze various segments/genes by ELISA-PTT.

Example 22

Cell-Free Protein Synthesis and ELISA-PTT Using Templates Obtained Using Universal PCR This example was carried out in accordance with Example 21.

The cell-free reaction mixture contained 8 µl of TNT T7 Quick Rabbit Reticulocyte lysate for PCR DNA (Promega, Madison, Wis.), 0.5 µl of a complete amino acid mix and 0.5 µl of DNA (approximately 200 ng). The translation reaction was allowed to proceed for 45 min at 30° C. After the translation, the reaction mixture was diluted 30-fold with TBS containing 0.05% Tween-20, 0.1% Triton X-100, 5% BSA, and both antibodies anti-VSV-G-HRP (Roche Applied Sciences, Indianapolis, Ind.) at 80 ng/mL and anti-HA-alkaline phosphatase (Sigma Chemicals, St. Louis, Mo.) at 100 ng/mL). Subsequently, 100 µl of the diluted reaction mixture was added to each well of an anti-HSV antibody coated 96-well plate (pre-blocked with 5% BSA) and incubated for 45 min on an orbital shaker. Anti-HSV antibody was obtained from Novagen (Madison, Wis.) and Microlite2+ multiwell plates were obtained from Dynex Technologies (Chantilly, Va.). The plate was washed 5× with TBS-T (TBS with 0.05% Tween-20) followed by 2× with TBS and developed using a chemiluminescent alkaline-phosphatase (AP) substrate (Roche Biochemicals, Indianapolis). After the AP readings, the plate was washed 2 times with TBS and the HRP signal was measured using chemiluminescent HRP substrate (Supersignal Femto, Pierce Chemicals, Rockford, Ill.). After normalization, C/N was calculated.

Figure 29:
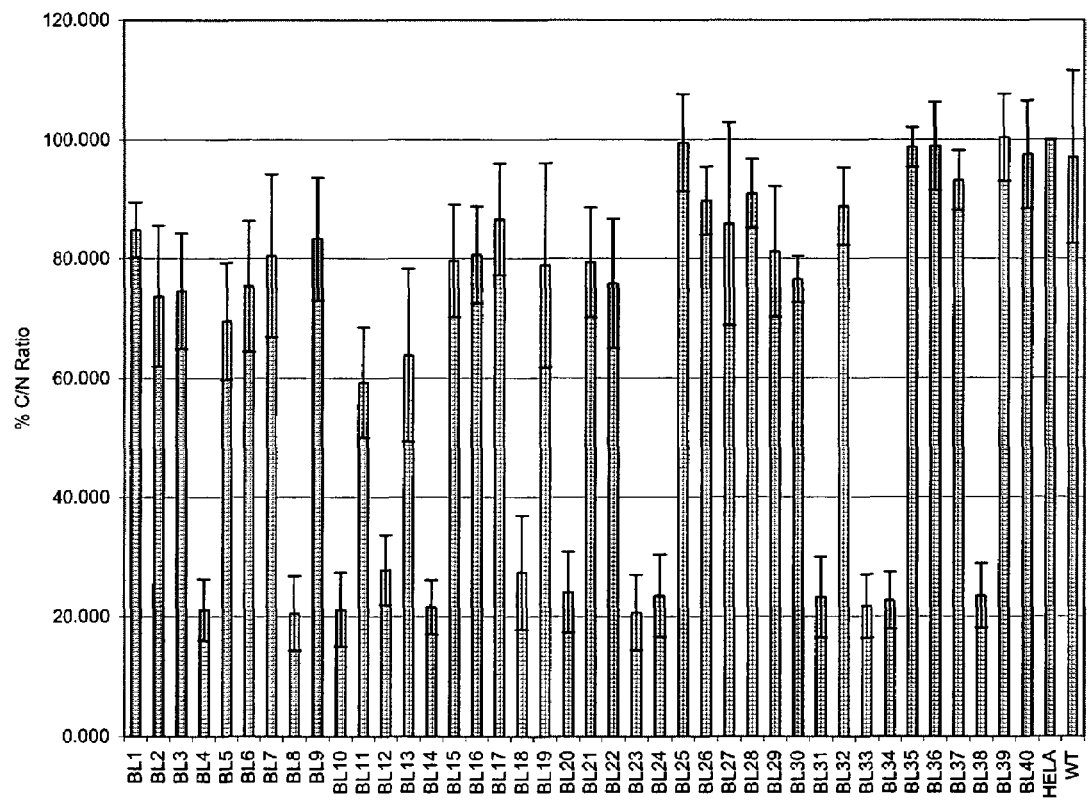
FIG. 29 shows exemplary example of ELISA PTT for APC segment 2 (PCR product obtained using universal primers) from FAP patients DNA (average of four independent experiments with standard deviations shown).

The results of ELISA-PTT using templates obtained from Universal PCR are shown in FIG. 29. It is clear from the Figure that WT and mutant samples can be clearly distinguished using percent C/N ratio. For example, percent C/N ratios for almost all the WT samples ranged from 80-100 while percent C/N ratio for mutant samples ranged from 15-45. This indicates the feasibility of using two-step universal PCR for generating the templates for ELSIA-PTT.

Example 23

Development of Long Primer Set for One-Step PCR

As described before, 2-step PCR was carried out successfully to obtain a good amplicon capable of producing a significant amount of nascent protein in cell-free translation systems. However, in an actual clinical setting 2-step PCR might pose a serious contamination problem. In order to avoid this problem, we have developed a primer set and used this set for one-step amplification of the target DNA. The forward primer, which is relatively long (133 bases), includes all the elements required for efficient in vitro (cell-free) translation (T7 promoter and Kozak sequence) as well as N-terminal detection tag (VSV epitope) and binding tag (HSV-Epitope). The reverse primer codes C-terminal detection tag (P53 epitope). The schematics are shown in FIG. 30. This avoids the need for two PCR reactions and minimizes the contamination problem. Apart from the contamination issue, this reduces the cost of the reaction in half since only a single PCR is necessary. The following are the details.

Primers: Sense (APC2-VH-Long): 5'-ggA TCC TAA TAC gAC TCA CTA TAg ggA gAC CAC CAT g TAC ACC gAC ATC gAg ATg AAC CgC CTg ggC AAg ggA ggA CAg CCT gAA CTC gCT CCA gAg gAT CCg gAA gAT AAT gCA TgT ggA ACT TTg Tgg AAT-3' (SEQ ID NO:80) and Antisense (BP53-APC2): 5'-TTA TTA CAG CAG CTT GTG CAG GTC GCT GAA GGT ACT TCT GCC TTC TGT AGG AAT GGT ATC-3' (SEQ ID NO:81).

Reaction mixture and cycling conditions: Each reaction was carried out in a total volume of 30 μL and contained: 0.25 μL of sense (APC2-VH-Long, 10 mM) and 0.5 μL of antisense (BP53-APC2, 10 mM) primers; 0.5 μL of genomic DNA; and 15 μL of Phusion High Fidelity PCR Master Mix (MJ Research, Waltham, Mass.). After an initial cycle of denaturation at 95° C. for 3 minutes; amplification was as follows: 40 cycles of denaturation at 95° C. for 45 seconds, annealing at 58° C. for 45 seconds, and extension at 72° C. for 2 minutes.

Gel Analysis: Samples (5 μL) were analyzed on a 2.0% agarose gel run at 150 volts for 30 minutes. 100 bp ladder was used as a DNA marker standard.

Figure 31:
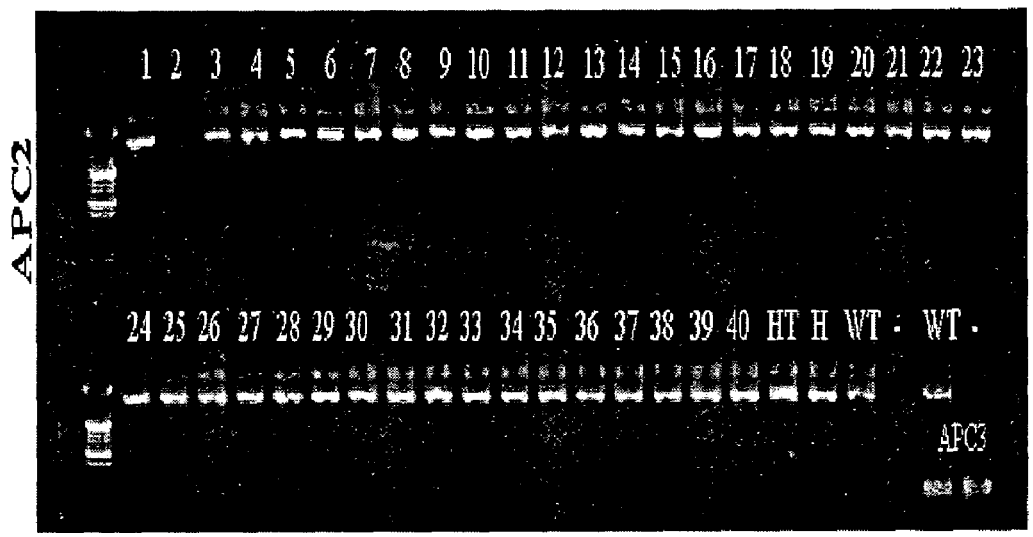
FIG. 31 shows exemplary example of PCR amplification of APC segment 2 from FAP patient DNA using Long primers. Lanes 1-40 correspond to different DNA samples. M is a marker.

The results of PCR are shown in FIG. 31. It is clear from the Figure that the amplification of genomic DNA works well and produces enough DNA for downstream applications. By using this approach, one can carry out single-step PCR to analyze various segments/genes by ELISA-PTT.

Example 24

Cell-Free Protein Synthesis and ELISA-PTT Using Templates Obtained Using One-Step PCR This example was carried out in accordance with Example 23.

The cell-free reaction mixture contained 4.35 μl of TNT T7 Quick Rabbit Reticulocyte lysate for PCR DNA (Promega, Madison, Wis.), 0.25 μl of a complete amino acid mix and 0.4 μl of DNA (approximately 200 ng). The translation reaction was allowed to proceed for 45 min at 30° C. After the translation, the reaction mixture was diluted 30-fold with TBS containing 0.05% Tween-20, 0.1% Triton X-100, 5% BSA, and both antibodies anti-VSV-G-HRP (Roche Applied Sciences, Indianapolis, Ind.) at 80 ng/mL and anti-p53-alkaline phosphatase (Santa Cruz Biotechnology, Santa Cruz, Calif.) at 100 ng/mL]. Subsequently, 100 μl of the diluted reaction mixture was added to each well of an anti-HSV antibody coated 96-well plate (pre-blocked with 5% BSA) and incubated for 45 min on an orbital shaker. Anti-HSV antibody was obtained from Novagen (Madison, Wis.) and Microlite2+ multiwell plates were obtained from Dynex Technologies (Chantilly, Va.). The plate was washed 5× with TBS-T (TBS with 0.05% Tween-20) followed by 2× with TBS and developed using a chemiluminescent alkaline-phosphatase (AP) substrate (Roche Biochemicals, Indianapolis). After the AP readings, the plate was washed 2 times with TBS and the HRP signal was measured using chemiluminescent HRP substrate (Supersignal Femto, Pierce, Rockford, Ill.). After normalization, C/N was calculated.

Figure 32:
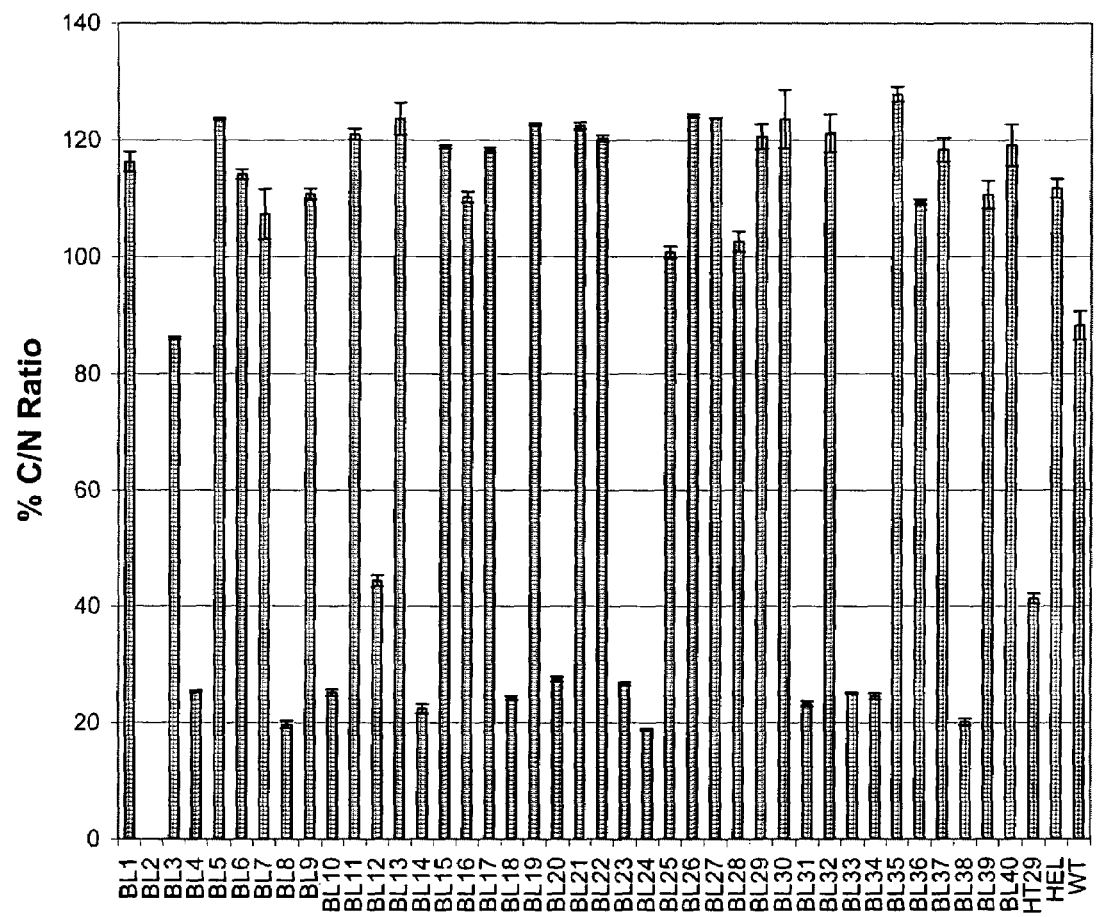
FIG. 32 shows exemplary example of ELISA PTT for APC segment 2 (PCR product obtained using one-step PCR) from FAP patients DNA (average of four independent experiments with standard deviations shown).

The results of ELISA-PTT using templates obtained from one-step PCR are shown in FIG. 32. It is clear from the Figure that WT and mutant samples can be clearly distinguished using percent C/N ratio. For example, percent C/N ratio for almost all the WT samples ranged between 80 and 100 while percent C/N ratio for mutant samples was in the range of 15 to 45. This indicates the feasibility of using one-step PCR for generating the templates for ELISA-PTT.

Example 25

FOBT-Plus Concept

Figure 34:
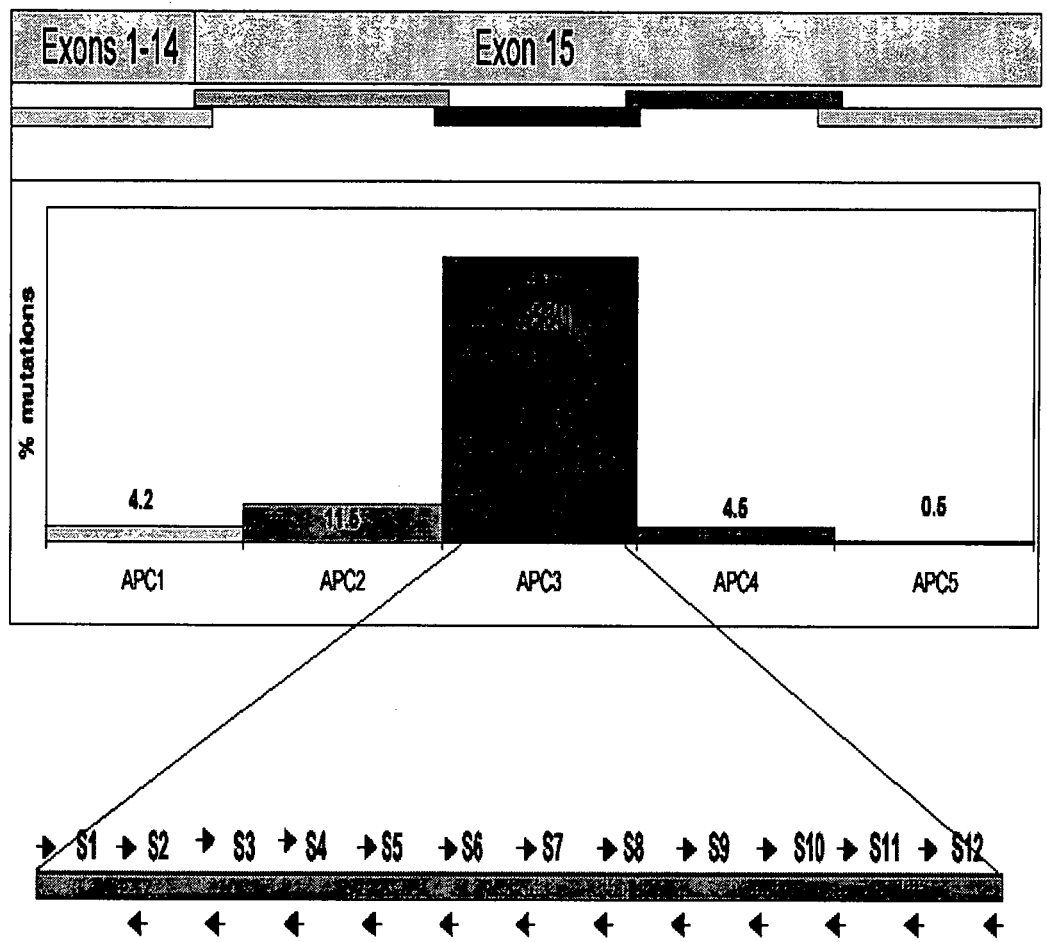
FIG. 34 shows one embodiment of a mutation cluster region within the APC gene used during a MASSIVE-PRO assay.
Figure 35:
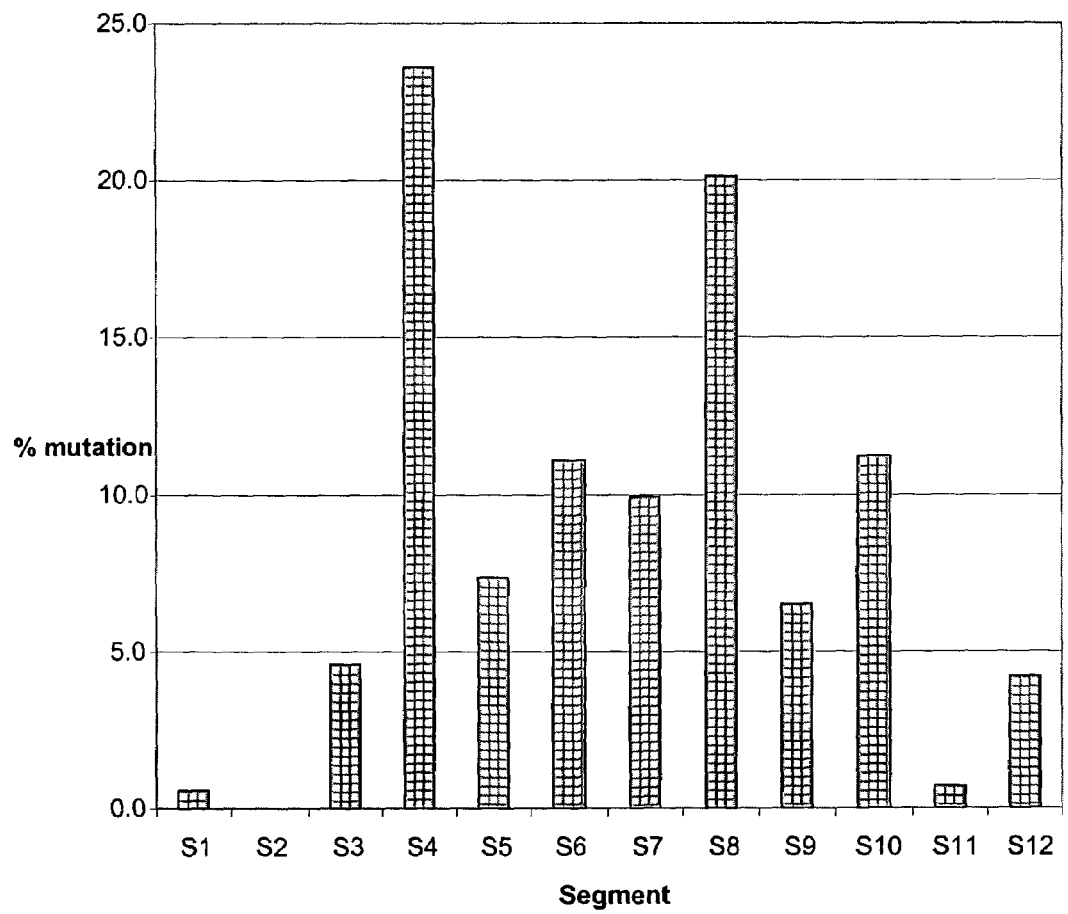
FIG. 35 shows exemplary example of mutation distribution over the APC gene's 12 mutation cluster segments that are used for MASSIVE-PRO assay.

Most of the mutations are clustered in MCR (Mutation Cluster Region). Current database analysis indicates that, out of 841 mutations reported in case of sporadic colorectal cancer; 695 (83%) resides in MCR. For Massive-Pro assay the MCR is further divided in 12 segments (FIG. 34). So accurate mutation scanning in MCR will itself results in high-sensitivity assay. Furthermore, mutations are not equally distributed over the 12 segments. For example, Segment 2 (S2) has virtually no mutation reported while Segment 4 (S4) has 23% mutations and Segment 7 (S7) has 20% (FIG. 35). So theoretically performing MASSIVE-PRO assay for two segments (S4 and S7) should yield approximately 43% mutation detection efficiency.

Example 26

Incorporation of FLAG and HA Epitopes in APC Segments

This example describes the incorporation of FLAG and HA epitopes in APC segments as N- and C-terminal markers, respectively.

DNA, RNA and PCR: Stool DNA was isolated using commercially available kits (Qiagen, Valencia, Calif.). PCR amplification of a selected region of the APC gene (APC segment 3-MS) was carried out using 250-500 ng of genomic DNA, 0.6 μM primer mix (forward and reverse) and 1×Taq PCR master mix (Qiagen, Valencia, Calif.).

Amplification was performed as follows: an initial denaturation step at 95° C. for 60 sec, forty cycles of denaturation at 95° C. for 20 sec, annealing at 55° C. for 20 sec, extension at 72° C. for 30 sec. and a final extension step at 72° C. for 5 min. Examples of the primer pairs are: APC-51 forward:

5'-TAA TAC GAC TCA CTA TAG GGA GGA GGA CAG CT ATG GAC TAC AAG GAC GAC GAT GAC AAG GGA CAA AGC AGT AAA ACC GAA-3' (SEQ ID NO:82); APC-51 reverse: 5'-TTT TTT TT TTA TGC GTA GTC TGG TAC GTC GTA TGG GTA TTTATTTAT AGC CTT TTG AGG CTG ACC ACT-3' (SEQ ID NO:83; APC-54 forward: 5'-TAA TAC GAC TCA CTA TAG GGA GGA GGA CAG CT ATG GAC TAC AAG GAC GAC GAT GAC AAG CAG GAA GCA GAT TCT GCT AAT-3' (SEQ ID NO:84) and APC-54 reverse: 5'-TTT TTT TT TTA TGC GTA GTC TGG TAC GTC GTA TGG GTA TTTATTTAT CTG CAG TCT GCT GGA TTT GGT-3 (SEQ ID NO:85). The italicized nucleotides in the forward primer correspond to the T7 promoter, the underlined ATG is the initiation codon, the boldface nucleotide region codes for the N-terminal FLAG-tag (DYKDDDDK) (SEQ ID NO:7) and the remaining nucleotide sequences correspond to the complementary region of the APC gene. In the reverse primer, the boldface nucleotides code for the C-terminal HA tag (YPYDVPDYA) (SEQ ID NO:9), the underlined TTT ATT TAT sequence codes for stop codons in the case of +1 and −1 frameshifts while the rest of the nucleotide sequence is complementary to the APC gene and nucleotides in italics (TTA) codes for a stop codon. After amplification, the quality and quantity of the PCR products was analyzed by agarose gel electrophoresis.

Example 27

Figure 36:
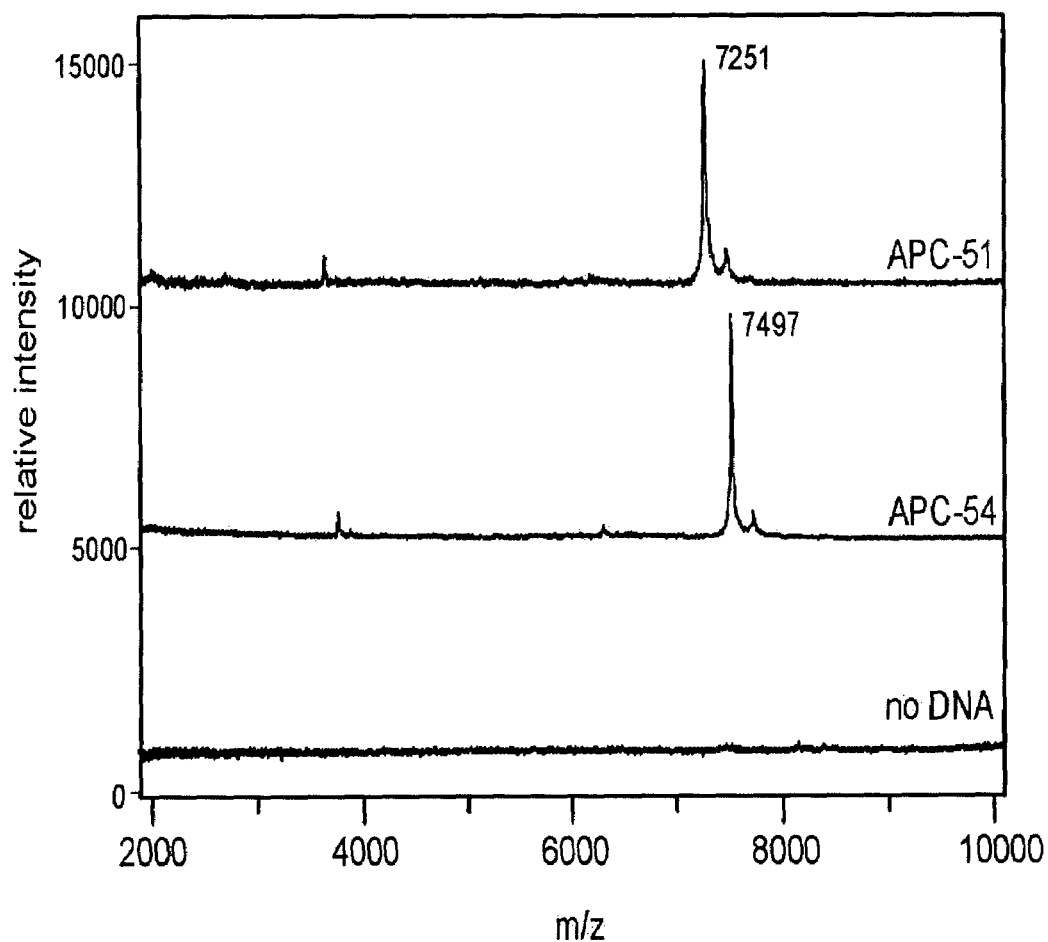
FIG. 36 shows exemplary example mass Spectrometric analysis of translation products derived from amplicons that are obtained from volunteer's stool DNA.

Cell-Free Protein Synthesis and Detection of Mutations in Nascent Proteins Using MALDI-Mass Spectrometry The cell-free reaction mixture contained 9 µl of PURESYSTEM classic II translation system (Post Genome Institute Co, Japan) and 1 µl of DNA (approximately 200 ng). A translation reaction was allowed to proceed for 45 min at 37° C. After the incubation, the reaction products were analyzed by MALDI-MS as described below. After a translation reaction, the reaction was terminated by addition of 100 µL of wash solution containing 100 mM EDTA, 1×PBS (phosphate buffered saline) and 0.1% Triton-X100 and immediately applied to the microcolumn containing 1 µL of packed beads (EZview™ Red ANTI-FLAG® M2 Affinity Gel; Sigma, St. Louis). The beads were then washed with 50 µL of wash solution followed by 50 µL of deionized H₂O and the bound peptide was eluted with ~2 µL of matrix solution (20 mg/mL sinapinic acid, 50% acetonitrile, 0.3% TFA) directly onto a MALDI plate. In a control experiment, translation was carried out without any added DNA (PCR product) and was processed as described above. When the translation was carried out using the PCR amplicons obtained from DNA isolated from volunteers' stool sample (Colonoscopy negative subjects), predominant peaks corresponding to the expected molecular weight of WT fragments were observed in all 12 fragments. The example for APC-51 and APC-54 is shown in FIG. 36. No peaks were observed in the control translation reaction i.e. translation performed in the absence of DNA.

Example 28

High Sensitivity Mutation Detection by MASSIVE-PRO

Detection of the low levels of mutant DNA that are expected to be present in fecal DNA is a critical requirement for MASSIVE-PRO. For example, it has been estimated that less than 1% mutant copies relative to WT are likely to be present in patients with CRC or large adenomas that are likely to transform into neoplastic polyps (Kinzler, K. W. and B. Vogelstein, Cancer-susceptibility genes. Gatekeepers and caretakers. Nature, 1997, 386(6627), 761-763). In order to test the feasibility of high sensitivity mutation detection using MASSIVE-PRO, we initially analyzed various mixtures of WT and mutant APC DNA obtained from cell lines.

Figure 37:
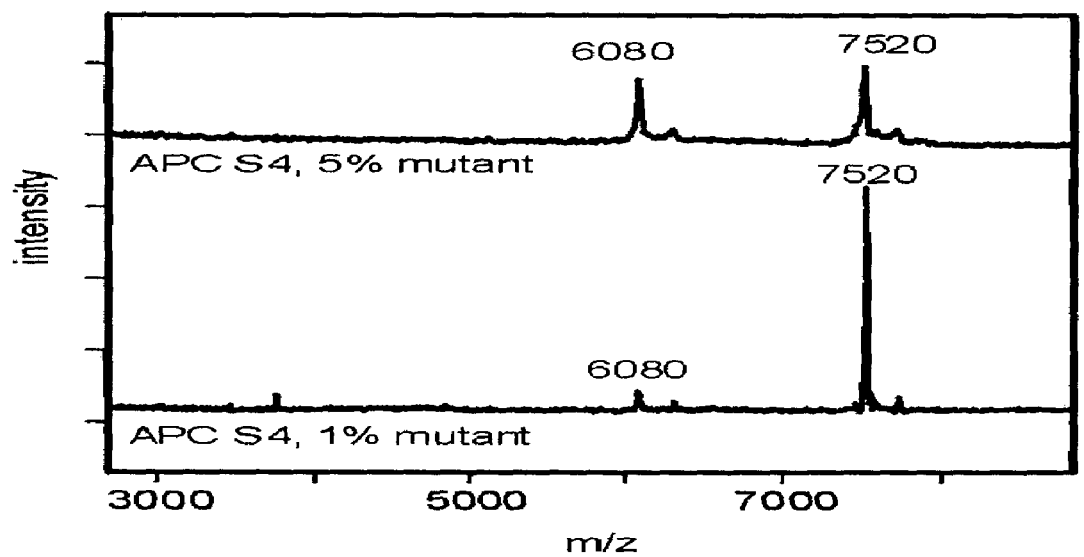
FIG. 37 shows exemplary example of high sensitivity MASSIVE-PRO. Mass spectra of 5% (top) & 1% (bottom) of APC mutant. Wild-Type predicted mass=6,082 Da. Mutant predicted mass=7,522 Da.

In one experiment, we utilized codons 1301-1331 of the APC gene as a test sequence (90 bases excluding primer sequences). The PCR products obtained from the WT and mutant cell-line DNA were mixed in various ratios (20:1 (5%) and 100:1 (1%)) and used for cell-free translation in the PURE system. After the translation, nascent peptides were purified by capture using the N-terminal FLAG-epitope. Our initial results (FIG. 37) show clearly that MASSIVE-PRO can unambiguously detect a 5% mutant population. A smaller band can even be seen (bottom trace) for the 1% population, thereby establishing that at least for this example, 1% detection is possible.

Figure 38:
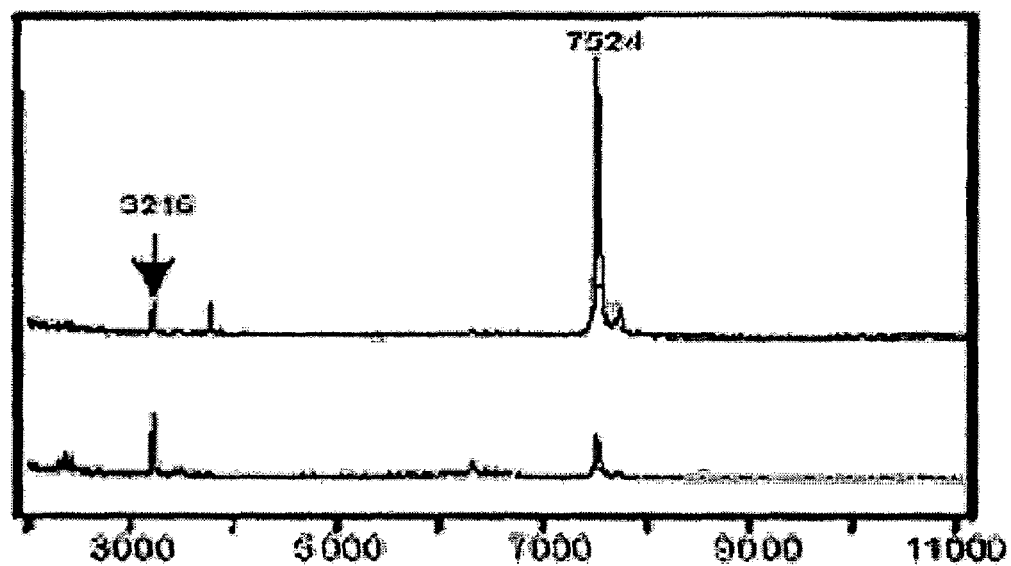
FIG. 38 shows exemplary example of sensitivity detection of MASSIVE-PRO can be achieved using WT depletion. Wild-Type predicted mass=7,509. Mutant predicted mass=3,202 Da.

In a second experiment, an even higher sensitivity was achieved with a proprietary technique we developed for reducing the presence of WT sequence. This is important because reduction of WT polypeptides allows more intensity to be achieved for mutant peaks. For this test, we have used a polypeptide encoded by codon 1301-1331 of the APC gene comprising the most common APC mutation, Δ5 at 1309. The PCR products obtained from the WT and mutant cell-line DNA were mixed in 100:1 ratio (WT: mutant) and used for cell-free translation in PURE system. After the translation, full-length peptides (WT) were removed by C-terminal based capture (HA-tag) prior to capture by N-terminal epitope (FLAG). Our results (FIG. 38) indicate that MASSIVE-PRO can easily detect 1 mutant copy in 100 total copies if the WT peptide is removed prior to mass spec analysis.

Example 29

Advanced Primer Design for MASSIVE-PRO

Figure 39:
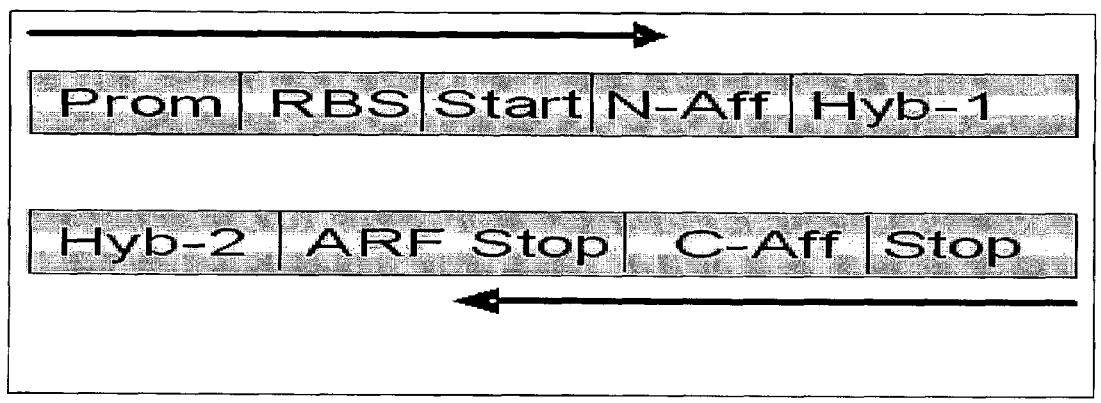
FIG. 39 shows exemplary example of design of forward (top) and reverse (bottom) primers for MASSIVE-PRO analysis of APC gene using fecal samples

The DNA template created by PCR amplification must contain elements that are essential for the efficient transcription, translation and purification of the polypeptide fragments to be analyzed by MASSIVE-PRO. Hence, as shown in FIG. 39, the forward primer (5'-primer) includes a promoter sequence (Prom) which should be appropriate for the particular cell-free translation system used (e.g. for PURE system a T7 promoter), a ribosome binding sequence (RBS), a start codon, N-terminal affinity tag (N-Aff; e.g. FLAG epitope). Similarly, the reverse primer (3'-primer) is designed to contain a C-terminal epitope tag (C-Aff) and a stop codon. An additional unique feature is the addition of an alternative reading frame (ARF) stop codon. The ARF stop is a unique proprietary universal sequence designed by AmberGen for out-of-frame mutants which are located at the 3'end of an amplicon and do not cause a mutant truncating stop codon before the C-terminal epitope tag. Mutations which result in out-of-frame reading can lead to longer polypeptides than that of WT if the ribosome does not encounter a chain truncating stop codon prior to the sequence for the C-terminal epitope. To avoid this we have developed a method which utilizes a proprietary alternative reading frame (ARF) stop codon. The reverse primers contain three codons TTT ATT TAT complementary to ATA AAT AAA in the 5'→3' sequence, which encode Ile-Asn-Lys. The ARF stop sequence contains a termination codon TAA in two alternative reading frames. The presence of these extra codons guarantees that any frame-shift mutation within the test sequence results in a premature termination of the peptide synthesis.

The C-terminal tag is designed to serve two purpose: i) it can be used for wild-type peptide depletion using affinity chromatography; and ii) it guarantees a minimum mass separation of 1100 Da for a wild type and mutant which occurs just before the 3'-end of the reading frame. The Hyb-1 and Hyb-2 sequences in the primer (FIG. 39) determines the region of the gene to be scanned for a particular segment. Primer pairs will be initially designed to maintain a test polypeptide length of less than 40 amino acids. This is important since in general shorter peptides produce more intense mass spectral peaks (Koomen, J. M., H. Zhao, D. Li, J. Abbruzzese, K. Baggerly, and R. Kobayashi, Diagnostic protein discovery using proteolytic peptide targeting and identification. Rapid Commun Mass Spectrom, 2004, 18(21), 2537-2548 and Leushner, J., MALDI TOF mass spectrometry: an emerging platform for genomics and diagnostics. Expert Rev Mol Diagn, 2001, 1(1), 11-18). Our initial experiments indicate that less than 40 amino acids results in sufficient signal intensity for high sensitivity detection.

Example 30

Removal of Short Polypeptides Which are Caused by Ribosomal Arrest in MASSIVE-PRO Our preliminary experiments revealed background peaks which can interfere with the detection of peaks arising from mutants. These peaks may arise from incomplete translation of the RNA due to ribosomal arrest, perhaps associated with secondary structure of the message. (Voges, D., M. Watzele, C. Nemetz, S. Wizemann, and B. Buchberger, Analyzing and enhancing mRNA translational efficiency in an *Escherichia coli* in vitro expression system. Biochem Biophys Res Commun, 2004, 318(2), 601-614; de Smit, M. H. and J. van Duin, Control of translation by mRNA secondary structure in *Escherichia coli*. A quantitative analysis of literature data. J Mol Biol, 1994, 244(2), 144-150 and Zama, M., Discontinuous translation and mRNA secondary structure. Nucleic Acids Symp Ser, 1995(34), 97-98). If so, these polypeptides are expected to remain bound to ribosome complexes. In agreement, we have found that we can partially reduce contributions of these background peaks to the mass spectrum by filtering the translation reaction mixture with a 100 kDa cut-off filter prior to analysis in order to remove large ribosome bound complexes.

Example 31

Optimization of Primers to Avoid mRNA Structure

The secondary structure of the transcript (mRNA) can reduce translation efficiency. In order to reduce this possibility we will continue to examine the effect of: Introducing silent substitutions in the 5' and 3' primers in order to avoid undesirable base paring and using additives that are known to interfere with RNA folding. These included $MgCl_2$ in the millimolar range and betaine (trimethylglycine) in the sub-molar range which we have shown does not interfere significantly with protein expression.

Example 32

Computer-Based Enhancement of Mutant Peaks

Initial studies revealed that there exists a constant background in typical MASSIVE-PRO spectra which survives purification steps discussed above. We have been able to successfully remove much of this background by utilizing standard spectral subtraction software, thus allowing small mutant peaks to be detected. In addition, special software can be utilized to analyze the data and detect new peaks in the mass spectra. Such software is already commercially available for proteomics research (for example ClinProTools software for biomarker detection and evaluation from Bruker Daltonics).

Example 33

High Sensitivity Detection of Chain Truncating Mutations "On the Edge"

Figure 40:
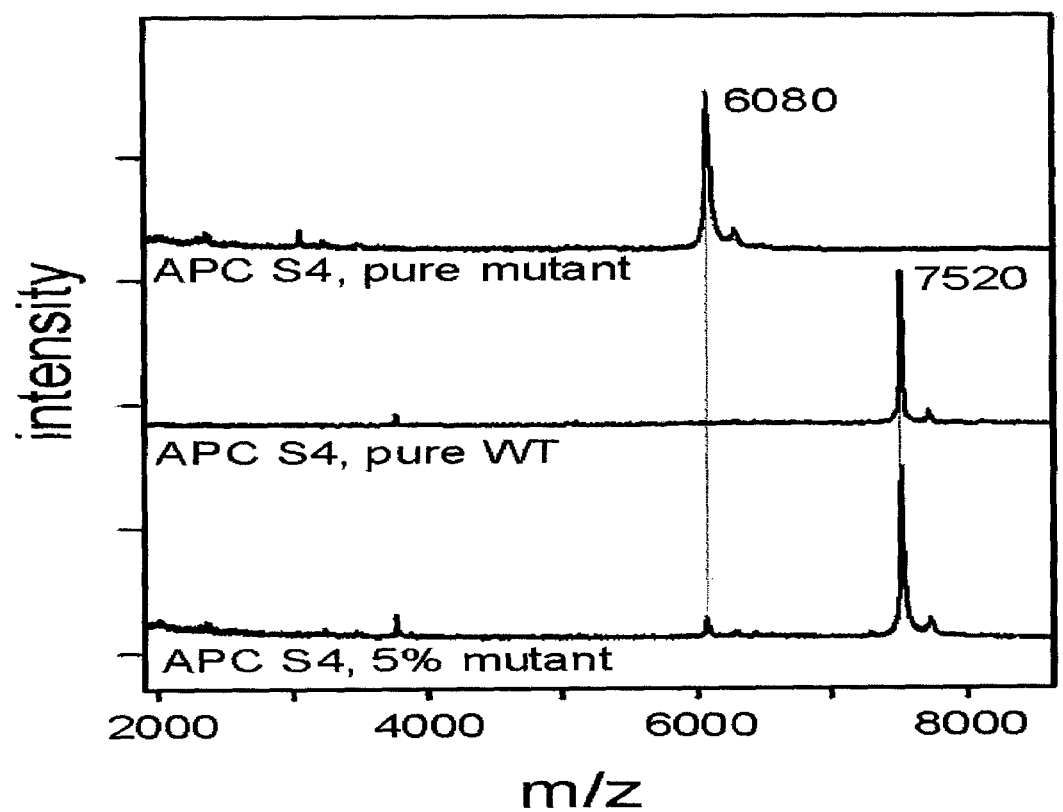
FIG. 40 shows exemplary example of high-sensitivity MASSIVE-PRO for detecting mutants at or near C-terminal.

The ability to detect chain truncation mutations in fecal DNA will require an assay sensitivity of greater than 1%. Furthermore, since in general smaller peptides produce higher signal intensity in the mass spectrum of polypeptides, the occurrence of a chain truncation should enhance the ability to detect the peptide. However, "a worse case scenario" is if the chain truncation occurs at or near C-terminal (edge mutation), thereby minimizing the mass difference and thus intensity of WT and mutant. In order to test the feasibility of high sensitivity detection of mutants, even in this worse case scenario we performed several preliminary measurements. In order to evaluate the ability to detect the S4 APC edge chain truncation at lower concentration, the WT and mutant DNA were premixed at various ratios and after cell-free translation in PURE subjected to MASSIVE-PRO as described above. The results, shown in FIG. 40, clearly indicate that even MASSIVE-PRO can detect this worst case mutation at the 5% level. It is evident from the Figure that, apart from mutant APC peak, one can clearly see the doubly charged species of WT peak.

Example 34

Multiplexing the MASSIVE-PRO CRC Assay

Figure 41:
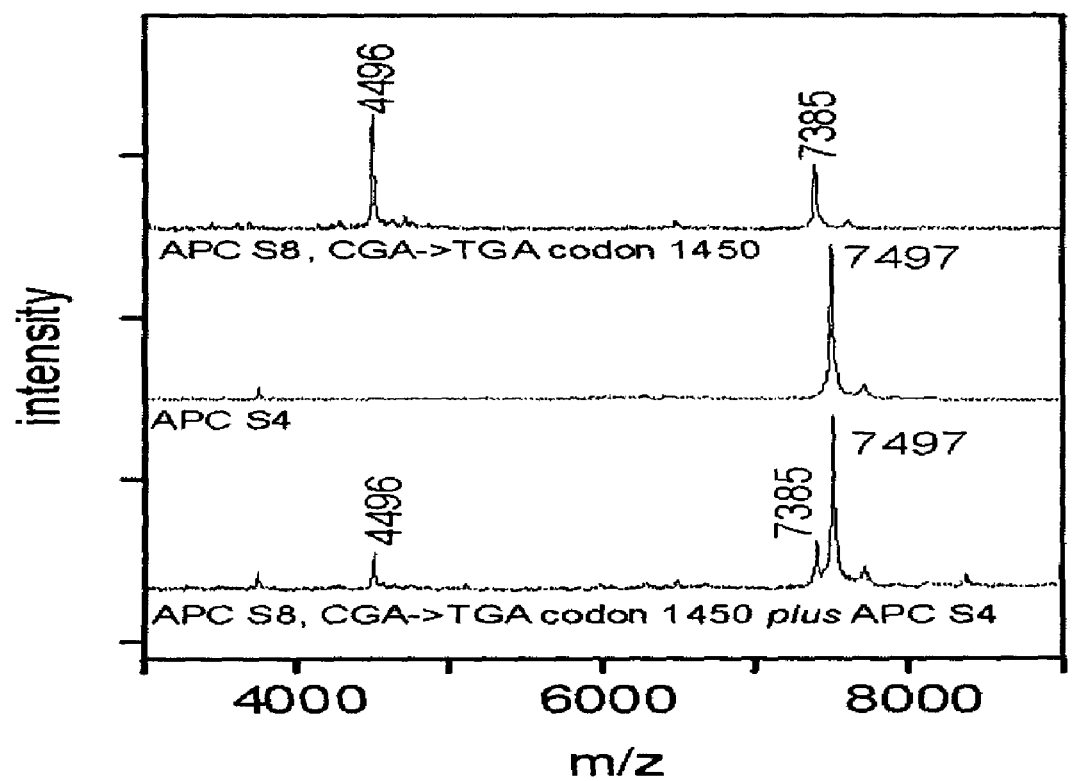
FIG. 41 shows exemplary example of multiplexing MASSIVE-PRO: Top and middle traces represent single-plex mass spectrum while the bottom trace corresponds to multiplex spectrum obtained from the single translation reaction containing DNA mixture.

Mass spectrometry has the ability to analyze simultaneously the mass of multiple polypeptides. When using MASSIVE-PRO, multiplex detection of several WT segments and simultaneous scanning for possible mutations can lower time and cost of ultimate CRC assay. As a first step toward multiplexing, 2 different APC segments which were translated in a single cell-free reaction. Note that one segment was derived from a heterozygous cell line containing a mutation in that segment. After the translation, nascent peptides were co-purified using a FLAG-antibody capture and analyzed by mass spectrometry. The results of one such experiment is shown in FIG. 41. The top two traces show mass spectra recorded of the individual WT APC S4 (middle trace) and the WT APC S8 with its chain truncating mutant at codon 1450 (top trace). The top trace represents single-plex mass spectrum of the heterozygous mutant CGA→TGA in codon 1450 in the segment S8. The middle trace represents single-plex mass spectrum of the wild type APC segment S4. The bottom trace corresponds to multiplex spectrum obtained from the single translation reaction containing DNA mixture (1:1) for segments S4 and S8. Peaks from both wild-type and mutant APC S8 as well as S4 are evident.

The two APC segments plus the mutant all exhibit the expected masses calculated from the nucleotide sequences. Importantly, all three bands can also be detected in the multiplexed reaction and measurement, demonstrating the feasibility of at least performing 2-fold multiplexing.

Example 35

Assay Validation Using Tumor Tissue Sample

One of the important criteria is to evaluate the ability of MASSIVE-PRO to detect specific mutations associated with CRC. For this purpose, mutations detected in tumor tissue removed from patients diagnosed with CRC during surgery are compared to the results from MASSIVE-PRO analysis of stool samples collected prior to surgery.

Figure 42:
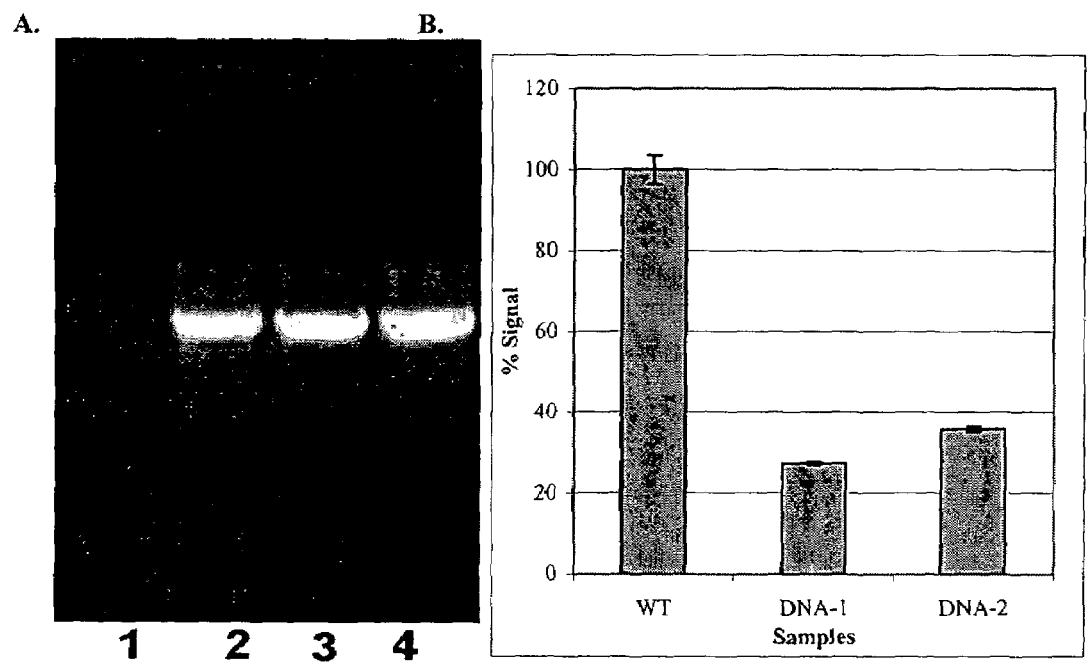
FIG. 42 shows exemplary example of analysis of Polyp Sample by APC PCR and ELISA-PTT. Panel A: APC PCR using DNA isolated from polyps. Lane 1: No template; Lane 2: WT HeLa DNA; Lane 3: Polyps DNA-1; and Lane 4: Polyps DNA-2. Panel B: Preliminary ELISA-PTT analysis. Both DNA-1 and DNA-2 show reduced C/N signal strength (indicates truncation mutation).

Compared to fecal samples, tumors tissues are expected to contain a significantly enriched APC mutant population. Moreover, micro-dissection of tumors allows further enrichment of cancerous cell populations which can then be subjected to conventional DNA sequencing of the APC gene. Overall, the approach of micro-dissection of tumors samples therefore provides us with a method to validate the results of MASSIVE-PRO. In order to confirm the feasibility of this approach, preliminary experiments were performed aimed at analyzing DNA recovered from polyps removed from patients diagnosed with FAP, an inherited form of colorectal cancer. DNA was isolated from two patients using 10 micron sections of paraffin-embedded polyp samples using the QIAamp DNA Mini Kit (Qiagen, Valencia, Calif.). These DNA samples were PCR amplified using specialized primers (31) for segment 2 in Exon 15 of the APC gene. PCR products of the expected size (1.5 Kb) were obtained (FIG. 42; A). DNA sequencing revealed the existence of truncation mutations at codon 876 and 1125 in this APC segment.

As a further confirmation of the ability to rapidly detect chain truncating mutations from tumor embedded tissue, the amplicons were subjected to ELISA-PTT, an advanced approach to the protein truncation test which does not utilize radioactivity or gel electrophoresis (Gite, S., M. Lim, R. Carlson, J. Olejnik, B. Zehnbauer, and K. Rothschild, A high-throughput nonisotopic protein truncation test. Nat Biotechnol, 2003, 21(2), 194-197). The results shown in FIG. 42 clearly indicate that the polyp samples from FAP patients contain chain-truncating mutations in agreement with the sequencing results. For example, compared to WT DNA (HeLa cell line), the C/N ratio of the FAP samples were 27 and 37 percent. However, note that since FAP is an inherited disease, all polyp cells from these patients should contain these specific APC mutations. This experiment shows the feasibility of using DNA isolated from polyps for either ELISA-PTT or DNA sequencing which can be used for MASSIVE-PRO result validation.

Example 36

Measuring Mutant Detection Sensitivity

The basic experimental protocol involves spiking fecal DNA with varying levels of mutant DNA derived from cell-lines. A basic requirement for these measurements is to determine the absolute amount of APC DNA present in the fecal DNA sample as well as mutant DNA added. Quantitation of human DNA in the total fecal DNA sample along with mutant DNA derived from cell-lines will be carried out using real-Time PCR as described below. Human female genomic DNA (Novagen, Madison, Wis.) was serially diluted 10-fold to 10,000-fold to achieve a starting copy number ranging from 30,000 to 3 copies per 5 µl of template.

These dilutions were subjected to real-time PCR on an ABI PRISM 7700 Sequence Detection System (Applied Biosystems, Foster City, Calif.) using the following primers: Forward: 5'-AGGCAAAGTCCTTCACAGAATG-3' (SEQ ID NO:86); Reverse: 5'-CTTGATTGTCTTTGCTCACTTTGT-3" (SEQ ID NO:87) and TaqMan Probe: 5'-6-FAM-AG-ATGGGCAAGACCCAAACACATA ATAGA AG-TAMRA-3' (SEQ ID NO:88). This primer pair results in an amplicon of 90 base pairs corresponding to the APC gene.

Figure 43:
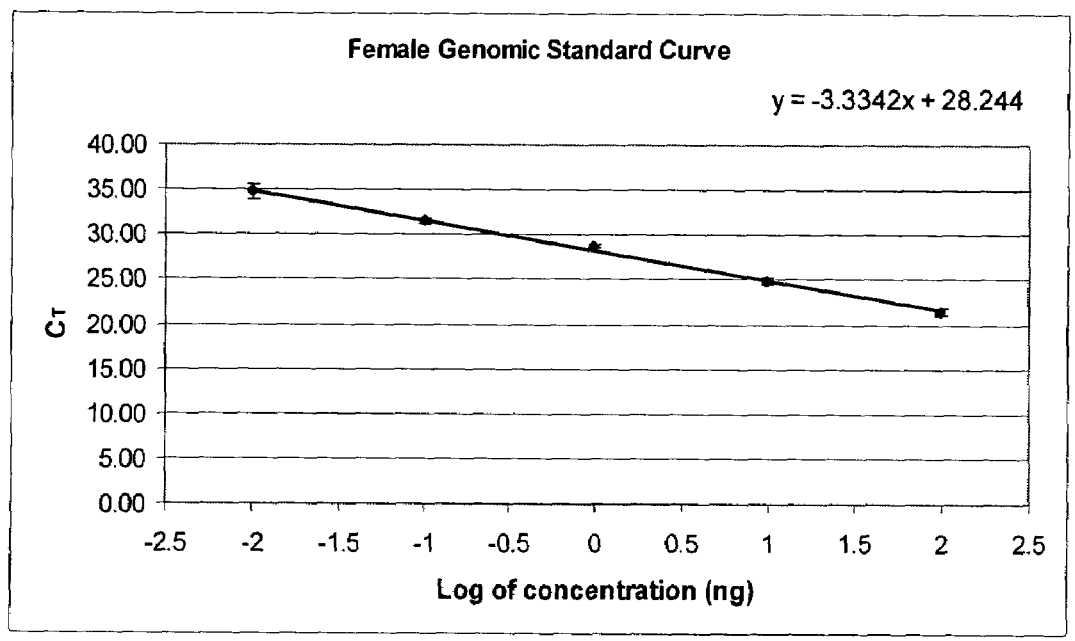
FIG. 43 shows exemplary example of real-time PCR for APC gene copy number determination in human DNA.

Reactions were performed in a 50 µl volume composed of forward and reverse primers (3 nM final concentration), TaqMan Probe (2 nM final concentration), 5 µL of template DNA, and TaqMan Universal PCR Master Mix (Applied Biosystems). The log of concentration versus the $C_T$ value was plotted to yield the result shown in FIG. 43. Two unknown DNA samples isolated from human stool were subjected to real-time PCR and their copy number determined from the female genomic standard curve. One sample (BUP-1) gave approximately 2,175 copies of the APC gene/µL of starting material with a total fecal DNA concentration of 67 ng/µL (approximately 33 copies per ng of total stool DNA). The other sample (BUP-2) gave approximately 472 copies of the APC gene/µl of starting material with a total DNA concentration of 75 ng/µl (approximately 7 copies per ng of total stool DNA).

Example 37

Measuring Cell-Free Protein Expression Yields

One application of MASSIVE-PRO analysis to the identification of low concentrations of chain truncating mutations in the APC gene:

(1) detects very weak peaks in the mass spectra that arise from the mutants; and (2) distinguishes them from background peaks and instrument noise.

Both of these factors can be addressed by optimizing cell-free expression of APC polypeptides. For this purpose, a quick assay quantitates the level of full-length (WT) polypeptides expressed based on a quick chemiluminescent ELISA measurement.

Figure 44:
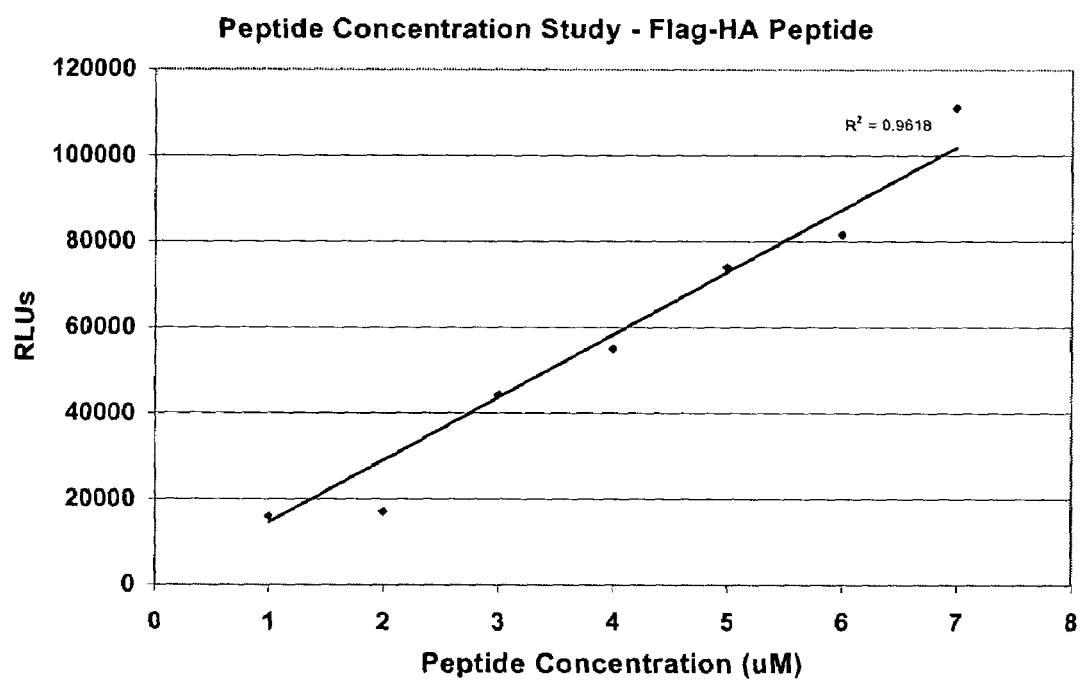
FIG. 44 shows exemplary example of quantitation of MASSIVE-PRO yield by ELISA using standard peptide.

The basis of the measurement is to capture the produced polypeptide fragments on an ELISA plate using the N-terminal flag epitope using an immobilized anti-flag antibody. The amount of peptide captured is then measured using the C-terminal HA epitope using an antibody directed against HA. The actual amount of peptide produced is then determined by comparing the chemiluminescent signal to a calibration curve derived using a test synthetic model peptide, FLAG-HA (MDYKDDDDKNFPFFFETLKLSSRVYPY-DVPDYA) (SEQ ID NO:89) having FLAG epitope sequence at N-terminal and HA at C-terminal. In one experiment, this peptide was serially diluted 25-fold to 200-fold (i.e. 25×, 37.5×, 50×, 75×, 100×, 150×, 200×). A 96-well ELISA plate (Thermoelectron, Labsystems Products, Franklin, Mass.) was coated with 250 ng/mL anti-Flag-M2 antibody (Sigma, St. Louis, Mo.). After binding, the plate was washed three times with TBS-T (TBS with 0.05% Tween 20) followed by two washes with TBS and developed using a chemiluminescent HRP substrate (Supersignal Femto, Pierce, Rockford, Ill.). The results, shown in FIG. 44, indicate the linearity in the range of 1-8 µM of peptide captured in a well verses chemiluminescent signal. From this signal, the amount of nascent peptide produced in the MASSIVE-PRO assay can be calculated. In one experiment we found perfect correlation between the mass spectrometer signal and the ELISA-quantization.

Example 38

Engineering Secondary Structure of the Transcript

This example describes optimization of primers in order to avoid mRNA structure in RBS and stop codon. This could be accomplished by:
1. Introducing silent substitutions in the 5' and 3' primers in order to avoid undesirable base paring
2. Varying reaction conditions such as temperature
3. Using additives that are known to interfere with RNA folding. These included $MgCl_2$ in the millimolar range and betaine (trimethylglycine) in the submolar range.

Figure 45:
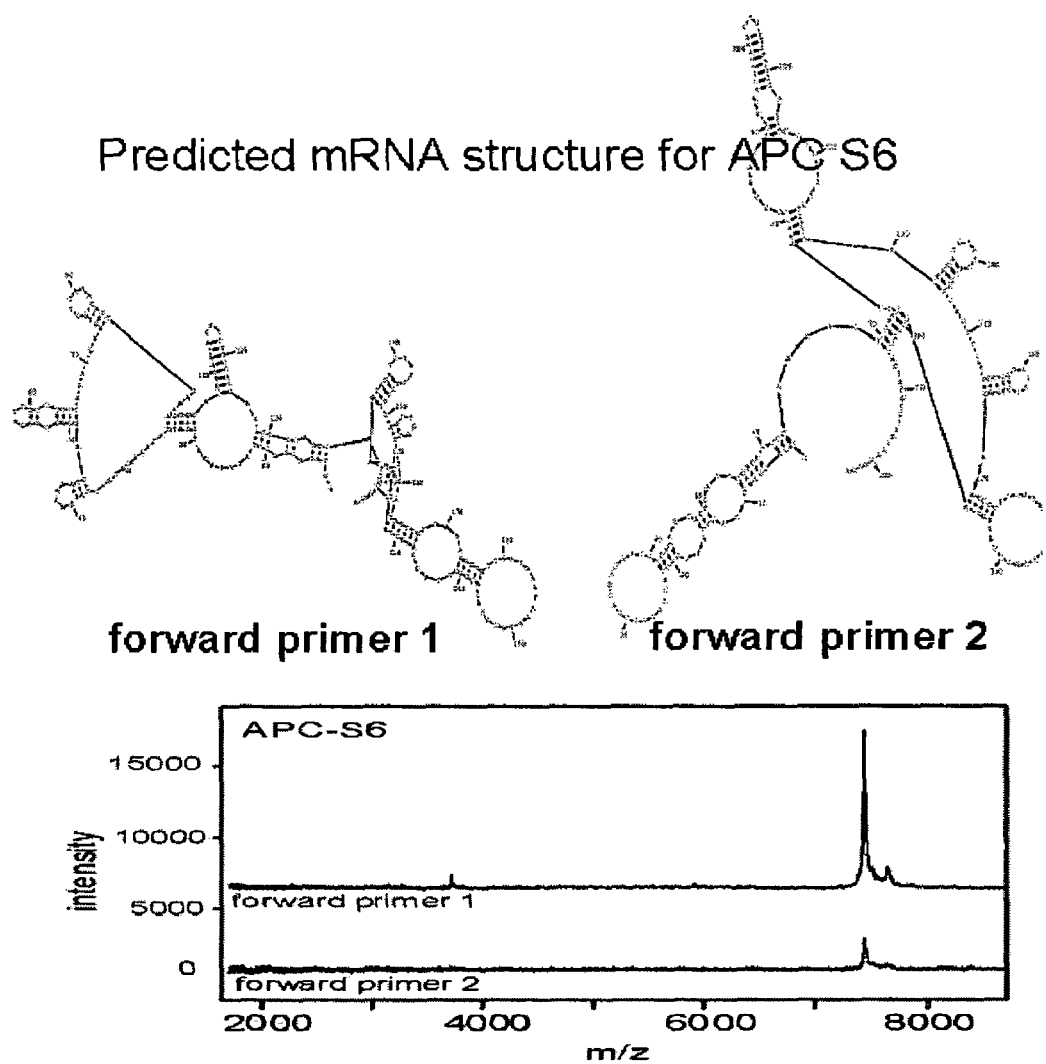
FIG. 45 shows exemplary example of relation between mRNA secondary structure at protein synthesis initiation site and yield of nascent protein.

For example, in a preliminary experiment two different forward primers were used in PCR amplification of segment S6 (see FIG. 45) and their influence on the translation yield was measured. The forward primers 1 and 2 contained several different nucleotides both in the 5'-UTR and in the FLAG tag sequence immediately downstream of the initiation codon. The mRNA structure of S6 segments encoded by the two primers was predicted by the program mfold (Zuker, M., Mfold web server for nucleic acid folding and hybridization prediction. Nucleic Acids Res, 2003, 31(13), 3406-3415) to have considerably different folding patterns which detect which will have a hair pin loop and which will have bubble like structures (FIG. 45, Top). We observed much higher yield in the case of forward primer 1 when measured by both mass-spectrometry (FIG. 45, bottom) and ELISA assay.

Example 39

High Sensitivity "Digital" ELISA-PTT

While heterozygous mutations in germ-line cells are expected to comprise 50% of the total DNA in a sample, polyp samples may contain a mixture of cell types in which only some of the cells contain mutations. The feasibility of detecting 25% mutant population has already been demonstrated by us (Gite, S., Lim, M., Carlson, R., Olejnik, J., Zehnbauer, B., and Rothschild, K. (2003) Nat Biotechnol 21, 194-197). Recently, Vogelstein and co-workers have demonstrated detection efficiencies of chain truncation mutations as low as 0.4% relative to WT (Traverso, G., Shuber, A., Levin, B., Johnson, C., Olsson, L., Schoetz, D. J., Jr., Hamilton, S. R., Boynton, K., Kinzler, K. W., and Vogelstein, B. (2002) N Engl J Med 346, 311-320). This is possible by first diluting genomic DNA samples so that no more than 2-4 DNA templates are present in each sample prior to PCR amplification. This step is followed by translation of the amplified DNA for over 100 samples and detection using radioactive-gel based PTT. At least two non-wild type bands are required out of the entire set for a positive (mutation present) in order to correct for possible polymerase error. As described in the above publication, radioactive-gel based detection is not suitable for automation of detection by gel and indeed problems are compounded for digital PTT.

Figure 46:
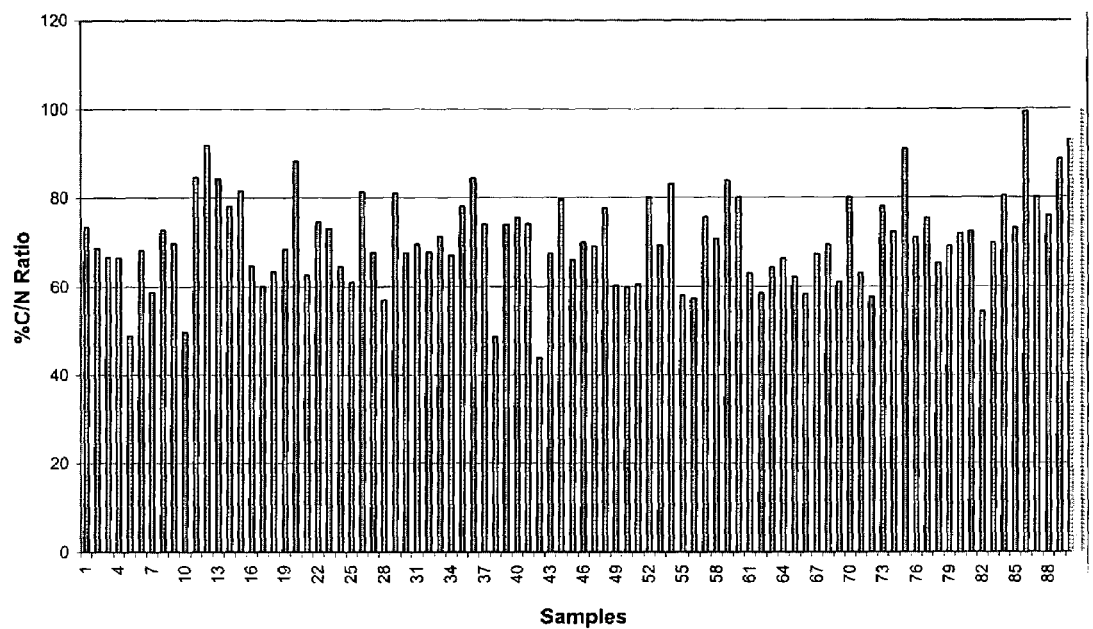
FIG. 46 shows exemplary example of digital ELISA-PTT analysis on a 1/100 mutant/WT DNA mixture from cell-lines. Each bar represents an individual patient sample.
Figure 47:
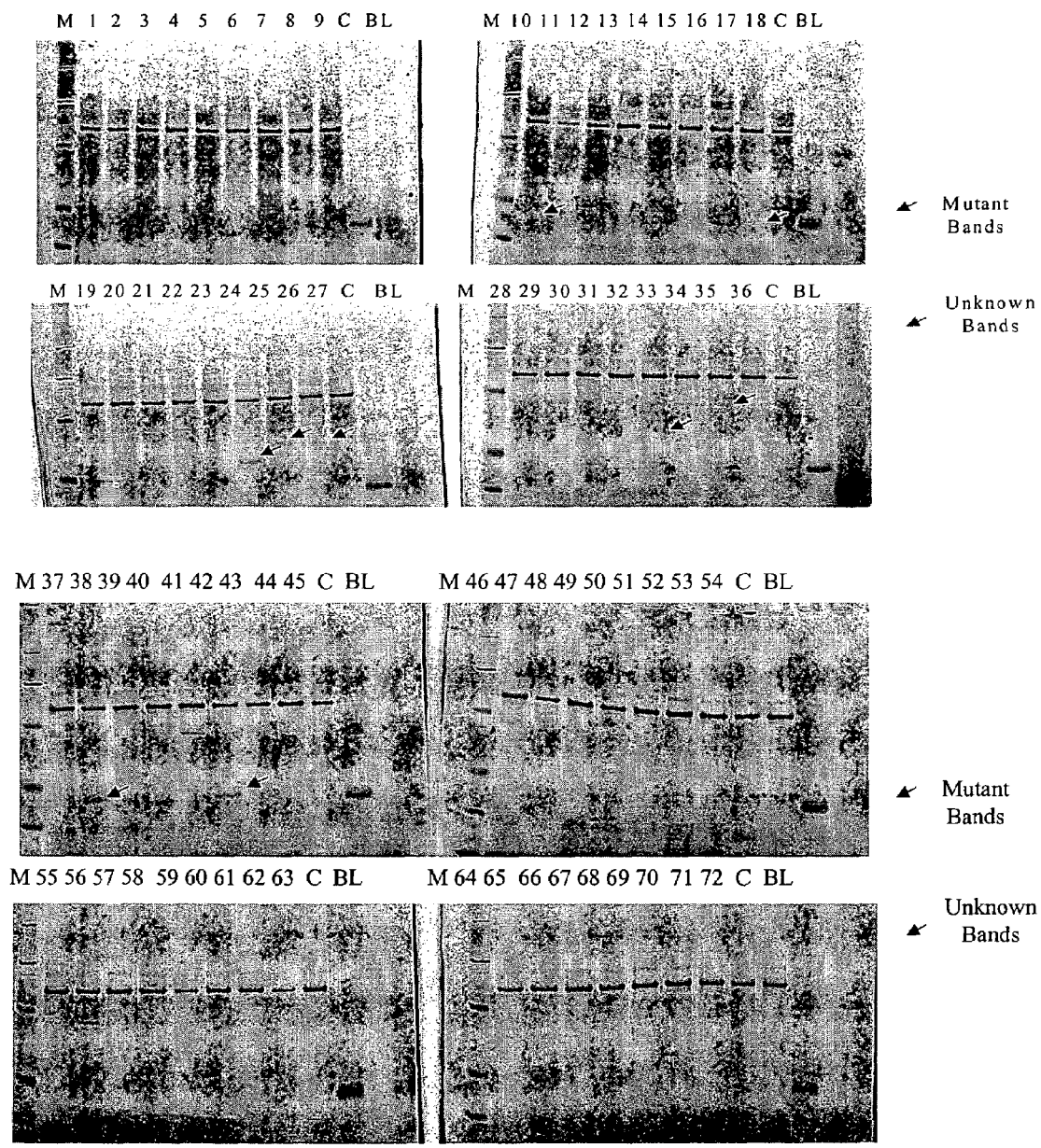
FIG. 47 shows exemplary example of digital Gel-PTT analysis on a 1/100 mutant/WT DNA mixture from cell-lines. Lanes 1-72 represent individual patient samples.

In order to demonstrate that ELISA-PTT can be run in a digital mode, we have now carried out preliminary work using a cell line DNA mixture (99% WT (HeLa) and 1% APC Mutant (SW-480/CCL-228). After performing the digital PCR step, ELISA-PTT was carried out as described in above examples. Out of 88 digital PCR samples, based on T-test, only 5 samples display a statistically significant reduction ($P<0.005$) of the C/N signal indicating the presence of a chain truncation mutation (red bars, FIG. 46). The mutation was then further analyzed by fluorescent-based gel-PTT, which confirmed the presence of the mutation in 5 of the 5 samples at the expected molecular weight (FIG. 47). Significantly, no evidence was found for a polymerase error (e.g. low C/N ratio with mutant at wrong MW). This experiment indicates that high sensitivity detection of mutations (e.g. <1%) can be achieved.

Example 40

Test of PCR Polymerase Fidelity with ELISA-PTT

Figure 48:
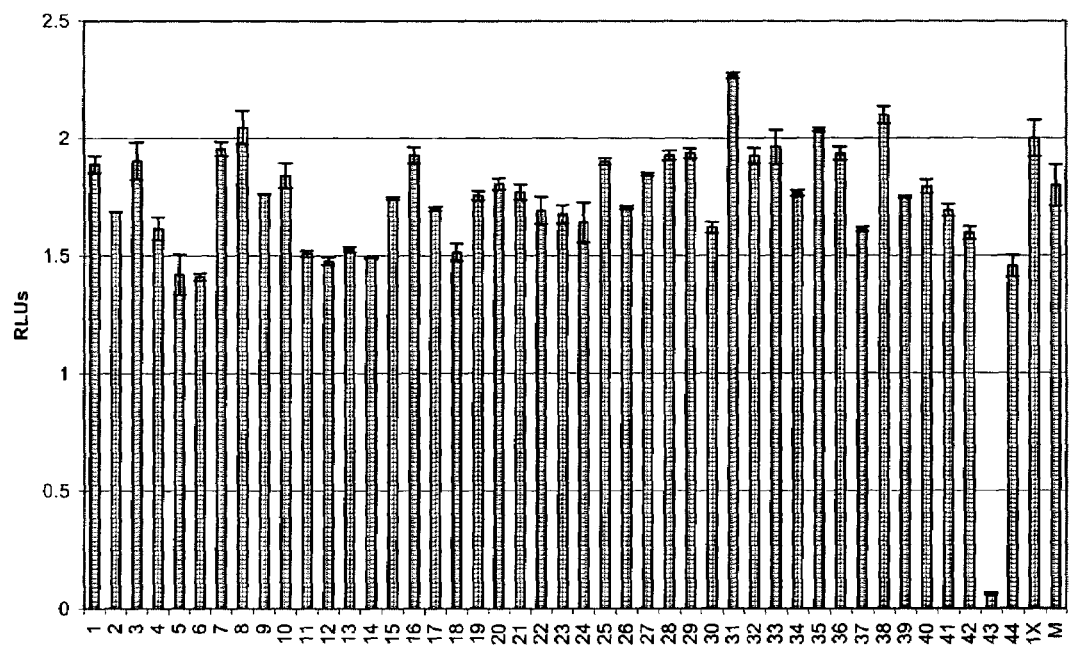
FIG. 48 shows exemplary example of digital ELISA-PTT analysis on a WT HeLa cell line DNA. Each bar represents an individual patient sample. Sample #43 had very little DNA.

One of the major requirements for the any PTT-method is to have a low-rate of PCR error that could potentially cause false positive detection of chain-truncations. Such a requirement is particularly important in the case of digital-PTT (see above), where PCR is performed from just a few DNA template molecules. For this reason we utilize for all assays an extremely high-fidelity polymerase (Phusion Polymerase, MJ research, Waltham, Mass.) which has a 52-times lower error rate compared to standard Taq polymerase. In order to detect possible false-chain truncations which might occur due to polymerase error, we performed digital-PTT for WT DNA isolated from HeLa cell-line using ELISA-PTT as the detection method. Significantly, out of the 43 test reactions based on 2-4 copies of DNA template no errors were detected on the basis of ELISA-PTT and gel electrophoresis. Instead, in all cases a normal C/N ratio and WT band was obtained indicating that polymerase error does not lead to the generation of false-positive chain truncations under these conditions. The data is shown in FIG. 48.

Example 41

Figure 50:
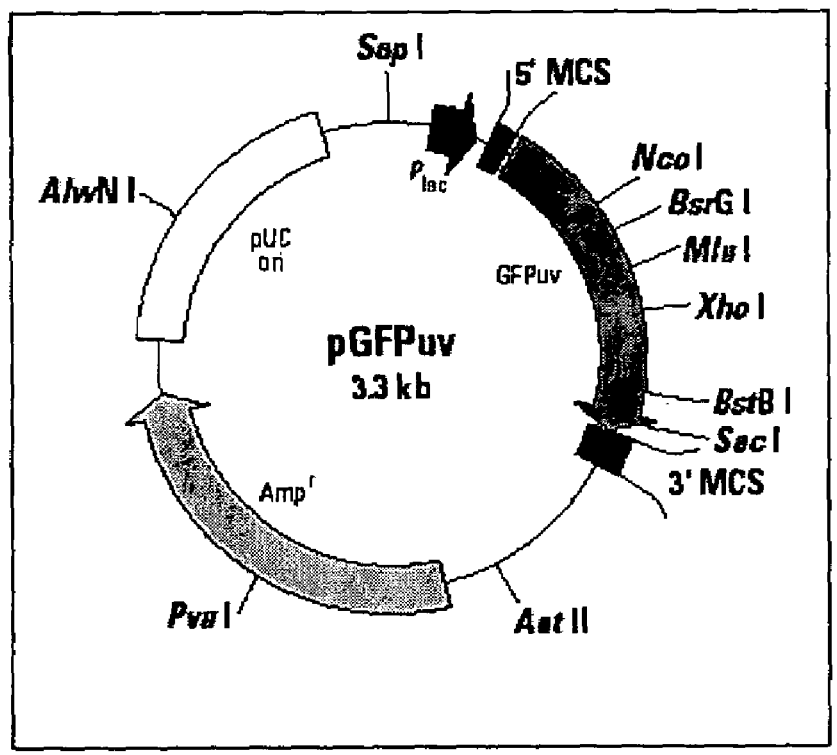
FIG. 50 shows exemplary map of vector pGFPuv.

Selection of Vector DNA, Optimization of Transformation and Detection Conditions In this study, pGFPuv vector (FIG. 50), was used which has GFPuv cloned into a multiple cloning site. This vector was purchased form BD Biosciences. After transformation of *E. coli* cells and overnight growth on the plates, several colonies were selected and used to prepare the DNA using Qiagen Midi-prep DNA Isolation Kit (Valencia, Calif.). This DNA was used as the source for all further work.

Example 42

Mutagenesis of pGFPUV Vector to Change the Start Codon (ATG) of GFP

Using a vector made in accordance with Example 41, there are two initiation codons, one for lacZ-GFP fusion and one for GFP alone. Since this screening assay has a first starting codon (ATG), the ATG of the GFP codon sequence is changed to something else utilizing Stratagene's QuikChange II Mutagenesis Kit. Briefly, pGFPUV plasmid was PCR amplified with specially prepared primers containing a point mutation which results in the ATG start codon of GFP to be changed to an ATC. The primer pairs are as follows: Sense (GFP-TOP): 5'-CCggTAgAAAAAATCAgTAAAggAgAA-3' (SEQ ID NO:90) and Antisense (GFP-BOTTOM): 5'-TTCTCCTTTTACTgATTTTTTCTACCgg-3' (SEQ ID NO:91. Each reaction was carried out in a total volume of 30 µL and contained: 0.5 µL of each sense (GFP-TOP, 10 µM) and antisense (GFP-BOTTOM, 10 µM) primers; 1.0 µL of template DNA; 5 ul 10× Buffer, 1 ul dNTPs, 1.0 ul PfuUltra™

High Fidelity DNA polymerase (Stratagene, La Jolla, Calif.). After an initial cycle of denaturation at 95° C. for 30 seconds; amplification was as follows: 12 cycles of denaturation at 95° C. for 30 seconds, annealing at 55° C. for 1 minute and extension at 68° C. for 4 minutes. After the PCR, samples (3 µL) were analyzed on a 2.0% agarose gel run at 160 volts for 70 minutes. 2-log ladder used as a DNA marker standard. After verification of amplification, the entire PCR reaction was digested by the addition of 1 µL of DpnI restriction enzyme for one hour at 37° C. 1 µL of digested DNA was then transformed into 50 µL XL1-Blue competent cells (Stratagene, La Jolla, Calif.), plated on LB-ampicillin, and incubated at 37° C. overnight. Multiple colonies were selected for sequencing to verify the proper mutation had occurred.

Figure 51:
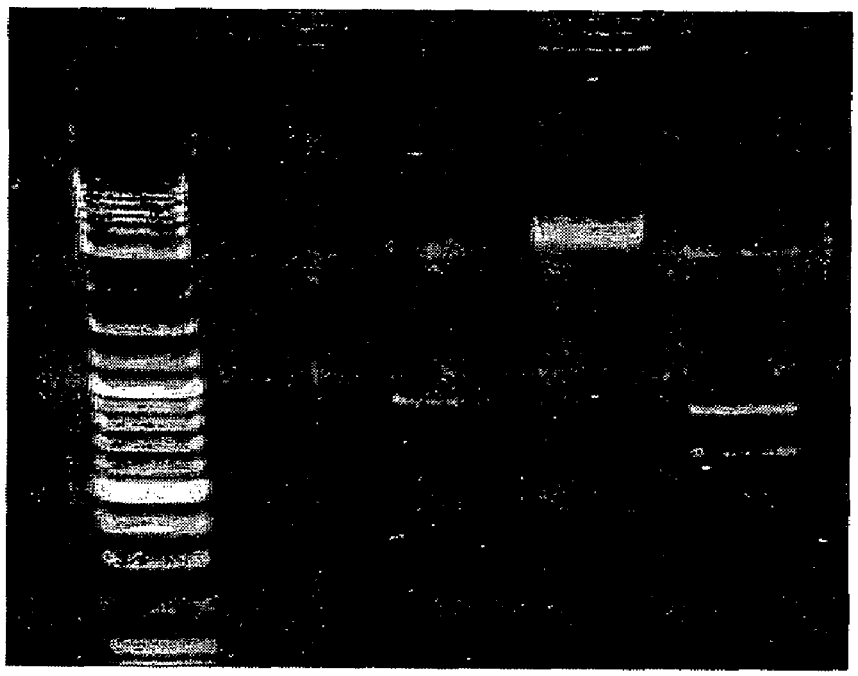
FIG. 51 shows exemplary results of agarose gel analysis of site-directed mutagenesis of pGFPuv.

The results of PCR amplification and digestion of the mutated pGFPuv plasmid are shown in FIG. 51. It is clear from the Figure that the amplification and digestion of DNA works well and produces enough DNA for downstream applications. DNA Sequencing of the recombinant plasmid showed that one plasmid contained the correct ATG→ATC change. Subsequently, this plasmid, named pGFPm, was used in all cloning experiments.

Example 43

Verification of GFP Translation by Introduction of Premature Stop Codon

Figure 52:
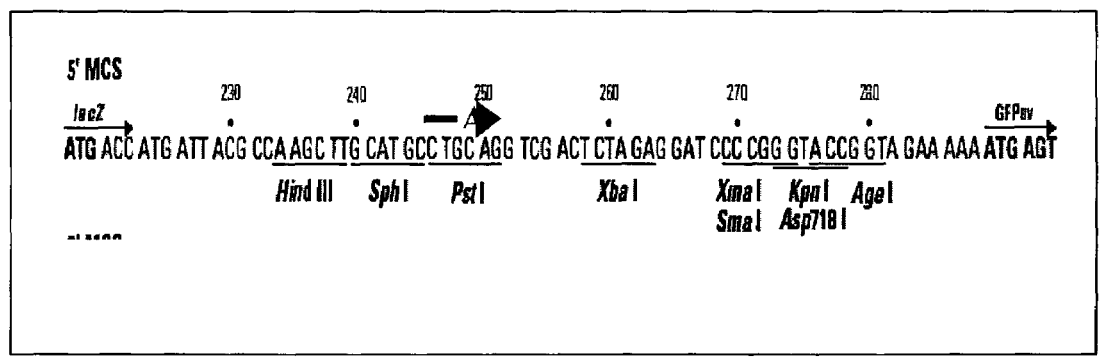
FIG. 52 (SEQ ID NO:105) shows exemplary example of creation of artificial stop in reading frame (TGC→TGA) concomitantly removing a pSTI restriction site.

In order to ensure that this novel approach will give the desired result, that of a loss of GFP production in the presence of a chain truncation mutation, initial studies were carried out on the pGFPm vector. Specially designed primers were constructed that would mutate the Pst I site in the 5'-MCS from a TGC→TGA, thus introducing a premature stop codon in frame with the reading sequence (FIG. 52).

The primers are as follows: Sense (H-A-MUT-TOP): 5'-AgCTTgC ATgCCTg AAggTCgACTCTAgAggATCCCCgggTA-3' (SEQ ID NO:92) and Anti-sense (H-A-MUT-BOT): 5'-ACCggTAC-CCggggATCCTCTAgAgTCgACCTTCAggCATgCA-3' (SEQ ID NO:93). The mutated base-pair is highlighted in bold and underline. Mutagenesis was carried out following the same procedure described in the above example for creating the GFPm vector. DNA was isolated from six colonies based upon the presence or absence of GFP fluorescence using the Qiagen Mini-prep DNA Isolation Kit (Valencia, Calif.). 1 µL of the isolated DNA was digested with Pst I for 30 min at 37° C. to verify the presence or absence of the Pst I restriction site.

Figure 53:
FIG. 53 shows exemplary example of restriction digestion analysis of recombinants clones. The uncut plasmid indicates the successful removal of the pSTI site.

The results of introducing a premature stop codon are shown in FIG. 53. DNA isolated from colonies 1 and 2, which were positive for GFP fluorescence, maintain the Pst I restriction site as indicated by the presence of a lower running band compared to control DNA. DNA isolated from colonies 3-6 were negative for GFP fluorescence and lack the Pst I site based upon the digestion results. These DNA samples do not exhibit any bans significantly different from the control suggesting no digestion has occurred.

Example 44

Preparation of Cloning Vector

The GFPm plasmid was digested with the following enzyme combinations: HindIII/AgeI, HindIII/XbaI, HindIII/KpnI, and HindIII/SmaI (New England Biolabs, Beverly, Mass.). The reaction mixture contained 20 µL of plasmid DNA, 2 µL 10× Buffer, and 0.5 µL of each restriction endonuclease in the above combinations. After digestion for one hour at 37° C./25° C., the DNA was run on a 2% agarose gel; and purified using the Novagen Spin-prep Kit (San Diego, Calif.).

Figure 54:
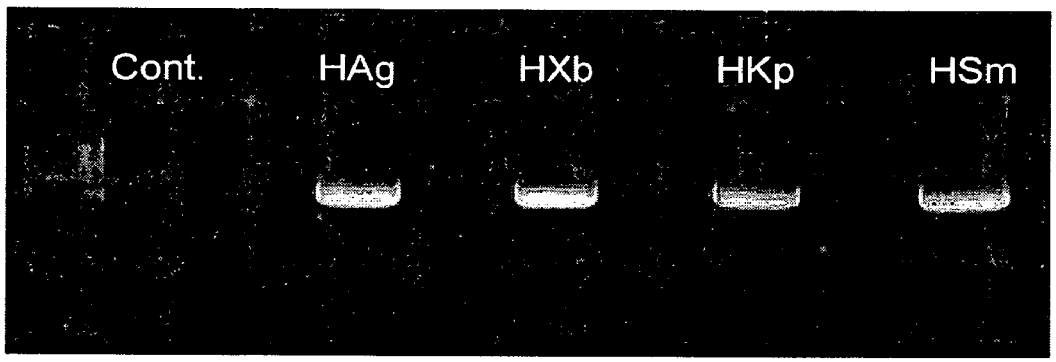
FIG. 54 shows exemplary example of digestion of pGFPm plasmid with various restriction endonuclease pairs.

The results of restriction digestion of the plasmid are shown in FIG. 54. It is clear from the Figure that the restriction endonucleases specifically cleave the desired sites. Purification from the gel allows for only digested plasmid to be isolated. There are no secondary bands indicative of multiple cut sites.

Example 45

PCR with Special Primers

DNA, RNA and PCR: Genomic DNA (WT and APC mutant) was isolated from WT and APC mutant cell lines as well as from FAP patients using commercially available kits (Qiagen, Valencia, Calif.). PCR amplification of a selected region of the APC gene (APC segment 3) was carried out using 250-500 ng of genomic DNA, 0.2 µM primer mix (forward and reverse) and 1×PCR master mix. After an initial cycle of denaturation at 95° C. for 3 minutes; amplification was as follows: 35 cycles of denaturation at 95° C. for 45 seconds, annealing at 56° C. for 45 seconds and extension at 72° C. for 4 minutes. Primer pairs used were: Sense (Hind3-APC3BV): 5'-ggAgCTCATAAgCTTCT CTggACAAAg-CAgTAAAACCgAA-3' (SEQ ID NO:94); Antisense-1 (APC3-Age1): 5'-ATgAg CTCCACCggTgCgCCTTCTg-TAggAATggTATCTCg-3' (SEQ ID NO:95); Antisense-2 (APC3BV-XbaI): 5'-ATgACgTCCTCTAgAgCACgTgAT-gACTTTgTTggCATggC-3' (SEQ ID NO:96); Anti sense-3 (APCBV-KpnI): 5'-ATgAgCCTCCggTACCgCACgTgAT-gACTTTgTTggC ATggC-3' (SEQ ID NO:97); Antisense-4 (APCBV-SmaI): 5'-ATgAgCCTCCCCCggggCAC g TgA TgACTTT gTTggCATggc-3' (SEQ ID NO:98. Bases highlighted in bold and italicized print are restriction endonuclease recognition sites. Each reaction was carried out in a total volume of 30 µL and contained: 0.5 µL of each sense (Hind3-APC3, 10 µM) and antisense (10 µM) primers; 0.5 µL of template DNA; and 15 µL Phusion High-Fidelity Polymerase Master Mix (MJ Research, Waltham, Mass.). After PCR, samples (3 µL) were analyzed on a 2.0% agarose gel run at 160 volts for 70 minutes. 2-log ladder used as a DNA marker standard.

Figure 55:
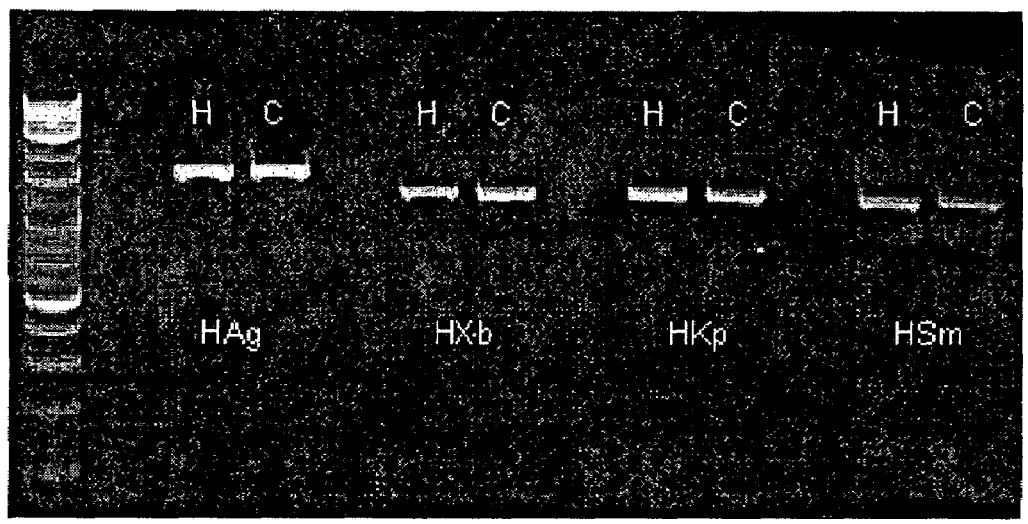
FIG. 55 shows exemplary example of PCR amplification of wild-type and mutant DNA templates with restriction primers.

The results of PCR amplification of WT and mutant DNA are shown in FIG. 55. It is clear from the Figure that the amplification of DNA with special primer works well and produces enough DNA for downstream applications.

Example 46

Digestion of PCR Products with Restriction Endonucleases

The digestion reaction consists of 30 ul of PCR product, 3 µL of 10× Buffer, 0.5 µL of each restriction endonuclease in the following combinations: HindIII/AgeI, HindIII/XbaI, HindIII/KpnI, and HindIII/SmaI (New England Biolabs, Beverly, Mass.); and was incubated for 30 minutes at 37° C./25° C. The enzymes were heat inactivated at 65° C. for 20 minutes; then purified using the Qiagen PCR Purification Kit (Valencia, Calif.).

Figure 56:
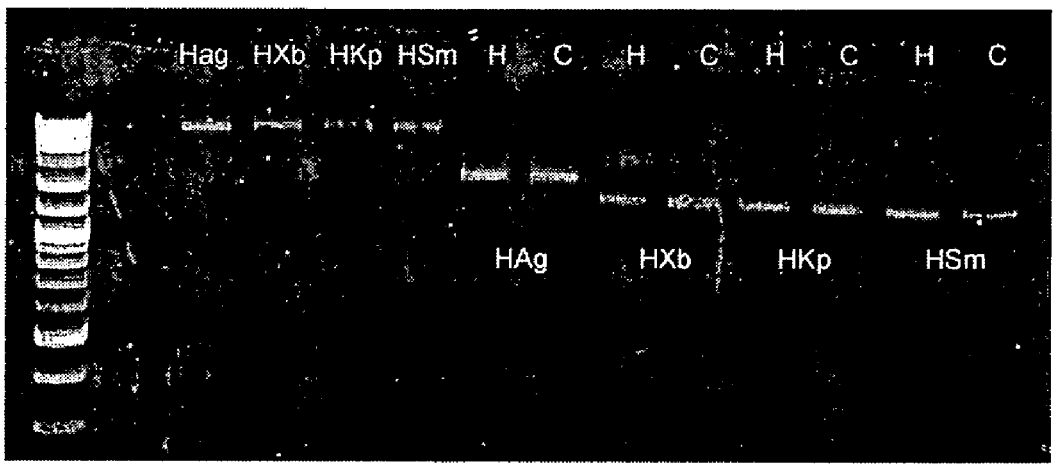
FIG. 56 shows exemplary example of restriction digestion analysis of GFPm plasmid and PCR products.

The results of restriction digestion of PCR products and GFPm plasmid are shown in FIG. 56. It is clear from the Figure that the restriction endonucleases specifically cleaves end sequences and leave the PCR product intact as no secondary band is found.

Example 47

Ligation of Insert to Digested Vector

Digested plasmid and insert (PCR product; 3-fold molar excess) was ligated using Quick Ligation Kit (New England Biolabs, Beverly, Mass.) for each of the four enzyme combinations. The reaction mixture contained 2 µL of plasmid and 2 µL of insert, 10 µL of 2× Buffer and 1 µL of Ligase enzyme; and was incubated for 30 minutes at 25° C. 1 µL of each ligation was transformed into 25 µL of Noveblue competent cells (Novagen, San Diego, Calif.) and plated at 37° C. overnight.

Figure 58:
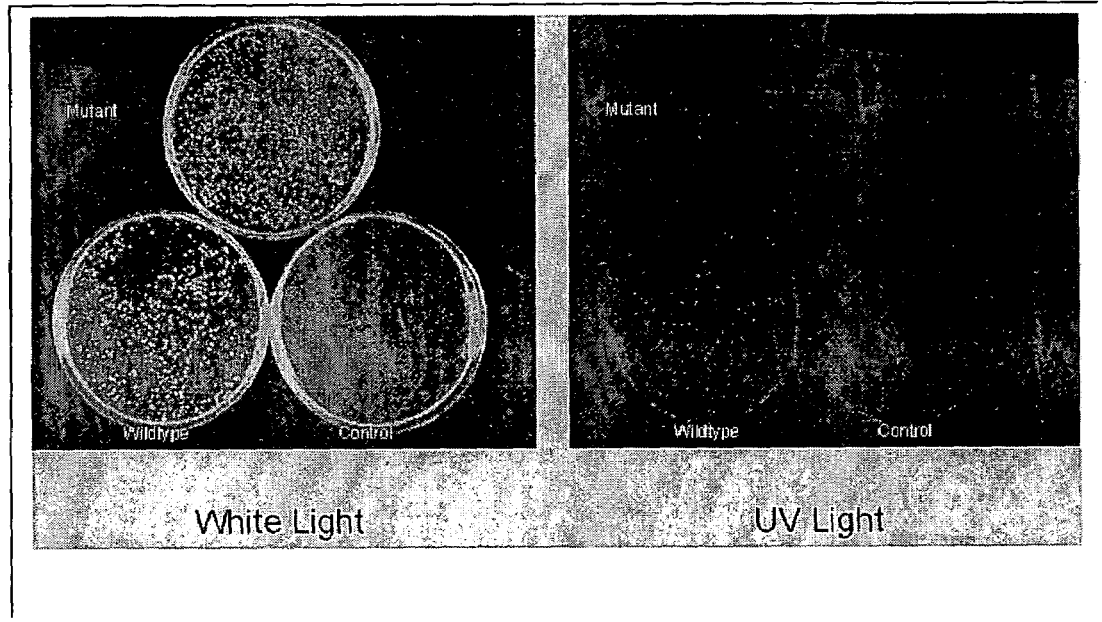
FIG. 58 shows exemplary example of screening of recombinants using white and UV-light. Colonies containing WT amplicon show green fluorescence while colonies containing mutant amplicon are white.

Transformation of pGFPuv and Empty (−GFP gene) vectors gave the expected results. GFP positive for pGFPuv and GFP negative for the Empty vector (FIG. 57). The results for the control and experimental ligation reactions were as expected i.e. Ligation reaction with insert gave 10-fold more colonies than reaction incubated without the insert (FIG. 58). Moreover, most of the colonies resulting from WT amplicon are green while colonies from mutant amplicons are white (FIG. 58).

Example 48

Alternative Method for Cloning Based on Fusion Cloning Protocol

Figure 59:
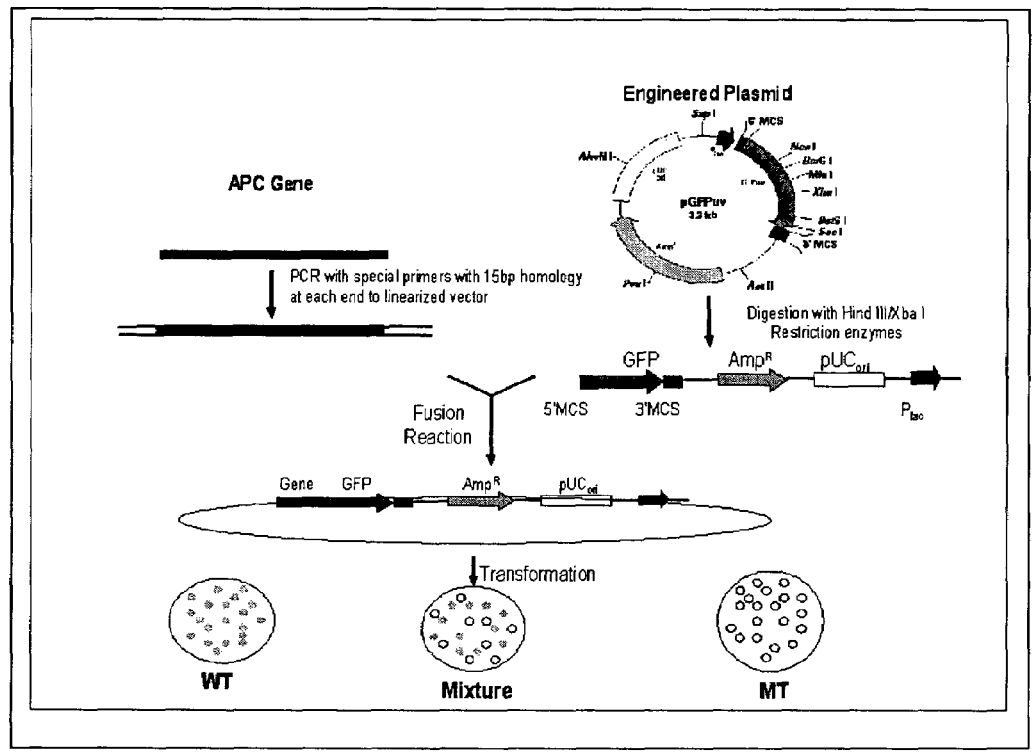
FIG. 59 shows one embodiment of a FISH-PTT assay based on a fusion cloning protocol.

This method is based on In-Fusion Cloning method (BD Biosciences, Palo Alto, Calif.). The schematic of Fusion cloning method is shown in FIG. 59. This technique allows high-throughput cloning of PCR products without the need for restriction enzymes and ligation. The major components of such a procedure involve a linear vector, PCR product, and In-Fusion enzyme mixture which are transformed into competent cells.

Example 49

Preparation of Cloning Vector for Fusion Method

The GFPm plasmid was digested with the following enzyme combination HindIII and XbaI (New England Biolabs, Beverly, Mass.) to create the linear vector necessary for the Fusion protocol. The initial digestion mixture contained 5 µL of plasmid DNA, 5 µL 10× Buffer, and 1.0 µL of HindIII in a total volume of 50 µL. The reaction was incubated at 37° C. and dosed with 1.0 µL of enzyme for a period of six hours. The resulting product was purified using Qaigen's PCR Purification Kit (Valencia, Calif.). The purified DNA was subjected to a second digestion reaction with the following conditions: 9 µL of HindIII digested plasmid, 5 µL 10× Buffer, and 1.0 µL of XbaI in a total volume of 50 µL. The reaction was incubated at 37° C. and dosed with 1.0 µL of enzyme for a period of six hours. The resulting product was purified using Qaigen's PCR Purification Kit (Valencia, Calif.). The DNA was run on a 2% agarose gel at each stage of digestion and purification.

Figure 60:
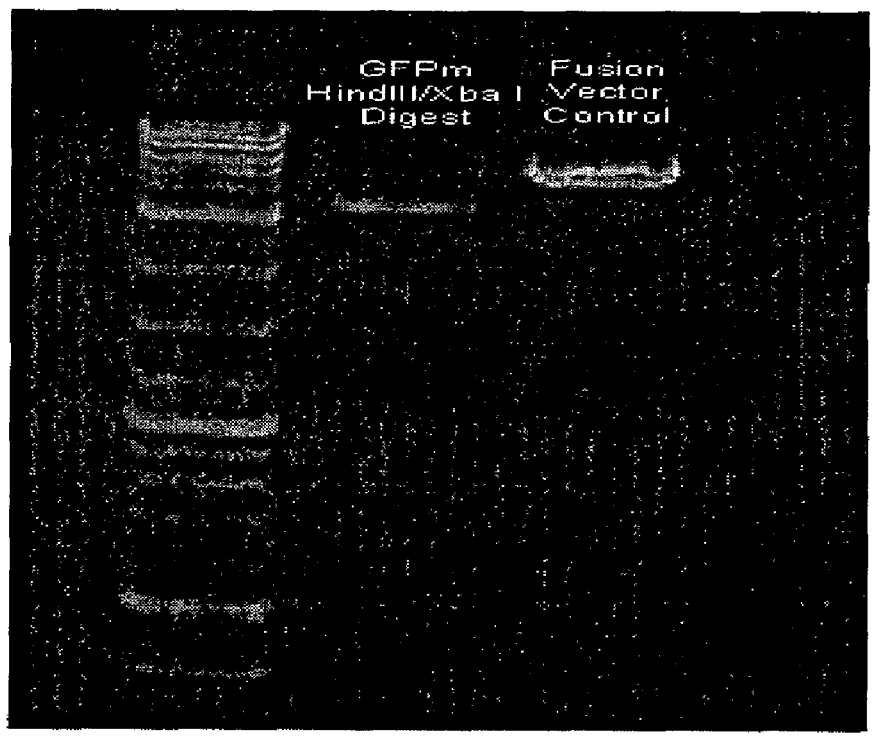
FIG. 60 shows exemplary example of restriction digestion analysis of vector pGFPm for fusion cloning method.

The results of restriction digestion of the plasmid, GFPm, are shown in FIG. 60. It is clear from the Figure that the restriction endonucleases specifically cleave the desired sites. In the initial digestion a large shift is apparent; caused by the opening of the vector from closed circular to linear. In the second digestion, a shift is not evident as only approximately 30 bp are removed, but the gel verifies the presence of a single DNA species at the correct molecular weight. There are no secondary bands indicative of multiple cut sites.

Example 50

Preparation of Amplicons for Fusion Cloning Method

PCR with Special Primer

Genomic DNA (WT and APC mutant) was isolated from WT and APC mutant cell lines using commercially available kits (Qiagen, Valencia, Calif.). PCR amplification of a selected region of the APC gene (APC segment 3) was carried out using 250-500 ng of genomic DNA, 0.2 µM primer mix (forward and reverse) and 1×PCR master mix. After an initial cycle of denaturation at 95° C. for 3 minutes; amplification was as follows: 35 cycles of denaturation at 95° C. for 45 seconds, annealing at 56° C. for 45 seconds and extension at 72° C. for 4 minutes. Primer pairs used were: Sense (Fusion-H5): 5'-TgATTACgCCAAgCTCATCTggACAAA gCAg-TAAAACCgAA-3' (SEQ ID NO:99) and Anti-sense (Fusion-X3): 5'-CCggggATCCT CTAgACgTgATgACTTTgTTggCATggC-3' (SEQ ID NO:100). Each primer contains 24 base-pairs complementary region to the APC gene (bold-faced), and 16 base-pairs homologous to the vector sequence surrounding the restriction sites. Reactions were carried out in a total volume of 30 µL and contained: 0.5 µL of each sense (Fusion-H5, 10 µM) and antisense (Fusion-X3, 10 µM) primers; 0.5 µL of template DNA; and 15 µL Phusion High-Fidelity Polymerase Master Mix (MJ Research, Waltham, Mass.). PCR products were purified using Qaigen's PCR Purification Kit (Valencia, Calif.). After purification, samples (1 µL) were analyzed on a 2.0% agarose gel run at 160 volts for 70 minutes. 2-log ladder used as a DNA marker standard.

Figure 61:
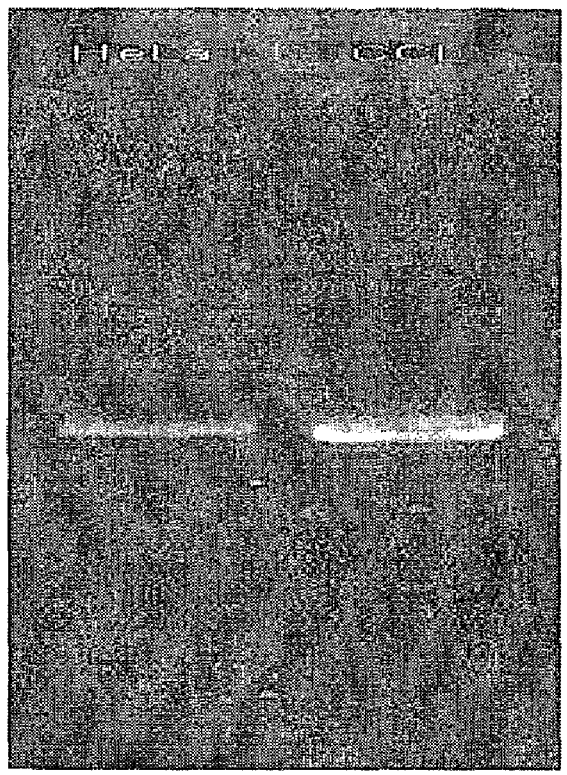
FIG. 61 shows exemplary example of agarose gel analysis of using PCR amplicons.

The results of PCR amplification of WT and mutant DNA are shown in FIG. 61. It is clear from the Figure that the amplification of DNA with special primers works well and produces enough DNA for downstream applications. Qiagen PCR purification removes any minor secondary bands.

Example 51

Fusion Cloning of Vector and PCR Products

This example uses vectors according to Example 49 and PCR procedures according to Example 50.

Fusion cloning was carried out according to BD Biosciences protocol. Each reaction contained 2 µL 10× Buffer, 2 µL 10×BSA, 6 µL linear GFPm vector (~2100 ng/µL), 2 µL PCR product (~75 ng/µL) either WT or MT, and 1 µL BD In-Fusion Enzyme. The components were mixed and incubated at room temperature for 30 minutes. After 30 minutes, reactions were placed on ice and 40 µL of 1×TE added. 2.5 µL of reaction mixture were transformed into 25 µL of Novablue competent cells (Novagen, San Diego, Calif.) and plated overnight at 37° C.

Figure 62:
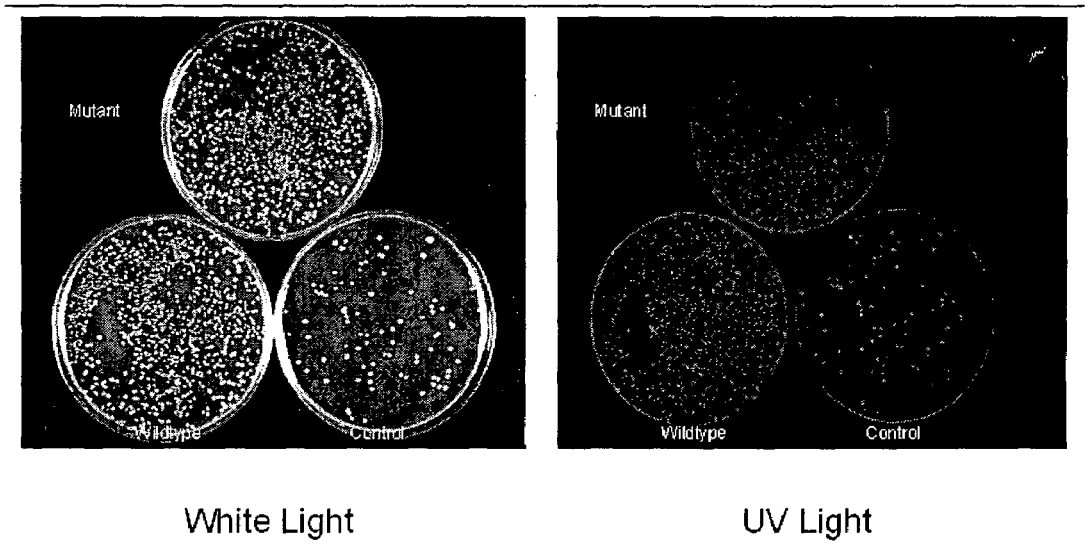
FIG. 62 shows exemplary example of screening of recombinants using white and UV-light. Colonies containing WT amplicon show green fluorescence while colonies containing mutant amplicon are white.

The results for Fusion Cloning methods are shown in FIG. 62. Transformation have yielded upwards of 400 colonies or more for each reaction. Wildtype insert plates yield a mixture of transformed colonies containing either weak or bright GFP fluorescence. Sequencing shows that weakly emitting GFP colonies contain the wildtype PCR insert in frame and bright GFP colonies contain no insert. In the case of mutant insert plates, a mixture of white and bright GFP colonies is seen. Sequencing indicates that the white colonies contain the proper mutant insert in frame and bright colonies contain no insert.

Example 52

Stool Sample Collection/DNA Isolation Using Standard Glass Slides

Figure 63:
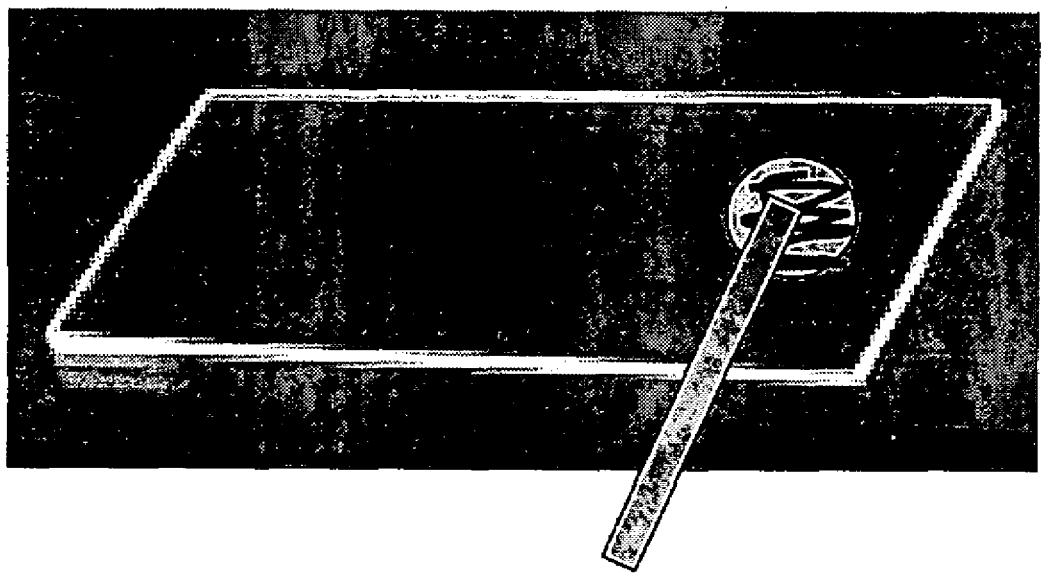
FIG. 63 demonstrates one embodiments for smearing a stool sample on a glass slide.

A small amount of stool sample (approximately 10 mg) is smeared on standard microscope glass slide (Corning, Ithaca, N.Y.) using thin wooden stick in a small area on one end (see FIG. 63). The quantity of stool sample deposited was measured by weighing the slide before and after deposition of the stool material. The glass slides were then kept closed in slide holder/storage box (Fisher Scientific, Atlanta, Ga.) and stored in laminar hood at room temperature till further use. Generally, it was allowed to dry for set period ranging from 1-4 days. Just prior to DNA isolation, 1.6 mL of ASL Buffer was added to the slide holder containing slide and left for 20-30 minutes in order to soak it. The stool smear was then gently scraped off the slide by pipetting ASL Buffer. Slides for later days were placed in slide holders and left to dry at RT prior to performing above procedure. After complete removal of sample from slide, the tube was mixed by vortexing and stool DNA isolation was performed using the QIAamp DNA Stool Mini Kit (Cat. No. 51504) following the protocol given on page 22 for Isolation of DNA from Stool for Human DNA Analysis. Note that, the volumes before adding the Inhibitex tablet must be brought up to 1.4 mL with ASL Buffer or else sample will be completely absorbed into the tablet and supernatant will not be recovered. The quality of the isolated DNA was then checked by Agarose gel electrophoresis. Furthermore, Isolated DNA was quantitated then using Molecular Probes PicoGreen DNA quantitation kit.

Figure 64:
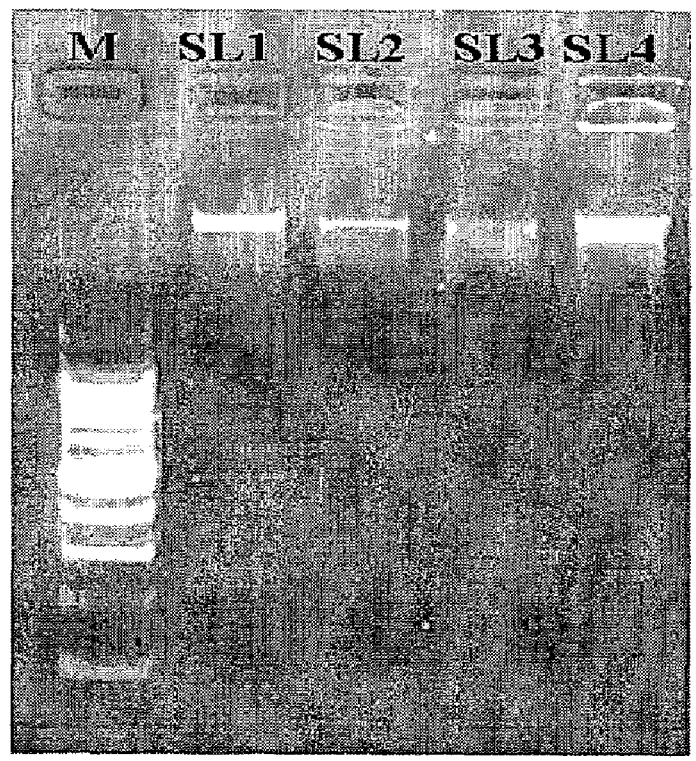
FIG. 64 shows exemplary data using agarose gel analysis of stool DNA isolated using a glass slide method.

The quantitation of total DNA isolated from glass slides from day 1 to day 4 ranged from 400-800 ng. Generally, using Qiagen Kit and 200 mg of stool samples, one get 15-60 ug DNA (15,000-60,000 ng DNA). Considering 20-30 times less starting stool material, one would expect 500-2000 ng of total DNA. Our total yield of 400-800 ng DNA was in the expected range. The result of agarose gel electrophoresis of DNA isolated from Stool deposited on glass slide is shown in FIG. 64, Lanes SL1-SL4. Lane M: molecular marker, Lane SL1 represents the DNA isolated on day 1, lane SL2 represents the DNA isolated on day 2, lane SL3 represents the DNA isolated on day 3 and lane SL4 is the DNA isolated on Day 4. The top band mainly represents the bacterial DNA, while most of the human DNA is generally degraded (smeared below).

The isolated stool DNA was then subjected to PCR analysis using various primer sets including primers that spanned an approximately 120-200 bases of the APC, P53 and k-ras gene.

A. APC PCR
1. Primers
Sense APC4-5: 5'-AGTGGCATTATAAGCCCCAGTGAT-3' (SEQ ID NO:60)
Antisense APC4-3: 5'-AGCATTTACTGCAGCTTGCT-TAGG-3' (SEQ ID NO:61)
2. PCR Cycling Conditions
After an initial cycle of denaturation at 94° C. for 2 minutes; amplification was as follows: 40 cycles of denaturation at 94° C. for 20 seconds, annealing at 61.8° C. for 30 seconds, and extension at 72° C. for 1 minute.

Figure 65:
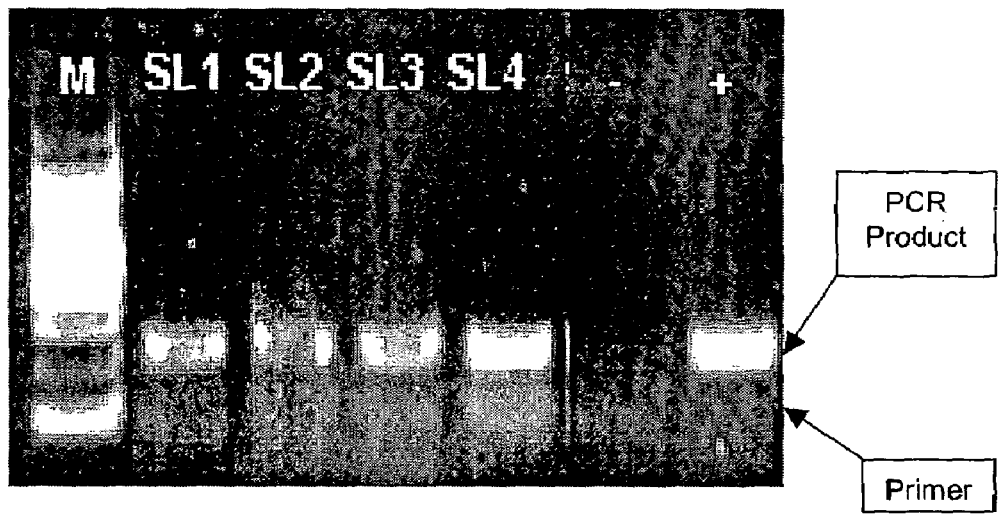
FIG. 65 shows exemplary data using APC PCR from various stool samples using a glass slide method (i.e., SL1 through SL4).

3. Reaction Mixture
Each reaction was carried out in a total volume of 30 μL and contained: 0.5 μL of each sense (APC4-5, 10 mM) and antisense (APC4-3, 10 mM) primers, 5 μL of template DNA and
4. Gel Analysis
After PCR, samples (5 μL) were analyzed on a 2.0% agarose gel that was run at 150V for 25 minutes. 100 bp ladder used as a DNA marker standard as well as quantitation standard. The PCR product visualized and quantitated using CCD-based imaging system and software (ChemImager, Alpha Innotech, San Leandro, Calif.).
5. Results
As seen in the FIG. 65, PCR product corresponding to 180 base pairs of APC gene is clearly seen in all the lanes (SL1-SL4) where the PCR was carried out using the DNA was isolated from slides on day 1 to 4. Lanes indicted with − and + are negative control and positive control, respectively. The quantitation of the above PCR product indicated the amount to be 40 ng to 80 ng per band (i.e. 8-16 ng per ul; total 240-480 ng per 30 ul PCR reaction).

Figure 66:
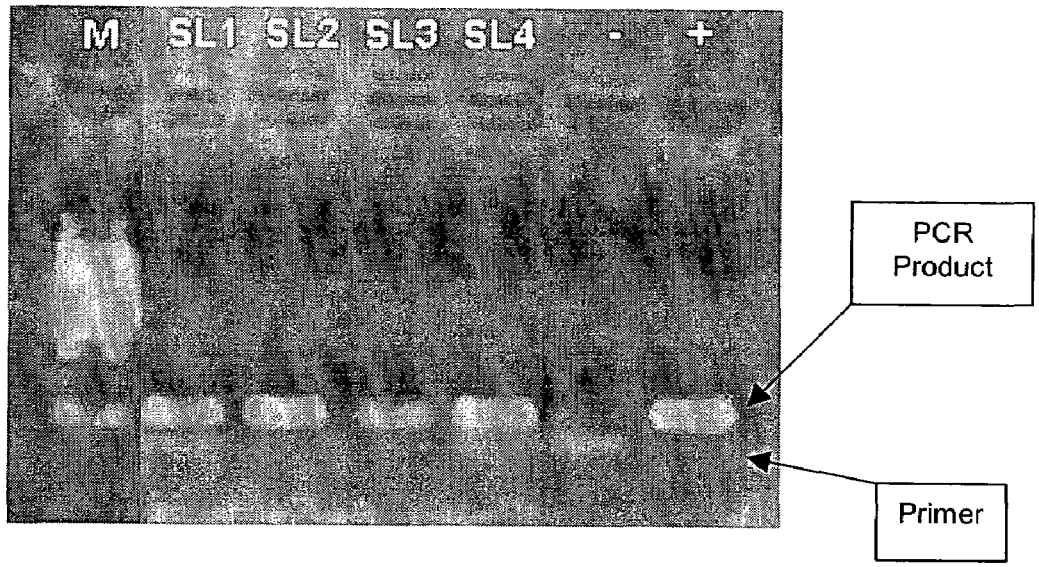
FIG. 66 shows exemplary data using P53 PCR from various stool samples using a glass slide method (i.e., SL1 through SL4).

B. P53 PCR
1. Primers
Sense P53-9-5: 5'-TGGTAACTCACTGGGACGGAACAG-3' (SEQ ID NO:62)
Antisense P53-9-3: 5'-CTCGCTTAGTGCTC-CCTGGGGGCA-3' (SEQ ID NO:63)
2. Cycle Conditions
After an initial cycle of denaturation at 94° C. for 2 minutes; amplification was as follows: 40 cycles of denaturation at 94° C. for 20 seconds, annealing at 61.8° C. for 30 seconds, and extension at 72° C. for 1 minute.
3. Reaction Mixture
Each reaction mixture was carried out in a total volume of 30 μL and contained: 0.5 μL of each sense (P53-9-5, 10 mM) and antisense (P53-9-3, 10 mM) primers, 5 μL of template DNA and 15 μL of High Fidelity PCR Master (Roche).
4. Gel Analysis
After PCR, samples (5 μL) were analyzed on a 2.0% agarose gel which was run at 150V for 25 minutes. 100 bp ladder used as a DNA marker standard as well as quantitation standard. The PCR product visualized and quantitated using CCD-based imaging system and software (ChemImager, Alpha Innotech, San Leandro, Calif.).
5. Results
As seen in the FIG. 66, PCR product corresponding to 137 base pairs of APC gene is clearly seen in all the lanes (SL1-SL4) where the PCR was carried out using the DNA was isolated from slides on day 1 to 4. Lanes indicted with − and + are negative control and positive control, respectively. The quantitation of the above PCR product indicated the amount to be 40 ng to 80 ng per band (i.e. 8-16 ng per ul; total 240-480 ng per 30 ul PCR reaction).

C. K-RAS
1. Primers
Sense KRAS-12F: 5'-GGCCTGCTGAAAATGACTGAA-3' (SEQ ID NO:64)
Antisense KRAS-12R: 5'-CTCTATTGTTGGATCATATTC-3' (SEQ ID NO:65)
2. Cycle Conditions
After an initial cycle of denaturation at 94° C. for 2 minutes; amplification was as follows: 40 cycles of denaturation at 94° C. for 20 seconds, annealing at 50.7° C. for 30 seconds, and extension at 72° C. for 1 minute.
3. Reaction Mixture
Each reaction mixture was carried out in a total volume of 30 μL and contained: 0.5 μL of each sense (KRAS-12F, 10 mM) and antisense (KRAS-12R, 10 mM) primers, 5 µL of template DNA and 15 µL of High Fidelity PCR Master (Roche).

4. Gel Analysis

After PCR, samples (5 µL) were analyzed on a 2.0% agarose gel which was run at 150V for 25 minutes. 100 bp ladder used as a DNA marker standard as well as quantitation standard. The PCR product visualized and quantitated using CCD-based imaging system and software (ChemImager, Alpha Innotech, San Leandro, Calif.).

5. Results

Figure 67:
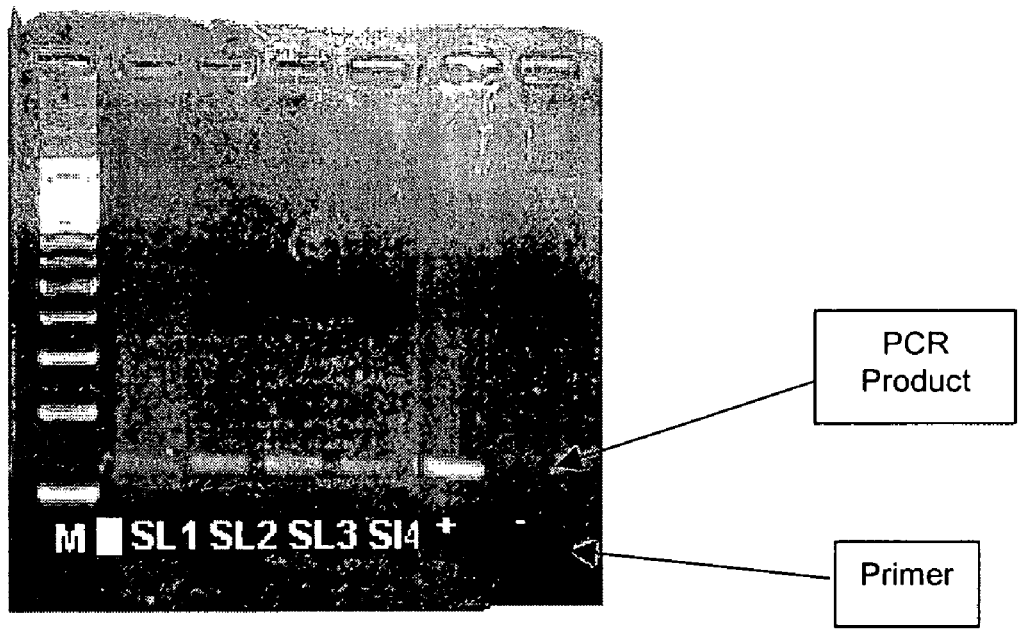
FIG. 67 shows exemplary data using K-ras PCR from various stool samples using a glass slide method (i.e., SL1 through SL4).

As seen in the FIG. 67, PCR product corresponding to 123 base pairs of K-ras gene is clearly seen in all the lanes (SL1-SL4) where the PCR was carried out using the DNA was isolated from slides on day 1 to 4. Lanes indicated with – and + are negative control and positive control, respectively. The quantitation of the above PCR product indicated the amount to be 10 ng to 20 ng per band (i.e. 2-4 ng per ul; total 60-120 ng per 30 ul PCR reaction).

Example 54

Stool Sample Collection/DNA Isolation Using STAR Buffer

Approximately 100 mg of stool sample is mixed with 500 ul of Stool Transport And Recovery Buffer (STAR; Roche Applied sciences, Indianapolis, Ind.). The tube was then kept closed and stored in laminar hood at room temperature till further use. Generally, it was stored for set period ranging from 1-4 days. Just prior to DNA isolation, the eppendorf tube was vortexed on high until the majority of stool sample was homogenized. It was then centrifuged for 1 min at maximum speed (13,000 RPM) and the supernatant was transferred to new tube. To this tube, $^1/_{10}$ volume of chloroform was added, vortexed briefly and centrifuged for 1 min at maximum speed. After centrifugation, supernatant was removed and volume of supernatant was adjusted to 1.4 mL using ASL Buffer. The stool DNA isolation was performed using the QIAamp DNA Stool Mini Kit (Cat. No. 51504) following the protocol given on page 22 for Isolation of DNA from Stool for Human DNA Analysis. Note that, the volumes before adding the Inhibitex tablet must be brought up to 1.4 mL with ASL Buffer or else sample will be completely absorbed into the tablet and supernatant will not be recovered. The quality of the isolated DNA was then checked by Agarose gel electrophoresis. Furthermore, Isolated DNA was quantitated then using Molecular Probes PicoGreen DNA quantitation kit.

Figure 68:
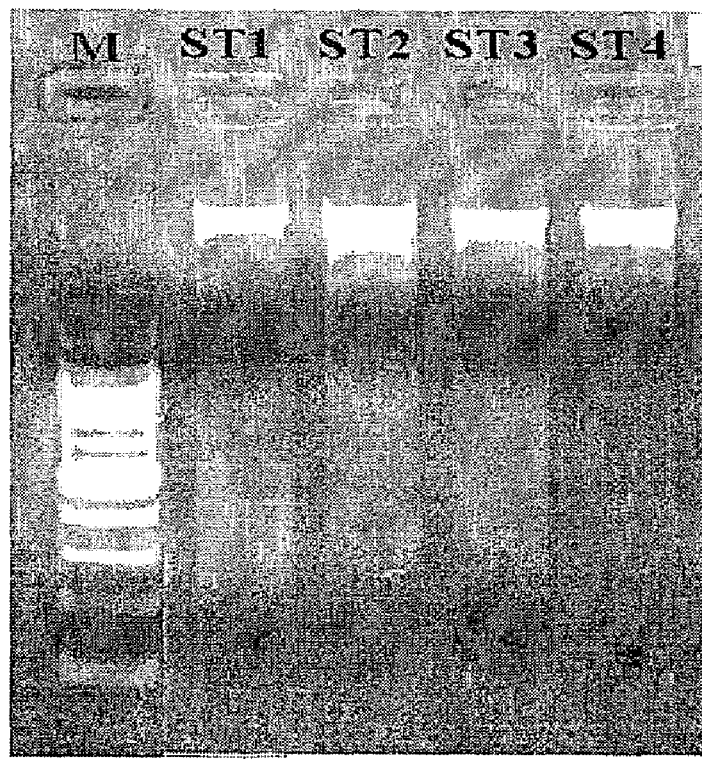
FIG. 68 shows exemplary data using agarose gel analysis of stool DNA isolated using a STAR buffer method (i.e., ST1 through ST4).

The quantitation of total DNA isolated from glass slides from day 1 to day 4 ranged from 10-25 ug. Generally, using Qiagen Kit and 200 mg of stool samples, one get 15-60 ug DNA (15,000-60,000 ng DNA). Considering 2-times less starting stool material, one would expect 7.5-30 ug of total DNA. Our total yield of 400-800 ng DNA was in the expected range. The result of agarose gel electrophoresis of DNA isolated from Stool stored in STAR buffer is shown in FIG. 68, Lanes ST1-ST4. Lane M: molecular marker, Lane ST1 represents the DNA isolated on day 1, lane ST2 represents the DNA isolated on day 2, lane ST3 represents the DNA isolated on day 3 and lane ST4 is the DNA isolated on Day 4. The top band mainly represents the bacterial DNA, while most of the human DNA is generally degraded (smeared below).

A. APC PCR

1. Primers
Sense APC4-5: 5'-AGTGGCATTATAAGCCCCAGTGAT-3' (SEQ ID NO:60)
Antisense APC4-3: 5'-AGCATTTACTGCAGCTTGCT-TAGG-3' (SEQ ID NO:61

2. PCR Cycling Conditions

After an initial cycle of denaturation at 94° C. for 2 minutes; amplification was as follows: 40 cycles of denaturation at 94° C. for 20 seconds, annealing at 61.8° C. for 30 seconds, and extension at 72° C. for 1 minute.

3. Reaction Mixture

Each reaction was carried out in a total volume of 30 µL and contained: 0.5 µL of each sense (APC4-5, 10 mM) and antisense (APC4-3, 10 mM) primers, 5 µL of template DNA and 15 µL of High Fidelity PCR Master (Roche).

4. Gel Analysis

After PCR, samples (5 µL) were analyzed on a 2.0% agarose gel that was run at 150V for 25 minutes. 100 bp ladder used as a DNA marker standard as well as quantitation standard. The PCR product visualized and quantitated using CCD-based imaging system and software (ChemImager, Alpha Innotech, San Leandro, Calif.).

5. Results

Figure 69:
FIG. 69 shows exemplary data using APC PCR from various stool samples isolated using a STAR buffer method (i.e., ST1 through ST4).

As seen in the FIG. 69, PCR product corresponding to 180 base pairs of APC gene is clearly seen in all the lanes (ST1-ST4) where the PCR was carried out using the DNA was isolated from stool stored in STAR buffer for 1 to 4 days. Lanes indicted with – and + are negative control and positive control, respectively. The quantitation of the above PCR product indicated the amount to be 40 ng to 80 ng per band (i.e. 8-16 ng per ul; total 240-480 ng per 30 ul PCR reaction).

B. P53 PCR

1. Primers
Sense P53-9-5: 5'-TGGTAACTCACTGGGACGGAACAG-3' (SEQ ID NO:62)
Antisense P53-9-3: 5'-CTCGCTTAGTGCTC-CCTGGGGGCA-3' (SEQ ID NO:63)

2. Cycle Conditions

After an initial cycle of denaturation at 94° C. for 2 minutes; amplification was as follows: 40 cycles of denaturation at 94° C. for 20 seconds, annealing at 61.8° C. for 30 seconds, and extension at 72° C. for 1 minute.

3. Reaction Mixture

Each reaction mixture was carried out in a total volume of 30 µL and contained: 0.5 µL of each sense (P53-9-5, 10 mM) and antisense (P53-9-3, 10 mM) primers, 5 µL of template DNA and 15 µL of High Fidelity PCR Master (Roche).

4. Gel Analysis

After PCR, samples (5 µL) were analyzed on a 2.0% agarose gel which was run at 150V for 25 minutes. 100 bp ladder used as a DNA marker standard as well as quantitation standard. The PCR product visualized and quantitated using CCD-based imaging system and software (ChemImager, Alpha Innotech, San Leandro, Calif.).

5. Results

Figure 70:
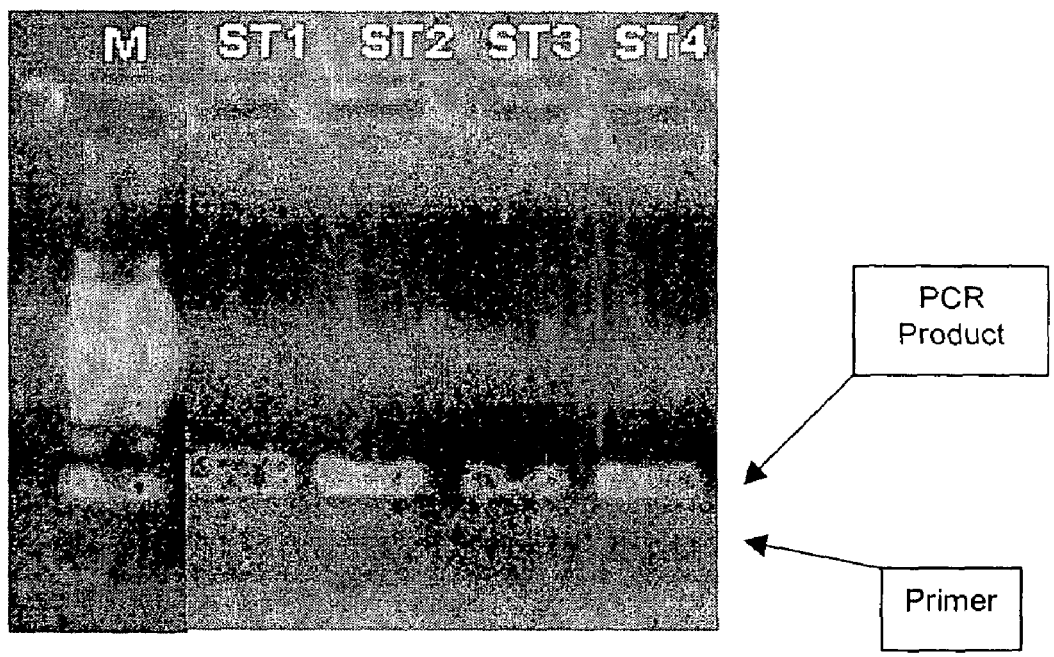
FIG. 70 shows exemplary data using P53 PCR from various stool samples using a STAR buffer method (i.e., ST1 through ST4).

As seen in the FIG. 70, PCR product corresponding to 137 base pairs of P53 gene is clearly seen in all the lanes (ST1-ST4) where the PCR was carried out using the DNA was isolated from stool stored in STAR buffer for 1 to 4 days. Lanes indicted with – and + are negative control and positive control, respectively. The quantitation of the above PCR product indicated the amount to be 40 ng to 80 ng per band (i.e. 8-16 ng per ul; total 240-480 ng per 30 ul PCR reaction).

C. K-RAS

Primers:
Sense KRAS-12F: 5'-GGCCTGCTGAAAATGACTGAA-3' (SEQ ID NO:64)
Antisense KRAS-12R: 5'-CTCTATTGTTGGATCATATTC-3' (SEQ ID NO:65)

1. Cycle Conditions

After an initial cycle of denaturation at 94° C. for 2 minutes; amplification was as follows: 40 cycles of denaturation at 94° C. for 20 seconds, annealing at 50.7° C. for 30 seconds, and extension at 72° C. for 1 minute.

2. Reaction Mixture

Each reaction mixture was carried out in a total volume of 30 µL and contained: 0.5 µL of each sense (KRAS-12F, 10 mM) and antisense (KRAS-12R, 10 mM) primers, 5 µL of template DNA and 15 µL of High Fidelity PCR Master (Roche).

3. Gel Analysis

After PCR, samples (5 µL) were analyzed on a 2.0% agarose gel which was run at 150V for 25 minutes. 100 bp ladder used as a DNA marker standard as well as quantitation standard. The PCR product visualized and quantitated using CCD-based imaging system and software (ChemImager, Alpha Innotech, San Leandro, Calif.).

4. Results

Figure 71:
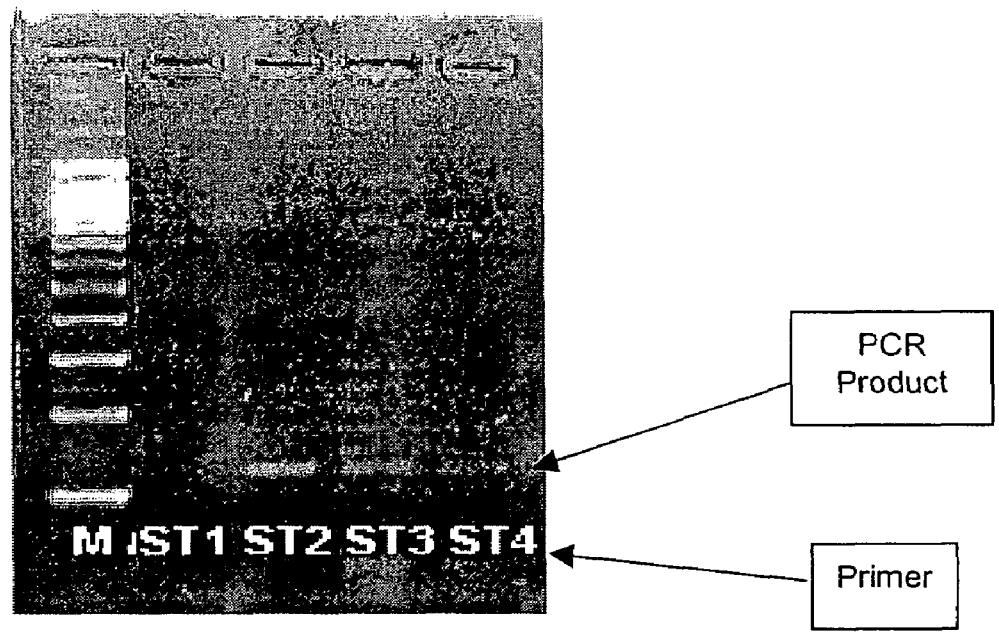
FIG. 71 shows exemplary data using K-RAS PCR from various stool samples using a STAR buffer method (i.e., ST1 through ST4).

As seen in the FIG. 71, PCR product corresponding to 123 base pairs of K-ras gene is clearly seen in all the lanes (SL1-SL4) where the PCR was carried out using the DNA was isolated from FOBT strips on day 1 to 4. Lanes indicted with – and + are negative control and positive control, respectively. The quantitation of the above PCR product indicated the amount to be 10 ng to 20 ng per band (i.e. 2-4 ng per ul; total 60-120 ng per 30 ul PCR reaction).

Example 55

Very Small Stool Sample Collection

Approximately 2-10 mg of stool sample is mixed with 100 ul of STAR buffer. The tube was then kept closed and stored in laminar hood at room temperature till further use. Just prior to DNA isolation, the eppendorf tube was vortexed on high until the majority of stool sample was homogenized. It was then centrifuged for 1 min at maximum speed (13,000 RPM) and the supernatant was transferred to new tube. To this tube, 1/10 volume of chloroform was added, vortexed briefly and centrifuged for 1 min at maximum speed. After centrifugation, supernatant was removed and volume of supernatant was adjusted to 1.4 mL using ASL Buffer. The stool DNA isolation was performed using the QIAamp DNA Stool Mini Kit (Cat. No. 51504) following the protocol given on page 22 for Isolation of DNA from Stool for Human DNA Analysis. Note that, the volumes before adding the Inhibitex tablet must be brought up to 1.4 mL with ASL Buffer or else sample will be completely absorbed into the tablet and supernatant will not be recovered. The quality of the isolated DNA was then checked by Agarose gel electrophoresis. This DNA was used for PCR amplification of APC and P53 gene segments.

Figure 72:
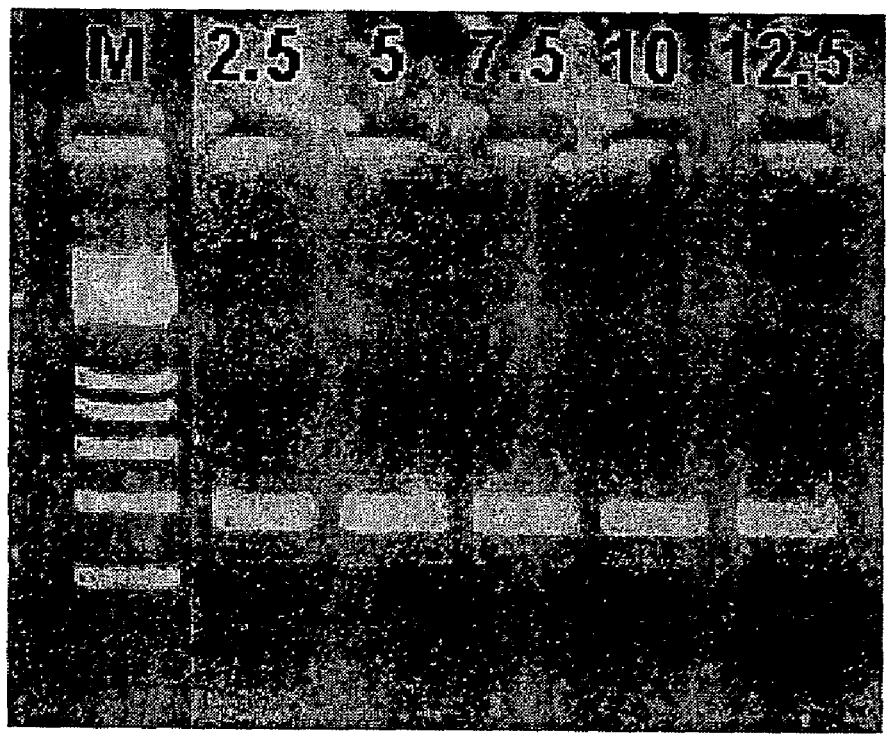
FIG. 72 shows exemplary data using APC PCR from very small stool samples using a STAR buffer method. M=molecular weight markers. 2.5-12.5 mg samples.
Figure 73:
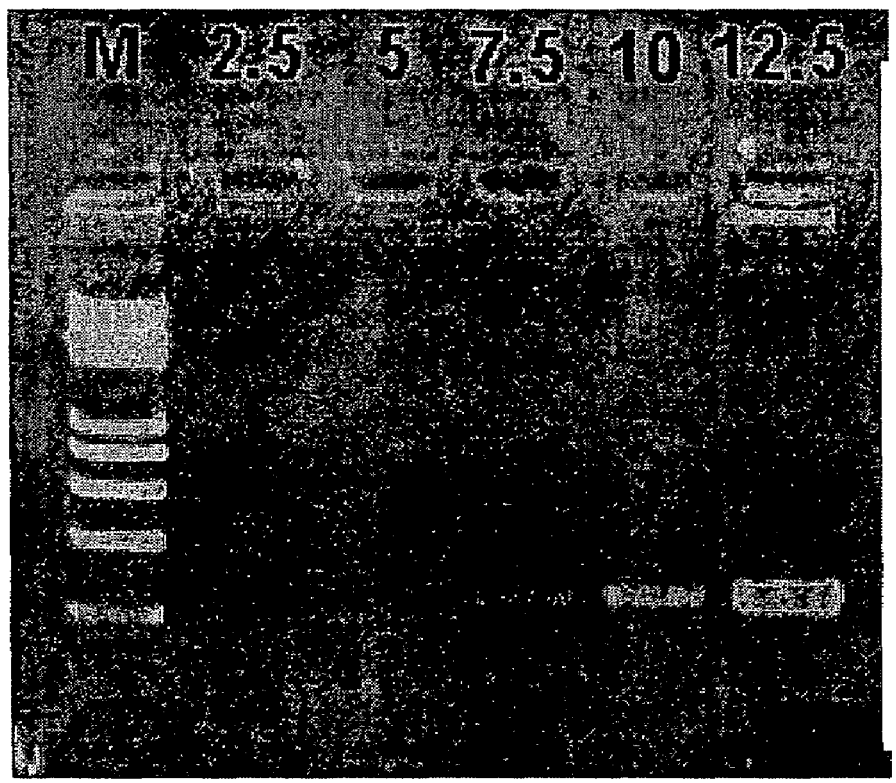
FIG. 73 shows exemplary data using P53 PCR from very small stool samples using a STAR buffer method. M=molecular weight markers. 2.5-12.5 mg samples.

As seen in the FIG. 72, PCR product corresponding to 180 base pairs of APC gene is clearly seen in all the lanes (2.5-12.5 mg) where the PCR was carried out using the DNA was isolated from various amount of stool material stored in STAR buffer (2.5 to 12.5 mg of stool material). Similarly, FIG. 73 shows PCR product corresponding to 137 base pairs of P53 gene is clearly seen in all the lanes (2.5-12.5 mg) where the PCR was carried out using the DNA was isolated from various amount of stool material stored in STAR buffer (2.5 to 12.5 mg of stool material).

Example 56

DNA Isolation from CRC Patients Using NIH Stool Repository

NIH stool repository contains archived stool samples collected from CRC patients over the past ten years. In one experiment, we have isolated DNA from small amounts of stool (100 mg of Stool) using QIAamp DNA Stool Mini Kit (Qiagen, Valencia, Calif.). The isolated DNA was analyzed on an agarose gel and the DNA was then quantitated using Molecular Probes PicoGreen DNA quantitation kit.

Figure 74:
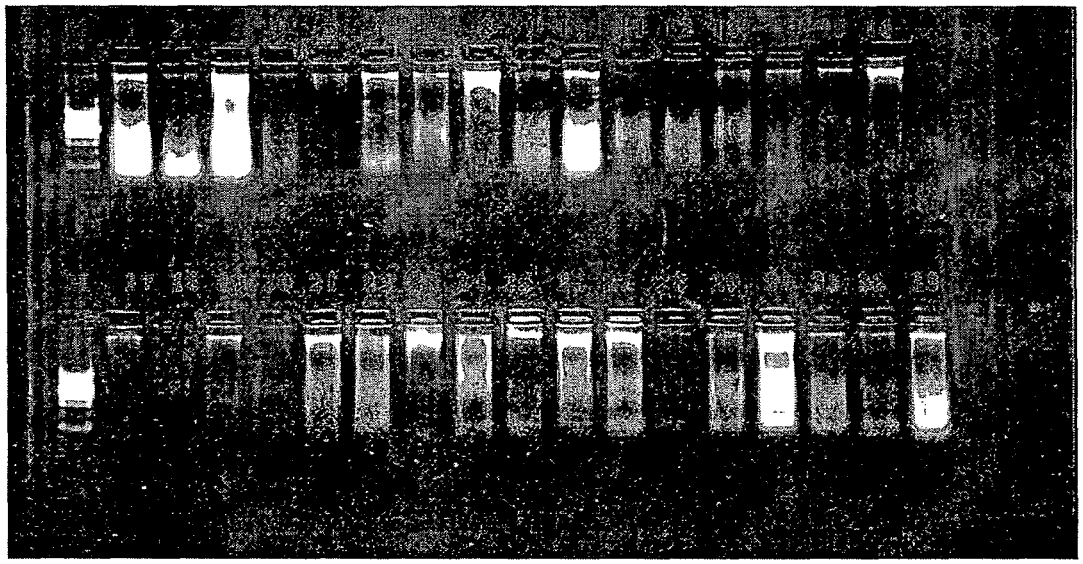
FIG. 74 shows exemplary data using agarose gel analysis of stool DNA isolated from an NIH stool sample repository.

The quantitation of total DNA isolated from NIH stool repository samples ranged from 0.3-5 ug. The result of agarose gel electrophoresis of DNA isolated from archived stool samples is shown in FIG. 74, Lanes 1-33). Lane M: molecular marker. The top band mainly represents the bacterial DNA, while most of the human DNA is generally degraded (smeared below).

A. APC PCR

1. Primers

Sense APC4-5: 5'-AGTGGCATTATAAGCCCCAGTGAT-3' (SEQ ID NO:60)
Antisense APC4-3: 5'-AGCATTTACTGCAGCTTGCT-TAGG-3' (SEQ ID NO:61)

2. PCR Cycling Conditions

After an initial cycle of denaturation at 94° C. for 2 minutes; amplification was as follows: 40 cycles of denaturation at 94° C. for 20 seconds, annealing at 61.8° C. for 30 seconds, and extension at 72° C. for 1 minute.

3. Reaction Mixture

Each reaction was carried out in a total volume of 30 µL and contained: 0.5 µL of each sense (APC4-5, 10 mM) and antisense (APC4-3, 10 mM) primers, 5 µL of template DNA and 15 µL of High Fidelity PCR Master (Roche).

4. Gel Analysis:

After PCR, samples (5 µL) were analyzed on a 2.0% agarose gel that was run at 150V for 25 minutes. 100 bp ladder used as a DNA marker standard. The PCR product visualized using CCD-based imaging system and software (ChemImager, Alpha Innotech, San Leandro, Calif.).

5. Results

Figure 75:
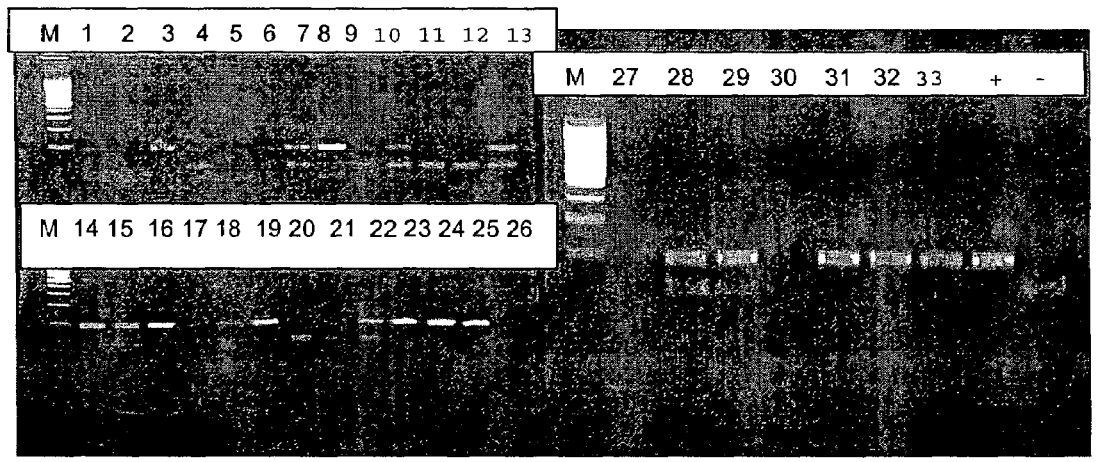
FIG. 75 shows exemplary data using APC PCR from various stool samples isolated from an NIH stool sample repository.

As seen in the FIG. 75, PCR product corresponding to 180 base pairs of APC gene is clearly seen in most of the lanes (1-33) where the PCR was carried out using the DNA was isolated from NIH stool repository samples. Lanes indicted with – and + are negative control and positive control, respectively.

B. P53 PCR

1. Primers

Sense P53-9-5: 5'-TGGTAACTCACTGGGACGGAACAG-3' (SEQ ID NO:62)
Antisense P53-9-3: 5'-CTCGCTTAGTGCTC-CCTGGGGGCA-3' (SEQ ID NO:63)

2. Cycle Conditions

After an initial cycle of denaturation at 94° C. for 2 minutes; amplification was as follows: 40 cycles of denaturation at 94° C. for 20 seconds, annealing at 61.8° C. for 30 seconds, and extension at 72° C. for 1 minute.

3. Reaction Mixture

Each reaction was carried out in a total volume of 30 µL and contained: 0.5 µL of each sense (P53-9-5, 10 mM) and antisense (P53-9-3, 10 mM) primers, 5 µL of template DNA and 15 µL of High Fidelity PCR Master (Roche).

4. Gel Analysis

After PCR, samples (5 µL) were analyzed on a 2.0% agarose gel which was run at 150V for 25 minutes. 100 bp ladder used as a DNA marker standard. The PCR product visualized using CCD-based imaging system and software (ChemImager, Alpha Innotech, San Leandro, Calif.).

5. Results

Figure 76:
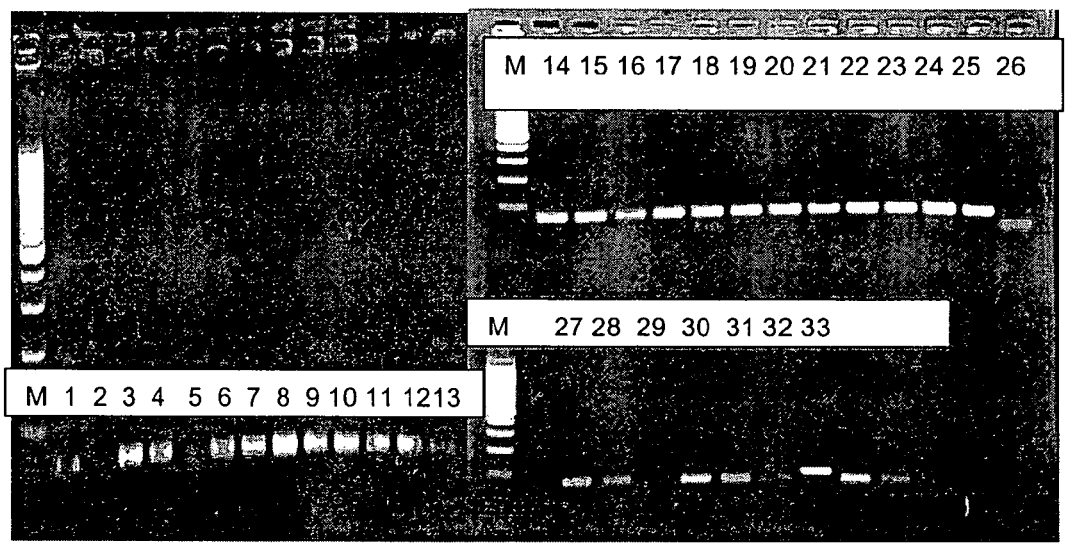
FIG. 76 shows exemplary data using P53 PCR from various stool samples isolated from an NIH stool sample repository.

As seen in the FIG. 76, PCR product corresponding to 137 base pairs of P53 gene is clearly seen in most of the lanes (1-33) where the PCR was carried out using the DNA was isolated from NIH stool repository samples. Lanes indicted with − and + are negative control and positive control, respectively.

C. K-RAS

1. Primers

Sense KRAS-12F: 5'-GGCCTGCTGAAAATGACTGAA-3' (SEQ ID NO:64)
Antisense KRAS-12R: 5'-CTCTATTGTTGGATCATATTC-3' (SEQ ID NO:65)

2. Cycle Conditions

After an initial cycle of denaturation at 94° C. for 2 minutes; amplification was as follows: 40 cycles of denaturation at 94° C. for 20 seconds, annealing at 50.7° C. for 30 seconds, and extension at 72° C. for 1 minute.

3. Reaction Mixture

Each reaction was carried out in a total volume of 30 μL and contained: 0.5 μL of each sense (KRAS-12F, 10 mM) and antisense (KRAS-12R, 10 mM) primers, 5 μL of template DNA and 15 μL of High Fidelity PCR Master (Roche).

4. Gel Analysis

After PCR, samples (5 μL) were analyzed on a 2.0% agarose gel which was run at 150V for 25 minutes. 100 bp ladder used as a DNA marker standard. The PCR product visualized using CCD-based imaging system and software (ChemImager, Alpha Innotech, San Leandro, Calif.).

5. Results

Figure 77:
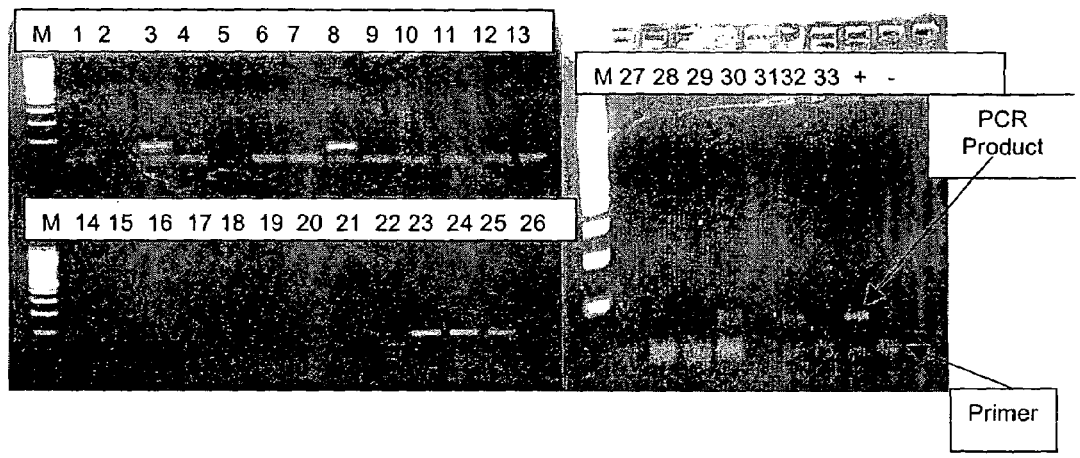
FIG. 77 shows exemplary data using K-RAS PCR from various stool samples isolated from an NIH stool sample repository.

As seen in the FIG. 77, PCR product corresponding to 123 base pairs of K-ras gene is clearly seen in most of the lanes (Lane 1-33) where the PCR was carried out using the DNA was isolated from NIH stool repository samples. Lanes indicted with − and + are negative control and positive control, respectively.

Example 3

APC PCR (Longer Size Amplicons)

D. Single Step PCR

1. Primers

Sense: APC-BV-VSV: 5'-GGATCCTAATACGACTCACTATAGG-GAGACCACCATGGGC TACACCGA CATCGAGAT-GAACCGCCTGGGCAAGTCTGGACAAAG-CAGTAAAACCG AACAT-3' (SEQ ID NO:101)
Antisense: APC-BV-P53: 5'-TTATTACAGCAGCTTGTGCAGGTCGCT-GAAGGTACG TGATGACTTTGTTG GCATGGCAGA-3' (SEQ ID NO:102)

2. PCR Cycling Conditions

After an initial cycle of denaturation at 94° C. for 3 minutes; amplification was as follows: 35 cycles of denaturation at 94° C. for 45 seconds, annealing at 56° C. for 45 seconds, and extension at 72° C. for 4 minute.

3. Reaction Mixture

Each reaction was carried out in a total volume of 30 μL and contained: 0.5 μL of each sense (APC-BV-VSV, 10 mM) and antisense (APC-BV-P53, 10 mM) primers, 1 μL of template DNA and 15 μL of High Fidelity PCR Master (Roche).

4. Gel Analysis

After PCR, samples (5 μL) were analyzed on a 2.0% agarose gel that was run at 150V for 25 minutes. 100 bp ladder used as a DNA marker standard. The PCR product visualized using CCD-based imaging system and software (ChemImager, Alpha Innotech, San Leandro, Calif.).

5. Results

Figure 78:
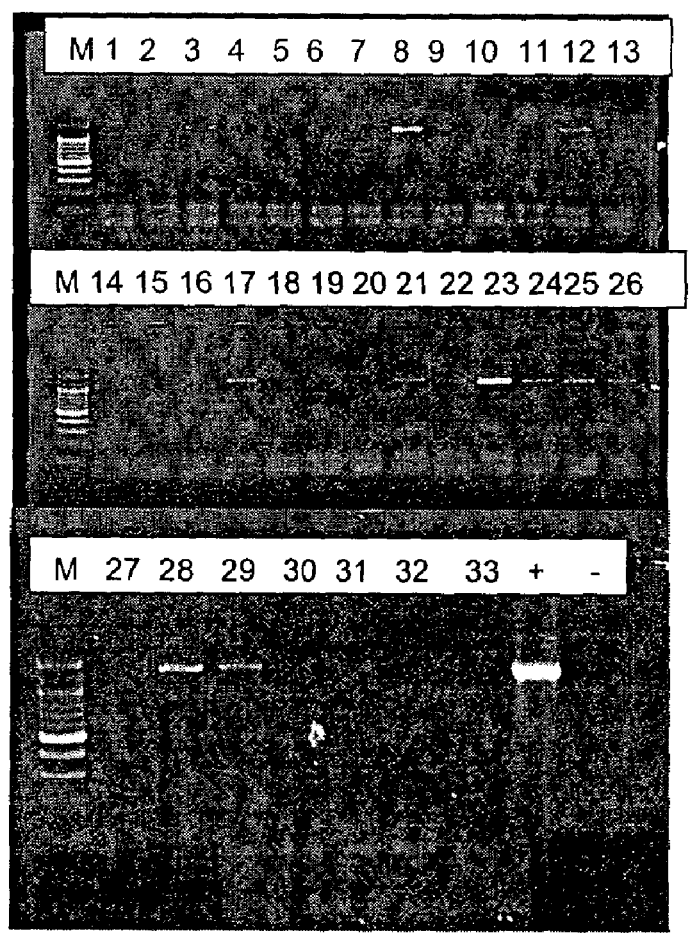
FIG. 78 shows exemplary data using single step APC (Long DNA) PCR from various stool samples isolated from an NIH stool sample repository.

As seen in the FIG. 78, PCR product corresponding to 1500 base pairs of APC gene is clearly seen in the several lanes when one-step PCR was carried out using the DNA was isolated from NIH stool repository samples.

E. Two Step Nested PCR

1. Primers

Primers for first PCR:
Sense APC-BV-F1: 5'-ACG TCA TGT GGA TCA GCC TAT TG-3' (SEQ ID NO:103), and
Antisense: APC-BV-R1: 5'-GGT AAT TTT GAA GCA GTC TGG GC-3' (SEQ ID NO:104); and, Primers for second PCR:
Sense: APC-BV-VSV: 5'-GGATCCTAATACGACTCAC-TATAGGGAGACCA CCATGGGCTACACCGACATC-GAGATGAACCGCCTGGGCAAGTCTGGA CAAAG-CAGTAAAACCGAACAT-3' (SEQ ID NO:101), and
Antisense: APC-BV-P53: 5'-TTATTACAGCAGCTTGTG-CAGGTCGCTGAAGG TACGTGATGACTTTGTTG-GCATGGCAGA-3' (SEQ ID NO:102)

2. PCR Cycling Conditions:

After an initial cycle of denaturation at 95° C. for 3 minutes; amplification was as follows: 40 cycles of denaturation at 95° C. for 30 seconds, annealing at 56° C. for 30 seconds, and extension at 72° C. for 90 seconds. After the completion of first PCR, 1 ul PCR product was used as a template for second PCR. The conditions were: an initial cycle of denaturation at 94° C. for 3 minutes; amplification was as follows: 35 cycles of denaturation at 94° C. for 45 seconds, annealing at 56° C. for 45 seconds, and extension at 72° C. for 4 minute.

3. Reaction Mixture

First PCR: Each reaction was carried out in a total volume of 30 μL and contained: 0.5 μL of each sense (APC-BV-VSV, 10 mM) and antisense (APC-BV-P53, 10 mM) primers, 1 μL of template DNA and 15 μL of High Fidelity PCR Master (Roche).

Second PCR: Each reaction was carried out in a total volume of 30 μL and contained: 0.5 μL of each sense (APC-BV-VSV, 10 mM) and antisense (APC-BV-P53, 10 mM) primers, 1 μL of template DNA (first PCR product) and 15 μL of High Fidelity PCR Master (Roche).

4. Gel Analysis

After second PCR, samples (5 μL) were analyzed on a 2.0% agarose gel that was run at 150V for 25 minutes. 100 bp ladder used as a DNA marker standard as well as quantitation standard. The PCR product visualized using CCD-based imaging system and software (ChemImager, Alpha Innotech, San Leandro, Calif.).

5. Results

Figure 79:
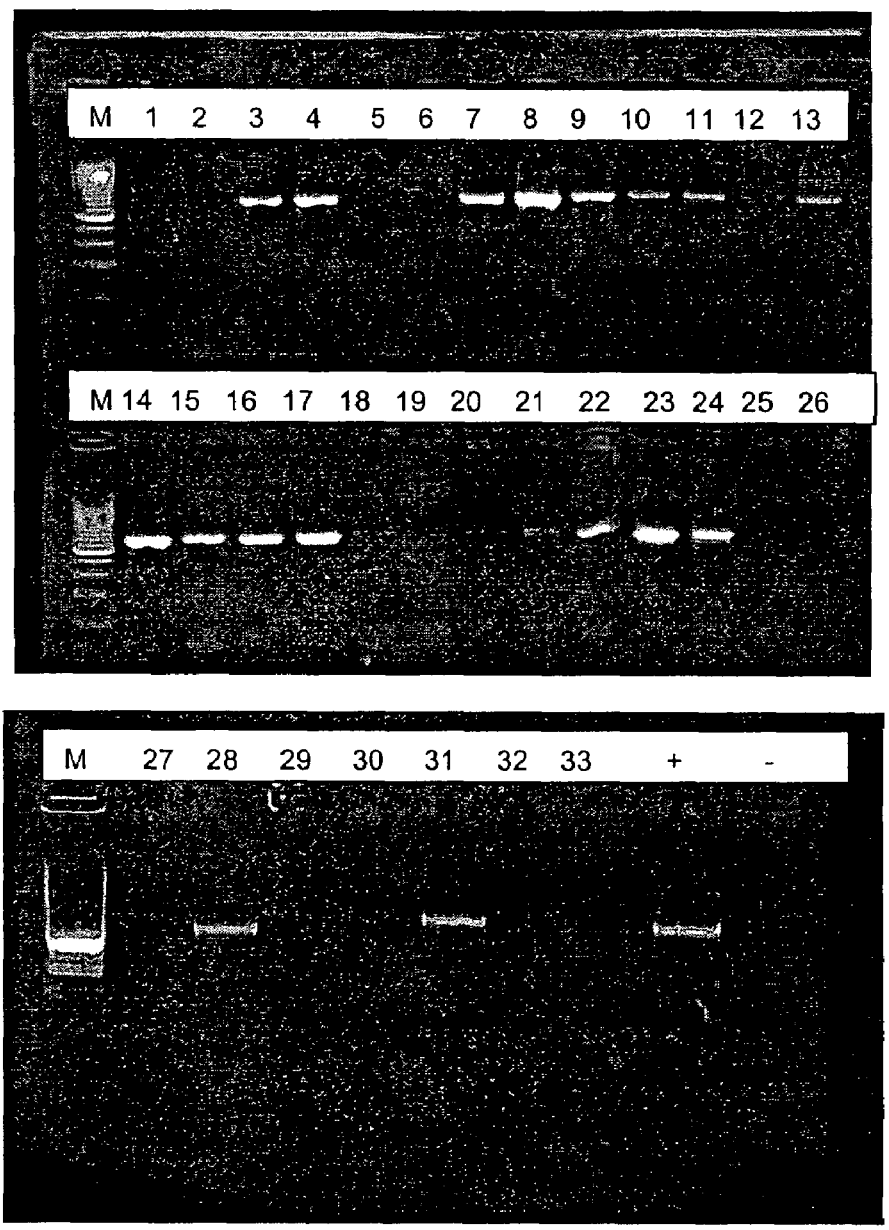
FIG. 79 shows exemplary data using two step nested APC (Long DNA) PCR from various stool samples isolated from an NIH stool sample repository.

As seen in the FIG. 79, strong PCR product corresponding to 1500 base pairs of APC gene is clearly seen in most of the lane the lanes (1-33) when 2-step PCR was carried out using the DNA was isolated from NIH stool repository samples.

Example 57

Isolation of DNA from Very Small Amounts of Stool Samples and PCR Amplification of Long DNA The DNA isolation and long DNA 2-step PCR was carried out exactly in a similar fashion as described in Example 56 except that a very small starting material was used (1-10 mg; FIG. 80).

Figure 81:
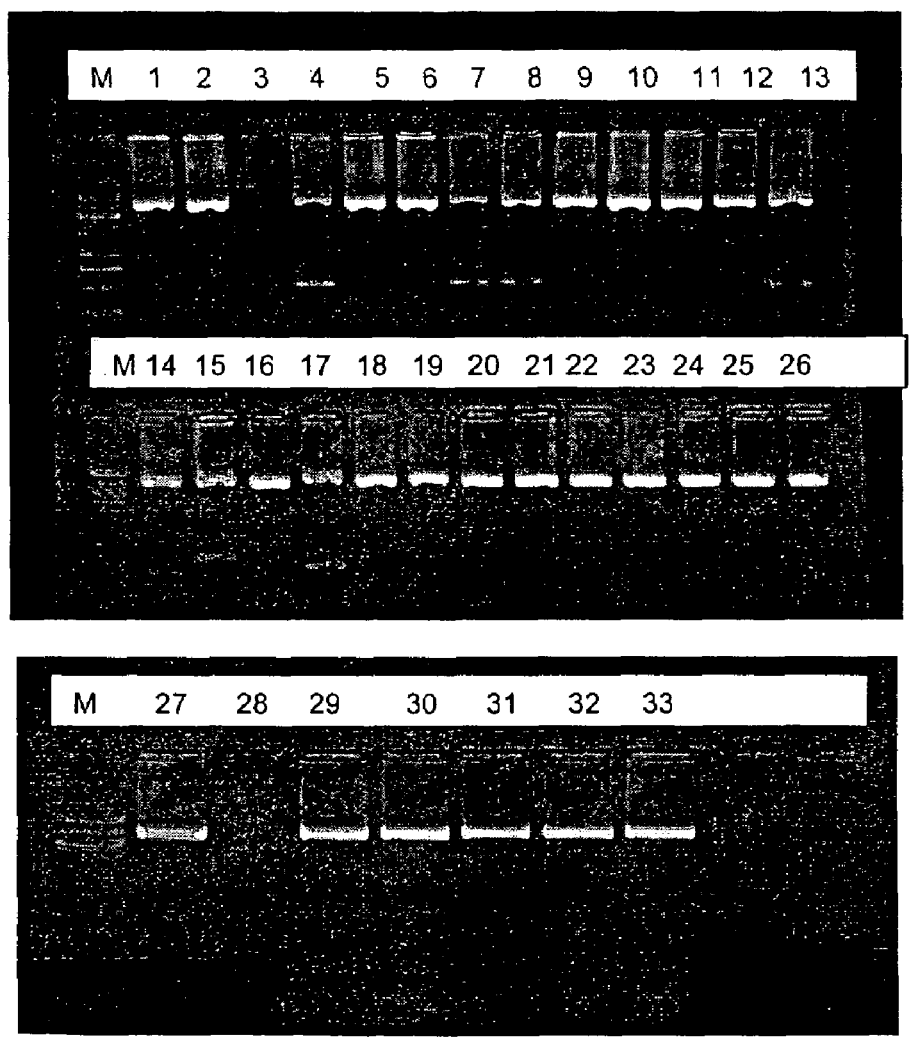
FIG. 81 shows exemplary data using very small amounts (i.e., 1-10 mg) of stool material using two step nested APC (Long DNA) PCR from various stool DNA isolated from an NIH stool sample repository.

As seen in the FIG. 81, strong PCR product corresponding to 1500 base pairs of APC gene is clearly seen in most of the lane the lanes (1-33) when 2-step PCR was carried out using the DNA that was isolated from small amount (1-10 mg) of NIH stool repository samples.

Example 58

FOBT on NIH Repository Stool Samples

FOBT was carried out using Hemoccult II FOBT kit (Beckman Coulter, Brea, Calif.). The slide was removed from paper dispensing envelope. Open front of section 1 and using one stick, small sample was collected and applied as a thin smear covering Box A. Second samples was collected from different part of stool was collected and applied as a thin smear covering Box B. Samples were then allowed to dry for 10-15 minutes and the developing reagent was added and the color appeared in the FOBT strip windows was noted immediately. A blue color indicated a positive FOBT test and samples were designated either (+) or (−). (see FIG. 80).

We claim:

1. A method, comprising:
   a) providing a fecal specimen on a surface, wherein the dry weight of said fecal specimen is less than 10 mg, said surface comprising guaiac, said specimen comprising DNA;
   b) extracting said DNA; and
   c) testing said DNA for mutations.

2. The method of claim 1, wherein the dry weight of said fecal specimen is between 1 and 3 mg.

3. The method of claim 1, wherein said testing of step (b) comprises using an assay with a sensitivity capable of measuring 1 mutant gene out of 50 wild type genes.

4. The method of claim 1, wherein, prior to step (b), the method comprises amplifying one or more regions of said DNA.

5. The method of claim 4, wherein said amplifying comprises performing a polymerase chain reaction.

6. The method of claim 1, wherein said testing results in the detection of a mutation.

7. The method of claim 6, wherein said detected mutation is in one or more of said gene selected from the group consisting of the APC, K-RAS, p53 and beta-catenine gene.

8. The method of claim 7, wherein said surface is part of a slide contained in a commercial kit used for fecal occult blood testing.

9. The method of claim 3, wherein said assay comprises a HTS-PTT assay.

10. The method of claim 3, wherein said assay comprises a Point-EXACCT assay.

11. A method, comprising:
    a) providing a fecal specimen on a surface, wherein the dry weight of said fecal specimen is less than 10 mg, said surface comprising guaiac, said specimen comprising DNA;
    b) extracting at least a portion of said DNA to create isolated DNA, and
    c) testing said isolated DNA for mutations.

12. The method of claim 11, wherein the dry weight of said fecal specimen is between 1 and 3 mg.

13. The method of claim 11, wherein said testing of step (c) comprises using an assay with a sensitivity capable of measuring 1 mutant gene out of 50 wild type genes.

14. The method of claim 11, wherein, prior to step (c), the method comprises amplifying one or more regions of said isolated DNA.

15. The method of claim 14, wherein said amplifying comprises performing a polymerase chain reaction.

16. The method of claim 11, wherein said testing results in the detection of a mutation.

17. The method of claim 16, wherein said detected mutation is in one or more of said gene selected from the group consisting of the APC, K-RAS, p53 and beta-catenine gene.

18. The method of claim 17, wherein said surface is part of a slide contained in a commercial kit used for fecal occult blood testing.

19. The method of claim 13, wherein said assay comprises a HTS-PTT assay.

20. The method of claim 13, wherein said assay comprises a Point-EXACCT assay.

21. A method, comprising:
    a) extracting DNA from a fecal specimen deposited on a surface, wherein the dry weight of said fecal specimen is less than 10 mg, said surface comprising guaiac, said specimen comprising DNA; and
    b) testing said isolated DNA for mutations.

* * * * *